(12) United States Patent
Kawata et al.

(10) Patent No.: US 8,791,266 B2
(45) Date of Patent: Jul. 29, 2014

(54) THYROID HORMONE β RECEPTOR AGONIST

(75) Inventors: Shinji Kawata, Osaka (JP); Koji Matsumoto, Osaka (JP); Maki Niijima, Osaka (JP); Taichi Takahashi, Osaka (JP)

(73) Assignee: Mitsubishi Tanabe Pharma Corporation, Osaka (JP)

(*) Notice: Subject to any disclaimer, the term of this patent is extended or adjusted under 35 U.S.C. 154(b) by 0 days.

(21) Appl. No.: 13/265,137

(22) PCT Filed: Apr. 19, 2010

(86) PCT No.: PCT/JP2010/056936
§ 371 (c)(1),
(2), (4) Date: Dec. 29, 2011

(87) PCT Pub. No.: WO2010/122980
PCT Pub. Date: Oct. 28, 2010

(65) Prior Publication Data
US 2012/0129812 A1 May 24, 2012

(30) Foreign Application Priority Data

Apr. 20, 2009 (JP) .................. 2009-102259

(51) Int. Cl.
*C07D 211/72* (2006.01)
*A61K 31/675* (2006.01)

(52) U.S. Cl.
USPC .......................... 546/290; 514/345

(58) Field of Classification Search
None
See application file for complete search history.

(56) References Cited

U.S. PATENT DOCUMENTS

| | | | |
|---|---|---|---|
| 6,395,784 B1 * | 5/2002 | Ryono | 514/563 |
| 6,656,957 B1 | 12/2003 | Allgeier et al. | |
| 7,199,265 B2 * | 4/2007 | Yi-Lin et al. | 562/426 |
| 7,557,143 B2 * | 7/2009 | Ryono et al. | 514/568 |
| 2001/0051645 A1 | 12/2001 | Chiang | |
| 2002/0035153 A1 | 3/2002 | Cornelius et al. | |
| 2002/0133005 A1 | 9/2002 | Iino et al. | |
| 2003/0007941 A1 | 1/2003 | Cornelius et al. | |
| 2003/0078288 A1 | 4/2003 | Haning et al. | |
| 2004/0039028 A1 | 2/2004 | Zhang et al. | |
| 2004/0097589 A1 | 5/2004 | Yi-Lin et al. | |
| 2004/0176425 A1 | 9/2004 | Washburn et al. | |
| 2005/0004184 A1 | 1/2005 | Ryono et al. | |
| 2005/0085541 A1 | 4/2005 | Shiohara et al. | |
| 2005/0107347 A1 | 5/2005 | Malm et al. | |
| 2005/0171104 A1 | 8/2005 | Rahimi-Ghadim et al. | |
| 2005/0282872 A1 | 12/2005 | Hangeland et al. | |
| 2007/0027215 A1 | 2/2007 | Baxter et al. | |
| 2009/0005383 A1 | 1/2009 | Haynes et al. | |

FOREIGN PATENT DOCUMENTS

| | | |
|---|---|---|
| RU | 2203889 C2 | 5/2003 |
| WO | WO 00/39077 A2 | 7/2000 |
| WO | WO 01/02359 A1 | 1/2001 |
| WO | WO 01/94293 A2 | 12/2001 |
| WO | WO 02/094319 A1 | 11/2002 |
| WO | WO 03/094845 A2 | 11/2003 |
| WO | WO 2004/066929 A2 | 8/2004 |
| WO | WO 2004/093799 A2 | 11/2004 |
| WO | WO 2004/103289 A2 | 12/2004 |
| WO | WO 2007/009913 A1 | 1/2007 |
| WO | WO 2007/018956 A2 | 2/2007 |
| WO | WO 2007/066784 A2 | 6/2007 |
| WO | WO 2007/132475 A1 | 11/2007 |

OTHER PUBLICATIONS

Silverman, R. "The Organic Chemistry of Drug Design and Drug Action," 2004, Elsevier, pp. 29-32.*
Stanton, J.L. et al., Bioorg. Med. Chem. Lett. 2000, vol. 10, pp. 1661-1663.*
Chiellini, G. et al., Bioog. Med. Chem., 2002, vol. 10, pp. 333-346.*
Baxter et al., "Selective modulation of thyroid receptor action," Journal of Steroid Biochemistry & Molecular Biology (2001) vol. 76, pp. 31-42
Gloss et al., "Cardiac Ion Channel Expression and Contractile Function in Mice with Deletion of Thyroid Hormone Receptor alpha or beta," Endocrinology (2001) vol. 142, No. 2, pp. 544-550
Grover et al., "Development of the Thyroid Hormone Receptor beta-Subtype Agonist KB-141: A Strategy for Body Weight Reduction and Lipid Lowering with Minimal Cardiac Side Effects," Cardiovascular Drug Reviews (2005) vol. 23, No. 2, pp. 133-148

(Continued)

*Primary Examiner* — Heidi Reese
(74) *Attorney, Agent, or Firm* — Birch, Stewart, Kolasch & Birch, LLP

(57) ABSTRACT

Provided is a heterocyclic derivative showing a thyroid hormone β receptor agonist action, which is effective for the prophylaxis or treatment of the diseases relating to the action. A compound represented by the formula [I]:

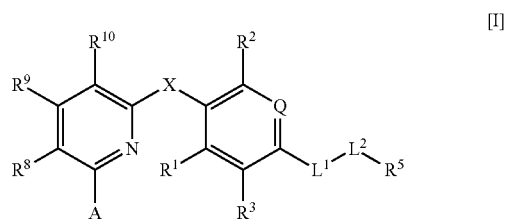

wherein each symbol is as defined in the specification, a pharmacologically acceptable salt thereof, and a medicament containing the compound as an active ingredient.

19 Claims, No Drawings

(56) References Cited

OTHER PUBLICATIONS

Schwartz et al., "Quantitation of Rat Tissue Thyroid Hormone Binding Receptor Isoforms by Immunoprecipitation of Nuclear Triiodothyronine Binding Capacity," The Journal of Biological Chemistry (1992) vol. 267, No. 17, pp. 11794-11799

Underwood et al., "A thyromimetic that decreases plasma cholesterol levels without increasing cardiac activity," Nature (Dec. 1986) vol. 324, pp. 425-429

Yen, "Physiological and Molecular Basis of Thyroid Hormone Action," Physiological Reviews (Jul. 2001) vol. 81, No. 3, pp. 1097-1142

Yoshihara et al., "Selective Thyroid Hormone Receptor Modulators," Current Topics in Medicinal Chemistry (2003) vol. 3 pp. 1601-1616.

International Search Report, dated Jun. 8, 2010, issued in PCT/JP2010/056936.

Supplementary European Search Report dated Sep. 18, 2012 issued in connection with corresponding European Application No. 10 76 7037.

Russian Decision on Grant of Patent for Invention for Russian Application No. 2011147069/04(070571) dated May 5, 2014 with English language translation.

* cited by examiner

# THYROID HORMONE β RECEPTOR AGONIST

TECHNICAL FIELD

The present invention relates to a novel heterocyclic compound and a novel thyroid hormone β receptor agonist containing the compound as an active ingredient, which is useful for hypercholesterolemia, hyperlipidemia, hypertriglyceridemia, familial hypercholesterolemia, dyslipidemia, atherosclerosis, hypothyroidism and/or latent hypothyroidism and the like.

BACKGROUND ART

Thyroid hormone is synthesized in vivo in the form of thyroxine (T4), which is an inactive form, released into the blood, converted to triiodothyronine (T3), which is an active form, in each target tissue, bound to α receptor (TRα) and β receptor (TRβ) of thyroid hormone receptor (TR) classified as a nuclear receptor, functions as a transcription factor in the cell nucleus and provides a physiological action characteristic of each target organ. T3 is metabolized in the target organ and primarily excreted in bile. The physiological action of thyroid hormone in mammals plays a very important role in the growth and differentiation, as well as maintenance of vital function such as control of heart rate, blood cholesterol and triglyceride concentration, systemic metabolic rate and body weight and the like. In terms of pathologic physiology, tachycardia, arrhythmia, cardiac failure, as well as feeling of fatigue, rapid breathing and beating, decreased skeletal muscle, osteoporosis and the like are observed in hyperthyroidism such as Graves' disease (non-patent document 1, non-patent document 2). On the contrary, beneficial phenomenon for the treatment of metabolic diseases such as decreased blood cholesterol, increased basal metabolism and the like are also observed. Conversely, decreased heart rate, increased blood cholesterol and increased body weight are observed in hypothyroid (thyroid hormone deficiency) caused by hypophysis disorder, congenital dysfunction and the like.

Assuming specific exertion of the advantageous aspects of thyroid hormone such as decreased blood cholesterol or increased basal metabolism while avoiding harmful event such as increased heartbeat and the like, and aiming at liver-specific accumulation of the compound, the development of several kinds of thyroid hormone analogues was tried (non-patent document 3, non-patent document 4). As a result, however, an influence primarily on the circulatory system could not be avoided, and the development thereof has not made any progress (non-patent document 5).

It has been reported that thyroid hormone receptors include receptor subtypes of TRα and TRβ (5 kinds of TRα1, TRα2, TRβ1, TRβ2 and TRβ3 including splice variants), and each receptor shows different tissue distribution. That is, it has been clarified that both TRα and TRβ are co-present in the liver wherein 70-80% is occupied by TRβ to be involved in the lipid metabolism and, in the heart, TRα receptor is involved in increased heartbeat and increased cardiac output (non-patent document 6, non-patent document 7).

As TRβ agonist (Thyromimetics), diphenylmethane derivative and diaryl ether derivative (patent documents 1-13), pyridazine derivative (patent document 14), pyridine derivative (patent document 15), and indole derivative (patent document 16) have been reported. However, these have different structures from that of the present invention.

DOCUMENT LIST

Patent Documents patent document 1: WO97/21993
patent document 2: WO2004/066929
patent document 3: WO2004/093799
patent document 4: WO2000/039077
patent document 5: WO2001/098256
patent document 6: WO2003/018515
patent document 7: WO2003/084915
patent document 8: WO2002/094319
patent document 9: WO2003/064369
patent document 10: JP-A-2002-053564
patent document 11: JP-A-2002-370978
patent document 12: JP-A-2000-256190
patent document 13: WO2007/132475
patent document 14: WO2007/009913
patent document 15: WO2003/094845
patent document 16: WO2002/051805

Non-Patent Documents non-patent document 1: Physiol. Rev., 81, 1097, 2001.
non-patent document 2: J. Steroid. Biochem. Mol. Biol., 76, 31, 2001.
non-patent document 3: Curr. Top Med. Chem., 3, 1601, 2003.
non-patent document 4: Nature, 324, 425, 1986.
non-patent document 5: Cardiovascular Drug Reviews, 23, 133, 2005.
non-patent document 6: Endocrinology, 142, 544, 2001.
non-patent document 7: J. Biol. Chem., 267, 11794, 1992.

SUMMARY OF THE INVENTION

Problems to be Solved by the Invention

The present invention relates to a novel heterocyclic compound and a novel thyroid hormone β receptor agonist containing the compound as an active ingredient, which is useful for hypercholesterolemia, hyperlipidemia, hypertriglyceridemia, familial hypercholesterolemia, dyslipidemia, atherosclerosis, hypothyroidism and/or latent hypothyroidism and the like.

Means of Solving the Problems

The present inventors have conducted intensive studies in an attempt to solve the above-mentioned problems and found that a particular heterocyclic derivative can solve a desired object, which resulted in the completion of the present invention.

The present invention relates to the following heterocyclic derivative or a pharmacologically acceptable salt thereof, and use thereof.

The present invention encompasses the following specific embodiments.

(1) A compound represented by the formula [I]:

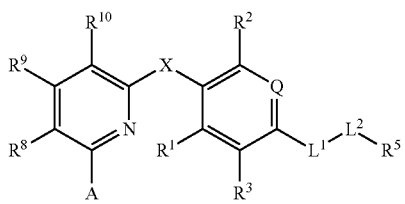

wherein
A is optionally substituted alkyl, optionally substituted carbocyclic group, optionally substituted aryl, optionally substituted heterocyclic group, optionally substituted heteroaryl, optionally substituted amino, or optionally substituted carbamoyl,
X is optionally substituted methylene, —O— or —S—,
Q is N or C—R⁴,
L¹ is single bond, methylene, —CH=CH—, —O—, —CO—, —NR¹¹—, —NR¹¹CO—, —CONR¹¹—, —CH₂NR¹¹— or —S—,
L² is single bond, —CR⁶R⁷—, or divalent heterocyclic group,
R¹ and R² are the same or different and each is hydrogen, alkyl, alkenyl or halogen,
R³ and R⁴ are the same or different and each is hydrogen, alkyl, alkoxy, cyano or halogen,
R¹ and R³ are optionally bonded to form carbocycle or heterocycle,
R⁵ is carboxyl group, an alkoxycarbonyl group or bioisosteric group of carboxyl group,
R⁶ and R⁷ are the same or different and each is hydrogen, optionally substituted alkyl or halogen, or
R⁶ and R⁷ are bonded to form cycloalkane or heterocycle,
R⁸ is hydroxy, alkanoylamino or alkylsulfonylamino,
R⁹ and R¹⁰ are the same or different and each is hydrogen, alkyl or halogen, and
R¹¹ is hydrogen or alkyl,
or a pharmacologically acceptable salt thereof.
(2) The compound of (1), wherein the substituent of the optionally substituted alkyl for A is the same or different 1-3 groups selected from
aryl optionally substituted by 1-3 groups selected from alkyl, halogen, alkoxy, alkanoyl, and cyano;
a heterocyclic group optionally substituted by 1-3 groups selected from alkyl, halogen, alkoxy, alkanoyl, and cyano;
heteroaryl optionally substituted by 1-3 groups selected from alkyl, halogen, alkoxy, alkanoyl, and cyano;
cycloalkyl optionally substituted by 1-3 groups selected from alkyl, halogen, alkoxy, alkanoyl, and cyano;
hydroxy;
alkoxy;
halogen;
an amino group optionally substituted by 1 or 2 alkyl; and
oxo,
the substituent of the optionally substituted aryl, an optionally substituted carbocyclic group, optionally substituted heterocyclic group and optionally substituted heteroaryl for A is the same or different 1-3 groups selected from
alkyl optionally substituted by hydroxy, alkoxy, cycloalkyl or halogen;
alkenyl optionally substituted by alkoxy or cycloalkyl;
cycloalkyl optionally substituted by alkyl, alkoxy or cycloalkyl;
alkoxy optionally substituted by alkoxy, cycloalkyl or halogen;
cycloalkyloxy optionally substituted by alkyl, alkoxy or cycloalkyl;
halogen;
cyano;
hydroxy;
oxo;
heterocycle;
alkylsulfonyl; and
mono or dialkylcarbamoyl,
the substituent of the optionally substituted amino for A is the same or different 1 or 2 alkyl optionally substituted by alkoxy, cycloalkyl or halogen;
alkenyl optionally substituted by alkoxy or cycloalkyl;
cycloalkyl optionally substituted by alkyl, alkoxy or cycloalkyl;
alkanoyl optionally substituted by alkoxy, cycloalkyl or halogen; or
aryl optionally substituted by alkyl, alkoxy or cycloalkyl,
the substituent of the optionally substituted carbamoyl for A is the same or different 1 or 2 alkyl optionally substituted by aryl,
the substituent of the optionally substituted alkyl for R⁶ or R⁷ is alkoxy, hydroxy or halogen, and
the substituent of the optionally substituted methylene for X is alkoxy or hydroxy, or a pharmacologically acceptable salt thereof.
(3) The compound of (1) or (2), wherein A is optionally substituted alkyl, optionally substituted carbocyclic group, optionally substituted aryl, optionally substituted heterocyclic group or optionally substituted heteroaryl,
Q is C—R⁴,
R¹ and R² are the same or different and each is alkyl or halogen,
R³ and R⁴ are the same or different and each is hydrogen, alkyl or halogen,
X is methylene, —O— or —S—,
R⁵ is carboxyl group, alkoxycarbonyl group, or bioisosteric group of carboxyl group,
L¹ is single bond, methylene, —CH=CH—, —O—, —NH—, —NHCO— or —S—,
L² is single bond, —CR⁶R⁷—, or divalent heterocyclic group,
R⁶ and R⁷ are the same or different and each is hydrogen, alkyl or halogen, or R⁶ and R⁷ form cycloalkane or heterocycle together with the adjacent carbon,
R⁸ is hydroxy, and
R⁹ and R¹⁰ are hydrogen, or a pharmacologically acceptable salt thereof.
(4) The compound of any of (1) to (3), wherein A is optionally substituted carbocyclic group, or a pharmacologically acceptable salt thereof.
(5) The compound of any of (1) to (3), wherein A is optionally substituted aryl, or a pharmacologically acceptable salt thereof.
(6) The compound of (4), wherein the optionally substituted carbocyclic group is optionally substituted cycloalkyl, or a pharmacologically acceptable salt thereof.
(7) The compound of any of (1) to (3), wherein A is optionally substituted alkyl, or a pharmacologically acceptable salt thereof.
(8) The compound of any of (1) to (3), wherein A is optionally substituted heterocyclic group, or a pharmacologically acceptable salt thereof.
(9) The compound of any of (1) to (3), wherein A is optionally substituted heteroaryl, or a pharmacologically acceptable salt thereof.
(10) The compound of any of (1) to (9), wherein X is methylene, or a pharmacologically acceptable salt thereof.

(11) The compound of any of (1) to (10), wherein $R^1$ and $R^2$ are the same group, or a pharmacologically acceptable salt thereof.

(12) The compound of any of (1) to (11), wherein $R^1$ and $R^2$ are the same or different and each is alkyl, or a pharmacologically acceptable salt thereof.

(13) The compound of any of (1) to (12), wherein $R^1$ and $R^3$ are bonded to form carbocycle or heterocycle, or a pharmacologically acceptable salt thereof.

(14) The compound of any of (1) to (13), wherein $R^8$ is hydroxy, or a pharmacologically acceptable salt thereof.

(15) (4-{[5-Hydroxy-6-(2-naphthyl)pyridin-2-yl]methyl}-3,5-dimethylphenoxy)acetic acid (Example 3);
{4-[(6-cyclopentyl-5-hydroxypyridin-2-yl)methyl]-2,3,5-trimethylphenoxy}acetic acid (Example 5);
{4-[(6-cyclohexyl-5-hydroxypyridin-2-yl)methyl]-2,3,5-trimethylphenoxy}acetic acid (Example 7);
{2-bromo-4-[(6-cyclohexyl-5-hydroxypyridin-2-yl)methyl]-3,5-dimethylphenoxy}acetic acid (Example 13);
3-({4-[(5-hydroxy-6-phenylpyridin-2-yl)methyl]-3,5-dimethylphenyl}amino)-3-oxopropanoic acid (Example 22);
3-({4-[(6-cyclohexyl-5-hydroxypyridin-2-yl)methyl]-3,5-dimethylphenyl}amino)-3-oxopropanoic acid (Example 23);
3-[(4-{[5-hydroxy-6-(2-naphthyl)pyridin-2-yl]methyl}-3,5-dimethylphenoxy)methyl]-1,2,4-oxadiazol-5(4H)-one (Example 29);
3-[(4-{[5-hydroxy-6-(5,6,7,8-tetrahydronaphthalen-2-yl)pyridin-2-yl]methyl}-3,5-dimethylphenoxy)methyl]-1,2,4-oxadiazol-5(4H)-one (Example 30);
({5-[(6-cyclohexyl-5-hydroxypyridin-2-yl)methyl]-3,4,6-trimethylpyridin-2-yl}oxy)acetic acid (Example 45);
3-({4-[(6-cycloheptyl-5-hydroxypyridin-2-yl)methyl]-3,5-dimethylphenyl}amino)-3-oxopropanoic acid (Example 52);
N-[2-chloro-4-(6-cyclohexyl-5-hydroxy-pyridin-2-ylmethyl)-3,5-dimethyl-phenyl]amino-3-oxopropanoic acid (Example 54);
3-[(2-fluoro-4-{[6-(2-fluoro-3-methylphenyl)-5-hydroxypyridin-2-yl]methyl}-3,5-dimethylphenoxy)methyl]-1,2,4-oxadiazol-5(4H)-one (Example 60);
{4-[(6-cyclohexyl-4-fluoro-5-hydroxypyridin-2-yl)methyl]-2,3,5-trimethylphenoxy}acetic acid (Example 65);
{4-[(6-cyclohexyl-3-fluoro-5-hydroxypyridin-2-yl)methyl]-2,3,5-trimethylphenoxy}acetic acid (Example 73);
{4-[(6-cycloheptyl-5-hydroxypyridin-2-yl)methyl]-2,3,5-trimethylphenoxy}acetic acid (Example 92);
3-({4-[(6-cycloheptyl-5-hydroxypyridin-2-yl)methyl]-2-fluoro-3,5-dimethylphenyl}amino)-3-oxopropanoic acid (Example 131);
{4-[6-(3-fluoro-phenyl)-5-hydroxy-pyridin-2-ylmethyl]-2,3,5-trimethyl-phenoxy}acetic acid (Example 171);
(4-{[6-(3-chlorophenyl)-5-hydroxypyridin-2-yl]methyl}-2,3,5-trimethylphenoxy)acetic acid (Example 173);
3-{2-fluoro-4-[5-hydroxy-6-(2,3,4-trifluoro-phenyl)-pyridin-2-ylmethyl]-3,5-dimethyl-phenoxymethyl}-1,2,4-oxadiazol-5(4H)-one (Example 191);
3-[(2-fluoro-4-{[5-hydroxy-6-(3-pyrrolidin-1-ylphenyl)pyridin-2-yl]methyl}-3,5-dimethylphenoxy)methyl]-1,2,4-oxadiazol-5(4H)-one (Example 206);
2-{4-[(5-hydroxy-6-phenylpyridin-2-yl)methyl]-3,5-dimethylphenyl}-3,5-dioxo-2,3,4,5-tetrahydro-1,2,4-triazine-6-carbonitrile (Example 216);
3-{2-fluoro-4-[5-hydroxy-6-(3-propoxy-phenyl)-pyridin-2-ylmethyl]-3,5-dimethyl-phenoxymethyl}-1,2,4-oxadiazol-5(4H)-one (Example 236);
[3,5-dibromo-2-fluoro-4-(5-hydroxy-6-phenyl-pyridin-2-ylmethyl)-phenoxy]acetic acid (Example 256);
(5-ethyl-4-{[6-(3-fluorophenyl)-5-hydroxypyridin-2-yl]methyl}-2,3-dimethylphenoxy)acetic acid (Example 269), or a pharmacologically acceptable salt thereof.

(16) A medicament comprising the compound of any of (1) to (15), or a pharmacologically acceptable salt thereof, as an active ingredient.

(17) The medicament of (16), which is a thyroid hormone β receptor agonist.

(18) The medicament of (16), which is for the treatment or prophylaxis of hypercholesterolemia, hyperlipidemia, hypertriglyceridemia, familial hypercholesterolemia, dyslipidemia, atherosclerosis, hypothyroidism and/or latent hypothyroidism.

(19) Use of the compound of any of (1) to (15) for the manufacture of a medicament for the treatment or prophylaxis of a disease that is improved by activating thyroid hormone β receptor.

(20) A method for the treatment or prophylaxis of a disease that is improved by activating thyroid hormone β receptor, which comprises administering the compound of any of (1) to (15).

(21) A compound represented by the formula [II]:

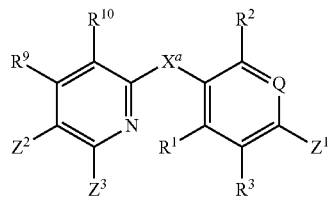

[II]

wherein $Z^1$ and $Z^2$ are the same or different and each is —O-PG (PG is a protecting group),
$Z^3$ is A or halogen,
$X^a$ is oxygen, sulfur or group represented by

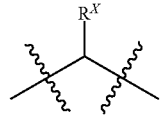

wherein $R^X$ is hydroxyl which is optionally protected by protecting group, and other symbols are as mentioned above, or a salt thereof.

Effect of the Invention

The heterocyclic derivative of the formula [I] of the present invention shows a thyroid hormone β receptor agonistic action, and can be a medicament effective for the prophylaxis or treatment of diseases relating to the action, for example, a medicament for the prophylaxis, reduction and/or treatment of hypercholesterolemia, hyperlipidemia, hypertriglyceridemia, familial hypercholesterolemia, dyslipidemia, hypothyroidism, latent hypothyroidism, atherosclerosis, metabolic syndrome, obesity, diabetes, cardiovascular disease, coronary artery disease, myocardial infarction, ventricular insufficiency, cardiac failure, fatty liver, cirrhosis, non-alcoholic steatohepatitis (NASH), non-alcoholic fatty liver diseases (NAFLD), melancholia, dementia, osteoporosis, alopecia, nail disease, dermatic diseases, renal diseases, chronic renal failure, and/or cancer and the like, particularly, hypercholesterolemia, hyperlipidemia, hypertriglyceridemia, familial hypercholesterolemia, dyslipidemia, atherosclerosis, hypothyroidism, and/or latent hypothyroidism and the like.

The compound of the formula [II] of the present invention is useful as intermediate for the heterocyclic derivative of the formula [I] of the present invention.

DESCRIPTION OF EMBODIMENTS

The groups represented by each term and each symbol in the present specification are explained in the following.

Examples of the "alkyl" include $C_{1-6}$, preferably $C_{1-4}$, straight chain or branched chain alkyl, specifically, methyl, ethyl, propyl, isopropyl, butyl, isobutyl, 1-methylpropyl, pentyl, hexyl and the like.

Alkoxy of "alkoxycarbonyl" and "alkoxy" includes $C_{1-6}$, preferably $C_{1-4}$, straight chain or branched chain alkoxy, specifically, methoxy, ethoxy, propoxy, isopropoxy, butoxy, isobutoxy, tert-butoxy, pentyloxy, hexyloxy and the like.

"Halogen" includes fluorine atom, chlorine atom, bromine atom and iodine atom.

"Alkanoyl" includes $C_{1-6}$, preferably $C_{1-4}$, straight chain or branched chain alkanoyl, specifically, formyl, acetyl, propionyl, butyryl, pentanoyl, hexanoyl and the like.

"Alkenyl" includes $C_{2-6}$, preferably $C_{2-4}$, straight chain or branched chain alkenyl, specifically, vinyl, allyl, 1-methyl-2-propenyl, 3-butenyl, 2-pentenyl, 3-hexenyl and the like.

Cycloalkyl of "cycloalkyloxy" and "cycloalkyl" includes $C_{3-8}$, preferably $C_{3-6}$, cycloalkyl, specifically cyclopropyl, cyclobutyl, cyclopentyl, cyclohexyl and the like.

"Cycloalkane" includes $C_{3-8}$, preferably $C_{3-6}$, cycloalkane, specifically, cyclopropane, cyclobutane, cyclopentane, cyclohexane and the like.

"Cycloalkene" includes $C_{3-8}$, preferably $C_{3-6}$, cycloalkene, specifically, cyclopropene, cyclobutene, cyclopentene, cyclohexene and the like.

"Carbocycle" includes $C_{6-14}$, preferably $C_{6-10}$, monocyclic, bicyclic or tricyclic nonaromatic carbocycle, which is optionally saturated partly or entirely.

"Carbocyclic group" includes $C_{3-14}$, preferably $C_{6-10}$, monocyclic, bicyclic or tricyclic nonaromatic carbocyclic group, which is optionally saturated partly or entirely.

"Aromatic ring" includes $C_{6-14}$ monocyclic, bicyclic or tricyclic aromatic ring, preferably $C_{6-10}$ monocyclic or bicyclic aromatic ring, specifically benzene, naphthalene, phenanthrene, anthracene and the like.

Aryl of "arylcarbonyl" and "aryl" includes $C_{6-14}$ monocyclic, bicyclic or tricyclic aryl, preferably $C_{6-10}$ monocyclic or bicyclic aryl. Specifically, phenyl, naphthyl, phenanthryl, anthryl and the like can be mentioned.

"Heterocycle" includes total 5- to 12-membered monocyclic or bicyclic nonaromatic heterocycle containing 1-4 hetero atoms selected from phosphorus atom, nitrogen atom, oxygen atom and sulfur atom (particularly, nitrogen atom, oxygen atom and sulfur atom), which is optionally saturated partly or entirely.

Preferable monocyclic heterocycle is total 5- to 7-membered heterocycle containing 1-4 hetero atoms selected from nitrogen atom, oxygen atom and sulfur atom, which is optionally saturated partly or entirely. Preferable example of the monocyclic heterocycle is total 5- to 7-membered heterocycle containing 1-4 hetero atoms selected from nitrogen atom, oxygen atom and sulfur atom, which is optionally saturated partly or entirely. Specific examples thereof include oxazoline, pyrrolidine, piperidine, piperazine, morpholine, tetrahydropyran, tetrahydrofuran, imidazolidine, oxazolidine and the like.

Bicyclic heterocycle includes bicyclic heterocycle wherein the same or different above-mentioned monocyclic heterocycles are fused, bicyclic heterocycle wherein the above-mentioned monocyclic heterocycle is fused with benzene ring, monocyclic heteroaromatic ring or cycloalkane, and bicyclic heterocycle wherein monocyclic heteroaromatic ring is fused with cycloalkane. Specific examples of the bicyclic heterocycle include indoline, isoindoline, tetrahydroquinoline, tetrahydrobenzofuran, tetrahydrobenzopyran and the like.

"Heterocyclic group" includes total 5- to 12-membered monocyclic or bicyclic nonaromatic heterocyclic group containing 1-4 hetero atoms selected from nitrogen atom, oxygen atom and sulfur atom, which is optionally saturated partly or entirely.

Monocyclic heterocyclic group includes a total 5 - 7-membered heterocyclic group containing 1-4 hetero atoms selected from nitrogen atom, oxygen atom and sulfur atom, which is optionally saturated partly or entirely. Specific examples include oxazolyl, pyrrolidinyl, piperidyl, piperazinyl, morpholyl, tetrahydropyranyl, tetrahydrofuryl, imidazolidinyl, oxazolidinyl and the like.

Bicyclic heterocyclic group includes 8- to 12-membered bicyclic heterocyclic group wherein the same or different, the above-mentioned monocyclic heterocycles are fused, 8- to 12-membered bicyclic heterocyclic group wherein the above-mentioned monocyclic heterocycle and benzene ring, monocyclic heteroaromatic ring or cycloalkane are fused, and 8- to 12-membered bicyclic heterocyclic group wherein monocyclic heterocyclic heterocyclic ring and cycloalkane are fused. Specific examples of the bicyclic heterocyclic group include indolyl, isoindolyl, tetrahydroquinolyl, tetrahydrobenzofuranyl, tetrahydrobenzopyranyl and the like.

"Heteroaromatic ring" is aromatic ring having at least one hetero atom (nitrogen, oxygen or sulfur) and carbon atom, which includes 5- or 6-membered monocyclic heteroaromatic ring, 8- to 10-membered bicyclic heteroaromatic ring wherein the same or different monocyclic heteroaromatic rings are fused, and 8- to 10-membered bicyclic heteroaromatic ring wherein monocyclic heteroaromatic ring is fused with benzene.

Specific examples of the heteroaromatic ring include furan, thiophene, pyrrole, imidazole, pyrazole, triazole, tetrazole, oxazole, triazole, isoxazole, isothiazole, oxadiazole, thiadiazole, furazan, pyridine, pyrazine, pyrimidine, pyridazine, triazine, indole, indazole, benzoimidazole, purine, quinoline, isoquinoline, phthalazine, quinoxaline, quinazoline, cinnoline, benzofuran, benzothiophene, benzoxazole, benzothiazole, benzoisoxazole, benzoisothiazole and the like.

"Heteroaryl" is aromatic cyclic group containing at least one hetero atom (nitrogen, oxygen or sulfur) and carbon atom, which includes 5- or 6-membered monocyclic compound, 8- to 10-membered bicyclic group wherein the same or different monocyclic heteroaromatic rings are fused and 8- to 10-membered bicyclic group wherein a monocyclic heteroaromatic ring is fused with benzene.

Specific examples of the heteroaryl group include furyl, thienyl, pyrrolyl, imidazolyl, pyrazolyl, triazolyl, tetrazolyl, oxazolyl, thiazolyl, isoxazolyl, isothiazolyl, oxadiazolyl, thiadiazolyl, furazanyl, pyridyl, pyrazinyl, pyrimidyl, pyridazinyl, triazinyl, indolyl, indazolyl, benzimidazolyl, purinyl, quinolyl, isoquinolyl, phthalazinyl, quinoxalinyl, quinazolinyl, cinnolinyl, benzofuranyl, benzothienyl, benzoxazolyl, benzothazolyl, benzoisoxazolyl, benzoisothiazolyl and the like.

"Bioisosteric group of carboxyl group" includes phosphoric acid, phosphate ester and groups represented by the following formulae

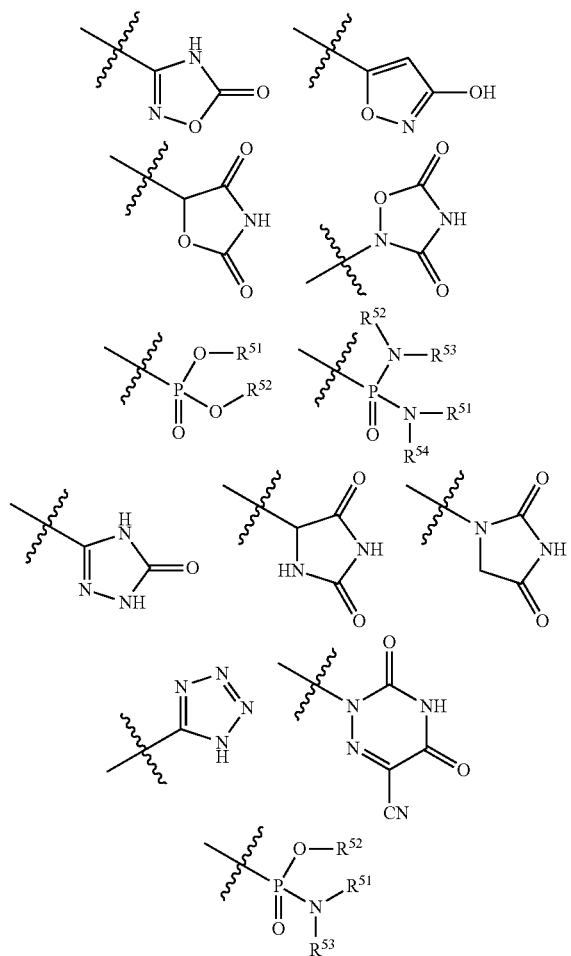

wherein $R^{51}$ and $R^{52}$ are the same or different and each is alkyl optionally substituted by alkanoyloxy or alkoxycarbonyl, or hydrogen, $R^{51}$ and $R^{52}$ may be bonded to form heterocycle optionally substituted by aryl optionally substituted by a halogen, and $R^{53}$ and $R^{54}$ are the same or different and each is alkyl or hydrogen (preferably hydrogen).

Preferable forms of each group are explained in the following.

"Optionally substituted alkyl" for A may be substituted by 1-5, preferably 1-3, substituents, and the substituents include (1) aryl optionally substituted by 1-3 groups selected from alkyl, halogen, alkoxy, alkanoyl, and cyano, (2) heterocyclic group optionally substituted by 1-3 groups selected from alkyl, halogen, alkoxy, alkanoyl, and cyano, (3) heteroaryl optionally substituted by 1-3 groups selected from alkyl, halogen, alkoxy, alkanoyl, and cyano, (4) cycloalkyl optionally substituted by 1-3 groups selected from alkyl, halogen, alkoxy, alkanoyl, and cyano, (5) hydroxy, (6) alkoxy, (7) halogen, (8) an amino group optionally substituted by 1 or 2 alkyl, and (9) oxo.

"Alkyl" for A is, for example, preferably 2-propyl, 2-methyl-1-propyl, 2-methyl-2-propyl, 2-butyl, 3-pentyl, 2-methyl-2-butyl and the like, more preferably 2-propyl, 2-methyl-2-propyl, 2-butyl and 3-pentyl, and alkyl of the "substituted alkyl" for A is, for example, preferably methyl, ethyl, 1-propyl, 2-methyl-1-propyl and the like.

Preferable substituent of the "optionally substituted alkyl" for A includes (1) aryl optionally substituted by 1-3 groups selected from alkyl, halogen, alkoxy, alkanoyl, and cyano (specifically, 4-fluorophenyl), (2) heterocyclic group optionally substituted by 1-3 groups selected from alkyl, halogen, alkoxy, alkanoyl, and cyano, (3) heteroaryl optionally substituted by 1-3 groups selected from alkyl, halogen, alkoxy, alkanoyl, and cyano, (4) cycloalkyl optionally substituted by 1-3 groups selected from alkyl, halogen, alkoxy, alkanoyl, and cyano, and (5) hydroxy, wherein the alkyl may be substituted by the same or different, 1-3, preferably 1-2, groups.

"Substituted alkyl" for A is, for example, preferably a group represented by the formula:

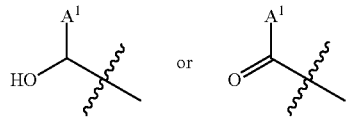

wherein $A^1$ is any group selected from (1) aryl optionally substituted by 1-3 groups selected from alkyl, halogen, alkoxy, alkanoyl, and cyano (specifically, 4-fluorophenyl), (2) heterocyclic group optionally substituted by 1-3 groups selected from alkyl, halogen, alkoxy, alkanoyl, and cyano, (3) heteroaryl optionally substituted by 1-3 groups selected from alkyl, halogen, alkoxy, alkanoyl, and cyano, (4) cycloalkyl optionally substituted by 1-3 groups selected from alkyl, halogen, alkoxy, alkanoyl, and cyano, and (5) alkyl group, particularly preferably a group represented by

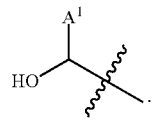

Preferable examples of the carbocyclic group of the "optionally substituted carbocyclic group" for A include a bicyclic group wherein an aromatic ring and cycloalkane are fused (specifically, tetrahydronaphthyl), and cycloalkyl, particularly preferably cycloalkyl. Among others, C5-C7 cycloalkyl is preferable, and cyclohexyl and cycloheptyl are particularly preferable.

Preferable aryl of "optionally substituted aryl" and "optionally substituted arylcarbonyl" for A includes naphthyl and phenyl.

Preferable heterocyclic group of "optionally substituted heterocyclic group" for A includes 5- or 6-membered monocyclic heterocyclic group optionally saturated partly or entirely and 9- to 12-membered bicyclic heterocyclic group optionally saturated partly or entirely, each of which has 1 to 3 hetero atoms (nitrogen, oxygen or sulfur) and carbon atom. Specific examples thereof include pyrrolidinyl, piperidinyl, tetrahydrofuranyl, tetrahydropyranyl, dioxanyl, dioxolanyl, and fused ring group of such group with monocyclic heteroaromatic ring or aromatic ring and the like.

Preferable heteroaryl of "optionally substituted heteroaryl" for A includes 5- or 6-membered aromatic monocyclic group and a 9- or 10-membered aromatic bicyclic group, each of which has 1 to 3 hetero atoms (oxygen or sulfur) and a carbon atom. Specific examples thereof include furanyl, thienyl, benzofuranyl, benzothienyl and the like.

"Optionally substituted aryl", "optionally substituted arylcarbonyl", "optionally substituted carbocyclic group", "optionally substituted heterocyclic group" and "optionally substituted heteroaryl" may respectively have the same or different, 1-3 substituents, and the substituent includes (1) alkyl optionally substituted by hydroxy, alkoxy, cycloalkyl or halogen, (2) alkenyl optionally substituted by alkoxy or cycloalkyl, (3) cycloalkyl optionally substituted by alkyl, alkoxy or cycloalkyl, (4) alkoxy optionally substituted by alkoxy, cycloalkyl or halogen, (5) cycloalkyloxy optionally substituted by alkyl, alkoxy or cycloalkyl, (6) halogen, (7) cyano, (8) hydroxy, (9) oxo, (10) heterocyclic group, (11) alkylsulfonyl, (12) mono or dialkylcarbamoyl and the like.

Preferable substituent of "optionally substituted aryl", "optionally substituted arylcarbonyl" and "optionally substituted heteroaryl" for A includes alkyl optionally substituted by alkoxy or halogen, alkoxy optionally substituted by halogen, heterocyclic group, mono or dialkylcarbamoyl, alkylsulfonyl, cyano and halogen, specifically methyl, ethyl, isopropyl, trifluoromethyl, methoxymethyl, methoxy, ethoxy, n-propoxy, isopropoxy, trifluoromethoxy, pyrrolidinyl, dimethylcarbamoyl, methanesulfonyl, cyano and halogen and the like, and preferably halogen, methyl, ethyl, methoxy, ethoxy, and cyano. The aryl and heteroaryl may be substituted by the same or different, 1-3, preferably 1-2, groups.

Preferable substituent of "optionally substituted carbocyclic group" and "optionally substituted heterocyclic group" for A includes halogen; alkyl optionally substituted by hydroxy, alkoxy or halogen; alkoxy; cyano; and hydroxy, specifically halogen, hydroxy, methyl, ethyl, hydroxymethyl, methoxymethyl, methoxy, ethoxy, and cyano. The carbocyclic group and heterocyclic group may be substituted by the same or different, 1-3, preferably 1-2, groups.

Preferable substituent of "optionally substituted amino" for A includes (1) alkyl optionally substituted by alkoxy, cycloalkyl or halogen (2) alkenyl optionally substituted by alkoxy or cycloalkyl (3) cycloalkyl optionally substituted by alkyl, alkoxy or cycloalkyl, (4) alkanoyl optionally substituted by alkoxy, cycloalkyl or halogen, (5) aryl optionally substituted by alkyl, alkoxy or cycloalkyl, with preference given to alkyl, cycloalkyl and aryl. Specifically, methyl, cyclohexyl and phenyl can be mentioned. The amino is optionally substituted by the same or different 1 or 2 groups.

Substituent of "optionally substituted carbamoyl" for A includes alkyl optionally substituted by aryl, specifically 2-phenylethyl and 2-phenyl-1-propyl. The carbamoyl may be substituted by the same or different, 1 or 2 groups.

"Alkyl" for $R^1$ or $R^2$ is, for example, particularly preferably methyl or ethyl.

"Alkenyl" for $R^1$ or $R^2$ is, for example, particularly preferably vinyl.

"Alkyl" for $R^3$ or $R^4$ is, for example, particularly preferably methyl or ethyl.

"Alkoxy" for $R^3$ or $R^4$ is, for example, particularly preferably methoxy.

$R^1$ and $R^2$ are preferably the same.

Preferably, one of $R^3$ and $R^4$ is hydrogen and the other is alkyl or halogen.

Carbocycle formed by $R^1$ and $R^3$ bonded to each other includes nonaromatic carbocycle, preferably 5- or 6-membered cycloalkane or 5- or 6-membered cycloalkene, particularly preferably cyclopentane.

Heterocycle formed by $R^1$ and $R^3$ bonded to each other includes 5- or 6-membered nonaromatic heterocycle containing 1 or 2 hetero atoms selected from oxygen, nitrogen and sulfur, preferably 5-membered nonaromatic heterocycle containing one hetero atom selected from oxygen, nitrogen and sulfur, particularly preferably tetrahydrofuran.

Specific examples of the formula:

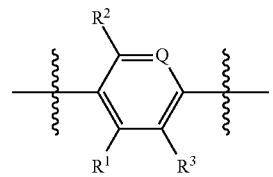

when $R^1$ and $R^3$ are bonded to form carbocycle or heterocycle include the formula:

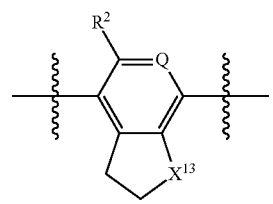

wherein $X^{13}$ is methylene, oxygen or sulfur and the other symbol is as mentioned above.

$R^5$ is preferably carboxyl group or 5-oxo-4,5-di-[1,2,4] oxadiazol-3-yl.

Alkyl of "optionally substituted alkyl" for $R^6$ or $R^7$ is particularly preferably methyl, and examples of the substituent include alkoxy, hydroxy and halogen.

Cycloalkane formed by $R^6$ and $R^7$ bonded to each other is particularly preferably $C_{3-5}$ cycloalkane (especially cyclopropane).

Heterocycle formed by $R^6$ and $R^7$ bonded to each other is preferably $C_{3-7}$, particularly preferably $C_{3-5}$ heterocycle. Examples thereof include tetrahydropyran, tetrahydrofuran and the like.

Alkanoylamino for $R^8$ is, for example, acetylamino, formylamino and the like.

Alkylsulfonylamino for $R^8$ is, for example, methanesulfonylamino, ethanesulfonylamino, isopropylsulfonylamino, n-propylsulfonylamino and the like.

$R^8$ is preferably hydroxy.

$R^9$ is preferably hydrogen or halogen (especially fluorine), particularly preferably hydrogen.

$R^{10}$ is preferably hydrogen or halogen (especially fluorine), particularly preferably hydrogen.

Alkyl for $R^{11}$ includes methyl and ethyl.

$L^1$ is preferably —O—.

"Divalent heterocyclic group" for $L^2$ includes a divalent monocyclic heterocyclic group preferably containing one or more nitrogen atoms, and examples thereof include pyrrolidinediyl, morpholinediyl, piperidinediyl and the like.

-$L^1$-$L^2$-$R^5$ is preferably $R^5$ ($L^1$ and $L^2$ are each a single bond) or group selected from groups represented by the following formulae:

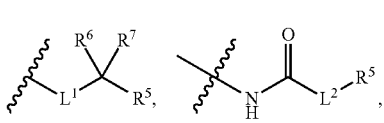

more preferably group represented by the formula:

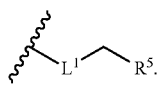

X is preferably optionally substituted methylene, particularly preferably methylene.

Substituent of "optionally substituted methylene" for X includes alkoxy and hydroxy.

Q is preferably C—R$^4$.

The compound the formula [I] or a pharmacologically acceptable salt thereof includes the compounds described in Examples and pharmacologically acceptable salts thereof, preferably (4-{[5-hydroxy-6-(2-naphthyl)pyridin-2-yl]methyl}-3,5-dimethylphenoxy)acetic acid (Example 3);

{4-[(6-cyclopentyl-5-hydroxypyridin-2-yl)methyl]-2,3,5-trimethylphenoxy}acetic acid (Example 5);

{4-[(6-cyclohexyl-5-hydroxypyridin-2-yl)methyl]-2,3,5-trimethylphenoxy}acetic acid (Example 7);

{2-bromo-4-[(6-cyclohexyl-5-hydroxypyridin-2-yl)methyl]-3,5-dimethylphenoxy}acetic acid (Example 13);

3-({4-[(5-hydroxy-6-phenylpyridin-2-yl)methyl]-3,5-dimethylphenyl}amino)-3-oxopropanoic acid (Example 22);

3-({4-[(6-cyclohexyl-5-hydroxypyridin-2-yl)methyl]-3,5-dimethylphenyl}amino)-3-oxopropanoic acid (Example 23);

3-[(4-{[5-hydroxy-6-(2-naphthyl)pyridin-2-yl]methyl}-3,5-dimethylphenoxy)methyl]-1,2,4-oxadiazol-5(4H)-one (Example 29);

3-[(4-{[5-hydroxy-6-(5,6,7,8-tetrahydronaphthalen-2-yl)pyridin-2-yl]methyl}-3,5-dimethylphenoxy)methyl]-1,2,4-oxadiazol-5(4H)-one (Example 30);

{4-[(6-cyclohexyl-5-hydroxypyridin-2-yl)methyl]-2,3,5-trimethylphenyl}acetic acid (Example 41);

({5-[(6-cyclohexyl-5-hydroxypyridin-2-yl)methyl]-3,4,6-trimethylpyridin-2-yl}oxy)acetic acid (Example 45);

3-({4-[(6-cycloheptyl-5-hydroxypyridin-2-yl)methyl]-3,5-dimethylphenyl}amino)-3-oxopropanoic acid (Example 52);

3-[(2-fluoro-4-{[6-(2-fluoro-3-methylphenyl)-5-hydroxypyridin-2-yl]methyl)-3,5-dimethylphenoxy)methyl]-1,2,4-oxadiazol-5(4H)-one (Example 60);

N-{4-[(6-cyclohexyl-5-hydroxypyridin-2-yl)methyl]-2,3,5-trimethylphenyl}glycine (Example 62);

{4-[(6-cyclohexyl-4-fluoro-5-hydroxypyridin-2-yl)methyl]-2,3,5-trimethylphenoxy}acetic acid (Example 65);

3-[(4-([6-(3-ethoxyphenyl)-5-hydroxypyridin-2-yl]methyl}-2-fluoro-3,5-dimethylphenoxy)methyl]-1,2,4-oxadiazol-5(4H)-one (Example 66);

3-({5-ethyl-2-fluoro-4-[(5-hydroxy-6-phenylpyridin-2-yl)methyl]-3-methylphenoxy}methyl)-1,2,4-oxadiazol-5 (4H)-one (Example 72);

{4-[(6-cyclohexyl-3-fluoro-5-hydroxypyridin-2-yl)methyl]-2,3,5-trimethylphenoxy}acetic acid (Example 73);

6-[4-(3-hydroxyisoxazol-5-yl)-2,3,6-trimethylbenzyl]-2-isopropylpyridin-3-ol (Example 81);

{4-[(6-cycloheptyl-5-hydroxypyridin-2-yl)methyl]-2-fluoro-3,5-dimethylphenoxy}acetic acid (Example 83);

3-[(2-fluoro-4-{[5-hydroxy-6-(2-naphthyl)pyridin-2-yl]methyl}-3,5-dimethylphenoxy)methyl]-1,2,4-oxadiazol-5 (4H)-one (Example 87);

{4-[(6-cycloheptyl-5-hydroxypyridin-2-yl)methyl]-2,3,5-trimethylphenoxy}acetic acid (Example 92);

3-({4-[(6-cyclohexyl-5-hydroxypyridin-2-yl)methyl]-2-fluoro-3,5-dimethylphenyl}amino)-3-oxopropanoic acid (Example 98);

3-({4-[(6-cyclohexyl-5-hydroxypyridin-2-yl)methyl]-2-methoxy-3,5-dimethylphenoxy}methyl)-1,2,4-oxadiazol-5(4H)-one (Example 107);

3-[({4-[(6-cyclohexyl-5-hydroxypyridin-2-yl)methyl]-5-methyl-2,3-dihydro-1-benzofuran-7-yl}oxy)methyl]-1,2,4-oxadiazol-5(4H)-one (Example 117);

3-({2-fluoro-4-[(5-hydroxy-6-piperidin-1-ylpyridin-2-yl)methyl]-3,5-dimethylphenoxy}methyl)-1,2,4-oxadiazol-5 (4H)-one (Example 118);

(4-{[6-(3,4-difluorophenyl)-5-hydroxypyridin-2-yl]methyl}-2,3,5-trimethylphenoxy)acetic acid (Example 120);

(4-{[5-hydroxy-6-(3-methylphenyl)pyridin-2-yl]methyl}-2,3,5-trimethylphenoxy)acetic acid (Example 122);

3-({4-[(6-cycloheptyl-5-hydroxypyridin-2-yl)methyl]-2-fluoro-3,5-dimethylphenyl}amino)-3-oxopropanoic acid (Example 131);

3-{4-[(6-cyclohexyl-5-hydroxypyridin-2-yl)methyl]-2,3,5-trimethylphenyl}-2-fluoropropanoic acid (Example 136);

3-{[2-fluoro-4-({5-hydroxy-6-[2-(trifluoromethyl)phenyl]pyridin-2-yl}methyl)-3,5-dimethylphenoxy]methyl}-1,2,4-oxadiazol-5(4H)-one (Example 148);

({7-[(6-cyclohexyl-5-hydroxypyridin-2-yl)methyl]-6-methyl-2,3-dihydro-1H-inden-4-yl}oxy)acetic acid (Example 152);

(4-{[6-(3-chlorophenyl)-5-hydroxypyridin-2-yl]methyl}-2,3,5-trimethylphenoxy)acetic acid (Example 173);

(4-{[6-(3-ethylphenyl)-5-hydroxypyridin-2-yl]methyl}-2,3,5-trimethylphenoxy)acetic acid (Example 176);

3-{[2-fluoro-4-({6-[4-fluoro-3-(trifluoromethyl)phenyl]-5-hydroxypyridin-2-yl}methyl)-3,5-dimethylphenoxy]methyl}-1,2,4-oxadiazol-5(4H)-one (Example 189);

3-[(2-fluoro-4-{[5-hydroxy-6-(3-pyrrolidin-1-ylphenyl)pyridin-2-yl]methyl}-3,5-dimethylphenoxy)methyl]-1,2,4-oxadiazol-5(4H)-one (Example 206);

2-{4-[(5-hydroxy-6-phenylpyridin-2-yl)methyl]-3,5-dimethylphenyl}-3,5-dioxo-2,3,4,5-tetrahydro-1,2,4-triazine-6-carbonitrile (Example 216);

3-[(4-{[6-(3-ethyl-2-fluorophenyl)-5-hydroxypyridin-2-yl]methyl}-2-fluoro-3,5-dimethylphenoxy)methyl]-1,2,4-oxadiazol-5(4H)-one (Example 249);

3-[(4-{[6-(3-ethyl-4-fluorophenyl)-5-hydroxypyridin-2-yl]methyl}-2-fluoro-3,5-dimethylphenoxy)methyl]-1,2,4-oxadiazol-5(4H)-one (Example 250);

3-{[2-fluoro-4-({5-hydroxy-6-[1-(methoxymethyl)cyclohexyl]pyridin-2-yl}methyl)-3,5-dimethylphenoxy]methyl}-1,2,4-oxadiazol-5(4H)-one (Example 268);

(5-ethyl-4-{[6-(3-fluorophenyl)-5-hydroxypyridin-2-yl]methyl}-2,3-dimethylphenoxy)acetic acid (Example 269);

(5-ethyl-4-{[5-hydroxy-6-(3-methylphenyl)pyridin-2-yl]methyl}-2,3-dimethylphenoxy)acetic acid (Example 270); and (4-{[6-(3-chlorophenyl)-5-hydroxypyridin-2-yl]methyl}-5-ethyl-2,3-dimethylphenoxy)acetic acid (Example 271), and pharmacologically acceptable salts thereof.

In a compound represented by the formula [II], preferable forms of A and R$^1$-R$^4$ are the same as those of A and R$^1$-R$^4$ in the formula [I].

$X^a$ is preferably a group represented by the formula:

wherein the symbols are as mentioned above.

Hydroxy-protecting group for $R^X$ includes those generally used for protection of hydroxy, for example, the hydroxy-protecting groups described in Protective Groups in Organic Synthesis Third Edition (Theodora W. Green and Peter G. Wuts). Specific examples thereof include alkanoyl, trialkylsilyl, alkyl and the like.

PG of —O-PG for $Z^1$ or $Z^2$ includes protecting groups generally used for phenolic hydroxy, for example, the hydroxy-protecting groups described in Protective Groups in Organic Synthesis Third Edition (Theodora W. Green and Peter G. Wuts). Specific examples thereof include methoxymethyl, ethoxymethyl, ethoxyethyl, benzyl, allyl, triisopropylsilyl and the like. In —O-PG for $Z^1$ or $Z^2$, PGs for $Z^1$ and $Z^2$ are desirably different protecting groups.

As a salt of a compound of the formula [I] in the above, an acid addition salt or a base addition salt can be used, where the kind of the salt is not particularly limited as long as it is physiologically acceptable.

Examples of the pharmacologically acceptable salt include, when it has a basic group, include inorganic acid salts such as hydrochloride, sulfate, phosphate, hydrobromide and the like, and organic acid salts such as acetate, fumarate, oxalate, citrate, methanesulfonate, benzenesulfonate, tosylate, maleate and the like. In addition, when it has an acidic group, examples of the salt include salts with bases such as alkali metal salts (sodium salt, potassium salt etc.), alkaline earth metal salts (calcium salt etc.) and the like.

When a compound of the formula [I], or a salt thereof contains an optically active form, it can be separated into each optical isomer by a general optical resolution means. Alternatively, an optically active form of a compound of the formula [I] or a salt thereof may be synthesized using an optically pure starting material or a compound whose steric configuration is known.

One or more kinds of the compound of the formula [I] of the present invention or a salt thereof may be directly administered to patients. Preferably, an active ingredient and a pharmacologically and pharmaceutically acceptable additive are mixed and provided as a preparation in a form well known to those of ordinary skill in the art.

The compound of the present invention is prepared into a suitable administration form (powder, injection, tablet, capsule or topical external preparation and the like) together with generally-used, suitable diluent and other additives, and can be administered to human or animal by a suitable administration method depending on the dosage form thereof (for example, intravenous administration, oral administration, transdermal administration or topical administration and the like).

As the pharmacologically and pharmaceutically acceptable additive, excipient, disintegrant, binder, lubricant, coating agent, dye, diluent, base, isotonicity agent and the like can be used.

Examples of a preparation suitable for oral administration include tablet, capsule, powder, fine granules, granule, liquid, syrup and the like. Examples of a preparation suitable for parenteral administration include injection, drip infusion, suppository and the like.

For a preparation suitable for oral administration, excipient, disintegrant, binder, lubricant, coating agent, base and the like can be used as additives. In addition, when the compound of the present invention is administered to patients to be the target of treatment, other agents appropriate for the treatment of the target disease and the compound of the present invention may be used in combination.

The administration route of the medicament of the present invention is not particularly limited, and can be administered orally or parenterally. The dose varies depending on the age, body weight, general health condition, sex, meal, administration time, administration method, clearance rate, drug combination, and level of the disease state for which the patient is treated, in consideration of them or other factors. The compound of the present invention, an optical isomer thereof and a pharmaceutically acceptable salt thereof are low toxic and can be used safely. The daily dose thereof varies depending on the conditions and body weight of patients, the kind of compound, administration route and the like. Parenterally, for example, about 0.0001-1000 mg/person/day, preferably about 0.001-1000 mg/person/day, particularly preferably 0.01-500 mg/person/day, is desirably administered subcutaneously, intravenously, intramuscularly or intrarectally, and about 0.0001-1000 mg/person/day, preferably 0.01-500 mg/person/day, is desirably administered orally.

Compounds represented by the formulas [I] and [II] can be produced by the following method.

Unless otherwise specified, the following symbols in the production methods, Examples and Reference Examples mean the following.

APCI: atmospheric chemical ionization
Ac: acetyl
BINAP: 2,2'-bis(diphenylphosphino)-1,1'-binaphthyl
Bn: benzyl
Boc: tertiary butoxycarbonyl
Bu: butyl
ESI: electrospray ionization
Et: ethyl
Me: methyl
MOM: methoxymethyl
Ms: methanesulfonyl
Ph: phenyl
Tf: trifluoromethanesulfonyl
TMS: trimethylsilyl
Ts: p-toluenesulfonyl A compound of the formula [II] can be produced according to the following method.

Production Method 1

-continued

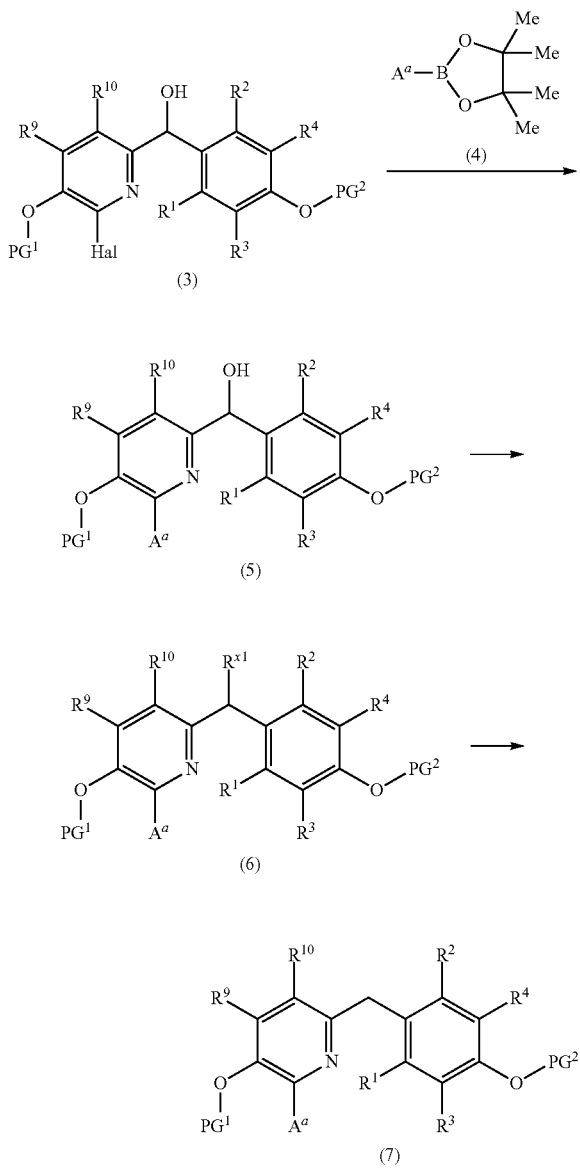

wherein PG¹ and PG² show different protecting groups, $A^a$ is aryl or heteroaryl optionally fused with cycloalkane, $R^{X1}$ is acetoxy or halogen, Hal is halogen, and other symbols are as mentioned above.

[Step 1]

Compound (3) can be obtained by reacting compound (2) with, for example, an organic metal reagent such as normal butyllithium reagent to allow halogen metal exchange, and adding compound (1) obtained by reference to Angew. Chem. Int. Ed. 2002, 41, 1062. This reaction preferably proceeds in a solvent inert to the reaction (for example, ether solvents such as tetrahydrofuran, diethyl ether and the like or hydrocarbon solvents such as toluene and the like) at −78° C. to room temperature.

As each of PG¹ and PG², protecting groups permitting selective deprotection may be selected. As PG¹, a methoxymethyl group is preferable, and as PG², a 1-ethoxy-1-ethyl group, a benzyl group and the like are preferable.

In addition, compound (3) can be reacted, without isolation, with a reagent for introduction of a protecting group such as acetic anhydride and the like.

[Step 2]

Compound (5) can be produced by reacting compound (3) with compound (4) in the presence of a base and a palladium catalyst. As the palladium catalyst, zero valent or divalent palladium catalysts such as tetrakis(triphenylphosphine)palladium(0), bis(triphenylphosphine)palladium(II) dichloride, palladium(II) acetate and the like can be preferably used. As the base, inorganic bases such as alkali metal carbonate, alkali metal hydroxide, alkali metal phosphate, alkali metal fluoride and the like, organic bases such as triethylamine etc. and the like can be preferably used.

This reaction can be carried out in a suitable solvent or without solvent. The solvent is not particularly limited as long as it does not adversely influence the reaction and, for example, dimethoxyethane, tetrahydrofuran, dimethylformamide, methanol, ethanol, toluene, benzene, chloroform and a mixed solvent thereof can be appropriately used. This reaction preferably proceeds at 60-150° C., particularly 80-120° C.

In addition, boric acid such as $A^a$-B(OH)$_2$ and ester thereof, a tin reagent such as $A^a$-SnBu$_4$, a magnesium reagent such as $A^a$-MgBr, and a zinc reagent such as $A^a$-ZnBr can be used instead of compound (4).

[Step 3]

A compound (6) wherein $R^{X1}$ is acetoxy can be produced by acetylating compound (5) and reducing the compound. The acetylation can be performed by a method generally used, for example, by reacting the compound with acetic anhydride in pyridine at room temperature.

A compound (6) wherein $R^{X1}$ is halogen can be produced by halogenating compound (5). The halogenation is not particularly limited as long as it is a method generally used and, for example, chlorination preferably proceeds at room temperature in the presence of a base such as triethylamine and N,N-dimethylaminopyridine, and using a chlorinating agent such as methanesulfonyl chloride and thienyl chloride, and optionally using a salt such as lithium chloride in a solvent inert to the reaction (for example, ester solvents such as ethyl acetate, halogenated solvents such as dichloromethane, hydrocarbon solvents such as toluene and the like).

[Step 4]

Compound (7) can be produced by reducing compound (6). The reduction proceeds fine by a catalytic hydrogenation reaction including reaction under a hydrogen atmosphere in the presence of a palladium catalyst, or by reduction using trialkylsilane in the presence of an acid catalyst. The catalytic hydrogenation reaction preferably proceeds in a solvent inert to the reaction (for example, ester solvents such as ethyl acetate, alcohol solvents such as ethanol, ether solvents such as tetrahydrofuran and the like), at room temperature under a hydrogen atmosphere (1-3 atm). The reduction using trialkylsilane preferably proceeds in a solvent inert to the reaction (for example, methylene chloride), in the presence of an acid catalyst such as BF$_3$.Et$_2$O, trifluoroacetic acid and silver trifluoromethanesulfonate, under ice-cooling.

By the reduction method using trialkylsilane, step 3 can be carried out before step 2, and thereafter step 2 can be carried out.

Production Method 2

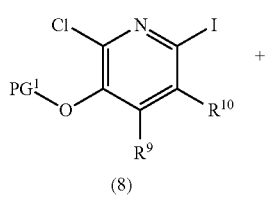
(8)

+

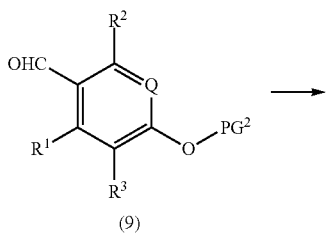
(9)

wherein each symbol is as mentioned above.

[Step 1]

Compound (10) can be produced by treating compound (8) with an alkyllithium reagent or an alkylmagnesium reagent to perform a halogen-metal exchange reaction, and reacting the compound with compound (9). This reaction can be carried out in a suitable solvent. The solvent is not particularly limited as long as it does not adversely influence the reaction and, for example, ether solvents such as tetrahydrofuran, hydrocarbon solvents such as toluene etc. and the like can be appropriately used. This reaction can be preferably carried out at −78° C. to room temperature.

A compound wherein $R^x$ is protected hydroxyl can also be produced by reaction with compound (9) and, without isolation, reaction with a reagent for introducing a protecting group such as acetic anhydride and the like.

Production Method 3

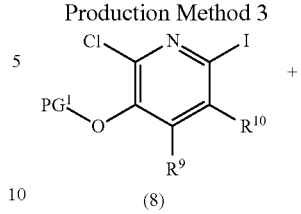
(8)

+

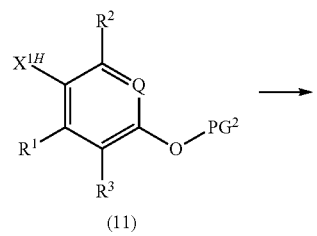
(11)

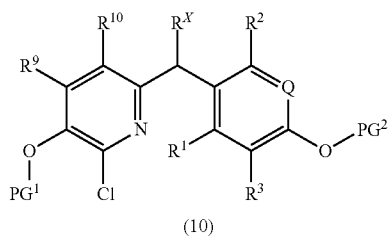
(10)

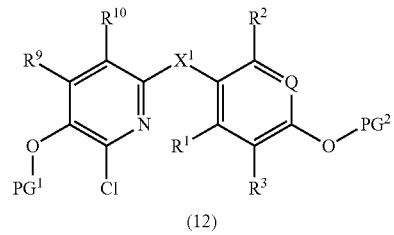
(12)

wherein $X^{1H}$ is OH or SH, $X^1$ is O or S, and other symbols are as mentioned above.

[Step 1]

Compound (12) can be produced by reacting compound (8) with compound (11) in the presence of a transition metal catalyst such as copper(I) iodide and the like, and a base. As the base, inorganic salts such as potassium carbonate, cesium carbonate and the like can be preferably used. This reaction can be carried out in a suitable solvent. The solvent is not particularly limited as long as it does not adversely influence the reaction and, for example, dimethyl sulfoxide and the like can be appropriately used. This reaction preferably proceeds at 60-150° C., particularly at 80-120° C.

Production Method 4

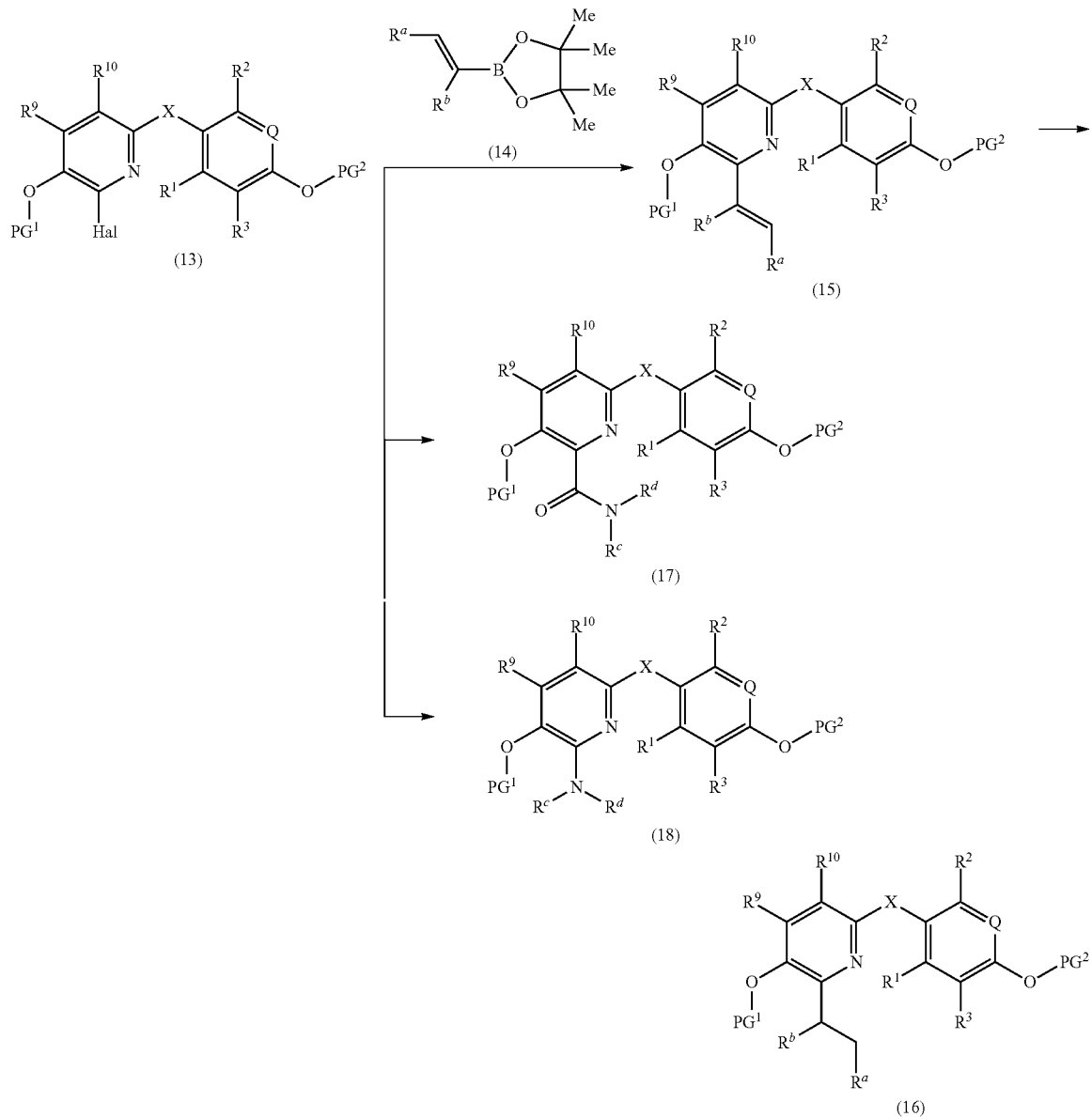

wherein $R^a$-$R^d$ are the same or different, and substituents such as hydrogen, optionally substituted alkyl, optionally substituted alkoxy, optionally substituted amino and the like, $R^d$ and $R^c$ may be bonded to form an optionally substituted cyclic group (e.g., heterocycle and carbocycle), and other symbols are as mentioned above.

[Step 1a]

Compound (16) can be produced by subjecting compound (15), which can be produced from compound (13) and compound (14) in the same manner as in production method 1, step 2, to a catalytic hydrogenation reaction including reduction under a hydrogen atmosphere in the presence of a palladium catalyst. The catalytic hydrogenation reaction preferably proceeds in a solvent inert to the reaction (for example, ester solvents such as ethyl acetate, alcohol solvents such as ethanol, ether solvents such as tetrahydrofuran and the like), at room temperature under a hydrogen atmosphere (1-3 atm).

Using the following compound (19) instead of compound (14), a compound represented by the formula [1] wherein A is cycloalkyl optionally fused with an aromatic ring or a heterocyclic group can also be synthesized.

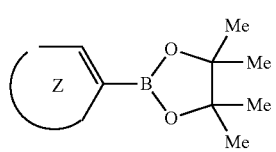

wherein Z is cycloalkenyl optionally fused with an optionally substituted aromatic ring, or a heterocyclic group.

Compound (16) can also be produced by using a boric acid reagent, borate, a tin reagent, a magnesium reagent and a zinc reagent corresponding to compound (14) and compound (19).

[Step 1b]

Compound (17) can be produced by reacting compound (13) in the presence of carbon monoxide, amine (NHR$^c$R$^d$), a base and a palladium catalyst. As the palladium catalyst, a zero valent or a divalent palladium catalyst such as tetrakis (triphenylphosphine)palladium(0), bis(triphenylphosphine) palladium(II) dichloride, palladium(II) acetate and the like can be preferably used. As the base, an inorganic base such as alkali metal carbonate, alkali metal hydroxide, alkali metal phosphate, alkali metal fluoride and the like, an organic base such as triethylamine etc. and the like can be preferably used. As the alcohol, methanol, ethanol and the like can be preferably used. Molybdenum hexacarbonyl and the like can be used instead of carbon monoxide.

This reaction can be carried out in a suitable solvent or without solvent. The solvent is not particularly limited as long as it does not adversely influence the reaction and, for example, dimethoxyethane, tetrahydrofuran, dimethylformamide, methanol, ethanol, toluene, benzene, chloroform and a mixed solvent thereof can be appropriately used. This reaction preferably proceeds at 60-150° C., particularly at 80-120° C.

[Step 1c]

Compound (18) can be produced by reacting compound (13) with amine (NHR$^c$R$^d$). A palladium catalyst and a base may also be used. For a reaction using a palladium catalyst, tris(benzylideneacetone)dipalladium(0), 4,5-bis(diphenylphosphino)-9,9-dimethylxanthene, sodium tert-butoxide and the like can be used in combination. As the base, an inorganic base such as alkali metal carbonate, alkali metal hydroxide, alkali metal phosphate, alkali metal fluoride and the like, an organic base such as triethylamine etc. and the like can be preferably used. This reaction can be carried out in a suitable solvent or without solvent. The solvent is not particularly limited as long as it does not adversely influence the reaction and, for example, dimethoxyethane, tetrahydrofuran, dimethyl sulfoxide and a mixed solvent thereof can be appropriately used. This reaction preferably proceeds at 60-150° C., particularly at 80-120° C.

Production Method 5

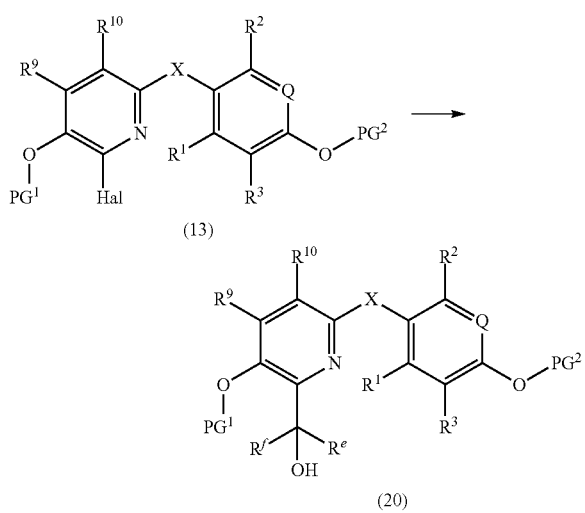

wherein R$^f$ and R$^e$ are the same or different and each is alkyl or alkenyl, or R$^f$ and R$^e$ may be bonded to form optionally substituted carbocycle or heterocycle, and other symbols are as mentioned above.

[Step 1]

Compound (20) can be produced by treating compound (13) with an alkyllithium reagent, or a mixed reagent of alkyllithium and alkylmagnesium halide to perform a halogen-metal exchange reaction, and reacting the compound with an electrophile (e.g., ketone: R$^f$C(=O)R$^e$ and the like).

The halogen-metal exchange reaction can be carried out in a solvent inert to the reaction (for example, ether solvents such as tetrahydrofuran and the like). This reaction can be preferably carried out at −78° C. to room temperature.

Production Method 6

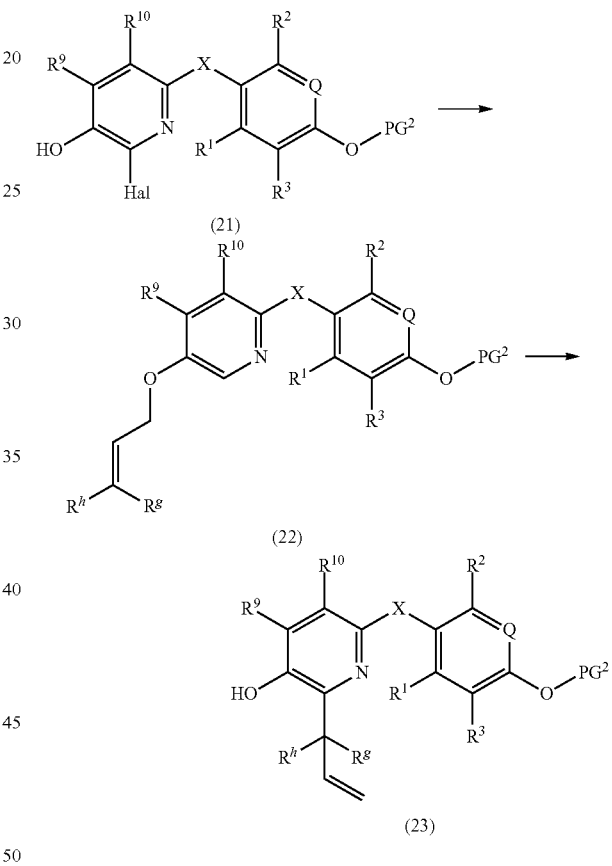

wherein R$^h$ and R$^g$ are the same or different and each is alkyl or alkenyl, R$^h$ and R$^g$ may be bonded to form carbocycle or heterocycle, and other symbols are as mentioned above.

[Step 1]

Compound (22) can be produced by dehalogenating compound (21) by a conventional method, and alkenylating the compound by a conventional method. This reaction can be carried out in a suitable solvent. The solvent is not particularly limited as long as it does not adversely influence the reaction and, for example, ether solvents such as tetrahydrofuran, amide solvents such as N,N-dimethylformamide, and mixed solvents with these can be used.

[Step 2]

Compound (23) can be produced by heating compound (22) in the presence of a base. As the base, sodium acetate can be preferably used and, as the solvent, acetic anhydride can be preferably used. This reaction preferably proceeds at 160° C.
-240° C., and preferably proceeds under microwave irradiation.

A compound represented by the formula [I] can be produced from a compound represented by the formula [II] and by the following method.

Production Method 7

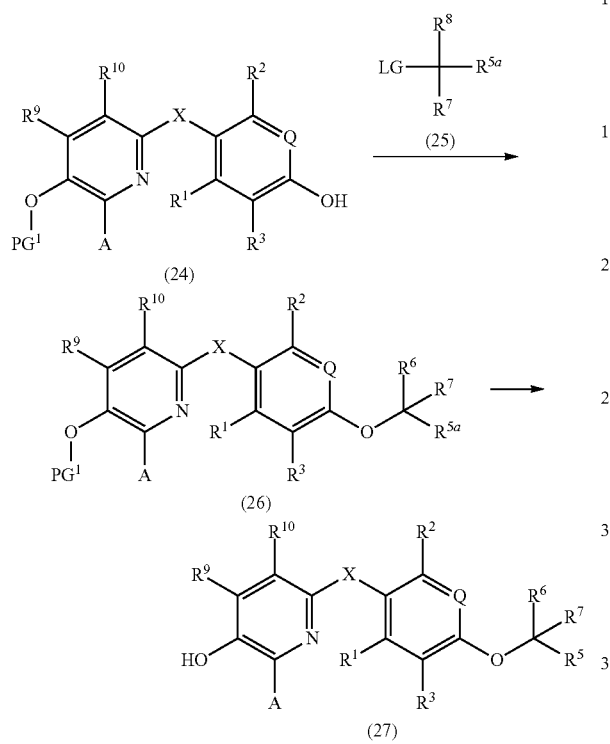

Production Method 8

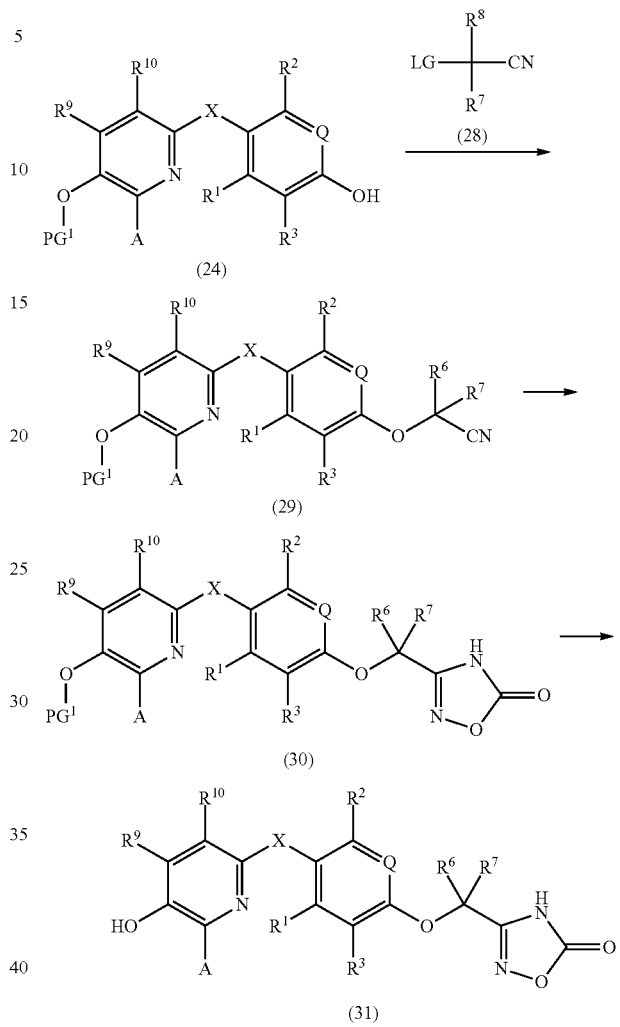

wherein $R^{5a}$ is a carboxyl group optionally protected by a protecting group or a bioisosteric group thereof optionally protected by a protecting group, LG is a leaving group (for example, halogen, arylsulfonyloxy such as tosyloxy, alkylsulfonyloxy and the like), and other symbols are as mentioned above.

[Step 1]

Compound (26) can be produced by reacting compound (24) with compound (25) in the presence of a base. This reaction can be carried out in a solvent inert to the reaction (for example, acetonitrile, ester solvents such as ethyl acetate, ether solvents such as tetrahydrofuran, amide solvents such as dimethylformamide and the like). As the base, an inorganic base such as cesium carbonate, potassium carbonate etc. and the like can be preferably used. This reaction preferably proceeds at 0° C.-80° C., particularly at room temperature—60° C.

[Step 2]

Compound (27) can be produced by deprotecting compound (26) by a conventional method.

wherein the symbols are as mentioned above.

[Step 1]

Compound (29) can be produced from compound (24) and compound (28) in the same manner as in production method 7, step 1.

[Step 2]

Compound (30) can be produced by reacting compound (29) with sodium hydrogen carbonate and hydroxyamine hydrochloride, and reacting the obtained compound with 1,1-carbonyldiimidazole (CDI).

The reaction with hydroxyamine can be carried out in a solvent inert to the reaction (for example, alcohol solvents such as methanol and the like), and preferably proceeds at 60° C.-100° C.

The reaction with CDI can be carried out in a solvent inert to the reaction (for example, ether solvents such as 1,4-dioxane and the like), and preferably proceeds at 80° C.-120° C.

[Step 3]

Compound (31) can be produced by deprotecting $PG^1$ of compound (30) by a conventional method.

Production Method 9

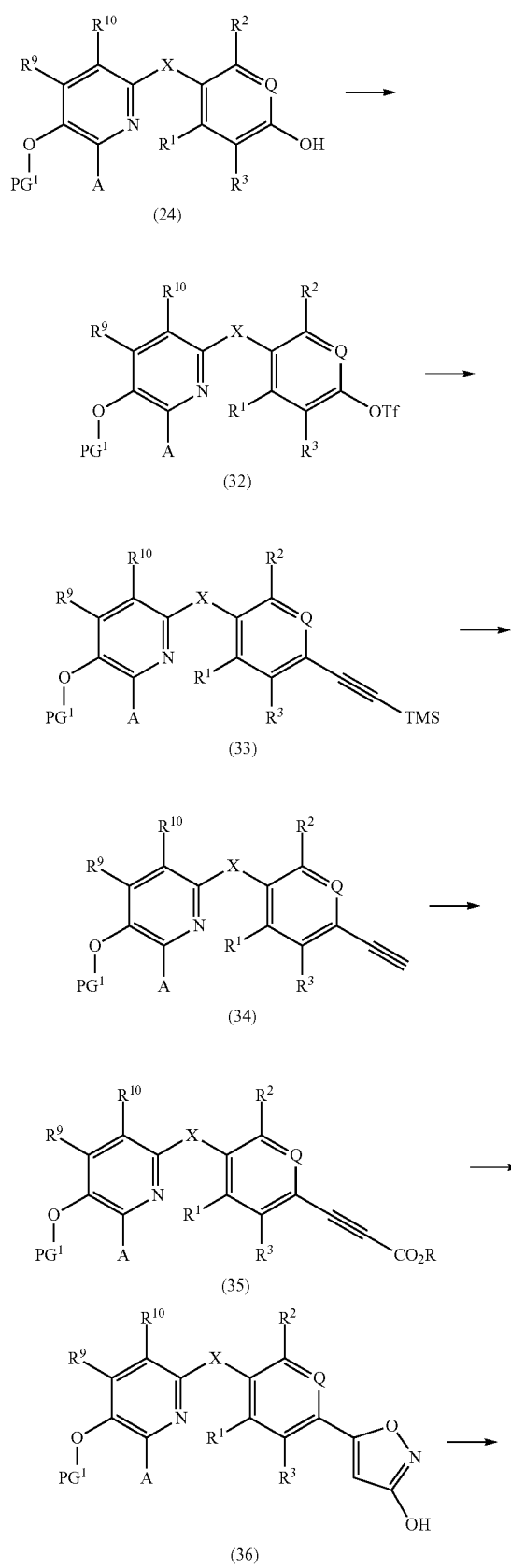

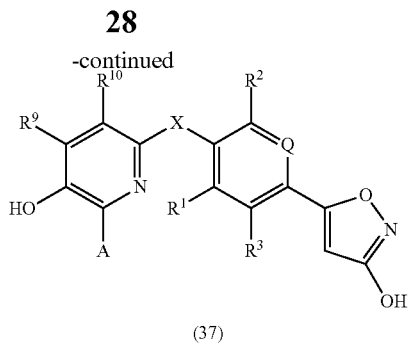

wherein R is alkyl, and other symbols are as mentioned above.

[Step 1]

Compound (32) can be produced by reacting compound (24) with trifluoromethanesulfonic anhydride in the presence of a base. This step preferably proceeds in a solvent inert to the reaction (for example, methylene chloride), in the presence of a base such as 2,6-lutidine, diisopropylethylamine and the like, under ice-cooling.

[Step 2]

Compound (33) can be produced by reacting compound (32) with trimethylsilylacetylene in the presence of a base, copper(I) iodide and a palladium catalyst (Sonogashira reaction). As the palladium catalyst, a zero valent or divalent palladium catalyst such as tetrakis(triphenylphosphine)palladium(0), bis(triphenylphosphine)palladium(II) dichloride, palladium(II) acetate and the like can be preferably used. As the base, an inorganic base such as alkali metal carbonate, alkali metal hydroxide, alkali metal phosphate, alkali metal fluoride and the like, an organic base such as triethylamine etc. and the like can be preferably used.

This reaction can be carried out in a suitable solvent or without solvent. The solvent is not particularly limited as long as it does not adversely influence the reaction and, for example, dimethoxyethane, tetrahydrofuran, dimethylformamide, methanol, ethanol, toluene, benzene, chloroform and a mixed solvent thereof can be appropriately used. This reaction preferably proceeds at 60-150° C., particularly at 80-120° C.

[Step 3]

Compound (34) can be produced by treating compound (33) with a base (for example, an inorganic base such as potassium carbonate) in a suitable solvent. This reaction can be carried out in a suitable solvent. The solvent is not particularly limited as long as it does not adversely influence the reaction and, for example, alcohol solvents such as methanol and the like can be used. This reaction preferably proceeds at 0° C.—room temperature.

[Step 4]

Compound (35) can be produced by treating compound (34) with a base (for example, metal amides such as lithium diisopropylamide, lithium hexamethyl disilazide and the like, alkyl metals such as butyllithium and the like) in a suitable solvent, and treating the compound with alkyl halocarbonate. This reaction can be carried out in a suitable solvent. The solvent is not particularly limited as long as it does not adversely influence the reaction and, for example, ether solvents such as tetrahydrofuran can be used. This reaction preferably proceeds at −78° C. to room temperature.

[Step 5]

Compound (36) can be produced by reacting compound (35) with hydroxyamine hydrochloride. This reaction can be carried out in a suitable solvent. The solvent is not particularly limited as long as it does not adversely influence the reaction and, for example, 10% aqueous sodium hydroxide solution, alcohol solvents such as ethanol, and aprotic solvents such as methylene chloride or a mixed solvent thereof can be used. This reaction preferably proceeds at 0° C.-80° C., particularly at 0° C.-60° C.

[Step 6]

Compound (37) can be produced by deprotecting $PG^1$ of compound (36) by a conventional method.

Production Method 10

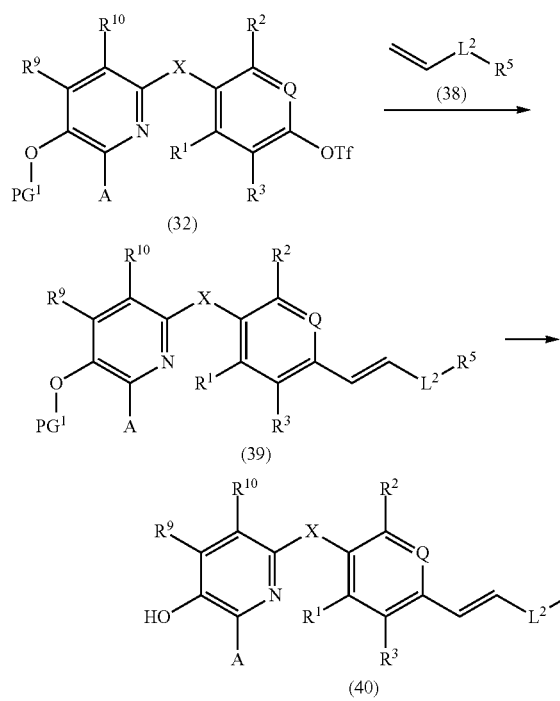

wherein the symbols are as mentioned above.

Compound (39) can be produced by reacting compound (32) with compound (38) in the presence of a palladium catalyst. As the palladium catalyst, a zero valent or divalent palladium catalyst such as tetrakis(triphenylphosphine)palladium(0), bis(triphenylphosphine)palladium(II) dichloride, palladium(II) acetate and the like can be preferably used. As additives, for example, lithium chloride, triethylammonium chloride, cesium fluoride, copper(I) iodide and the like may be added.

This reaction can be carried out in a suitable solvent or without solvent. The solvent is not particularly limited as long as it does not adversely influence the reaction and, for example, dimethoxyethane, tetrahydrofuran, dimethylformamide, methanol, ethanol, toluene, benzene, chloroform and a mixed solvent thereof can be appropriately used. This reaction preferably proceeds at 60-150° C., particularly at 80-120° C.

[Step 3]

Compound (40) can be produced by deprotecting $PG^1$ of compound (39) by a conventional method.

Production Method 11

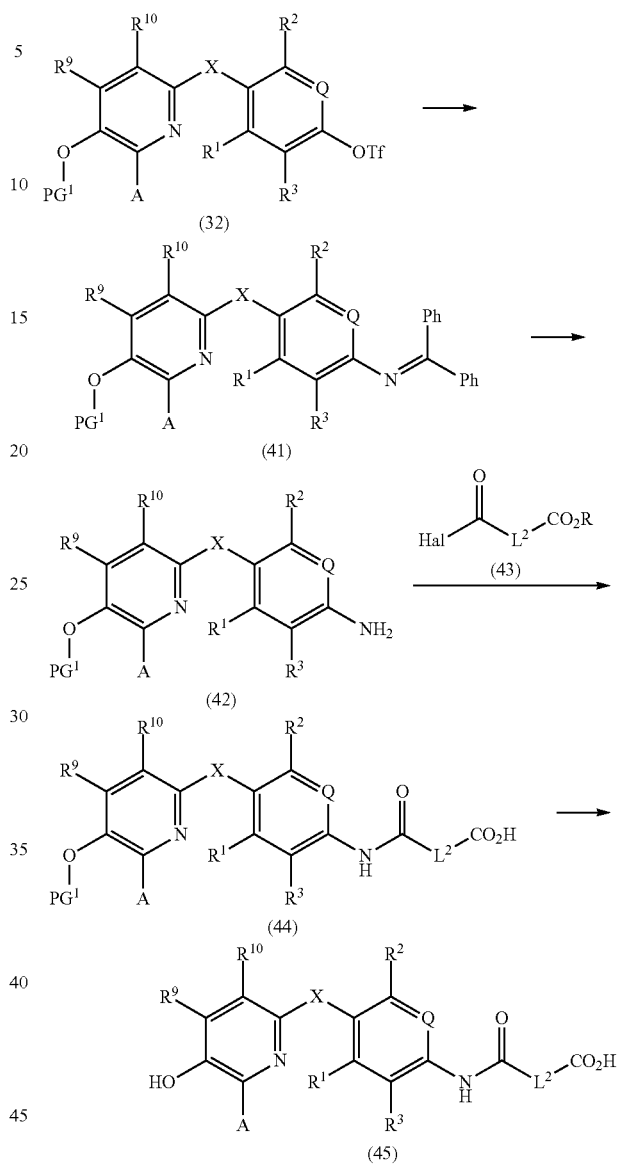

wherein the symbols are as mentioned above.

[Step 1]

Compound (41) can be produced by reacting compound (32) with benzophenone imine in the presence of a palladium catalyst. As the palladium catalyst, palladium(II) acetate, BINAP and cesium carbonate can be used in combination. As the base, an inorganic base such as alkali metal carbonate, alkali metal hydroxide, alkali metal phosphate, alkali metal fluoride and the like, an organic base such as triethylamine etc. and the like can be preferably used. This reaction can be carried out in a suitable solvent or without solvent. The solvent is not particularly limited as long as it does not adversely influence the reaction and, for example, dimethoxyethane, tetrahydrofuran, and a mixed solvent thereof can be appropriately used. This reaction preferably proceeds at 60-150° C., particularly at 80-120° C.

[Step 2]

Compound (42) can be produced by elimination of debenzophenone of compound (41) by a conventional method. The elimination of debenzophenone can be carried out by, for example, reacting compound (41) with hydroxyamine hydrochloride in a suitable solvent, in the presence of sodium acetate at room temperature. The solvent is not particularly limited as long as it does not adversely influence the reaction and, for example, an alcohol solvent can be appropriately used.
[Step 3]
Compound (44) can be produced by acylating compound (42) and compound (43) by a conventional method, followed by hydrolysis.
[Step 4]
Compound (45) can be produced by deprotecting $PG^1$ of compound (44) by a conventional method.
Production Method 12

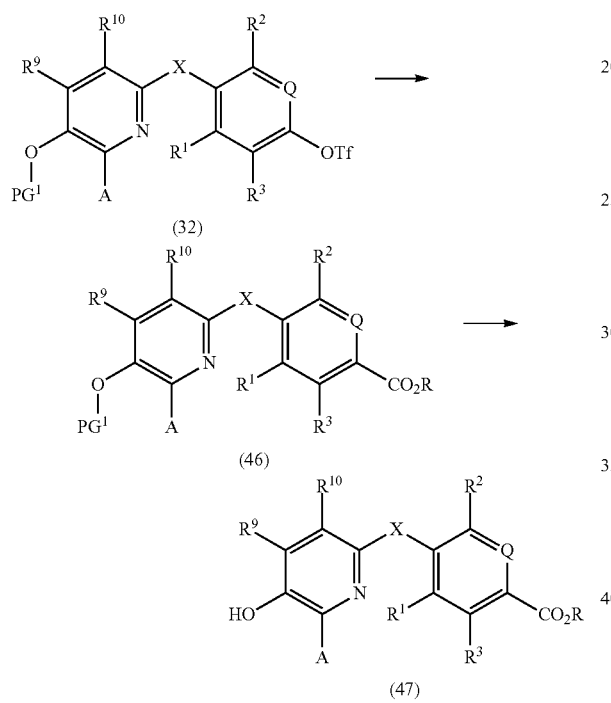

wherein the symbols are as mentioned above.

Compound (46) can be produced by reacting compound (32) in the presence of carbon monoxide, alcohol (ROH: R is alkyl), a base and a palladium catalyst. As the palladium catalyst, zero valent or divalent palladium catalysts such as tetrakis(triphenylphosphine)palladium(0), bis(triphenylphosphine)palladium(II) dichloride, palladium(II) acetate and the like can be preferably used. As the base, inorganic bases such as alkali metal carbonate, alkali metal hydroxide, alkali metal phosphate, alkali metal fluoride and the like, organic bases such as triethylamine and the like, and the like can be preferably used. As alcohol, methanol, ethanol and the like can be preferably used. Molybdenum hexacarbonyl and the like can be used instead of carbon monoxide.

This reaction can be carried out in a suitable solvent or without solvent. The solvent is not particularly limited as long as it does not adversely influence the reaction and, for example, dimethoxyethane, tetrahydrofuran, dimethylformamide, methanol, ethanol, toluene, benzene, chloroform and a mixed solvent thereof can be appropriately used. This reaction preferably proceeds at 60-150° C., particularly 80-120° C.

[Step 2]
Compound (47) can be produced by deprotecting $PG^1$ of compound (46) by a conventional method.
Production Method 13

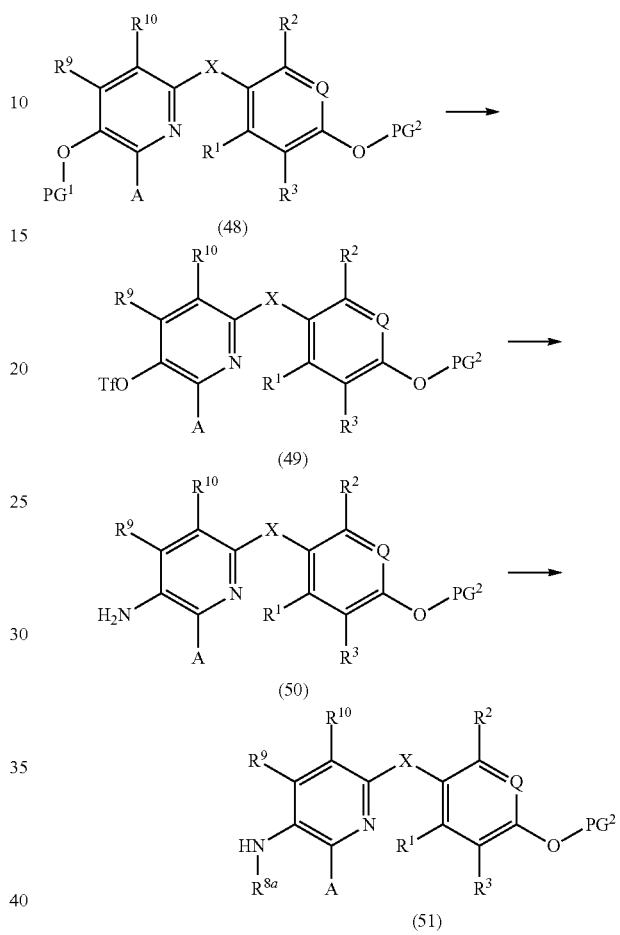

wherein $R^{8a}$ is alkanoyl or alkylsulfonyl, and other symbols are s as mentioned above.
[Step 1]
Compound (49) can be produced by selectively deprotecting $PG^1$ of compound (48) by a conventional method, and reacting the compound with trifluoromethanesulfonic anhydride in the presence of a base. The reaction with trifluoromethanesulfonic anhydride preferably proceeds in a solvent inert to the reaction (for example, methylene chloride) in the presence of a base such as 2,6-lutidine, under ice-cooling.
[Step 2]
Compound (50) can be produced in the same manner as in production method 11, step 1 and step 2.
[Step 3]
Compound (51) can be produced by subjecting compound (50) to alkanoylation or alkylsulfonylation by a method generally used.
Production Method 14

The functional groups contained in the compound of the present invention, synthetic intermediate or starting compound can be converted by techniques generally used, for example, the following methods and the like.
(1) When the compound of the present invention, synthetic intermediate or starting compound has a functional group (hydroxy, amino, carboxy and the like), the reaction can be performed after protecting the functional group with a protecting group generally used in the organic synthesis chemistry (for example, the method described in Protective Groups in Organic Synthesis Third Edition (Theodora W. Green and Peter G. Wuts)). The object compound can be obtained by removing the protecting group after the reaction. Examples of the hydroxy-protecting group include tetrahydropyranyl, TMS, alkanoyl, benzoyl and the like, examples of the amino-protecting group include Boc, benzyloxycarbonyl and the like, and examples of the carboxy-protecting group include alkyl such as methyl, ethyl and the like, benzyl and the like.

(2) When the compound of the present invention, synthetic intermediate or starting compound has an amino, a compound wherein optionally substituted alkyl has mono- or di-substituted amino can be obtained by protecting amino as necessary, (i) reacting with alkyl halide in the presence of a base (sodium hydride, triethylamine, sodium carbonate, potassium carbonate and the like), or (ii) subjecting alcohol to the Mitsunobu reaction using dialkyl azodicarboxylate and triphenylphosphine, and deprotecting amino as necessary.

(3) When the compound of the present invention, synthetic intermediate or starting compound has an amino, amide can be produced by any conventional method generally used for amide formation in peptide synthesis and the like. Examples thereof include a method comprising reaction with carboxylic acid in the presence of a condensing agent, and a method comprising reaction with acid halide or acid anhydride. In the method using a condensing agent, any of N-ethyl-N'-(3-diethylaminopropyl)carbodiimide, N,N'-dicyclohexylcarbodiimide, 1-methyl-2-bromopyridinium iodide, N,N'-carbonyldiimidazole, diphenylphosphoryl azide, benzotriazol-1-yloxytris(dimethylamino)phosphonium hexafluorophosphate, 4-(4,6-dimethoxy-1,3,5-triazin-2-yl)-4-methylmorphorinium chloride, fluoro-N,N,N',N'-tetramethylformamidinium hexafluorophosphate and the like can be preferably used as the condensing agent. As the solvent, any of water, methanol, isopropanol, ethanol, methylene chloride, THF, dioxane, DMF, dimethylacetamide, chloroform and the like can be preferably used singly or as a mixed solvent. This reaction preferably proceeds at −78° C.-100° C., more preferably −25° C.-25° C. The progress of this reaction can be promoted by adding, as the base, inorganic bases such as potassium carbonate, sodium carbonate, sodium hydrogen carbonate and the like or organic bases such as triethylamine, diisopropylethylamine, N-methylmorpholine, pyridine, N,N-dimethylaminopyridine, picoline, lutidine and the like and, as the additive, N-hydroxysuccinimide, 3-hydroxy-3,4-dihydro-4-oxo-1,2,3-benzotriazole, N,N-dimethylaminopyridine or N-hydroxybenzotriazole and the like. In the method using acid halide or acid anhydride, methylene chloride, chloroform, THF, DMF and the like can be preferably used, as the solvent, singly or as a mixed solvent. This reaction preferably proceeds at −78° C.-100° C., more preferably −25° C.-25° C. This reaction proceeds in the presence of a base such as pyridine, triethylamine, N,N-dimethylaminopyridine, diisopropylethylamine and the like, preferably at −78° C.-100° C., more preferably −25° C.-25° C. and, as a solvent, any of methylene chloride, chloroform, THF, DMF and the like can be preferably used singly or as a mixed solvent.

(4) When the compound of the present invention, synthetic intermediate or starting compound has a double bond, it can be converted to the corresponding single bond by catalytic reduction using a transition metal (platinum, palladium, rhodium, ruthenium, nickel) catalyst.

(5) When the compound of the present invention, synthetic intermediate or starting compound has an ester group, it can be converted to the corresponding carboxy by hydrolysis using alkali (sodium hydroxide, potassium hydroxide and the like).

(6) When the compound of the present invention, synthetic intermediate or starting compound has carbamoyl, it can be converted to the corresponding nitrile by reaction with trifluoroacetic anhydride.

(7) When the compound of the present invention, synthetic intermediate or starting compound has carboxy, it can be converted to the corresponding 4,5-dihydrooxazol-2-yl by reaction with 2-haloethylamine in the presence of a condensing agent.

(8) When the compound of the present invention, synthetic intermediate or starting compound has hydroxy, it can be converted to the corresponding halogen by a treatment with a halogenating agent. In addition, when the compound of the present invention or starting compound has halogen, it can be converted to the corresponding alkoxy by a treatment with alcohol.

(9) When the compound of the present invention, synthetic intermediate or starting compound has ester, it can be converted to the corresponding hydroxy by reduction with a reducing agent (metal reducing reagent such as lithium aluminum hydride, sodium borohydride, lithium borohydride and the like, diborane and the like).

(10) When the compound of the present invention, synthetic intermediate or starting compound has hydroxy, it can be converted to aldehyde, ketone or carboxy by oxidation with an oxidant.

(11) When the compound of the present invention, synthetic intermediate or starting compound has carbonyl or aldehyde, it can be converted to optionally mono- or di-substituted aminomethyl by reductive amination reaction in the presence of an amine compound and a reducing agent (sodium borohydride, sodium cyanoborohydride and the like).

(12) When the compound of the present invention, synthetic intermediate or starting compound has carbonyl or aldehyde, it can be converted to a double bond by subjecting to a Wittig reaction.

(13) When the compound of the present invention, synthetic intermediate or starting compound has sulfonamide, it can be converted to the corresponding salt of sulfonamide (sodium salt, potassium salt and the like) by a treatment with alkali (sodium hydroxide, potassium hydroxide and the like) in alcohol (methanol, ethanol and the like).

(14) When the compound of the present invention, synthetic intermediate or starting compound has aldehyde, it can be converted to the corresponding oxime by reaction with hydroxylamine or O-alkylhydroxylamine in alcohol (methanol, ethanol and the like), in the presence of a base (sodium hydrogen carbonate and the like).

(15) When the compound of the present invention, synthetic intermediate or starting compound has halogen, it can be converted to the corresponding cyano group by a treatment with a cyanating agent.

(16) When the compound of the present invention, synthetic intermediate or starting compound has halogen, it can be converted to the corresponding amine by reaction according to the method described in Tetrahedron, 2041-2075, 2002.

(17) When the compound of the present invention, synthetic intermediate or starting compound has a cyano group, it can be converted to an aldehyde group by using a reducing agent (diisobutylaluminum hydride and the like).
(18) When the compound of the present invention, synthetic intermediate or starting compound has a vinyl group, it can be converted to a formyl group by ozone oxidation or osmium oxidation followed by periodate oxidation.
(19) The amino group of compound (38) of production method 8 can be converted to a 6-cyano-3,5-dioxo-1,2,4-triazin-2-yl group by a method similar to the method described in J. Med. Chem., 1983, 26, 96.
(20) When the compound of the present invention, synthetic intermediate or starting compound has phenolic hydroxy, it can be converted to a phosphonomethyloxy group by a method similar to the method described in Tetrahedron Lett., 1986, 27, 1477.
(21) When the compound of the present invention, synthetic intermediate or starting compound has an aldehyde group, it can be converted to a 1,3-oxazolidine-2,4-dion-5-yl group by a method similar to the method described in J. Med. Chem., 2002, 45, 1518.
(22) When the compound of the present invention, synthetic intermediate or starting compound has an aldehyde group, it can be converted to a 1,2,4-oxadiazolidine-3,5-dion-2-yl group by a method similar to the method described in Eur. J. Med. Chem., 2001, 36, 31.
(23) When the compound of the present invention, synthetic intermediate or starting compound has an aldehyde group, it can be converted to semicarbazone by using semicarbazide, and semicarbazone can be converted to a 1,2,4-triazol-3-on-5-yl group by a method similar to the method described in J. Heterocyclic. Chem., 1986, 23, 881.
(24) When the compound of the present invention, synthetic intermediate or starting compound has an aldehyde group, it can be converted to a 1,3-imidazolidine-2,4-dion-5-yl group by using hydantoin and a reducing agent.
(25) When the compound of the present invention, synthetic intermediate or starting compound has an amino group, it can be converted to a 1,3-imidazolidine-2,4-dion-1-yl group by using chloroacetyl isocyanate.
(26) When the compound of the present invention, synthetic intermediate or starting compound has a cyano group, it can be converted to a tetrazolyl group by using sodium azide.
(27) When the compound of the present invention, synthetic intermediate or starting compound has a phosphono group, it can be converted to a dialkylphosphono group by reaction with alkyl halide.
(28) When the compound of the present invention, synthetic intermediate or starting compound has a phosphono group, phosphonate ester or phosphonic amide can be produced by converting the group to a dihalophosphoryl group by treating with a halogenating agent (e.g., phosphorus trichloride, phosphorus pentachloride, thionyl chloride, oxalyl chloride etc.), and reacting same with a desired alcohol or desired amine.
(29) When the compound of the present invention, synthetic intermediate or starting compound has a phosphono group, it can be converted to phosphonate ester or phosphonic amide by reacting with alcohol or amine in the presence of a condensing agent. As an example of the condensing agent, any of N-ethyl-N'-(3-diethylaminopropyl)carbodiimide, N,N'-dicyclohexylcarbodiimide, 1-methyl-2-bromopyridinium iodide, N,N'-carbonyldiimidazole, diphenylphosphoryl azide, benzotriazol-1-yloxytris(dimethylamino)phosphonium hexafluorophosphate, 4-(4,6-dimethoxy-1,3,5-triazin-2-yl)-4-methylmorpholinium chloride, fluoro-N,N,N',N'-tetramethylformamidinium hexafluorophosphate and the like can be used preferably.

The compounds of the formulae [I] and [II] obtained above and each synthetic intermediate are isolated and purified by conventional chemical operations such as extraction, crystallization, recrystallization, various chromatographys and the like.

Pharmacologically acceptable salts of the compounds of the formulae [I] and [II] obtained above can be produced using the prior art, and salts are purified by conventional chemical operations such as recrystallization and the like.

The compounds [I] and [II] of the present invention encompass a mixture of stereoisomers, or each stereoisomer which is pure or in a substantially pure form. For example, when the compound of the present invention has one or more asymmetric centers at any carbon atom, compounds [I] and [II] may contain an enantiomer or a diastereomer or a mixture thereof. The compound of the present invention encompasses such isomers and mixtures thereof. In addition, when the compounds [I] and [II] of the present invention have a double bond, a geometric isomer (cis form, trans form) may be present and, when the compounds [I] and [II] of the present invention contain an unsaturated bond such as carbonyl and the like, a tautomer may be present. The compound of the present invention encompasses all such isomers and mixtures thereof.

EXAMPLES

The present invention is explained in more detail in the following by referring to Examples; however, the scope of the present invention is not limited to the following Examples.

Example 1

{4-[(5-hydroxy-6-isopropylpyridin-2-yl)methyl]-3,5-dimethylphenoxy}acetic acid

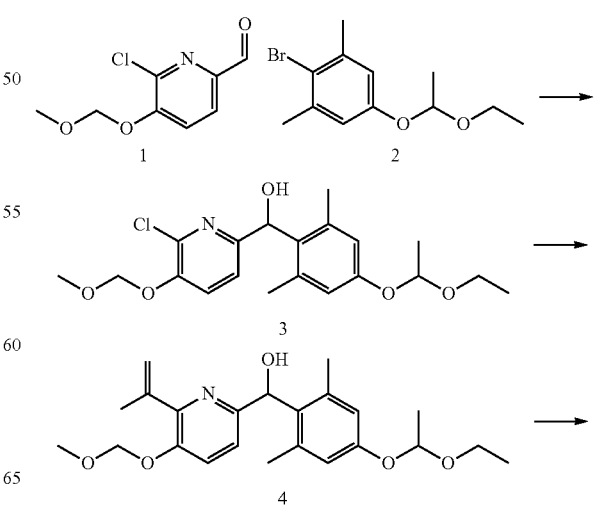

-continued

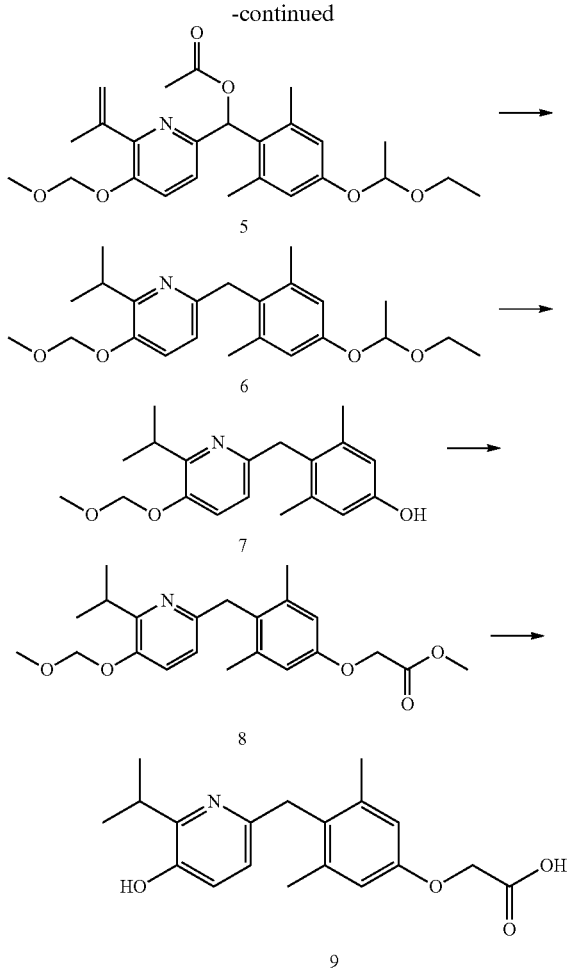

Compound 2 (CAS No. 848442-41-1, 3.58 g, 13.1 mmol) was dissolved in tetrahydrofuran (15 ml), and the mixture was cooled to −78° C. n-Butyllithium (1.6 M hexane solution, 8.8 mL, 14.1 mmol) was slowly added dropwise, and the mixture was stirred for 1 hr. Compound 1 (CAS No. 939430-71-4, 2.03 g, 10.0 mmol) was dissolved in tetrahydrofuran (17 mL), and the mixture was cooled to −78° C. The lithium reagent prepared earlier was added dropwise over 30 min. After stirring for 80 min, the mixture was heated to room temperature. After 1 hr, water was added, and the mixture was extracted with ethyl acetate. The organic layer was washed with saturated brine, dried over anhydrous sodium sulfate, filtered and concentrated. The residue was purified by silica gel column chromatography to give compound 3 (2.07 g, 52%).

MS m/z 396/398 [M+H]+, APCI(+)

Compound 3 (508 mg, 1.28 mmol) was dissolved in dimethoxyethane (5 mL), water (0.5 mL), cesium carbonate (1.25 g, 3.85 mmol) and isopropenylboronic acid pinacol ester (539 mg, 3.20 mmol) were added, and the mixture was purged with argon. Tetrakistriphenylphosphinepalladium(0) (44 mg, 0.038 mmol) was added, and the mixture was heated to 90° C. After stirring for 11 hr, the mixture was allowed to cool to room temperature. Water was added, and the mixture was extracted with chloroform. The organic layer was dried over anhydrous sodium sulfate, filtered and concentrated. The residue was purified by silica gel column chromatography to give compound 4 (449 mg, 87%).

MS m/z 402 [M+H]+, APCI(+)

Compound 4 (444 mg, 1.10 mmol) was dissolved in pyridine (0.54 mL), acetic anhydride (0.31 mL, 9.3 mmol) and dimethylaminopyridine (13.5 mg, 0.111 mmol) were added. After stirring for 6.5 hr, 0.5N hydrochloric acid was added, and the mixture was extracted with ethyl acetate. The organic layer was washed with saturated aqueous sodium hydrogen carbonate and saturated brine, dried over anhydrous sodium sulfate, filtered, and concentrated. The residue was purified by silica gel column chromatography to give compound 5 (454 mg, 93%).

MS m/z 444 [M+H]+, APCI(+)

Compound 5 (450 mg, 1.01 mmol) was dissolved in ethyl acetate (5 mL) and acetic acid (1 mL), and 10% Pd/C (200 mg) was added. After purging with hydrogen, the mixture was stirred for 14 hr. The mixture was filtered through radiolite, and washed well with ethyl acetate. The filtrate was concentrated and the residue was purified by silica gel column chromatography to give compound 6 (225 mg, 57%).

MS m/z 388 [M+H]+, APCI(+)

Compound 6 (450 mg, 1.01 mmol) was dissolved in ethanol (4.5 mL) and acetic acid (0.9 mL), and the mixture was stirred at room temperature for 14 hr. Acetic acid (3.6 mL) was added, and the mixture was heated to 50° C. After 1 hr, the mixture was allowed to cool to room temperature, and neutralized with 2N aqueous sodium hydroxide solution. The filtrate was extracted with ethyl acetate, washed with saturated brine, dried over anhydrous sodium sulfate, filtered and concentrated. The residue was purified by silica gel column chromatography to give compound 7 (213 mg, 67%).

MS m/z 316 [M+H]+, APCI(+)

Compound 7 (20 mg, 0.063 mmol) was dissolved in acetonitrile (0.54 mL), and methyl bromoacetate (29.0 mg, 0.190 mmol) and cesium carbonate (124 mg, 0.380 mmol) were added. After stirring for 1 hr, water was added, and the mixture was extracted with chloroform. The organic layer was dried over anhydrous sodium sulfate, filtered, and concentrated. The residue was purified by silica gel column chromatography, and the obtained compound 8 (23.8 mg) was dissolved in methanol (0.7 mL) and tetrahydrofuran (0.7 mL). 6N Hydrochloric acid (0.7 mL) was added, and the mixture was stirred at room temperature for 1 hr, and heated to 60° C. After 2.5 hr, the mixture was allowed to cool to room temperature, 4N aqueous sodium hydroxide solution (2 mL) was added, and the mixture was heated to 60° C. After 3 hr, the mixture was allowed to cool to room temperature, and neutralized with 2N hydrochloric acid. The mixture was extracted with tetrahydrofuran, dried over anhydrous sodium sulfate, filtered, concentrated and suspension washed with diethyl ether to give compound 9 (20 mg, 97%).

MS m/z 328 [M−H]−, ESI(−)

Hydrobromide, hydrochloride, para-toluenesulfonate, methanesulfonate, benzenesulfonate, maleate and the like of the present compound can be produced by a general salt formation step.

Example 2

{4-[(6-cyclohexyl-5-hydroxypyridin-2-yl)methyl]-3,5-dimethylphenoxy}acetic acid

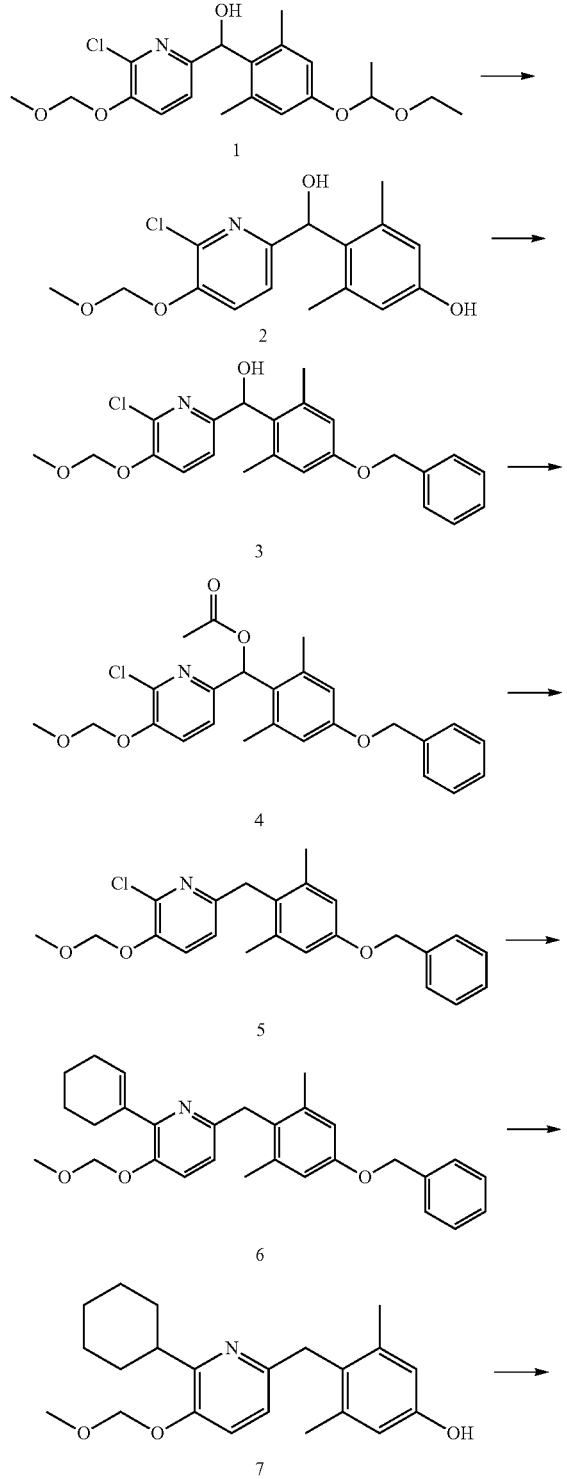

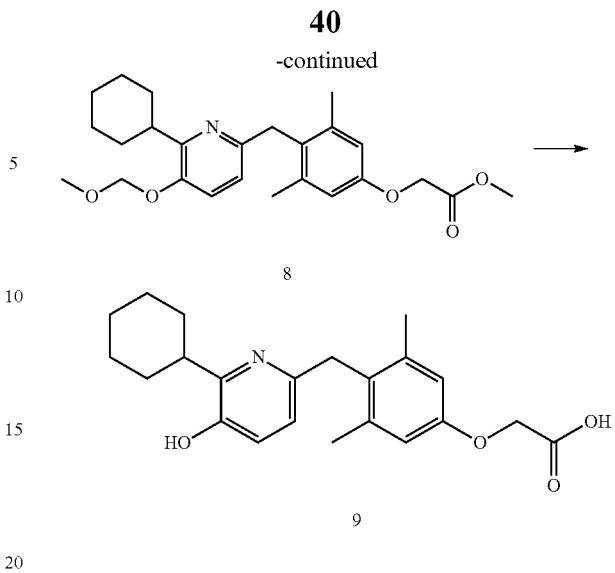

Compound 1 (1.20 g, 3.04 mmol) was dissolved in ethanol (12 mL) and acetic acid (2.4 mL), and the mixture was heated to 50° C. After 7 hr, the mixture was allowed to cool to room temperature and the precipitated solid was collected by filtration, dissolved in ethyl acetate, and neutralized with 2N aqueous sodium hydroxide solution. The filtrate was concentrated under reduced pressure, the residue was dissolved in ethyl acetate, and neutralized with 2N aqueous sodium hydroxide solution. The organic layers were combined, washed with saturated brine, dried over anhydrous sodium sulfate, filtered, and concentrated to give compound 2 (874 mg, 89%).

MS m/z 324/326 [M+H]+, APCI(+)

Compound 2 (872 mg, 2.69 mmol) was dissolved in acetonitrile (16 mL) and tetrahydrofuran (8 mL), benzyl bromide (552 mg, 3.23 mmol) and cesium carbonate (2.63 g, 8.08 mmol) were added. After stirring for 4 hr, water was added, and the mixture was extracted with chloroform. The organic layer was dried over anhydrous sodium sulfate, filtered, and concentrated. The residue was purified by silica gel column chromatography to give compound 3 (971 mg, 87%).

MS m/z 414/416 [M+H]+, APCI(+)

Compound 3 (969 mg, 2.34 mmol) was dissolved in pyridine (1.5 mL), and acetic anhydride (0.88 mL, 9.3 mmol) and dimethylaminopyridine (28.6 mg, 0.234 mmol) were added. After stirring for 18 hr, 1N hydrochloric acid was added, and the mixture was extracted with ethyl acetate. The organic layer was washed with saturated brine, dried over anhydrous sodium sulfate, filtered, and concentrated. The residue was purified by silica gel column chromatography to give compound 4 (1.03 g, 97%).

MS m/z 428/430 [M−OCOCH$_3$+CH$_3$OH]+, APCI(+)

Compound 4 (190 mg, 0.418 mmol) was dissolved in methylene chloride (6 mL), triethylsilane (72.8 mg, 0.627 mmol) was added, and the mixture was ice-cooled. Boron trifluoride-diethyl ether complex (88.9 mg, 0.627 mmol) was slowly added dropwise. After stirring for 10 min, saturated aqueous sodium hydrogen carbonate was added, and the mixture was neutralized with 2N hydrochloric acid, and extracted with ethyl acetate. The organic layer was washed with saturated brine, dried over anhydrous sodium sulfate, filtered, and concentrated. The residue was purified by silica gel column chromatography to give compound 5 (119 mg, 72%).

MS m/z 398/400 [M+H]+, APCI(+)

Compound 5 (497 mg, 1.24 mmol) was dissolved in dimethoxyethane (10 mL), water (1 mL), cesium carbonate (1.22 g, 3.74 mmol), cyclohexenylboronic acid pinacol ester (649 mg, 3.12 mmol) were added, and the mixture was purged with argon. Tetrakistriphenylphosphinepalladium(0) (72 mg, 0.062 mmol) was added, and the mixture was heated to 90° C. After stirring for one day, the mixture was allowed to cool to room temperature. Water was added, and the mixture was extracted with chloroform. The organic layer was dried over anhydrous sodium sulfate, filtered, and concentrated. The residue was purified by silica gel column chromatography to give compound 6 (480 mg, 87%).

MS m/z 444 [M+H]+, ESI(+)

Compound 6 (477 mg, 1.07 mmol) was dissolved in ethanol (14 mL) and, after purging with argon, 10% Pd/C (250 mg) was added. After purging with hydrogen, the mixture was stirred for 9 hr, radiolite filtered, and washed with ethyl acetate. The filtrate was concentrated to give compound 7 (369 mg, 1.03 mmol, 97%). A part (248 mg, 0.700 mmol) of the obtained compound 7 was dissolved in acetonitrile (0.54 mL), and methyl bromoacetate (160 mg, 1.04 mmol) and cesium carbonate (683 mg, 2.09 mmol) were added. After stirring for 2 hr, water was added, and the mixture was extracted with chloroform. The organic layer was dried over anhydrous sodium sulfate, filtered, and concentrated. The residue was purified by silica gel column chromatography to give compound 8 (242 mg, 81%).

MS m/z 428 [M+H]+, APCI(+)

Compound 8 (239 mg, 0.559 mmol) was dissolved in methanol (2.4 mL) and tetrahydrofuran (2.4 mL). 6N Hydrochloric acid (2.4 mL) was added, and the mixture was stirred for 5.5 hr at room temperature, and heated to 60° C. After 1 hr, the mixture was allowed to cool to room temperature, and neutralized with 2N aqueous sodium hydroxide solution. After extraction with ethyl acetate, the organic layer was dried over anhydrous sodium sulfate, filtered, and concentrated. The obtained residue was dissolved in methanol (5 mL) and tetrahydrofuran (4 mL), and 1N sodium hydroxide (1.5 mL) was added. The mixture was heated to 50° C. and, 1 hr later, allowed to cool to room temperature, and neutralized with 1N hydrochloric acid. The mixture was extracted with ethyl acetate-tetrahydrofuran mixed solvent, and the extract was washed with saturated brine, dried over anhydrous sodium sulfate, filtered, and concentrated. The obtained residue was suspension washed with hexane-diethyl ether mixed solvent to give compound 9 (204 mg, 99%).

MS m/z 368 [M−H]−, ESI(−)

Hydrobromide, hydrochloride, para-toluenesulfonate, methanesulfonate, benzenesulfonate, maleate and the like of the present compound can be produced by a general salt formation step.

Example 3

(4-{[5-hydroxy-6-(2-naphthyl)pyridin-2-yl]methyl}-3,5-dimethylphenoxy)acetic acid

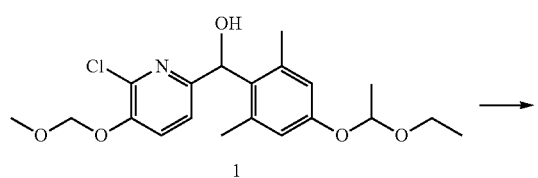

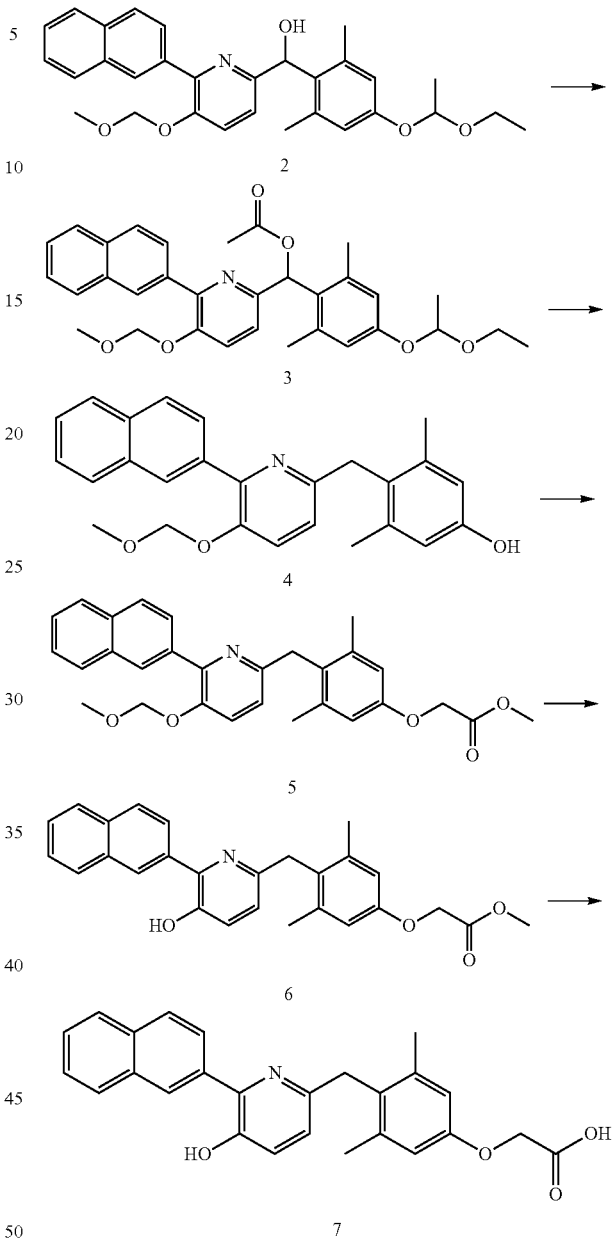

Compound 1 (416 mg, 1.05 mmol) was dissolved in dioxane (7 mL), and water (2 mL), potassium carbonate (435 mg, 3.15 mmol), and 2-naphthaleneboronic acid (271 mg, 1.57 mmol) were added, and the mixture was purged with argon. Tetrakistriphenylphosphinepalladium(0) (36 mg, 0.032 mmol) was added, and the mixture was heated to 90° C. After stirring for 7.5 hr, the mixture was allowed to cool to room temperature. Water was added, and the mixture was extracted with chloroform. The organic layer was dried over anhydrous sodium sulfate, filtered, and concentrated. The residue was purified by silica gel column chromatography to give compound 2 (515 mg, 99%).

MS m/z 488 [M+H]+, APCI(+)

Compound 2 (510 mg, 1.04 mmol) was dissolved in pyridine (0.50 mL), and acetic anhydride (0.29 mL, 3.1 mmol) and dimethylaminopyridine (12.8 mg, 0.105 mmol) were added. After stirring for 3 hr, 0.5N hydrochloric acid was added, and the mixture was extracted with ethyl acetate. The organic layer was washed with saturated aqueous sodium hydrogen carbonate and saturated brine, dried over anhydrous sodium sulfate, filtered, and concentrated. The residue was purified by silica gel column chromatography to give compound 3 (492 mg, 89%).

MS m/z 530 [M+H]+, APCI(+)

Compound 3 (497 mg, 1.01 mmol) was dissolved in methylene chloride (5 mL), triethylsilane (0.17 g, 1.5 mmol) was added, and the mixture was ice-cooled. Boron trifluoride-diethyl ether complex (0.21 mg, 1.5 mmol) was slowly added dropwise. After 20 min, triethylsilane (0.087 g, 0.95 mmol) and boron trifluoride-diethyl ether complex (0.11 g, 0.79 mmol) were slowly added dropwise. After 10 min, triethylsilane (0.17 g, 1.9 mmol) and boron trifluoride-diethyl ether complex (0.22 g, 1.6 mmol) were slowly added dropwise. After stirring for 10 min, water and saturated aqueous sodium hydrogen carbonate were added, and the mixture was extracted with ethyl acetate. The organic layer was washed with saturated brine, dried over anhydrous sodium sulfate, filtered, and concentrated. The residue was purified by silica gel column chromatography to give compound 4 (189 mg, 47%).

MS m/z 400 [M+H]+, APCI(+)

Compound 4 (86.0 mg, 0.215 mmol) was dissolved in acetonitrile (4 mL), and methyl bromoacetate (65.9 mg, 0.431 mmol) and cesium carbonate (280 mg, 0.861 mmol) were added. After stirring for 14 hr, water was added, and the mixture was extracted with chloroform. The organic layer was dried over anhydrous sodium sulfate, filtered, and concentrated. The residue was purified by silica gel column chromatography to give compound 5 (79 mg). To the obtained compound 5 was added 2N hydrogen chloride-methanol solution (2 mL), and the mixture was stirred at room temperature for 5.5 hr. The mixture was heated to 60° C. and, after 1.5 hr, allowed to cool to room temperature, and neutralized with saturated aqueous sodium hydrogen carbonate. The mixture was extracted with ethyl acetate, and the extract was dried over anhydrous sodium sulfate, filtered, and concentrated. The residue was purified by silica gel column chromatography to give compound 6 (57.5 mg, 63%).

MS m/z 428 [M+H]+, APCI(+)

Compound 6 (57 mg, 0.135 mmol) was dissolved in methanol (6 mL), and 1N sodium hydroxide (1 mL) was added. After 12.5 hr, the mixture was heated to 60° C. and, after 1 hr, the mixture was allowed to cool to room temperature, and neutralized with 1N hydrochloric acid. The mixture was extracted with ethyl acetate, and the extract was washed with saturated brine, dried over anhydrous sodium sulfate, filtered, and concentrated. The obtained residue was suspension washed with water and diethyl ether to give compound 7 (41.3 mg, 74%).

MS m/z 412 [M−H]−, ESI(−)

Hydrobromide, hydrochloride, para-toluenesulfonate, methanesulfonate, benzenesulfonate, maleate and the like of the present compound can be produced by a general salt formation step.

Example 4

{4-[(5-hydroxy-6-isopropylpyridin-2-yl)methyl]-2,3,5-trimethylphenoxy}acetic acid

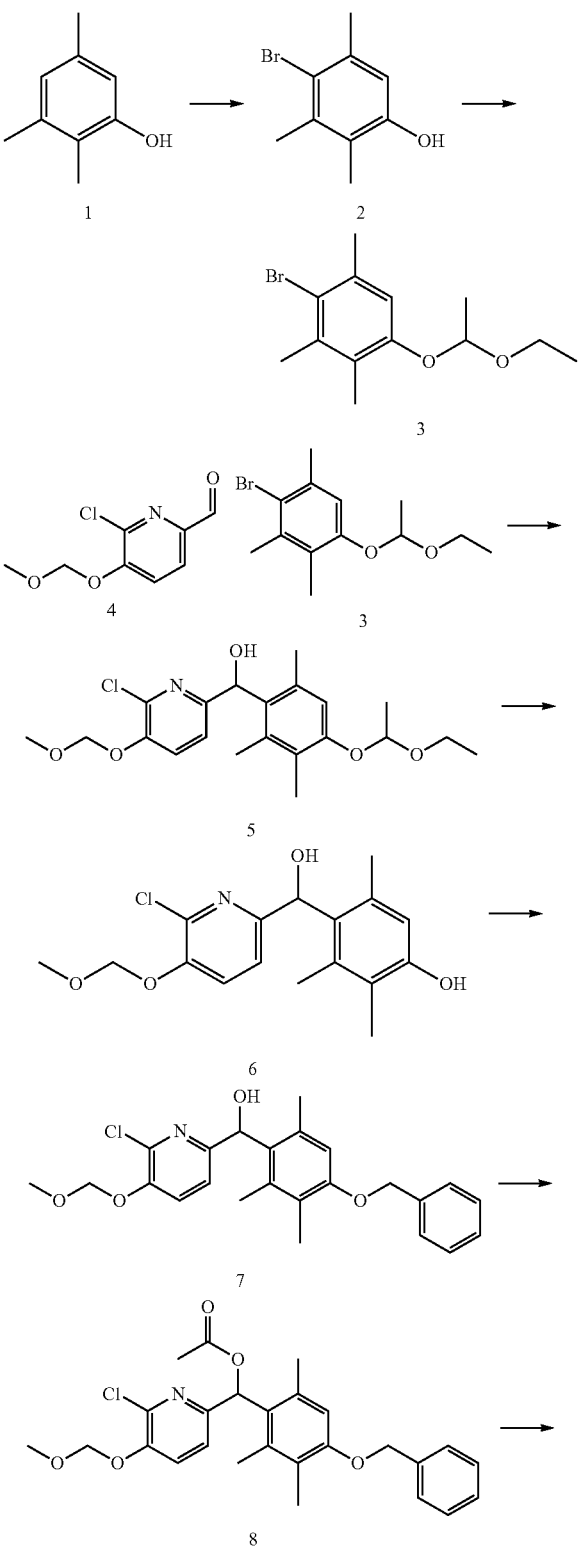

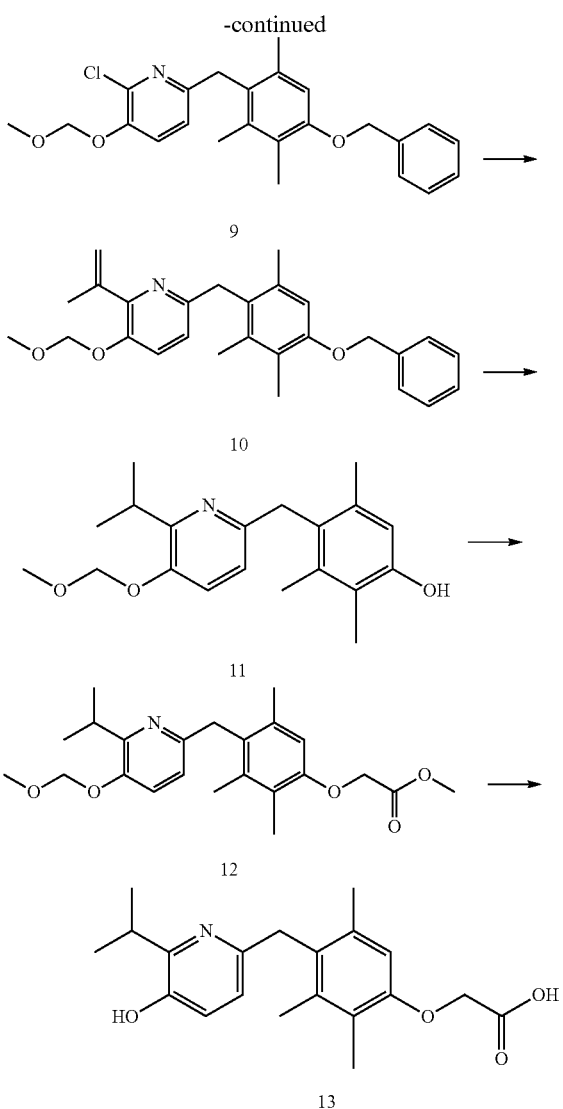

2,3,5-Trimethylphenol (3.23 g, 23.7 mmol) was dissolved in methylene chloride (48 mL) and methanol (32 mL), and tetra-n-butylammonium tribromide (11.5 g, 23.9 mmol) was added. After 20 min, the mixture was concentrated, water was added, and the mixture was extracted with diethyl ether. The organic layer was washed with saturated brine, dried over anhydrous magnesium sulfate, filtered and concentrated. The residue was washed with hexane to give compound 2 (4.87 g, 95%).

MS m/z 213/215 [M−H]−, ESI(−)

Compound 2 (4.87 g, 22.6 mmol) was dissolved in methylene chloride (48 mL), and ethyl vinyl ether (8.16 g, 113 mmol) and pyridinium p-toluenesulfonate (569 mg, 2.26 mmol) were added. After 4 hr, triethylamine (11.4 g, 113 mmol) was added, and the mixture was concentrated. The residue was purified by silica gel column chromatography to give compound 3 (6.43 g, 20 99%).

MS m/z 304/306 [M+NR$_4$]+, APCI(+)

Compound 3 (3.39 g, 11.8 mmol) was dissolved in tetrahydrofuran (15 mL), and the mixture was cooled to −78° C. n-Butyllithium (1.6 M hexane solution, 8.0 mL, 12.8 mmol) was slowly added dropwise, and the mixture was stirred for 1 hr. Compound 4 (CAS No. 939430-71-4, 2.07 g, 10.2 mmol) was dissolved in tetrahydrofuran (16 mL), and the mixture was cooled to −78° C. The lithium reagent prepared earlier was added dropwise over 30 min, and the mixture was stirred for 45 min and heated to room temperature. After 1 hr, water was added, and the mixture was extracted with ethyl acetate. The organic layer was washed with saturated brine, dried over anhydrous sodium sulfate, filtered and concentrated. The residue was purified by silica gel column chromatography to give compound 5 (1.73 g, 41%).

MS m/z 410/412 [M+H]+, APCI(+)

Compound 5 (2.02 g, 4.94 mmol) was dissolved in ethanol (20 mL), and acetic acid (4 mL) was added. After stirring at room temperature for one day, the mixture was stirred at 60° C. for 1 hr, and allowed to cool to room temperature. After concentration, the residue was purified by silica gel column chromatography to give compound 6 (1.19 g, 71%).

MS m/z 338/340 [M+H]+, APCI(+)

Compound 6 (1.19 g, 3.52 mmol) was dissolved in acetonitrile (23 mL), and benzyl bromide (663 mg, 3.87 mmol) and cesium carbonate (3.44 g, 10.5 mmol) were added. After stirring at room temperature for 2.5 hr, water was added, and the mixture was extracted with ethyl acetate. The organic layer was washed with saturated brine, dried over anhydrous magnesium sulfate, filtered and concentrated. The residue was purified by silica gel column chromatography to give compound 7 (1.39 g, 93%).

MS m/z 428/430 [M+H]+, APCI(+)

To compound 7 (1.39 g, 3.25 mmol) were added pyridine (1.05 mL), acetic anhydride (0.613 mL), and dimethylaminopyridine (39.7 mg). After 15 hr, water and 1N hydrochloric acid were added, and the mixture was extracted with ethyl acetate. The organic layer was dried over anhydrous magnesium sulfate, filtered and concentrated. The residue was purified by silica gel column chromatography to give compound 8 (1.40 g, 92%).

MS m/z 442/444 [M−CH$_3$COC+CH$_3$OH]+, APCI(+)

Compound 8 (1.40 g, 2.99 mmol) was dissolved in methylene chloride (28 mL), and triethylsilane (0.521 g, 4.48 mmol) was added. Boron trifluoride-diethyl ether complex (0.636 g, 4.48 mmol) was added at 0° C. After 10 min, saturated aqueous sodium hydrogen carbonate was added, and the mixture was extracted with chloroform. The organic layer was dried over anhydrous magnesium sulfate, filtered and concentrated. The residue was purified by silica gel column chromatography to give compound 9 (996 mg, 81%).

MS m/z 412/414 [M+H]+, APCI(+)

Compound 9 (505 mg, 1.23 mmol) was dissolved in dimethoxyethane (12 mL), and water (1.2 mL), cesium carbonate (1.20 g, 3.68 mmol), and isopropenylboronic acid pinacol ester (515 mg, 3.06 mmol) were added, and the mixture was purged with argon. Tetrakistriphenylphosphine-palladium(0) (142 mg, 0.123 mmol) was added, and the mixture was heated to 90° C. After stirring for 17 hr, the mixture was allowed to cool to room temperature. Water was added, and the mixture was extracted with ethyl acetate. The organic layer was washed with saturated brine, dried over anhydrous magnesium sulfate, filtered and concentrated. The residue was purified by silica gel column chromatography to give compound 10 (503 mg, 98%).

MS m/z 418 [M+H]+, APCI(+)

Compound 10 (500 mg, 1.20 mmol) was dissolved in tetrahydrofuran (12 ml) and, after purging with argon, 10% Pd/C (255 mg) was added. After purging with hydrogen, the mixture was stirred for 8 hr, filtered through celite and thoroughly washed with ethyl acetate. The filtrate was concentrated, and the obtained residue was dissolved in tetrahydrofuran (12 mL). After purging with argon, 10% Pd/C (255 mg)

was added. After purging with hydrogen, the mixture was stirred for 17 hr, filtered through celite and thoroughly washed with ethyl acetate. The filtrate was concentrated and the obtained residue was dissolved in tetrahydrofuran (12 mL) and, after purging with argon, 10% Pd/C (255 mg) was added. After purging with hydrogen, the mixture was stirred for 5 hr, filtered through celite and thoroughly washed with ethyl acetate. The filtrate was concentrated, and the residue was purified by silica gel column chromatography to give compound 11 (375 mg, 95%).

MS m/z 330 [M+H]+, APCI(+)

Compound 11 (157 mg, 0.477 mmol) was dissolved in acetonitrile (5 ml), and methyl bromoacetate (109 mg, 0.715 mmol) and cesium carbonate (465 mg, 1.43 mmol) were added. After stirring for 20 hr, water was added, and the mixture was extracted with ethyl acetate. The organic layer was washed with saturated brine, dried over anhydrous magnesium sulfate, filtered and concentrated. The residue was purified by silica gel column chromatography to give compound 12 (180 mg, 94%).

MS m/z 402 [M+H]+, APCI(+)

Compound 12 (178 mg, 0.443 mmol) was dissolved in methanol (2.5 mL) and tetrahydrofuran (2.5 mL). 6N Hydrochloric acid (2.5 mL) was added, and the mixture was stirred for 20 hr at room temperature, and heated to 60° C. After 2 hr, the mixture was allowed to cool to room temperature, and neutralized with 2N aqueous sodium hydroxide solution. After extraction with ethyl acetate, the organic layer was washed with saturated brine, dried over anhydrous magnesium sulfate, filtered and concentrated. The obtained residue was dissolved in methanol (5 mL), and 2N sodium hydroxide (0.67 mL) was added and the mixture was heated at 60° C. After 2.5 hr, the mixture was allowed to cool to room temperature, neutralized with 2N hydrochloric acid, and extracted with ethyl acetate-tetrahydrofuran mixed solvent. The extract was dried over anhydrous magnesium sulfate, filtered and concentrated. The obtained residue was suspension washed with hexane-diethyl ether mixed solvent to give compound 13 (145 mg, 95%).

MS m/z 342 [M−H]−, ESI(−)

Hydrobromide, hydrochloride, para-toluenesulfonate, methanesulfonate, benzenesulfonate, maleate and the like of the present compound can be produced by a general salt formation step.

Example 5

{4-[(6-cyclopentyl-5-hydroxypyridin-2-yl)methyl]-2,3,5-trimethylphenoxy}acetic acid

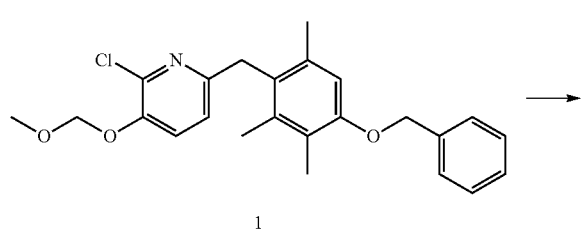

Compound 1 (539 mg, 1.31 mmol) was dissolved in 1,4-dioxane (8 mL), and water (2 mL), potassium carbonate (543 mg, 3.93 mmol), and 1-cyclopenteneboronic acid (220 mg, 1.96 mmol) were added, and the mixture was purged with argon. Tetrakistriphenylphosphinepalladium(0) (45 mg, 0.039 mmol) was added, and the mixture was heated to 90° C. After stirring for 4 hr, the mixture was allowed to cool to room temperature. Water was added, and the mixture was extracted with ethyl acetate. The organic layer was washed with saturated brine, dried over anhydrous magnesium sulfate, filtered and concentrated. The residue was purified by silica gel column chromatography to give compound 2 (449 mg, 77%).

MS m/z 444 [M+H]+, APCI(+)

Compound 2 (446 mg, 1.01 mmol) was dissolved in tetrahydrofuran (10 mL) and, after purging with argon, 10% Pd/C (214 mg) was added. After purging with hydrogen, the mixture was stirred for 7 hr, filtered through celite and thoroughly washed with ethyl acetate. The filtrate was concentrated, and the residue was purified by silica gel column chromatography to give compound 3 (349 mg, 98%).

MS m/z 356 [M+H]+, APCI(+)

Compound 3 (140 mg, 0.394 mmol) was dissolved in acetonitrile (4 mL), and methyl bromoacetate (90 mg, 0.591 mmol) and cesium carbonate (385 mg, 1.18 mmol) were added. After stirring for 20 hr, water was added, and the mixture was extracted with ethyl acetate. The organic layer was washed with saturated brine, dried over anhydrous magnesium sulfate, filtered and concentrated. The residue was purified by silica gel column chromatography to give compound 4 (155 mg, 92%).

MS m/z 428 [M+H]+, APCI(+)

Compound 4 (153 mg, 0.358 mmol) was dissolved in methanol (2 mL) and tetrahydrofuran (2 mL). 6N Hydrochloric acid (2 mL) was added, and the mixture was stirred for 18 hr at room temperature stirred, and heated to 60° C. After 2 hr, the mixture was allowed to cool to room temperature, and neutralized with 2N aqueous sodium hydroxide solution. After extraction with ethyl acetate, the organic layer was washed with saturated brine, dried over anhydrous magnesium sulfate, filtered and concentrated. The obtained residue was dissolved in methanol (4 mL), 2N sodium hydroxide (0.5 mL) was added and the mixture was heated to 60° C. After 2.5 hr, the mixture was allowed to cool to room temperature, and neutralized with 2N hydrochloric acid. Water and saturated brine were added, and the mixture was extracted with ethyl acetate-tetrahydrofuran mixed solvent. The extract was dried over anhydrous magnesium sulfate, filtered and concentrated. The obtained residue was suspension washed with hexane-diethyl ether mixed solvent to give compound 5 (132 mg, 100%).

MS m/z 368 [M–H]–, ESI(–)

Hydrobromide, hydrochloride, para-toluenesulfonate, methanesulfonate, benzenesulfonate, maleate and the like of the present compound can be produced by a general salt formation step.

Example 6

(4-{[5-hydroxy-6-(tetrahydrofuran-2-yl)pyridin-2-yl]methyl}-2,3,5-trimethylphenoxy)acetic acid

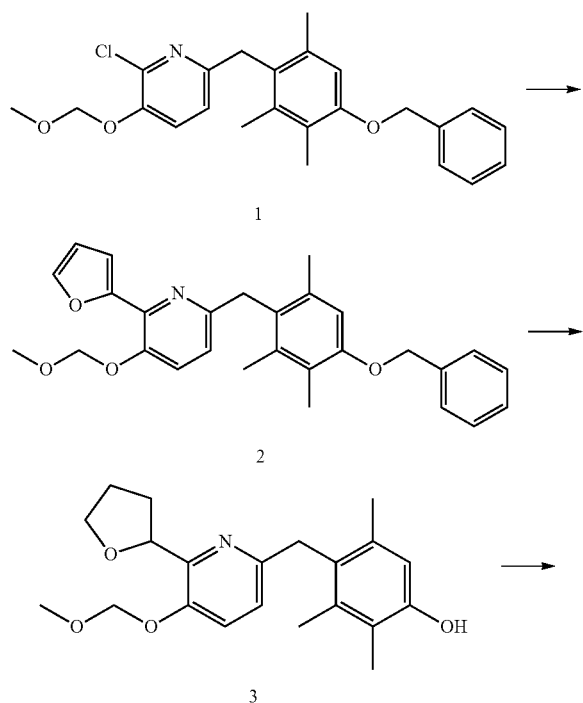

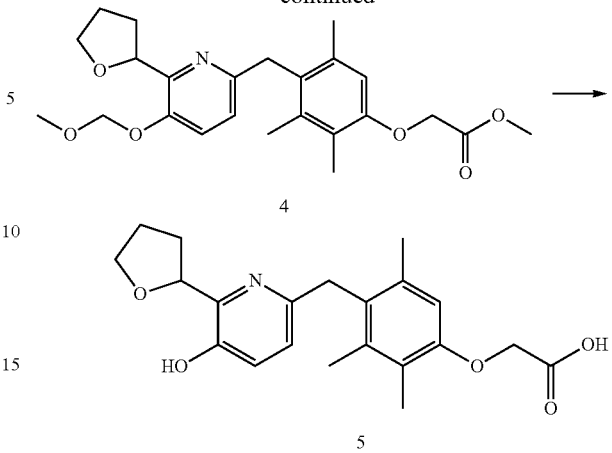

Compound 1 (522 mg, 1.27 mmol) was dissolved in 1,4-dioxane (8 mL), and water (2 mL), potassium carbonate (525 mg, 3.80 mmol), and 2-furanboronic acid (213 mg, 1.90 mmol) were added, and the mixture was purged with argon. Tetrakistriphenylphosphinepalladium(0) (44 mg, 0.038 mmol) was added, and the mixture was heated to 90° C. After stirring for 2.5 hr, the mixture was allowed to cool to room temperature. Water was added, and the mixture was extracted with ethyl acetate. The organic layer was washed with saturated brine, dried over anhydrous magnesium sulfate, filtered and concentrated. The residue was purified by silica gel column chromatography to give compound 2 (441 mg, 78%).

MS m/z 444 [M+H]+, APCI(+)

Compound 2 (330 mg, 0.744 mmol) was dissolved in tetrahydrofuran (10 mL) and, after purging with argon, 10% Pd/C (158 mg) was added. After purging with hydrogen, the mixture was stirred for 19 hr, filtered through celite and thoroughly washed with ethyl acetate. The filtrate was concentrated, and the residue was purified by silica gel column chromatography to give compound 3 (238 mg, 89%).

MS m/z 358 [M+H]+, APCI(+)

Compound 3 (124 mg, 0.347 mmol) was dissolved in acetonitrile (4 mL), and methyl bromoacetate (80 mg, 0.520 mmol) and cesium carbonate (339 mg, 1.04 mmol) were added. After stirring for 5 hr, water was added, and the mixture was extracted with ethyl acetate. The organic layer was washed with saturated brine, dried over anhydrous magnesium sulfate, filtered and concentrated. The residue was purified by silica gel column chromatography to give compound 4 (139 mg, 93%).

MS m/z 430 [M+H]+, APCI(+)

Compound 4 (116 mg, 0.270 mmol) was dissolved in methanol (1.5 mL) and tetrahydrofuran (1.5 mL). 6N Hydrochloric acid (1.5 mL) was added, and the mixture was heated to 40° C. After stirring for 2.5 hr, the mixture was stirred for 16 hr at room temperature, and heated again to 40° C. After 3 hr, the mixture was allowed to cool to room temperature, and neutralized with 2N aqueous sodium hydroxide solution. After extraction with ethyl acetate, the organic layer was washed with saturated brine, dried over anhydrous magnesium sulfate, filtered and concentrated. The obtained residue was dissolved in methanol (3 mL), and 2N sodium hydroxide (0.4 mL) was added. The mixture was heated to 40° C. and, after 5 hr, allowed to cool to room temperature, and neutralized with 1N hydrochloric acid. Water and saturated brine were added, and the mixture was extracted with ethyl acetate-tetrahydrofuran mixed solvent. The extract was dried over anhydrous magnesium sulfate, filtered and concentrated. The obtained residue was suspension washed with hexane-diethyl ether mixed solvent to give compound 5 (73 mg, 73%).

MS m/z 370 [M–H]–, ESI(–)

Hydrobromide, hydrochloride, para-toluenesulfonate, methanesulfonate, benzenesulfonate, maleate and the like of the present compound can be produced by a general salt formation step.

Example 7

{4-[(6-cyclohexyl-5-hydroxypyridin-2-yl)methyl]-2,3,5-trimethylphenoxy}acetic acid

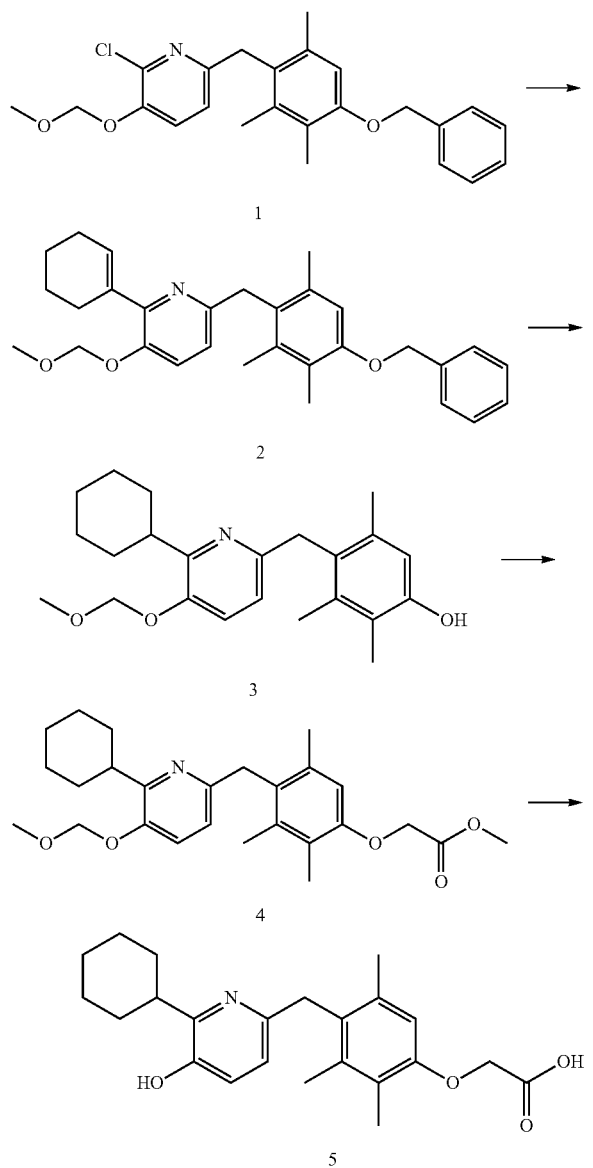

Compound 1 (313 mg, 0.762 mmol) was dissolved in dimethoxyethane (6 mL), and cesium carbonate (744 mg, 2.28 mmol), cyclohexenylboronic acid pinacol ester (396 mg, 1.90 mmol) were added, and the mixture was purged with argon. Tetrakistriphenylphosphinepalladium(0) (44.0 mg, 0.0380 mmol) was added, and the mixture was heated to 90° C. After stirring for 7 hr, the mixture was allowed to cool to room temperature. Water was added, and the mixture was extracted with ethyl acetate. The organic layer was washed with saturated brine, dried over anhydrous sodium sulfate, filtered, and concentrated. The residue was purified by silica gel column chromatography to give compound 2 (331 mg, 95%).

MS m/z 474 [M+NH$_4$]+, APCI(+)

Compound 2 (331 mg, 0.725 mmol) was dissolved in ethanol (10 mL) and, after purging with argon, 10% Pd/C (165 mg) was added. After purging with hydrogen, the mixture was stirred for 7 hr, filtered through radiolite, and washed with ethyl acetate. The filtrate was concentrated to give compound 3.

MS m/z 370 [M+H]+, APCI(+)

Compound 3 was dissolved in acetonitrile (3 mL), and methyl bromoacetate (94.4 mg, 0.617 mmol) and cesium carbonate (402 mg, 1.23 mmol) were added. After stirring for 30 min, water was added, and the mixture was extracted with ethyl acetate. The organic layer was washed with saturated brine, dried over anhydrous magnesium sulfate, filtered and concentrated. The residue was purified by silica gel column chromatography to give compound 4 (134 mg, 76%).

MS m/z 442 [M+H]+, APCI(+)

Compound 4 (131 mg, 0.297 mmol) was dissolved in methanol (1 mL) and tetrahydrofuran (1 mL). 6N Hydrochloric acid (1 mL) was added, and the mixture was stirred for 15 hr at room temperature. The mixture was heated to 60° C. and, after 1 hr, allowed to cool to room temperature, and neutralized with 2N aqueous sodium hydroxide solution. After extraction with ethyl acetate, the organic layer was washed with saturated brine, dried over anhydrous sodium sulfate, and concentrated. The obtained residue was dissolved in methanol (5 mL), and 2N sodium hydroxide (0.5 mL) was added. The mixture was heated to 60° C. and, after 2 hr, allowed to cool to room temperature, and neutralized with 2N hydrochloric acid. The mixture was extracted with ethyl acetate-tetrahydrofuran mixed solvent, and the extract was dried over anhydrous sodium sulfate, filtered, and concentrated. The obtained residue was washed with diethyl ether to give compound 5 (85.1 mg, 75%).

MS m/z 382 [M–H]–, ESI(–)

Hydrobromide, hydrochloride, para-toluenesulfonate, methanesulfonate, benzenesulfonate, maleate and the like of the present compound can be produced by a general salt formation step.

Example 8

(4-{[5-hydroxy-6-(tetrahydro-2H-pyran-2-yl)pyridin-2-yl]methyl}-2,3,5-trimethylphenoxy)acetic acid

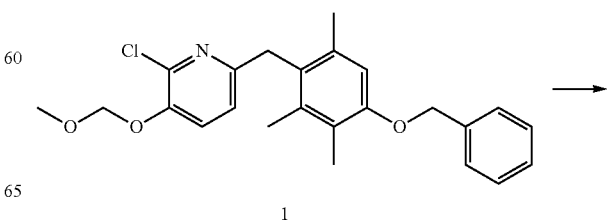

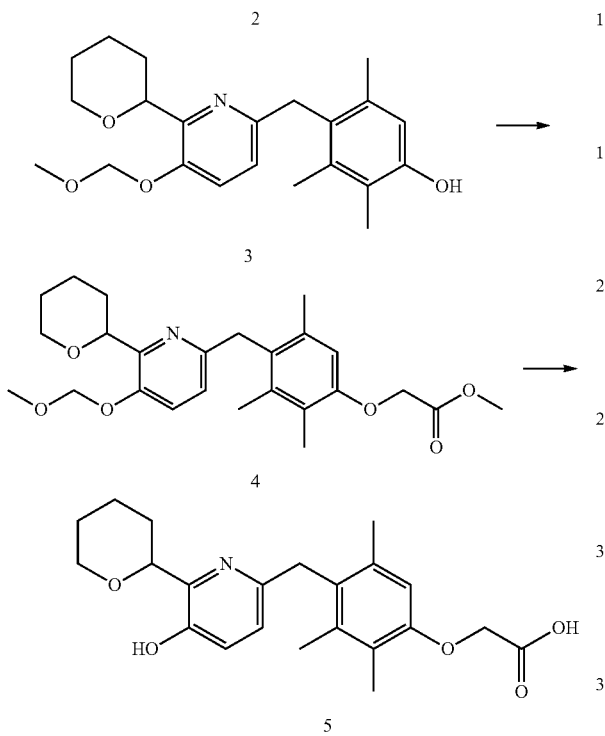

Compound 1 (564 mg, 1.37 mmol) was dissolved in dimethoxyethane (14 mL), and water (1.4 mL), cesium carbonate (1.34 g, 4.11 mmol), and dihydropyranylboronic acid pinacol ester (719 mg, 3.42 mmol) were added, and the mixture was purged with argon. Tetrakistriphenylphosphinepalladium(0) (158 mg, 0.137 mmol) was added, and the mixture was heated to 90° C. After stirring for 5.5 hr, the mixture was allowed to cool to room temperature. Water was added, and the mixture was extracted with ethyl acetate. The organic layer was washed with saturated brine, dried over anhydrous magnesium sulfate, filtered and concentrated. The residue was purified by silica gel column chromatography to give compound 2 (375 mg, 60%).

MS m/z 460 [M+H]+, APCI(+)

Compound 2 (372 mg, 0.809 mmol) was dissolved in tetrahydrofuran (8 mL) and, after purging with argon, 10% Pd/C (172 mg) was added. After purging with hydrogen, the mixture was stirred for 7 hr, filtered through celite and thoroughly washed with ethyl acetate. The filtrate was concentrated, and the obtained residue was dissolved in tetrahydrofuran (8 mL). After purging with argon, 10% Pd/C (172 mg) was added. After purging with hydrogen, the mixture was stirred for 15 hr, filtered through celite and thoroughly washed with ethyl acetate. The filtrate was concentrated, and the residue was purified by silica gel column chromatography to give compound 3 (254 mg, 84%).

MS m/z 372 [M+H]+, APCI(+)

Compound 3 (104 mg, 0.280 mmol) was dissolved in acetonitrile (3 mL), and methyl bromoacetate (64 mg, 0.420 mmol) and cesium carbonate (274 mg, 0.840 mmol) were added. After stirring for 20 hr, water was added, and the mixture was extracted with ethyl acetate. The organic layer was washed with saturated brine, dried over anhydrous magnesium sulfate, filtered and concentrated. The residue was purified by silica gel column chromatography to give compound 4 (125 mg, 100%).

MS m/z 444 [M+H]+, APCI(+)

Compound 4 (123 mg, 0.277 mmol) was dissolved in methanol (1.5 mL) and tetrahydrofuran (1.5 mL). 6N Hydrochloric acid (1.5 mL) was added, and the mixture was heated to 40° C. After stirring for 2.5 hr, the mixture was stirred for 16 hr at room temperature, and heated again to 40° C. After 3 hr, the mixture was allowed to cool to room temperature, and neutralized with 2N aqueous sodium hydroxide solution. After extraction with ethyl acetate, the organic layer was washed with saturated brine, dried over anhydrous magnesium sulfate, filtered and concentrated. The obtained residue was dissolved in methanol (3 mL), and 2N sodium hydroxide (0.4 mL) was added. The mixture was heated to 40° C. and, after 5 hr, allowed to cool to room temperature, and neutralized with 1N hydrochloric acid. Water and saturated brine were added, and the mixture was extracted with ethyl acetate-tetrahydrofuran mixed solvent. The extract was dried over anhydrous magnesium sulfate, filtered and concentrated. The obtained residue was suspension washed with hexane-diethyl ether mixed solvent to give compound 5 (106 mg, 99%).

MS m/z 384 [M−H]−, ESI(−)

Hydrobromide, hydrochloride, para-toluenesulfonate, methanesulfonate, benzenesulfonate, maleate and the like of the present compound can be produced by a general salt formation step.

Example 9

{4-[(5-hydroxy-6-isopropylpyridin-2-yl)oxy]-2,3,5-trimethylphenoxy}acetic acid

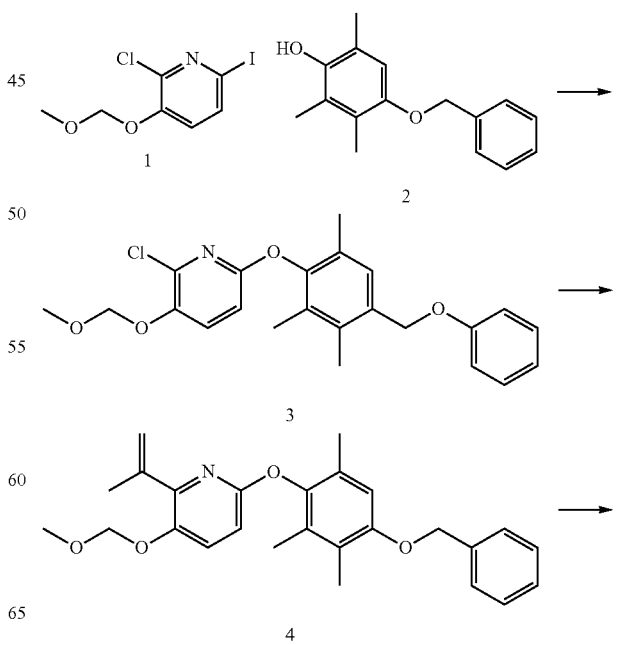

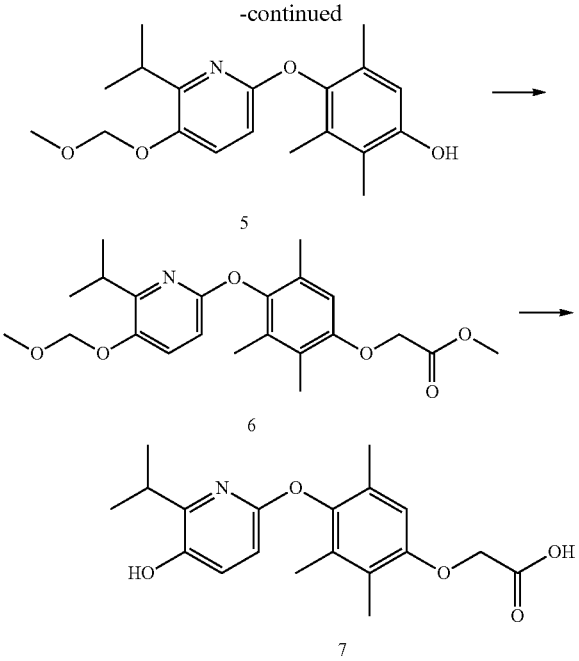

Compound 1 (CAS No. 199168-10-0, 3.41 g, 11.4 mmol) and compound 2 (CAS No. 36592-80-0, 2.76 g, 11.4 mmol) were dissolved in dimethylsulfoxide (17 mL). Potassium carbonate (3.15 g, 22.8 mmol) was added, and the mixture was purged with argon. Copper iodide (1.08 g, 5.7 mmol) was added, and the mixture was heated to 90° C. After 1 day, the mixture was allowed to cool to room temperature, and water and ethyl acetate were added. Ammonium chloride was added, and the mixture was thoroughly stirred, filtered through radiolite, and extracted with ethyl acetate. The extract was washed with saturated brine, dried over anhydrous sodium sulfate, filtered, and concentrated. The residue was purified by silica gel column chromatography to give compound 3 (3.23 g, 68%).

MS m/z 414/416 [M+H]+, APCI(+)

Compound 3 (1.14 g, 2.76 mmol) was dissolved in dimethoxyethane (11 mL), and water (1 mL), cesium carbonate (2.70 g, 8.29 mmol) and isopropenylboronic acid pinacol ester (1.16 g, 6.91 mmol) were added, and the mixture was purged with argon. Tetrakistriphenylphosphinepalladium(0) (95.9 mg, 0.0829 mmol) was added, and the mixture was heated under reflux. After 21.5 hr, the mixture was allowed to cool to room temperature. Water was added, and the mixture was extracted with ethyl acetate. The organic layer was washed with saturated brine, dried over anhydrous sodium sulfate, filtered, and concentrated. The residue was purified by silica gel column chromatography to give compound 4 (616 mg, 53%).

MS m/z 420 [M+H]+, APCI(+)

Compound 4 (370 mg, 0.913 mmol) was dissolved in ethanol (4 mL) and, after purging with argon, 10% Pd/C (185 mg) was added. After purging with hydrogen, the mixture was stirred for 17.5 hr, filtered through radiolite, and thoroughly washed with ethyl acetate. The filtrate was concentrated to give compound 5. The obtained compound 5 was dissolved in acetonitrile (6 mL), and methyl bromoacetate (209 mg, 1.36 mmol) and cesium carbonate (890 mg, 2.73 mmol) were added. After stirring for 15.5 hr, water was added, and the mixture was extracted with chloroform. The organic layer was dried over anhydrous magnesium sulfate, filtered, and concentrated. The residue was purified by silica gel column chromatography to give compound 6 (292 mg, 79%).

MS m/z 404 [M+H]+, APCI(+)

Compound 6 (290 mg, 0.719 mmol) was dissolved in methanol (3 mL) and tetrahydrofuran (3 mL). 6N Hydrochloric acid (3 mL) was added and, after 1 day, 4N aqueous sodium hydroxide solution (5 mL) was added, and the mixture was heated to 60° C. After 6 hr, the mixture was allowed to cool to room temperature, and neutralized with 2N hydrochloric acid. The mixture was extracted with ethyl acetate, and the extract was dried over anhydrous sodium sulfate, filtered, and concentrated. The obtained residue was washed with diethyl ether. The obtained residue was dissolved in methanol (3 mL) and tetrahydrofuran (3 mL) and 6N hydrochloric acid (3 mL) was added. The mixture was heated to 60° C. and, after 2 hr, allowed to cool to room temperature, and neutralized with 4N aqueous sodium hydroxide solution. The mixture was extracted with ethyl acetate, and the extract was washed with saturated brine, dried over anhydrous sodium sulfate, filtered, and concentrated. The obtained residue was washed with diethyl ether to give compound 7 (180 mg, 73%).

MS m/z 344 [M−H]−, ESI(−)

Hydrobromide, hydrochloride, para-toluenesulfonate, methanesulfonate, benzenesulfonate, maleate and the like of the present compound can be produced by a general salt formation step.

Example 10

{4-[(6-cyclohexyl-5-hydroxypyridin-2-yl)oxy]-2,3,5-trimethylphenoxy}acetic acid

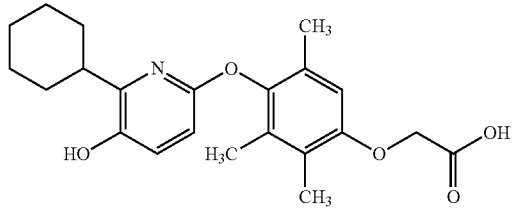 [SMILES: Cc1cc(OCC(=O)O)c(C)c(C)c1Oc1ccc(O)c(C2CCCCC2)n1]

The compound was synthesized by a method similar to that in Example 9.

MS m/z 384 [M−H]−, ESI(−)

Hydrobromide, hydrochloride, para-toluenesulfonate, methanesulfonate, benzenesulfonate, maleate and the like of the present compound can be produced by a general salt formation step.

Example 11

{2-fluoro-4-[(5-hydroxy-6-isopropylpyridin-2-yl)methyl]-3,5-dimethylphenoxy}acetic acid

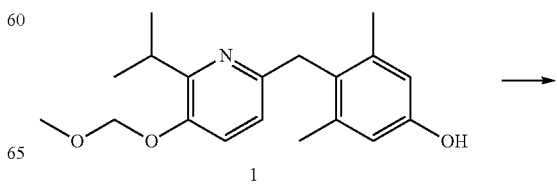

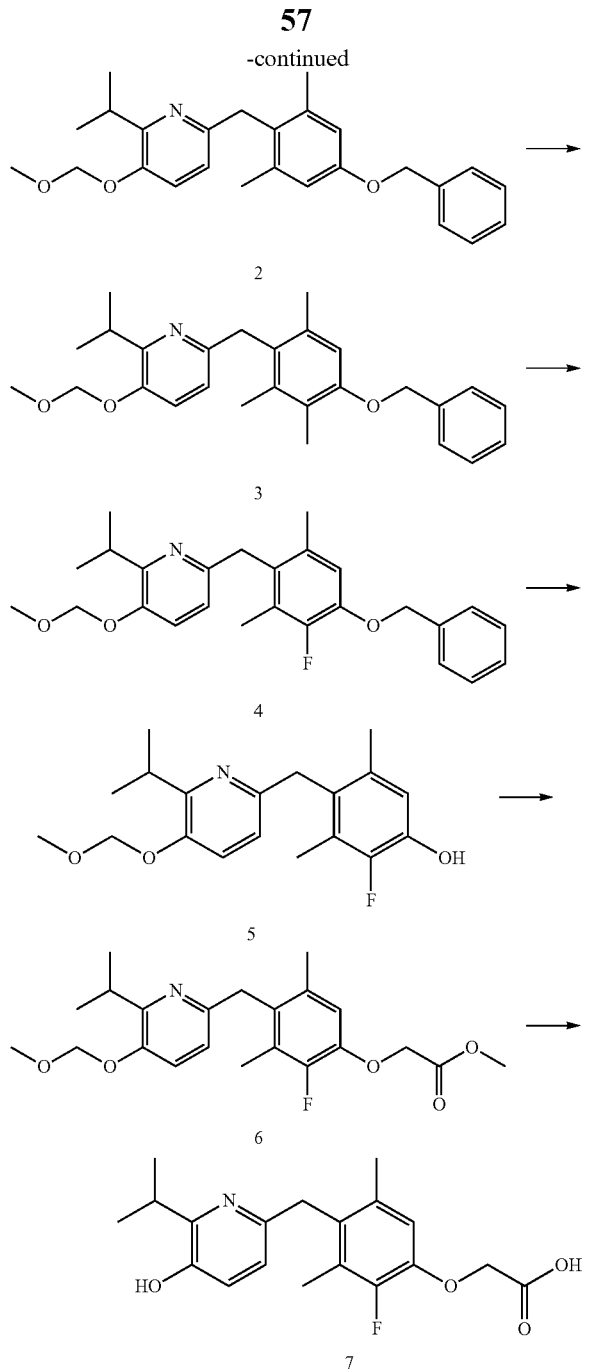

Compound 1 (500 mg, 1.59 mmol) was dissolved in acetonitrile (10 mL), and benzyl bromide (299 mg, 1.75 mmol) and cesium carbonate (777 mg, 2.38 mmol) were added. After stirring for 2 hr, the mixture was filtered and concentrated. The residue was purified by silica gel column chromatography to give compound 2 (642 mg, 100%).

MS m/z 406 [M+H]+, APCI(+)

Compound 2 (300 mg, 0.740 mmol), silver acetate (207 mg, 0.815 mmol) and iodine (207 mg, 0.816 mmol) were dissolved in methylene chloride (6 mL). Under light shielding conditions at room temperature, the mixture was stirred for 3 hr, silver acetate (25 mg, 0.150 mmol) and iodine (38 mg, 0.150 mmol) were added, and the mixture was stirred under light shielding conditions again for 2 hr at room temperature. The mixture was filtered, chloroform was added, and the mixture was washed successively with saturated aqueous sodium thiosulfate solution, saturated aqueous sodium hydrogen carbonate, water and saturated brine, dried over anhydrous magnesium sulfate, filtered and concentrated. The residue was purified by silica gel column chromatography to give compound 3 (355 mg, 90%).

MS m/z 532 [M+H]+, APCI(+)

Compound 3 (354 mg, 0.666 mmol) and N-fluorobenzenesulfonimide (845 mg, 2.68 mmol) were dissolved in tetrahydrofuran (7 mL), and the mixture was cooled to −78° C. n-Butyllithium (1.59 M hexane solution, 1.7 ml, 2.70 mmol) was slowly added dropwise, and the mixture was stirred for 1 hr. Saturated aqueous ammonium chloride solution was added at −78° C., and the mixture was heated to room temperature. The mixture was extracted with ethyl acetate, and the extract was washed with water and saturated brine, dried over anhydrous magnesium sulfate, filtered, and concentrated. The residue was purified by silica gel column chromatography to give compound 4 (158 mg, 56%).

MS m/z 424 [M+H]+, APCI(+)

Compound 4 (158 mg, 0.374 mmol) was dissolved in ethanol (10 mL) and, after purging with argon, 5% Pd/C (100 mg) was added. After purging with hydrogen, the mixture was stirred for 8 hr, filtered through radiolite, and thoroughly washed with ethyl acetate. The filtrate was concentrated to give 5. The obtained compound 5 was dissolved in acetonitrile (4 mL), and methyl bromoacetate (100 mg, 0.977 mmol) and cesium carbonate (210 mg, 0.645 mmol) were added. After stirring for 3 hr, water was added, and the mixture was extracted with ethyl acetate and washed with saturated brine. The organic layer was dried over anhydrous magnesium sulfate, filtered, and concentrated. The residue was purified by silica gel column chromatography to give compound 6 (122 mg, 80%).

MS m/z 406 [M+H]+, APCI(+)

Compound 6 (122 mg, 0.300 mmol) was dissolved in methanol (1.4 mL) and tetrahydrofuran (1.4 mL). 6N Hydrochloric acid (1.4 mL) was added, and the mixture was stirred at 50° C. for 1 hr. The mixture was allowed to cool to room temperature, and neutralized with 1N aqueous sodium hydroxide solution. After extraction with ethyl acetate, the organic layer was washed with saturated brine, dried over anhydrous magnesium sulfate, filtered and concentrated. The obtained residue was dissolved in methanol (1.4 mL) and tetrahydrofuran (1.4 mL), and 1N sodium hydroxide (1.4 mL) was added, and the mixture was stirred at 50° C. for 1 hr. The mixture was allowed to cool to room temperature, neutralized with 1N hydrochloric acid, and extracted with ethyl acetate-tetrahydrofuran mixed solvent. The extract was dried over anhydrous magnesium sulfate, filtered and concentrated. The obtained residue was recrystallized from methanol to give compound 7 (51 mg, 42%).

MS m/z 346 [M−H]−, ESI(−)

Hydrobromide, hydrochloride, para-toluenesulfonate, methanesulfonate, benzenesulfonate, maleate and the like of the present compound can be produced by a general salt formation step.

Example 12

{4-[(6-cyclohexyl-5-hydroxypyridin-2-yl)methyl]-2-fluoro-3,5-dimethylphenoxy}acetic acid

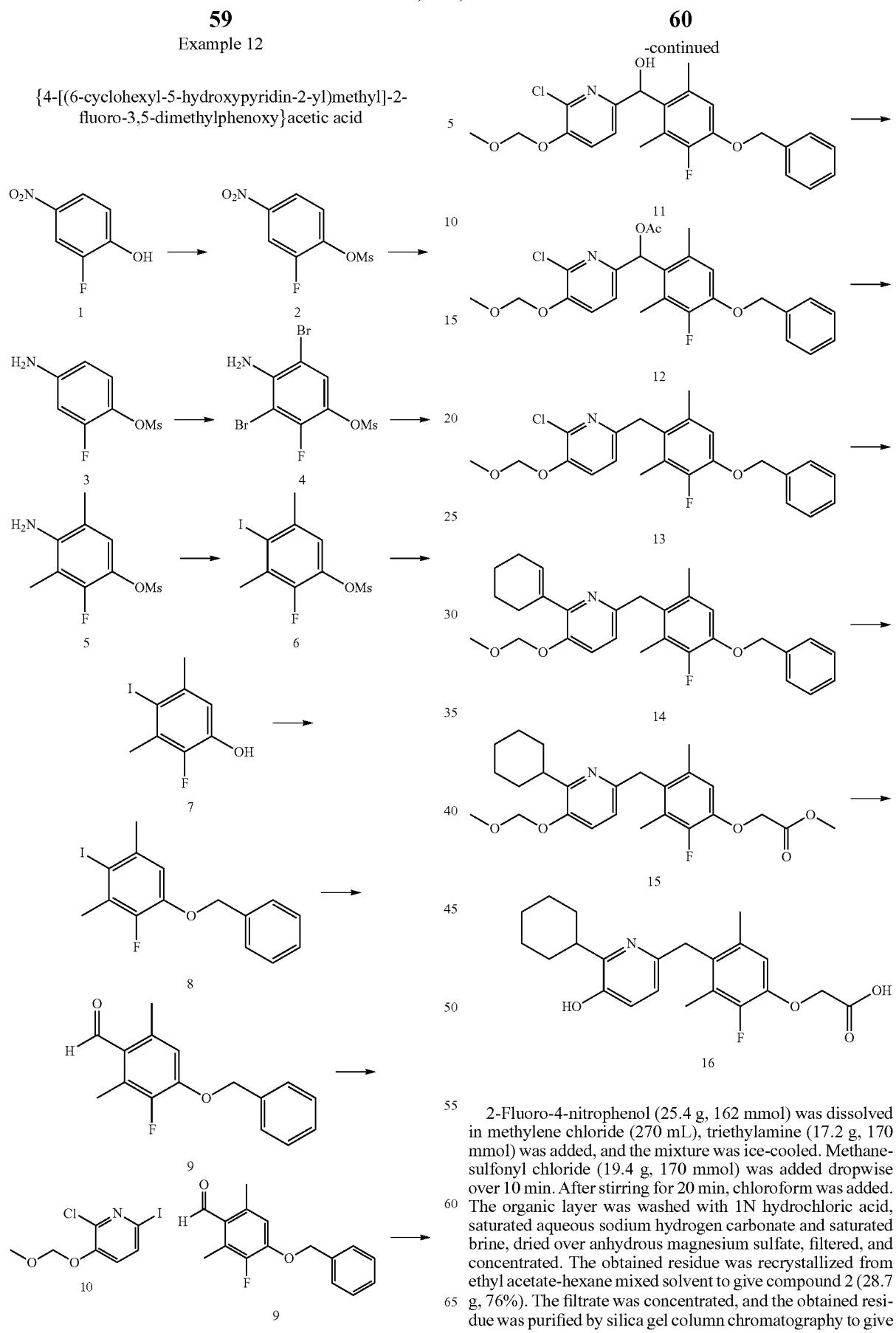

2-Fluoro-4-nitrophenol (25.4 g, 162 mmol) was dissolved in methylene chloride (270 mL), triethylamine (17.2 g, 170 mmol) was added, and the mixture was ice-cooled. Methanesulfonyl chloride (19.4 g, 170 mmol) was added dropwise over 10 min. After stirring for 20 min, chloroform was added. The organic layer was washed with 1N hydrochloric acid, saturated aqueous sodium hydrogen carbonate and saturated brine, dried over anhydrous magnesium sulfate, filtered, and concentrated. The obtained residue was recrystallized from ethyl acetate-hexane mixed solvent to give compound 2 (28.7 g, 76%). The filtrate was concentrated, and the obtained residue was purified by silica gel column chromatography to give compound 2 (8.80 g, 23%).

MS m/z 253 [M+NH$_4$]+, APCI(+)

Compound 2 (33.2 g, 141 mmol) was dissolved in methylene chloride (280 mL), zinc powder (92.3 g, 1.41 mol) was added, and the mixture was ice-cooled. Acetic acid (59.3 g, 0.988 mol) was added dropwise over 2 hr. The mixture was stirred for 5 min, filtered through celite, and thoroughly washed with chloroform and ethyl acetate. The filtrate was neutralized with saturated aqueous sodium hydrogen carbonate, and the organic layer was washed with saturated brine, dried over anhydrous magnesium sulfate, filtered, and concentrated. The obtained residue was suspension washed with chloroform-hexane mixed solvent to give compound 3 (12.4 g, 43%). The filtrate was concentrated to give compound 3 (15.8 g, 54%).

MS m/z 206 [M+H]+, APCI(+)

Compound 3 (14.6 g, 71.1 mmol) was dissolved in methylene chloride (120 mL) and methanol (120 mL), and calcium carbonate (15.7 g, 157 mmol) was added, and the mixture was ice-cooled. Bromine (22.7 g, 142 mmol) was dissolved in methylene chloride (30 mL), and added dropwise over 20 min. After stirring for 5 min, the mixture was heated to room temperature. After 15 hr, the mixture was filtered through celite. To the filtrate was added saturated aqueous sodium thiosulfate solution, and the mixture was neutralized with saturated aqueous sodium hydrogen carbonate. After concentration, the residue was extracted with ethyl acetate, and the organic layer was washed with saturated brine, dried over anhydrous magnesium sulfate, filtered, and concentrated. The obtained residue was recrystallized from ethyl acetate-hexane mixed solvent to give compound 4 (19.7 g, 76%). The filtrate was concentrated, and the obtained residue was purified by silica gel column chromatography to give compound 4 (4.66 g, 18%).

MS m/z 360/362/364 [M−H]−, ESI(−)

Compound 4 (12.4 g, 34.2 mmol) was dissolved in 1,4-dioxane (170 mL), and potassium carbonate (11.8 g, 85.4 mmol) and trimethylboroxine (3.22 g, 25.6 mmol) were added, and the mixture was purged with argon. [1,1'-Bis(diphenylphosphino)ferrocene]dichloropalladium(II)dichloromethane complex (1.39 g, 1.71 mmol) was added, and the mixture was heated to 110° C. After stirring for 1 hr, trimethylboroxine (3.22 g, 25.6 mmol) was added, and the mixture was further stirred for 1 hr and trimethylboroxine (3.22 g, 25.6 mmol) was added. After stirring for 16 hr, trimethylboroxine (3.22 g, 25.6 mmol) and [1,1'-bis(diphenylphosphino)ferrocene]dichloropalladium(II) methylene chloride complex (1.39 g, 1.71 mmol) were added. After stirring for 3 hr, trimethylboroxine (4.29 g, 34.2 mmol) was added. The mixture was further stirred for 3 hr, and trimethylboroxine (4.29 g, 34.2 mmol) was added. After stirring for 2 hr, the mixture was allowed to cool to room temperature, celite filtered, and thoroughly washed with ethyl acetate. The filtrate was concentrated, and the residue was purified by silica gel column chromatography to give compound 5 (5.30 g, 66%).

MS m/z 234 [M+H]+, APCI(+)

Compound 5 (6.95 g, 29.8 mmol) was dissolved in acetonitrile (150 mL), sulfuric acid (7.31 g, 74.5 mmol) was added and the mixture was ice-cooled. Sodium nitrite (4.11 g, 59.6 mmol) was dissolved in water (15 mL) and, after cooling with ice, the mixture was added dropwise over 10 min. After stirring for 30 min, ice-cooled aqueous potassium iodide (19.8 g, 119 mmol) solution (15 mL) was added dropwise. After stirring for 5 min, cold water (75 mL) was added, and the mixture was heated to room temperature. After stirring for 40 min, saturated aqueous sodium thiosulfate solution was added, and the mixture was extracted with ethyl acetate. The organic layer was washed with saturated aqueous sodium hydrogen carbonate and saturated brine, dried over anhydrous magnesium sulfate, filtered and concentrated. The residue was purified by silica gel column chromatography to give compound 6 (8.96 g, 5 87%).

MS m/z 362 [M+NH$_4$]+, APCI(+)

Compound 6 (11.8 g, 34.3 mmol) was dissolved in methylene chloride (170 mL), and potassium hydroxide (5.77 g, 103 mmol) suspended in methanol (40 mL) was added. After 1 hr, the mixture was neutralized with 1N hydrochloric acid, and extracted with chloroform. The organic layer was washed with saturated aqueous sodium hydrogen carbonate and saturated brine, dried over anhydrous magnesium sulfate, filtered and concentrated. The residue was purified by silica gel column chromatography to give compound 7 (7.98 g, 88%).

MS m/z 265 [M−H]−, ESI(−)

Compound 7 (7.98 g, 30.0 mmol) was dissolved in acetonitrile (150 mL), and benzyl bromide (5.13 g, 30.0 mmol) and cesium carbonate (11.7 g, 36.0 mmol) were added. After stirring for 15 hr, the mixture was filtered through celite, and thoroughly washed with ethyl acetate. The filtrate was concentrated, and the residue was purified by silica gel column chromatography to give compound 8 (10.4 g, 97%).

MS m/z 357 [M+H]+, APCI(+)

Compound 8 (10.4 g, 29.2 mmol) was dissolved in tetrahydrofuran (100 mL), cooled to −78° C., n-butyllithium (1.3 M hexane solution, 33.7 mL, 43.8 mmol) was added dropwise over 15 min, and the mixture was stirred for 25 min. Dimethylformamide (10.7 g, 146 mmol) was added dropwise over 5 min. After stirring for 5 min, the mixture was heated to room temperature. After 1 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 9 (6.24 g, 83%).

MS m/z 259 [M+H]+, APCI(+)

Compound 10 (7.60 g, 25.4 mmol) was dissolved in toluene (180 mL), and the mixture was cooled to −78° C., n-butyllithium (1.65 M hexane solution, 15.4 mL, 25.4 mmol) was added dropwise over 10 min, and the mixture was stirred for 1 hr. Compound 9 (6.24 g, 24.2 mmol) was dissolved in toluene (70 mL), and the mixture was added dropwise over 35 min. After 15 min, saturated aqueous ammonium chloride solution was added, and the mixture was heated to room temperature. The reaction mixture was extracted with ethyl acetate, and the organic layer was washed with saturated brine, dried over anhydrous magnesium sulfate, filtered and concentrated. The residue was purified by silica gel column chromatography to give compound 11 (8.78 g, 84%).

MS m/z 432/434 [M+H]+, APCI(+)

Compound 11 (8.78 g, 20.3 mmol) was dissolved in pyridine (35 mL), and acetic anhydride (35 mL) was added. After stirring for 14 hr, the reaction mixture was concentrated, and the residue was dried azeotropically with toluene. The residue was purified by silica gel column chromatography to give compound 12 (9.60 g, 100%).

MS m/z 414/416 [M+H—CH₃CO₂H]+, ESI(+)

Compound 12 (9.60 g, 20.3 mmol) was dissolved in methylene chloride (130 mL), triethylsilane (5.89 g, 50.6 mmol) was added and the mixture was ice-cooled. Boron trifluoride-diethyl ether complex (7.19 g, 50.6 mmol) was added dropwise over 5 min. After stirring for 20 min, saturated aqueous sodium hydrogen carbonate was added, and the mixture was extracted with ethyl acetate. The organic layer was washed with saturated brine, dried over anhydrous magnesium sulfate, filtered and concentrated. The residue was dissolved in acetonitrile (100 mL), and chloromethyl methyl ether (1.30 g, 16.2 mmol) and cesium carbonate (13.2 g, 40.5 mmol) were added. After stirring for 16 hr, the mixture was filtered through celite, and thoroughly washed with ethyl acetate. The filtrate was concentrated, and the residue was purified by silica gel column chromatography to give compound 13 (7.67 g, 91%).

MS m/z 416/418 [M+H]+, APCI(+)

Compound 13 (296 mg, 0.712 mmol) was dissolved in 1,4-dioxane (4 mL), and water (1 mL), potassium carbonate (295 mg, 2.14 mmol), and 1-cyclohexeneboronic acid (134 mg, 1.07 mmol) were added, and the mixture was purged with argon. Tetrakistriphenylphosphinepalladium(0) (25 mg, 0.021 mmol) was added, and the mixture was heated to 90° C. After stirring for 40 min, the mixture was allowed to cool to room temperature, filtered through celite, and thoroughly washed with ethyl acetate. To the filtrate was added saturated brine, and the mixture was extracted with ethyl acetate, and the extract was dried over anhydrous magnesium sulfate, filtered and concentrated. The residue was purified by silica gel column chromatography to give compound 14 (329 mg, 100%).

MS m/z 462 [M+H]+, APCI(+)

Compound 14 (326 mg, 0.706 mmol) was dissolved in tetrahydrofuran (8 mL) and, after purging with argon, 5% Pd/C (301 mg) was added. After purging with hydrogen, the mixture was stirred for 1 hr, filtered through celite and thoroughly washed with ethyl acetate. The filtrate was concentrated, and the residue was dissolved in acetonitrile (4 mL), and methyl bromoacetate (156 mg, 1.02 mmol) and cesium carbonate (665 mg, 2.04 mmol) were added. After stirring for 18 hr, the mixture was filtered through celite, and thoroughly washed with ethyl acetate. The filtrate was concentrated, and the residue was purified by silica gel column chromatography to give compound 15 (282 mg, 90%).

MS m/z 446 [M+H]+, APCI(+)

Compound 15 (280 mg, 0.628 mmol) was dissolved in methanol (3 mL) and tetrahydrofuran (3 mL). 6N Hydrochloric acid (3 mL) was added, and the mixture was heated to 60° C. After 2 hr, the mixture was allowed to cool to room temperature, and neutralized with 2N aqueous sodium hydroxide solution. After extraction with ethyl acetate, the organic layer was washed with saturated brine, dried over anhydrous magnesium sulfate, filtered and concentrated. The obtained residue was dissolved in methanol (6 mL), and 2N sodium hydroxide (0.9 mL) was added. The mixture was heated to 60° C. and, after 2 hr, allowed to cool to room temperature, and neutralized with 1N hydrochloric acid. Water and saturated brine were added, and the mixture was extracted with ethyl acetate-tetrahydrofuran mixed solvent, and the extract was dried over anhydrous magnesium sulfate, filtered and concentrated. The obtained residue was suspension washed with hexane-diethyl ether mixed solvent to give compound 16 (232 mg, 95%).

MS m/z 386 [M−H]−, ESI(−)

Hydrobromide, hydrochloride, para-toluenesulfonate, methanesulfonate, benzenesulfonate, maleate and the like of the present compound can be produced by a general salt formation step.

Example 13

{2-bromo-4-[(6-cyclohexyl-5-hydroxypyridin-2-yl)methyl]-3,5-dimethylphenoxy}acetic acid

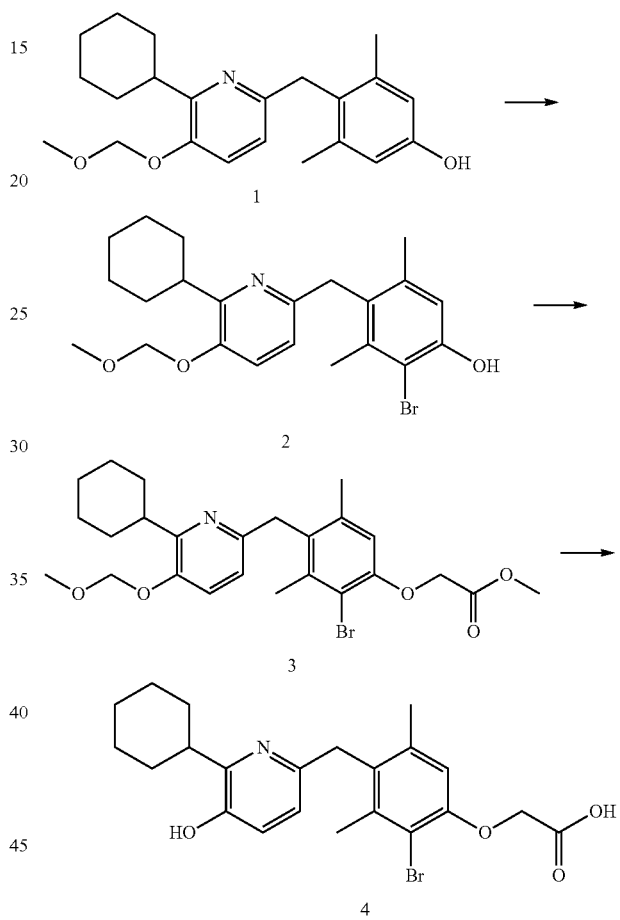

Compound 1 (200 mg, 0.563 mmol) was dissolved in methylene chloride (4.0 mL), and the mixture was cooled to −50° C. 1,3-Dibromo-5,5-dimethylhydantoin (82.1 mg, 0.281 mmol) was added by small portions. After stirring for 3 hr, saturated aqueous sodium hydrogen carbonate was added, and the mixture was extracted with chloroform. The organic layer was washed with saturated brine, dried over anhydrous sodium sulfate, filtered and concentrated. The residue was purified by silica gel column chromatography to give compound 2 (144 mg, 59%).

MS m/z 434/436 [M+H]+, APCI(+)

Compound 2 (260 mg, 0.598 mmol) was dissolved in acetonitrile (5.2 mL), and cesium carbonate (584 mg, 1.79 mmol) and methyl bromoacetate (137 mg, 0.897 mmol) were added. After stirring for 4 hr, water was added, and the mixture was extracted with ethyl acetate. The organic layer was washed with saturated brine, dried over anhydrous magnesium sulfate, filtered and concentrated. The residue was purified by silica gel column chromatography to give compound 3 (252 mg). The obtained compound 3 was dissolved in methanol (4.0 mL) and tetrahydrofuran (4.0 mL). 6N Hydrochloric acid (4.0 mL) was added, and the mixture was heated to 60° C. After stirring for 1.5 hr, the mixture was allowed to cool to room temperature. The mixture was neutralized with 4N aqueous sodium hydroxide solution, and extracted with ethyl acetate. The organic layer was washed with saturated brine, and dried over anhydrous sodium sulfate. After filtration, the filtrate was concentrated, and the residue was dissolved in methanol (5.0 mL). 2N Sodium hydroxide (1.0 mL) was added, and the mixture was heated to 60° C., and stirred for 2 hr. After allowing to cool to room temperature, the mixture was neutralized with 2N hydrochloric acid, and extracted with ethyl acetate-tetrahydrofuran mixed solvent. The organic layer was washed with saturated brine, dried over anhydrous sodium sulfate, filtered, and concentrated. The obtained residue was suspension washed with hexane-diethyl ether mixed solution to give compound 4 (206 mg, 88%).

MS m/z 446/448 [M−H]−, ESI(−)

Hydrobromide, hydrochloride, para-toluenesulfonate, methanesulfonate, benzenesulfonate, maleate and the like of the present compound can be produced by a general salt formation step.

Example 14

2-{4-[(6-cyclohexyl-5-hydroxypyridin-2-yl)methyl]-3,5-dimethylphenoxy}propanoic acid

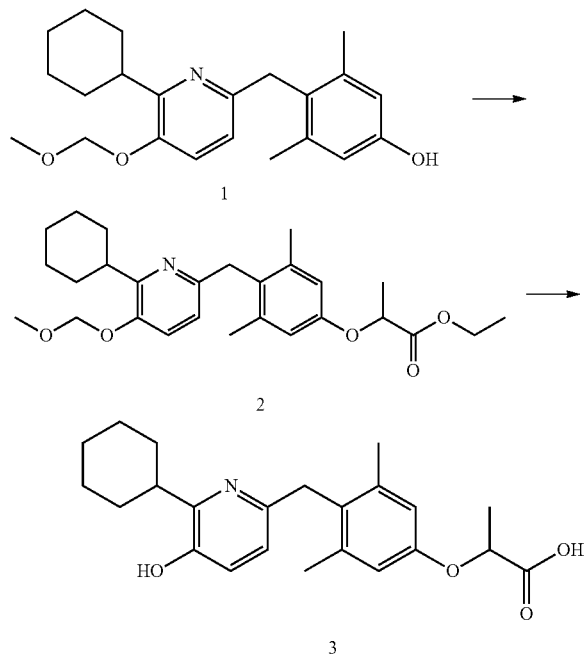

Compound 1 (200 mg, 0.563 mmol) was dissolved in acetonitrile (4.0 mL), and cesium carbonate (275 mg, 0.844 mmol) and ethyl 2-bromopropionate (250 mg, 0.995 mmol) were added. After stirring for 4 hr, water was added, and the mixture was extracted with ethyl acetate. The organic layer was washed with saturated brine, dried over anhydrous magnesium sulfate, filtered and concentrated. The residue was purified by silica gel column chromatography to give compound 2 (213 mg, 83%).

MS m/z 456 [M+H]+, APCI(+)

Compound 2 (213 mg, 0.468 mmol) was dissolved in methanol (2.0 mL) and tetrahydrofuran (2.0 mL). 6N Hydrochloric acid (2.0 mL) was added, and the mixture was heated to 60° C. After stirring for 1.5 hr, the mixture was allowed to cool to room temperature. The mixture was neutralized with 4N aqueous sodium hydroxide solution, and extracted with ethyl acetate. The organic layer was washed with saturated brine, and dried over anhydrous sodium sulfate. After filtration, the filtrate was concentrated, and the residue was dissolved in methanol (4.3 mL). 2N Sodium hydroxide (1.0 mL) was added, and the mixture was heated to 60° C., and stirred for 2 hr. The mixture was allowed to cool to room temperature, and neutralized with 2N hydrochloric acid, and extracted with ethyl acetate-tetrahydrofuran mixed solvent. The organic layer was washed with saturated brine, dried over anhydrous sodium sulfate, filtered and concentrated. The obtained residue was suspension washed with diethyl ether to give compound 3 (173 mg, 97%). MS m/z 382 [M−H]−, ESI(−)

Hydrobromide, hydrochloride, para-toluenesulfonate, methanesulfonate, benzenesulfonate, maleate and the like of the present compound can be produced by a general salt formation step.

Example 15

2-{4-[(6-cyclohexyl-5-hydroxypyridin-2-yl)methyl]-2,3,5-trimethylphenoxy}propanoic acid

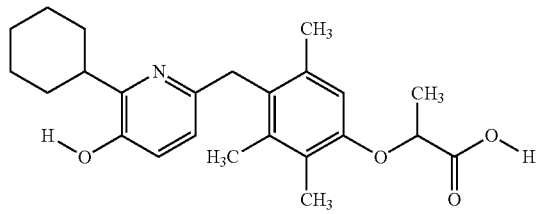 [SMILES: Cc1cc(OC(C)C(=O)O)c(C)c(C)c1Cc1ccc(O)c(C2CCCCC2)n1]

The compound was synthesized from compound 3 of Example 7 by a method similar to that in Example 14.

MS m/z 396 [M−H]−, ESI(−)

Hydrobromide, hydrochloride, para-toluenesulfonate, methanesulfonate, benzenesulfonate, maleate and the like of the present compound can be produced by a general salt formation step.

Example 16

2-{4-[(6-cyclohexyl-5-hydroxypyridin-2-yl)methyl]-3,5-dimethylphenoxy}-2-methylpropanoic acid

67

-continued

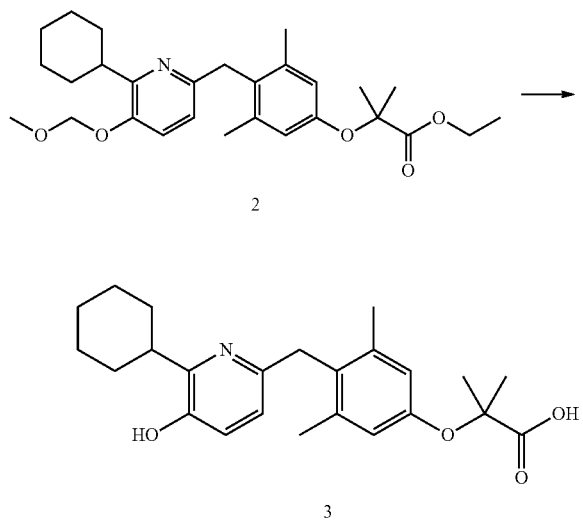

Compound 1 (200 mg, 0.563 mmol) was dissolved in acetonitrile (4.0 mL), and cesium carbonate (275 mg, 0.844 mmol) and ethyl 2-bromoisobutyrate (158 mg, 0.788 mmol) were added. The mixture was heated under reflux and, after stirring for 4 hr, allowed to cool to room temperature. Water was added, and the mixture was extracted with ethyl acetate. The organic layer was washed with saturated brine, dried over anhydrous magnesium sulfate, filtered and concentrated. The residue was purified by silica gel column chromatography to give compound 2 (264 mg, 62%).

MS m/z 470 [M+H]+, APCI(+)

Compound 2 (163 mg, 0.348 mmol) was dissolved in methanol (2.0 mL) and tetrahydrofuran (2.0 mL). 6N Hydrochloric acid (2.0 mL) was added, and the mixture was heated to 60° C. After stirring for 1.5 hr, the mixture was allowed to cool to room temperature. The mixture was neutralized with 4N aqueous sodium hydroxide solution, and extracted with ethyl acetate. The organic layer was washed with saturated brine, and dried over anhydrous sodium sulfate. After filtration, the filtrate was concentrated, and the residue was dissolved in methanol (3.3 mL). 2N Sodium hydroxide (1.0 mL) was added, and the mixture was heated to 60° and stirred overnight. The mixture was allowed to cool to room temperature, neutralized with 2N hydrochloric acid, and extracted with ethyl acetate-tetrahydrofuran mixed solvent. The organic layer was washed with saturated brine, dried over anhydrous sodium sulfate, filtered and concentrated. The obtained residue was suspension washed with diethyl ether to give compound 3 (128 mg, 93%).

MS m/z 396 [M−H]−, ESI(−)

Hydrobromide, hydrochloride, para-toluenesulfonate, methanesulfonate, benzenesulfonate, maleate and the like of the present compound can be produced by a general salt formation step.

68

Example 17

2-{4-[(6-cyclohexyl-5-hydroxypyridin-2-yl)methyl]-2,3,5-trimethylphenoxy}-2-methylpropanoic acid

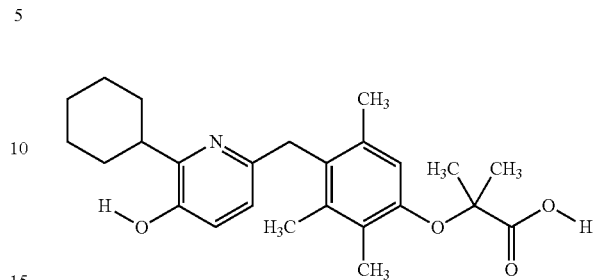

The compound was synthesized from compound 3 of Example 7 by a method similar to that in Example 16.

MS m/z 410 [M−H]−, ESI(−)

Hydrobromide, hydrochloride, para-toluenesulfonate, methanesulfonate, benzenesulfonate, maleate and the like of the present compound can be produced by a general salt formation step.

Example 18

1-{4-[(6-cyclohexyl-5-hydroxypyridin-2-yl)methyl]-3,5-dimethylphenoxy}cyclopropanecarboxylic acid

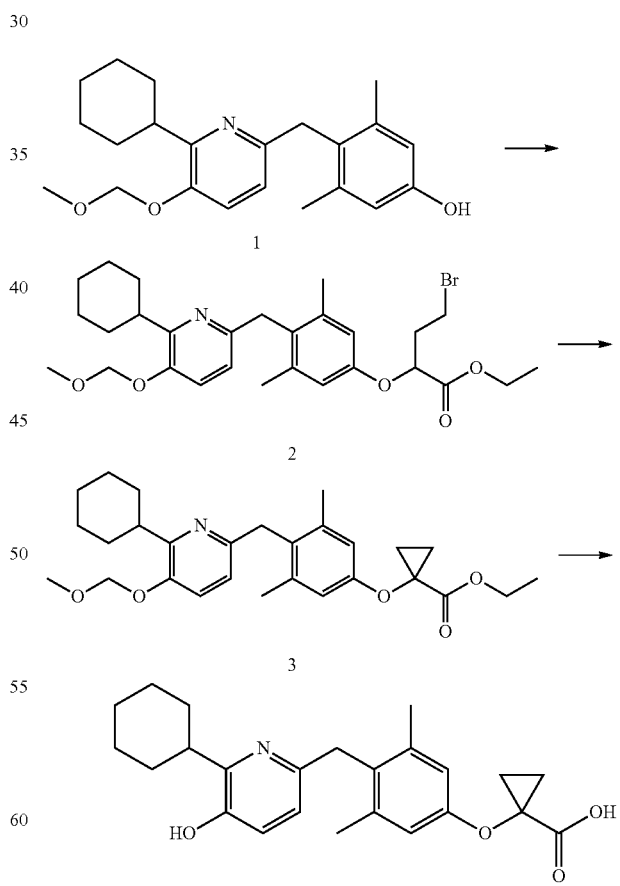

Compound 1 (400 mg, 1.13 mmol) was dissolved in acetonitrile (8.0 mL), and cesium carbonate (550 mg, 1.69 mmol)

and ethyl 2,4-dibromobutyrate (462 mg, 1.69 mmol) were added. After stirring overnight, water was added, and the mixture was extracted with ethyl acetate. The organic layer was washed with saturated brine, dried over anhydrous magnesium sulfate, filtered and concentrated. The residue was purified by silica gel column chromatography to give compound 2 (414 mg, 67%).

MS m/z 54B/550 [M+H]+, APCI(+)

Compound 2 (414 mg, 0.755 mmol) was dissolved in tetrahydrofuran (8.3 mL), and potassium t-butoxide (127 mg, 1.13 mmol) was added. The mixture was heated under reflux, and stirred overnight. The mixture was allowed to cool to room temperature, and cesium carbonate (738 mg, 2.26 mmol) and ethyl iodide (177 mg, 1.13 mmol) were added. After stirring overnight, water was added, and the mixture was extracted with ethyl acetate. The organic layer was washed with saturated brine, dried over anhydrous sodium sulfate, filtered and concentrated. The residue was purified by silica gel column chromatography to give compound 3 (211 mg, 60%).

MS m/z 468 [M+H]+, APCI(+)

Compound 3 (207 mg, 0.443 mmol) was dissolved in methanol (4.0 mL) and tetrahydrofuran (4.0 mL). 6N Hydrochloric acid (4.0 mL) was added, and the mixture was heated to 60° C. After stirring for 2 hr, the mixture was allowed to cool to room temperature. The mixture was neutralized with 4N aqueous sodium hydroxide solution, and extracted with ethyl acetate. The organic layer was washed with saturated brine, and dried over anhydrous sodium sulfate. After filtration, the filtrate was concentrated, and the residue was dissolved in methanol (5.0 mL). 2N Sodium hydroxide (1.0 mL) was added, and the mixture was heated to 60° and stirred overnight. The mixture was allowed to cool to room temperature, and neutralized with 2N hydrochloric acid, and extracted with ethyl acetate-tetrahydrofuran mixed solvent. The organic layer was washed with saturated brine, dried over anhydrous sodium sulfate, filtered and concentrated. The obtained residue was suspension washed with hexane-diethyl ether mixed solvent to give compound 4 (125 mg, 71%).

MS m/z 394 [M–H]–, ESI(–)

Hydrobromide, hydrochloride, para-toluenesulfonate, methanesulfonate, benzenesulfonate, maleate and the like of the present compound can be produced by a general salt formation step.

Example 19

({4-[(6-cyclohexyl-5-hydroxypyridin-2-yl)methyl]-3,5-dimethylphenyl}amino)(oxo)acetic acid

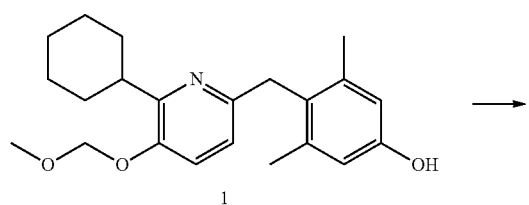

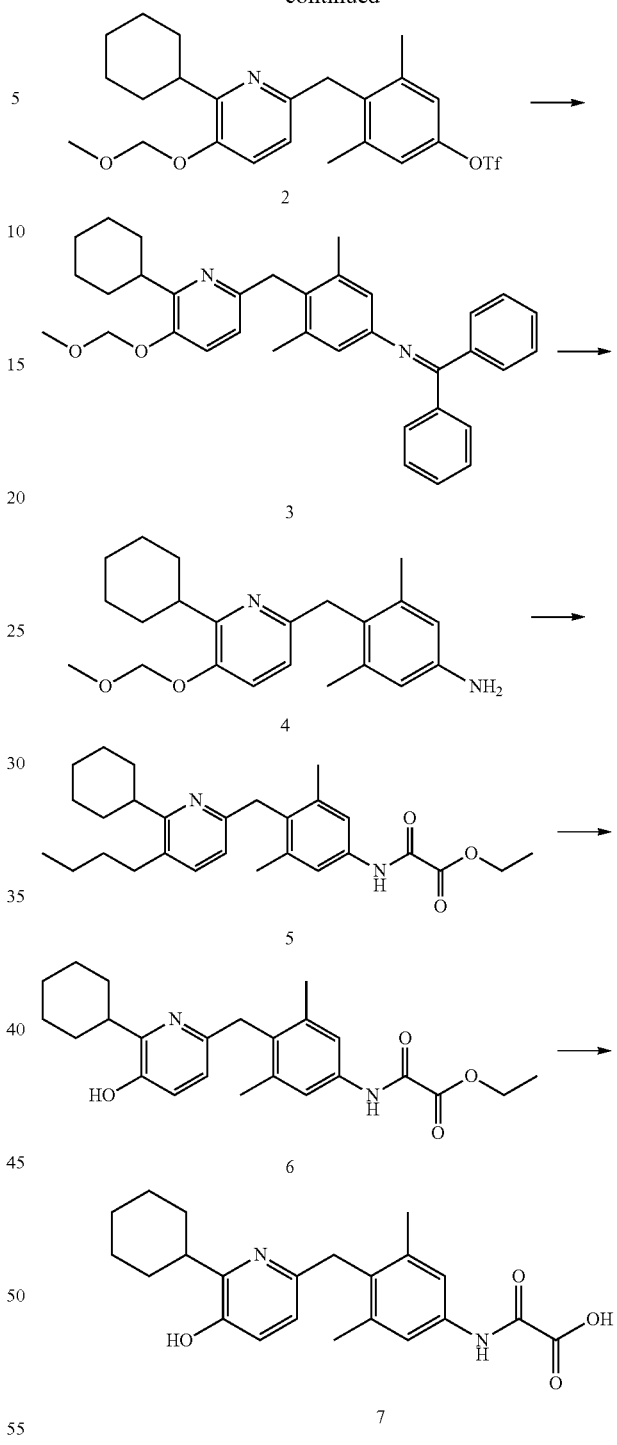

Compound 1 (4.00 g, 11.3 mmol) was dissolved in methylene chloride (80 mL), and ice-cooled. Diisopropylethylamine (4.36 g, 33.8 mmol) and trifluoromethanesulfonic anhydride (4.76 g, 16.9 mmol) were added. After stirring for 4 hr, the mixture was stirred overnight while allowing to warm. Water was added, and the mixture was extracted with ethyl acetate. The organic layer was washed with saturated brine, dried over anhydrous sodium sulfate, filtered and concentrated. The residue was purified by silica gel column chromatography to give compound 2 (4.76 g, 87%).

MS m/z 488 [M+H]+, APCI(+)

Compound 2 (4.75 g, 9.73 mmol) was dissolved in tetrahydrofuran (95 mL), and cesium carbonate (4.76 g, 14.6 mmol), benzophenone imine (2.12 g, 11.7 mmol), (R)-BINAP (937 mg, 1.46 mmol), and palladium acetate (219 mg, 0.973 mmol) were added. The mixture was purged with argon, heated under reflux, and stirred overnight. The mixture was allowed to cool to room temperature, water was added, and the mixture was extracted with ethyl acetate. The organic layer was washed with saturated brine, dried over anhydrous sodium sulfate, filtered and concentrated. The residue was purified by silica gel column chromatography to give compound 3 (2.08 g, 40%).

MS m/z 519 [M+H]+, APCI(+)

Compound 3 (2.08 g, 4.01 mmol) was dissolved in methanol (20 mL) and dimethylformamide (20 mL). Hydroxyamine hydrochloride (557 mg, 8.02 mmol) and sodium acetate (987 mg, 12.0 mmol) were added. After stirring overnight, water was added, and the mixture was extracted with ethyl acetate. The organic layer was washed with saturated brine, dried over anhydrous sodium sulfate, filtered and concentrated. The residue was purified by silica gel column chromatography to give compound 4 (1.14 g, 80%).

MS m/z 355 [M+H]+, APCI(+)

Compound 4 (300 mg, 0.846 mmol) was dissolved in methylene chloride (6.0 mL), and ice-cooled. Triethylamine (103 mg, 1.02 mmol) and ethyl chloroglyoxylate (142 mg, 1.02 mmol) were added. After stirring overnight while allowing to warm to room temperature, water was added, and the mixture was extracted with chloroform. The organic layer was washed with saturated brine, dried over anhydrous sodium sulfate, filtered and concentrated. The residue was purified by silica gel column chromatography to give compound 5 (359 mg, 93%).

MS m/z 455 [M+H]+, APCI(+)

Compound 5 (359 mg, 0.789 mmol) was dissolved in methylene chloride (3.5 mL). Thioanisole (980 mg, 7.89 mmol), and trifluoromethanesulfonic acid (3.5 mL) were added. After stirring for 4 hr, the mixture was heated to 40° C., and stirred for 30 min. The mixture was allowed to cool to room temperature, and concentrated. Water was added, and the mixture was neutralized with saturated aqueous sodium hydrogen carbonate, and extracted with chloroform. The organic layer was washed with saturated brine, dried over anhydrous sodium sulfate, filtered and concentrated. The residue was purified by silica gel column chromatography to give compound 6 (330 mg, 100%).

MS m/z 411 [M+H]+, APCI(+)

Compound 6 (330 mg, 0.804 mmol) was dissolved in methanol (6.6 mL) and tetrahydrofuran (4.0 mL). 1N Sodium hydroxide (2.0 mL) was added, and the mixture was stirred overnight, neutralized with 1N hydrochloric acid, and extracted with ethyl acetate-diethyl ether-acetone-methanol mixed solvent. The organic layer was washed with saturated brine, dried over anhydrous sodium sulfate, filtered and concentrated. The obtained residue was suspension washed with methylene chloride-hexane mixed solvent to give compound 7 (258 mg, 84%).

MS m/z 381 [M−H]−, ESI(−)

Hydrobromide, hydrochloride, para-toluenesulfonate, methanesulfonate, benzenesulfonate, maleate and the like of the present compound can be produced by a general salt formation step.

Example 20

({4-[(6-cyclohexyl-5-hydroxypyridin-2-yl)methyl]-2,3,5-trimethylphenyl}amino)(oxo)acetic acid

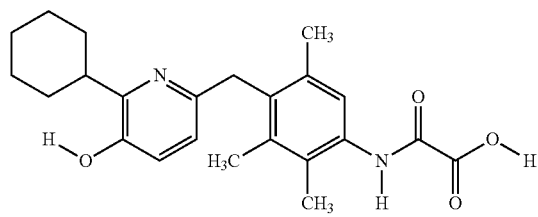 [SMILES: Cc1cc(NC(=O)C(=O)O)c(C)c(C)c1Cc1ccc(O)c(C2CCCCC2)n1]

The compound was synthesized from compound 3 of Example 7 by a method similar to that in Example 19.

MS m/z 395 [M−H]−, ESI(−)

Hydrobromide, hydrochloride, para-toluenesulfonate, methanesulfonate, benzenesulfonate, maleate and the like of the present compound can be produced by a general salt formation step.

Example 21

3-({4-[(5-hydroxy-6-isopropylpyridin-2-yl)methyl]-3,5-dimethylphenyl}amino)-3-oxopropanoic acid

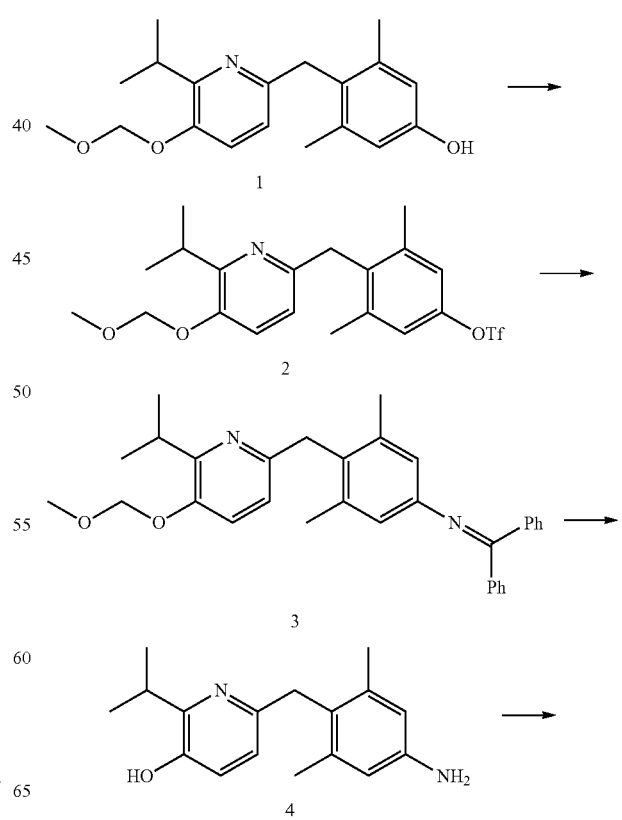

-continued

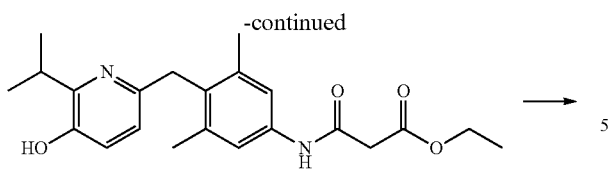

5

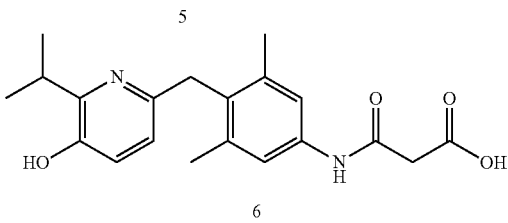

6

Compound 1 (919 mg, 2.92 mmol) was dissolved in methylene chloride (18.4 mL), and ice-cooled. Diisopropylethylamine (1.13 g, 8.74 mmol) and trifluoromethanesulfonic anhydride (863 mg, 3.06 mmol) were added. After stirring overnight while allowing to warm to room temperature, water was added, and the mixture was extracted with chloroform. The organic layer was washed with saturated brine, dried over anhydrous sodium sulfate, filtered and concentrated. The residue was purified by silica gel column chromatography to give compound 2 (1.00 g, 77%).

MS m/z 448 [M+H]+, APCI(+)

Compound 2 (1.00 g, 2.24 mmol) was dissolved in tetrahydrofuran (20 mL), and cesium carbonate (1.10 g, 3.36 mmol), benzophenone imine (488 mg, 2.69 mmol), (R)-BINAP (216 mg, 0.336 mmol), and palladium acetate (50.3 mg, 0.224 mmol) were added, and the mixture was purged with argon. The mixture was heated under reflux, and stirred overnight. The mixture was allowed to cool to room temperature, water was added, and the mixture was extracted with ethyl acetate. The organic layer was washed with saturated brine, dried over anhydrous sodium sulfate, filtered and concentrated. The residue was purified by silica gel column chromatography to give compound 3 (488 mg, 46%).

MS m/z 479 [M+H]+, APCI(+)

Compound 3 (482 mg, 1.01 mmol) was dissolved in methanol (4.8 mL) and tetrahydrofuran (4.8 mi). 6N Hydrochloric acid (5.5 mL) was added, and the mixture was heated to 60° C. After stirring for 2 hr, the mixture was allowed to cool to room temperature. The mixture was neutralized with 4N aqueous sodium hydroxide solution, and extracted with ethyl acetate. The organic layer was washed with saturated brine, and dried over anhydrous sodium sulfate. After filtration, the filtrate was concentrated, and the residue was dissolved in tetrahydrofuran (9.6 mL), and ice-cooled. 1N Sodium hydroxide (6.0 mL) was added, and ethyl 3-chloro-3-oxopropionate (910 mg, 6.04 mmol) was added by small portions. After stirring for 2 hr, the mixture was stirred overnight while allowing to warm to room temperature. After ice-cooling, 10N sodium hydroxide (3.0 mL) was added, and the mixture was stirred for 2 hr. Water was added, and the aqueous layer was washed with ethyl acetate, neutralized with 2N hydrochloric acid, and extracted with ethyl acetate. The organic layer was washed with saturated brine, dried over anhydrous sodium sulfate, filtered and concentrated. The obtained residue was suspension washed with diethyl ether-hexane mixed solvent to give compound 6 (188 mg, 61%).

MS m/z 355 [M−H]−, ESI(−)

Hydrobromide, hydrochloride, para-toluenesulfonate, methanesulfonate, benzenesulfonate, maleate and the like of the present compound can be produced by a general salt formation step.

Example 22

3-({4-[(5-hydroxy-6-phenylpyridin-2-yl)methyl]-3,5-dimethylphenyl}amino)-3-oxopropanoic acid

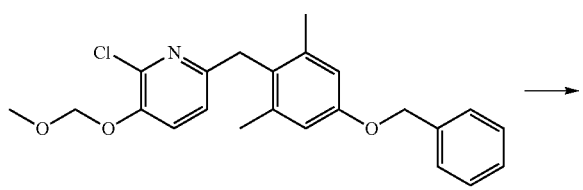

1

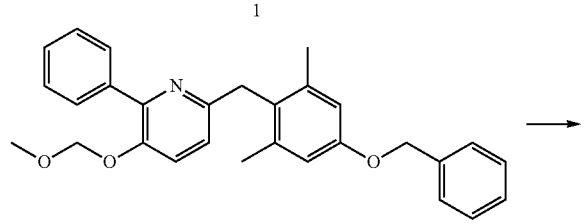

2

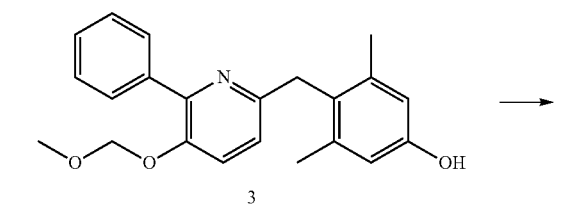

3

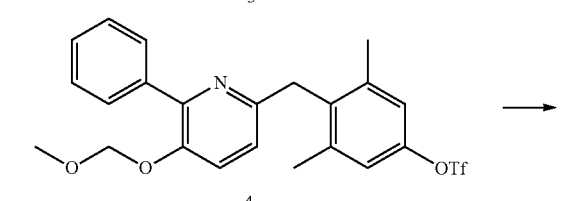

4

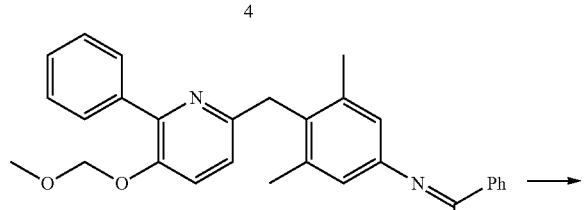

5

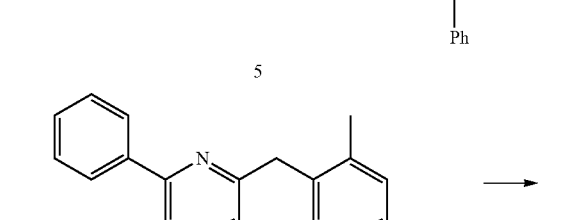

6

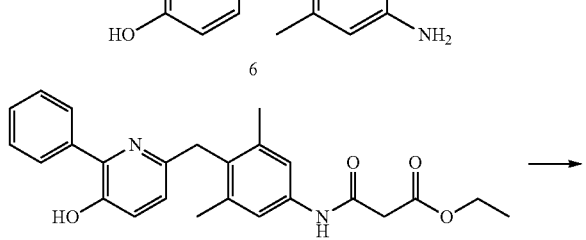

7

-continued

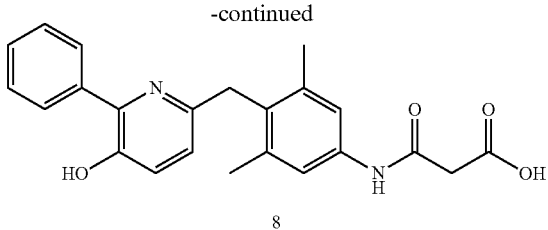

8

The compound 3 was synthesized by a method similar to that of Compound 7 of Example 2.

Compound 8 was synthesized from compound 3 by a method similar to that in Example 21.

MS m/z 389 [M−H]−, ESI(−)

Hydrobromide, hydrochloride, para-toluenesulfonate, methanesulfonate, benzenesulfonate, maleate and the like of the present compound can be produced by a general salt formation step.

Example 23

3-({4-[(6-cyclohexyl-5-hydroxypyridin-2-yl)methyl]-3,5-dimethylphenyl}amino)-3-oxopropanoic acid

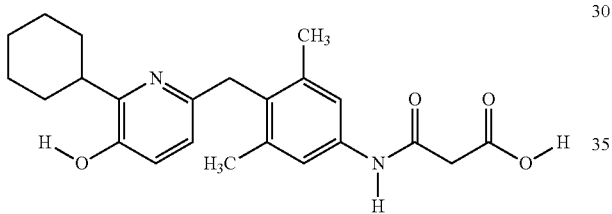

The compound was synthesized from compound 7 of Example 2 by a method similar to that in Example 21.

MS m/z 395 [M−H]−, ESI(−)

Hydrobromide, hydrochloride, para-toluenesulfonate, methanesulfonate, benzenesulfonate, maleate and the like of the present compound can be produced by a general salt formation step.

Example 24

3-({4-[(6-cyclohexyl-5-hydroxypyridin-2-yl)methyl]-2,3,5-trimethylphenyl}amino)-3-oxopropanoic acid

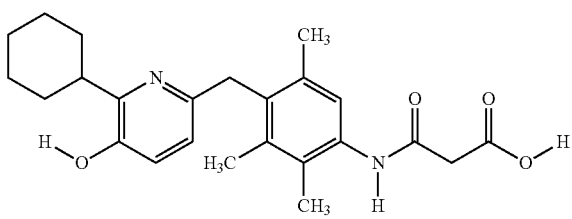 [SMILES: Cc1cc(NC(=O)CC(=O)O)c(C)c(C)c1Cc1ccc(O)c(C2CCCCC2)n1]

The compound was synthesized from compound 3 of Example 7 by a method similar to that in Example 21.

MS m/z 409 [M−H]−, ESI(−)

Hydrobromide, hydrochloride, para-toluenesulfonate, methanesulfonate, benzenesulfonate, maleate and the like of the present compound can be produced by a general salt formation step.

Example 25

(2E)-3-{4-[(6-cyclohexyl-5-hydroxypyridin-2-yl)methyl]-2,3,5-trimethylphenyl}acrylic acid

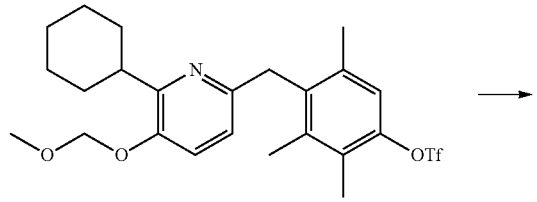

1

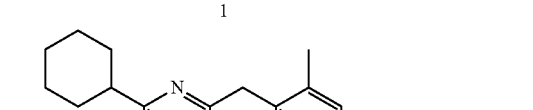

2

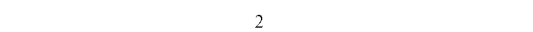

3

Under an argon atmosphere, compound 1 (295 mg, 0.588 mmol) was dissolved in dimethylformamide (2 mL), and triethylamine (65 mg, 0.647 mmol) and methyl acrylate (253 mg, 2.94 mmol) and 1,3-bis(diphenylphosphino)propane (27 mg, 0.065 mmol) and palladium acetate (13 mg, 0.059 mmol) were added. The mixture was tightly sealed and stirred overnight at 100° C. Methyl acrylate (127 mg, 1.47 mmol) and 1,3-bis(diphenylphosphino)propane (27 mg, 0.065 mmol) and palladium acetate (13 mg, 0.059 mmol) were added. The mixture was tightly sealed and stirred overnight at 100° C. The mixture was allowed to cool to room temperature, chloroform and 5% hydrochloric acid were added and the mixture was stirred, and filtered through celite. The organic layer was washed successively with 5% hydrochloric acid and water and saturated brine, dried over anhydrous sodium sulfate, filtered, and concentrated. The residue was purified by silica gel column chromatography to give compound 2 (127 mg, 49%).

MS m/z 438 [M+H]+, APCI(+)

Compound 2 (42 mg, 0.096 mmol) was dissolved in methanol (0.2 mL) and tetrahydrofuran (0.6 mL). 6N Hydrochloric acid (0.2 mL) was added, and the mixture was heated to 50° C. After 2 hr, the mixture was allowed to cool to room temperature, and neutralized with saturated aqueous sodium hydrogen carbonate. After extraction with ethyl acetate, the organic layer was dried over anhydrous sodium sulfate, filtered, and concentrated. The obtained residue was dissolved in methanol (1 mL) and tetrahydrofuran (0.6 mL), and 1N sodium hydroxide (0.2 mL) was added. The mixture was heated to 50° C. After stirring overnight, the mixture was allowed to cool to room temperature, and neutralized with saturated aqueous ammonium chloride solution. The mixture was extracted with ethyl acetate, and washed successively with water and saturated brine, dried over anhydrous sodium sulfate, filtered and concentrated to give compound 3 (28 mg, 77%).

MS m/z 378 [M−H]−, ESI(−)

Hydrobromide, hydrochloride, para-toluenesulfonate, methanesulfonate, benzenesulfonate, maleate and the like of the present compound can be produced by a general salt formation step.

Example 26

3-{4-[(6-cyclohexyl-5-hydroxypyridin-2-yl)methyl]-2,3,5-trimethylphenyl}propanoic acid

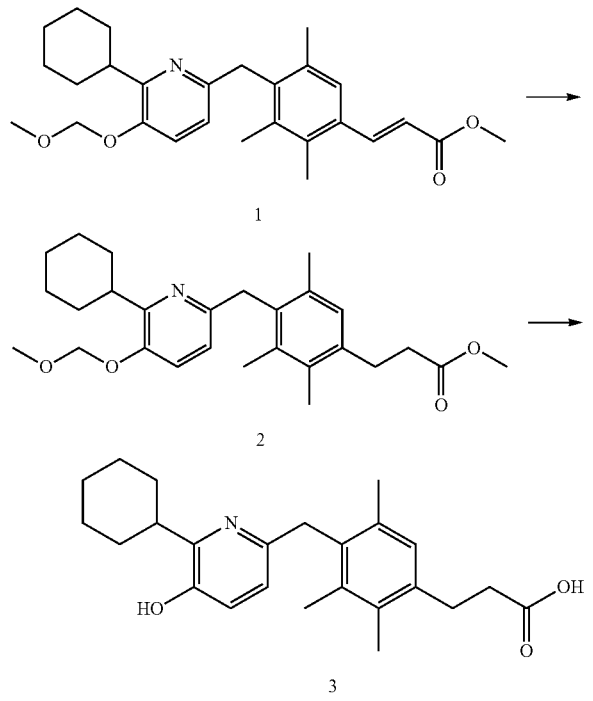

Compound 1 (125 mg, 0.286 mmol) was dissolved in ethanol (3 mL) and acetic acid (0.8 mL), 10% Pd/C (63 mg) was added, and the mixture was purged with hydrogen. The mixture was stirred at room temperature overnight, filtered through celite, and concentrated. The residue was purified by silica gel column chromatography to give compound 2 (102 mg, 81%).

MS m/z 440 [M+H]+, APCI(+)

Compound 2 (100 mg, 0.227 mmol) was dissolved in tetrahydrofuran (2 mL), 6N hydrochloric acid (0.45 mL) was added, and the mixture was stirred at 50° C. for 3 hr. 6N Hydrochloric acid (0.23 mL) was added, and the mixture was further stirred at 50° C. for 2 hr. The mixture was allowed to cool to room temperature, saturated aqueous sodium hydrogen carbonate and ethyl acetate were added and the mixture was stirred. After extraction with ethyl acetate, saturated aqueous ammonium chloride solution was added and the mixture was stirred. The mixture was extracted with ethyl acetate, and the extract was washed successively with water and saturated brine, dried over anhydrous sodium sulfate, filtered, and concentrated. The residue was purified by silica gel column chromatography to give compound 3 (63 mg, 73%).

MS m/z 380 [M−H]−, ESI(−)

Hydrobromide, hydrochloride, para-toluenesulfonate, methanesulfonate, benzenesulfonate, maleate and the like of the present compound can be produced by a general salt formation step.

Example 27

3-({4-[(5-hydroxy-6-isopropylpyridin-2-yl)methyl]-3,5-dimethylphenoxy}methyl)-1,2,4-oxadiazol-5(4H)-one

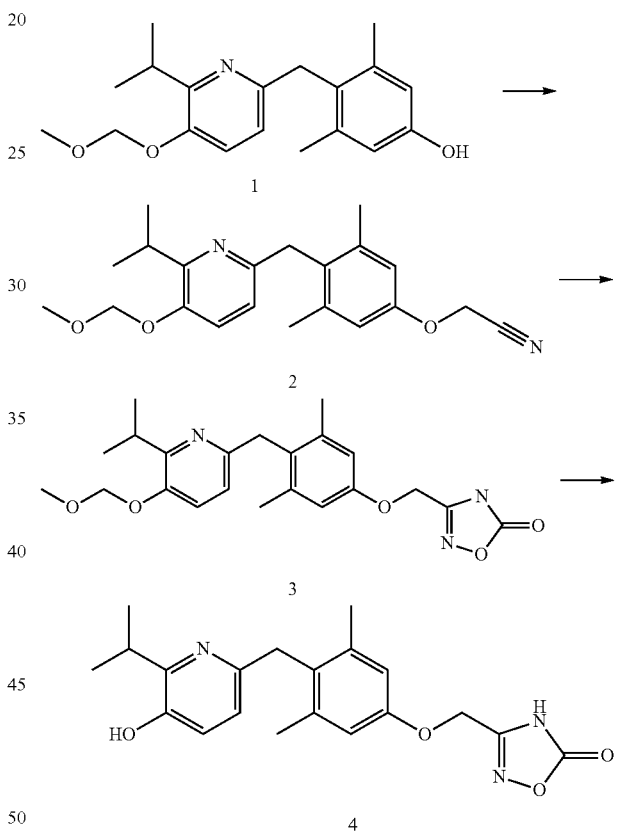

Compound 1 (93.0 mg, 0.295 mmol) was dissolved in acetonitrile (3 mL), and bromoacetonitrile (53.1 mg, 0.442 mmol) and cesium carbonate (192 mg, 0.590 mmol) were added. After stirring at room temperature for 4 hr, water was added, and the mixture was extracted with chloroform. The organic layer was dried over anhydrous sodium sulfate, filtered, and concentrated. The residue was purified by silica gel column chromatography to give compound 2 (84.3 mg, 81%).

MS m/z 355 [M+H]+, APCI(+)

Compound 2 (80.0 mg, 0.226 mmol) was dissolved in methanol (2 mL), and hydroxyamine hydrochloride (23.5 mg, 0.339 mmol) and sodium hydrogen carbonate (47.4 mg, 0.564 mmol) were added. After heating under reflux for 1.5 hr, the mixture was allowed to cool to room temperature. Water was added, and the mixture was extracted with ethyl acetate. The organic layer was dried over anhydrous sodium sulfate, filtered, and concentrated, and 1,4-dioxane (2 mL) was added. 1,1'-Carbonyldiimidazole (43.9 mg, 0.271 mmol) was added. After heating under reflux for 4 hr, the mixture was allowed to cool to room temperature, water was added, and the mixture was neutralized with 0.5N hydrochloric acid. The mixture was extracted with ethyl acetate, and the organic layer was dried over anhydrous sodium sulfate, and concentrated. The residue was purified by silica gel column chromatography to give compound 3 (80.8 mg, 86%).

MS m/z 412 [M−H]−, ESI(−)

Compound 3 (77.0 mg, 0.186 mmol) was dissolved in isopropanol (1 mL) and tetrahydrofuran (1 mL). 6N Hydrochloric acid (1 mL) was added, and the mixture was stirred for 12 hr at room temperature. The mixture was heated to 60° C. and, after 30 min, allowed to cool to room temperature, and neutralized with 2N sodium hydroxide. The mixture was extracted with ethyl acetate, and the extract was concentrated and the obtained residue was washed with diethyl ether to give compound 4 (35.3 mg, 51%).

MS m/z 368 [M−H]−, ESI(−)

Hydrobromide, hydrochloride, para-toluenesulfonate, methanesulfonate, benzenesulfonate, maleate and the like of the present compound can be produced by a general salt formation step.

Example 28

3-({4-[(6-cyclohexyl-5-hydroxypyridin-2-yl)methyl]-3,5-dimethylphenoxy}methyl)-1,2,4-oxadiazol-5(4H)-one

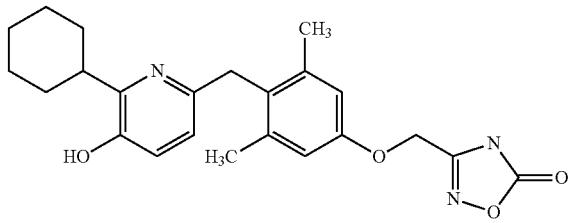 [SMILES: Cc1cc(OCc2noc(=O)[nH]2)cc(C)c1Cc1ccc(O)c(C2CCCCC2)n1]

The compound was synthesized from compound 7 of Example 2 by a method similar to that in Example 27.

MS m/z 408 [M−H]−, ESI(−)

Hydrobromide, hydrochloride, para-toluenesulfonate, methanesulfonate, benzenesulfonate, maleate and the like of the present compound can be produced by a general salt formation step.

Example 29

3-[(4-{[5-hydroxy-6-(2-naphthyl)pyridin-2-yl]methyl}-3,5-dimethylphenoxy)methyl]-1,2,4-oxadiazol-5(4H)-one

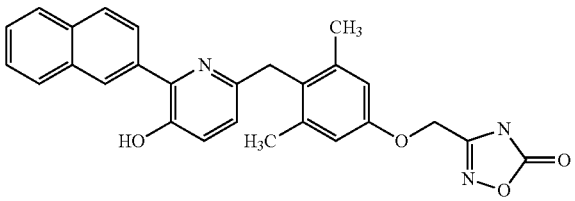 [SMILES: Cc1cc(OCc2noc(=O)[nH]2)cc(C)c1Cc1ccc(O)c(-c2ccc3ccccc3c2)n1]

The compound was synthesized from compound 4 of Example 3 by a method similar to that in Example 27.

MS m/z 452 [M−H]−, ESI(−)

Hydrobromide, hydrochloride, para-toluenesulfonate, methanesulfonate, benzenesulfonate, maleate and the like of the present compound can be produced by a general salt formation step.

Example 30

3-[(4-{[5-hydroxy-6-(5,6,7,8-tetrahydronaphthalen-2-yl)pyridin-2-yl]methyl}-3,5-dimethylphenoxy)methyl]-1,2,4-oxadiazol-5(4H)-one

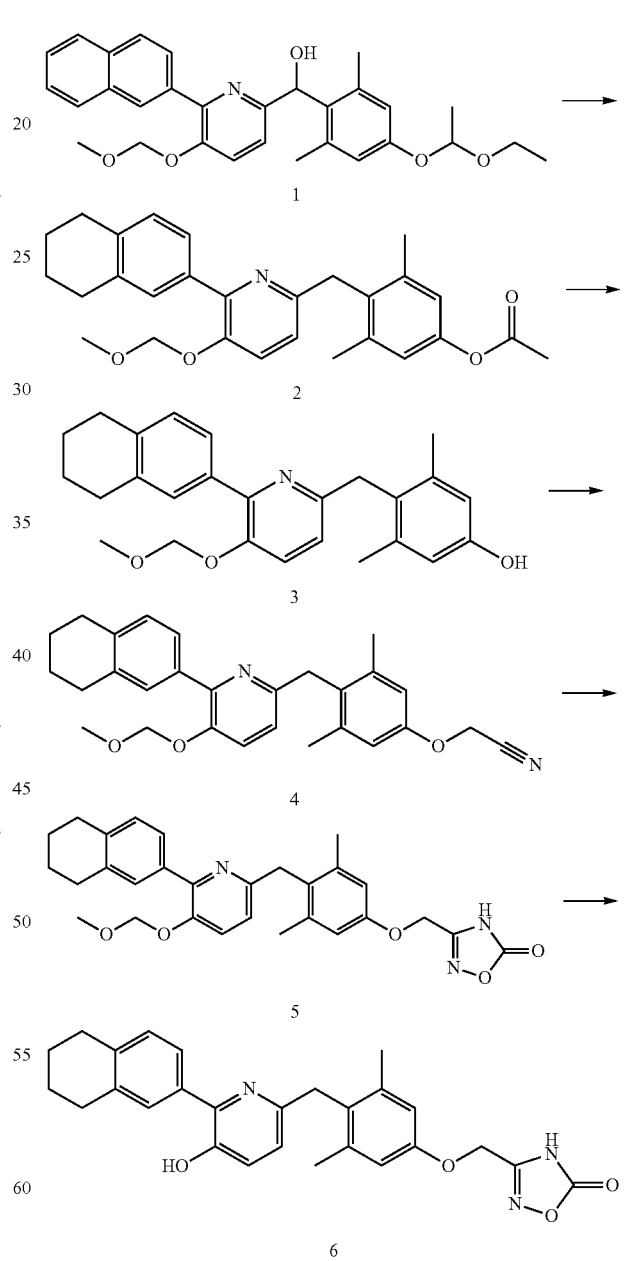

Compound 1 (425 mg, 0.873 mmol) was dissolved in ethanol (9 mL) and acetic acid (1 mL). 5% Pd/C (510 mg) was added, and the mixture was purged with hydrogen. After 16 hr, the mixture was filtered through radiolite, and washed with ethyl acetate. After concentration, acetic anhydride (0.71 mL) and pyridine (0.41 mL) were added to the obtained residue. After stirring for 21 hr, ethyl acetate was added, and the mixture was washed with 1N hydrochloric acid and saturated brine, dried over anhydrous sodium sulfate, filtered, and concentrated. The obtained residue was dissolved in ethanol (10 mL) and acetic acid (1 mL). 20% Pd(OH)$_2$/C (403 mg) was added, and the mixture was purged with hydrogen. After 5 hr, the mixture was filtered through radiolite, washed with ethanol, and concentrated. This operation of catalytic reduction was repeated twice. The obtained residue was purified by silica gel column chromatography to give compound 2 (185 mg, 48%).

MS m/z 446 [M+H]+, APCI(+)

Compound 2 (174 mg, 0.392 mmol) was dissolved in methanol (6 mL), and potassium carbonate (108 mg, 0.785 mmol) was added. After 2.5 hr, water and 1N hydrochloric acid were added, and the mixture was extracted with chloroform. The organic layer was dried over anhydrous sodium sulfate, and concentrated. The residue was purified by silica gel column chromatography to give compound 3 (151 mg, 96%).

MS m/z 404 [M+H]+, APCI(+)

Compound 6 was synthesized from compound 3 by a method similar to that in Example 27.

MS m/z 456 [M−H]−, ESI(−)

Hydrobromide, hydrochloride, para-toluenesulfonate, methanesulfonate, benzenesulfonate, maleate and the like of the present compound can be produced by a general salt formation step.

Example 31

3-({4-[(5-hydroxy-6-isopropylpyridin-2-yl)methyl]-2,3,5-trimethylphenoxy}methyl)-1,2,4-oxadiazol-5(4H)-one

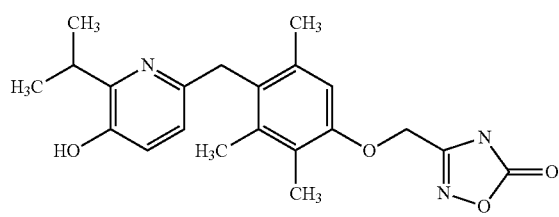 [SMILES: Cc1cc(OCc2noc(=O)[nH]2)c(C)c(C)c1Cc1ccc(O)c(C(C)C)n1]

The compound was synthesized from compound 11 of Example 4 by a method similar to that in Example 27.

MS m/z 382 [M−H]−, ESI(−)

Hydrobromide, hydrochloride, para-toluenesulfonate, methanesulfonate, benzenesulfonate, maleate and the like of the present compound can be produced by a general salt formation step.

Example 32

3-({4-[(6-cyclopentyl-5-hydroxypyridin-2-yl)methyl]-2,3,5-trimethylphenoxy}methyl)-1,2,4-oxadiazol-5(4H)-one

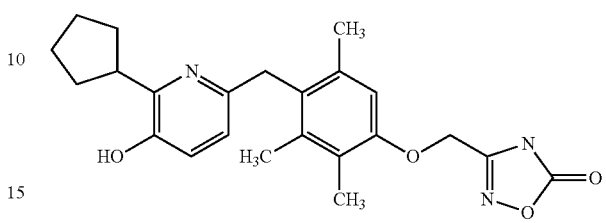

The compound was synthesized from compound 3 of Example 5 by a method similar to that in Example 27.

MS m/z 408 [M−H]−, ESI(−)

Hydrobromide, hydrochloride, para-toluenesulfonate, methanesulfonate, benzenesulfonate, maleate and the like of the present compound can be produced by a general salt formation step.

Example 33

3-[(4-{[5-hydroxy-6-(tetrahydrofuran-2-yl)pyridin-2-yl]methyl}-2,3,5-trimethylphenoxy)methyl]-1,2,4-oxadiazol-5(4H)-one

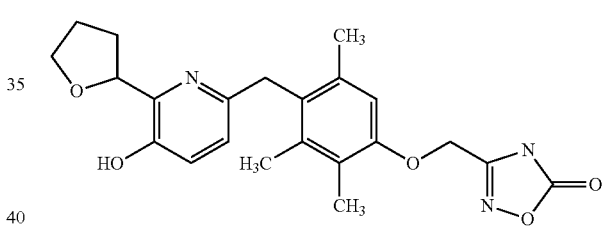

The compound was synthesized from compound 3 of Example 6 by a method similar to that in Example 27.

MS m/z 410 [M−H]−, ESI(−)

Hydrobromide, hydrochloride, para-toluenesulfonate, methanesulfonate, benzenesulfonate, maleate and the like of the present compound can be produced by a general salt formation step.

Example 34

3-({4-[(6-cyclohexyl-5-hydroxypyridin-2-yl)methyl]-2,3,5-trimethylphenoxy}methyl)-1,2,4-oxadiazol-5(4H)-one

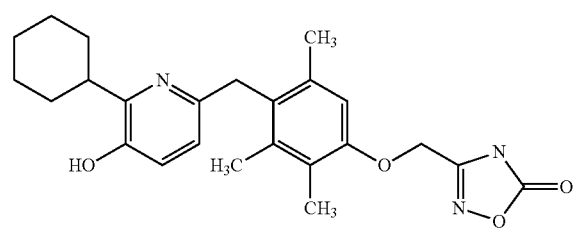

The compound was synthesized from compound 3 of Example 7 by a method similar to that in Example 27.

MS m/z 422 [M–H]–, ESI(–)

Hydrobromide, hydrochloride, para-toluenesulfonate, methanesulfonate, benzenesulfonate, maleate and the like of the present compound can be produced by a general salt formation step.

Example 35

3-[(4-{[5-hydroxy-6-(tetrahydro-2H-pyran-2-yl)pyridin-2-yl]methyl}-2,3,5-trimethylphenoxy)methyl]-1,2,4-oxadiazol-5(4H)-one

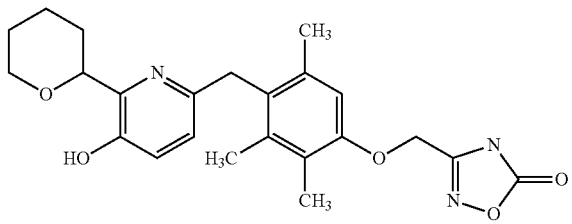 [SMILES: Cc1cc(OCc2noc(=O)[nH]2)c(C)c(C)c1Cc1ccc(O)c(C2CCCCO2)n1]

The compound was synthesized from compound 3 of Example 8 by a method similar to that in Example 27.

MS m/z 424 [M–H]–, ESI(–)

Hydrobromide, hydrochloride, para-toluenesulfonate, methanesulfonate, benzenesulfonate, maleate and the like of the present compound can be produced by a general salt formation step.

Example 36

3-({4-[(5-hydroxy-6-isopropylpyridin-2-yl)oxy]-2,3,5-trimethylphenoxy}methyl)-1,2,4-oxadiazol-5(4H)-one

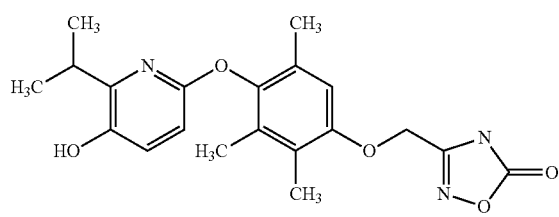 [SMILES: Cc1cc(OCc2noc(=O)[nH]2)c(C)c(C)c1Oc1ccc(O)c(C(C)C)n1]

The compound was synthesized from compound 5 of Example 9 by a method similar to that in Example 27.

MS m/z 384 [M–H]–, ESI(–)

Hydrobromide, hydrochloride, para-toluenesulfonate, methanesulfonate, benzenesulfonate, maleate and the like of the present compound can be produced by a general salt formation step.

Example 37

3-({2-fluoro-4-[(5-hydroxy-6-isopropylpyridin-2-yl)methyl]-3,5-dimethylphenoxy}methyl)-1,2,4-oxadiazol-5(4H)-one

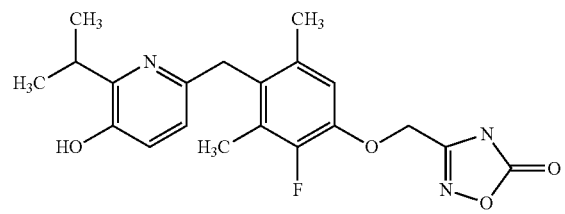 [SMILES: Cc1cc(OCc2noc(=O)[nH]2)c(F)c(C)c1Cc1ccc(O)c(C(C)C)n1]

The compound was synthesized from compound 5 of Example 11 by a method similar to that in Example 27.

MS m/z 386 [M–H]–, ESI(–)

Hydrobromide, hydrochloride, para-toluenesulfonate, methanesulfonate, benzenesulfonate, maleate and the like of the present compound can be produced by a general salt formation step.

Example 38

(4-{[5-hydroxy-6-({[(2R)-2-phenylpropyl]amino}carbonyl)pyridin-2-yl]methyl}-2,3,5-trimethylphenoxy)acetic acid

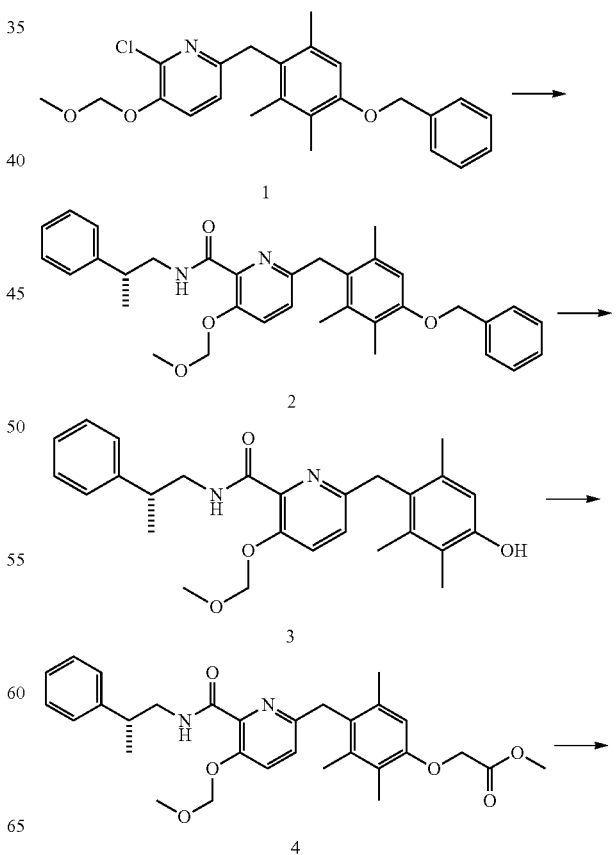

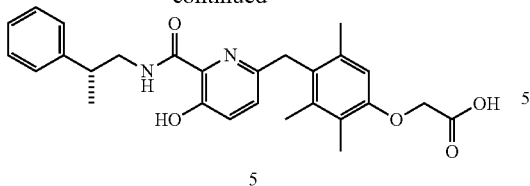

Compound 1 (309 mg, 0.75 mmol), molybdenum hexacarbonyl (396 mg, 1.5 mmol), palladium(II) acetate (34 mg, 0.15 mmol), BINAP (93 mg, 0.15 mmol), cesium carbonate (269 mg, 0.825 mmol) were suspended in toluene (7.5 mL) and, after purging with argon, (R)-β-methylphenethylamine (132 mg, 0.975 mmol) and acetonitrile (3.75 mL) were added, and the mixture was stirred at 80° C. for 1 hr. The mixture was allowed to cool to room temperature, and iodine (381 mg, 1.5 mmol) was added. The mixture was stirred for 1 hr and filtered through celite. Ethyl acetate, and aqueous sodium sulfite solution were added, and the mixture was stirred for 30 min and filtered through celite. The mixture was extracted with ethyl acetate, and the organic layer was washed with water and saturated brine, dried over anhydrous sodium sulfate, filtered, and concentrated. The residue was purified by silica gel column chromatography to give compound 2 (241 mg, 60%).

MS m/z 539 [M+H]+, APCI(+)

Compound 3 was synthesized by a method similar to that for compound 11 of Example 4.

MS m/z 449 [M+H]+, APCI(+)

Compound 4 was synthesized by a method similar to that for compound 12 of Example 4.

MS m/z 521 [M+H]+, APCI(+)

Compound 5 was synthesized by a method similar to that for compound 13 of Example 4.

MS m/z 461 [M−H]−, ESI(−)

Hydrobromide, hydrochloride, para-toluenesulfonate, methanesulfonate, benzenesulfonate, maleate and the like of the present compound can be produced by a general salt formation step.

Example 39

2-cyclohexyl-6-[4-(3-hydroxyisoxazol-5-yl)-2,3,6-trimethylbenzyl]pyridin-3-ol

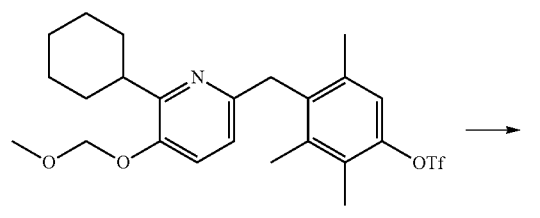

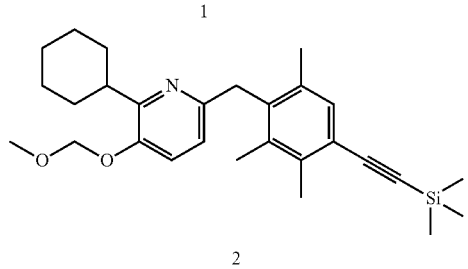

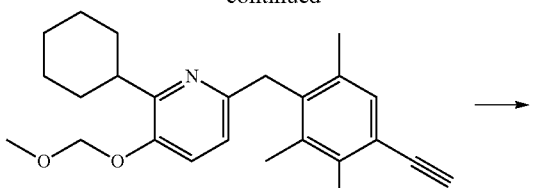

Compound 1 (355 mg, 0.708 mmol) was dissolved in N,N-dimethylformamide (5 mL), triethylamine (1.5 mL), trimethylsilylacetylene (104 mg, 1.06 mmol), dichlorobis(triphenylphosphine)palladium(II) (25 mg, 0.035 mmol), copper iodide (20 mg, 0.106 mmol), and tetrabutylammonium iodide (392 mg, 1.06 mmol) were added, and the mixture was purged with argon. The mixture was stirred at 70° C. for 4 hr, and heated to 80° C. After stirring for 1 hr, the mixture was allowed to cool to room temperature, saturated aqueous ammonium chloride solution was added, and the mixture was extracted with ethyl acetate. The organic layer was washed with saturated aqueous sodium hydrogen carbonate, and saturated brine, dried over anhydrous magnesium sulfate, filtered and concentrated. The residue was purified by silica gel column chromatography to give compound 2 (299 mg, 94%).

MS m/z 450 [M+H]+, APCI(+)

Compound 2 (295 mg, 0.656 mmol) was dissolved in methanol (6 mL) and dichloromethane (3 mL), and ice-cooled. Potassium carbonate (136 mg, 0.984 mmol) was added, and the mixture was heated to room temperature. After stirring for 1 hr, potassium carbonate (136 mg, 0.984 mmol) was added. After stirring for 2.5 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 3 (237 mg, 96%).

MS m/z 378 [M+H]⁺, APCI(+)

Compound 3 (233 mg, 0.617 mmol) was dissolved in tetrahydrofuran (6 mL), and the mixture was cooled to −78° C. Lithium hexamethyl disilazide (1M tetrahydrofuran solution, 0.741 mL, 0.741 mmol) was added dropwise. After stirring for 2 hr, ethyl chloroformate (134 mg, 1.23 mmol) was added dropwise, and the mixture was heated to room temperature. After 1.5 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 4 (210 mg, 76%).

MS m/z 450 [M+H]⁺, APCI(+)

Compound 4 (207 mg, 0.460 mmol) was dissolved in ethanol (5 mL) and dichloromethane (0.5 mL), and added dropwise to a mixed solution of ice-cooled hydroxylamine hydrochloride (96 mg, 1.38 mmol) and 10% aqueous sodium hydroxide solution (1.84 mL, 4.60 mmol) over 5 min. After stirring for 10 min, the mixture was heated to 40° C. After stirring for 16 hr, the mixture was allowed to cool to room temperature, and neutralized with 2N hydrochloric acid. Saturated brine was added, the mixture was extracted with ethyl acetate, and the organic layer was dried over anhydrous magnesium sulfate, filtered and concentrated. The residue was purified by silica gel column chromatography to give compound 5 (171 mg, 85%).

MS m/z 435 [M−H]−, ESI(−)

Compound 5 (169 mg, 0.387 mmol) was dissolved in methanol (1.5 mL) and tetrahydrofuran (1.5 mL), 6N hydrochloric acid (1.5 mL) was added, and the mixture was heated to 50° C. After stirring for 6.5 hr, the mixture was allowed to cool to room temperature, and neutralized with 2N aqueous sodium hydroxide solution. After extraction with ethyl acetate, the organic layer was washed with saturated brine, dried over anhydrous magnesium sulfate, filtered and concentrated. The obtained residue was suspension washed with chloroform to give compound 6 (122 mg, 80%).

MS m/z 391 [M−H]−, ESI(−)

Hydrobromide, hydrochloride, para-toluenesulfonate, methanesulfonate, benzenesulfonate, maleate and the like of the present compound can be produced by a general salt formation step.

Example 40

{4-[(5-hydroxy-6-pyrrolidin-1-ylpyridin-2-yl)methyl]-2,3,5-trimethylphenoxy}acetic acid

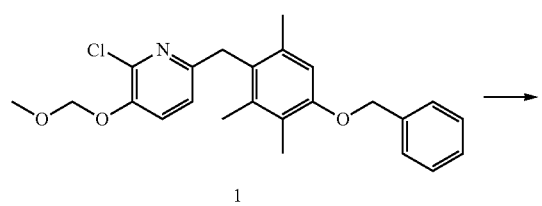

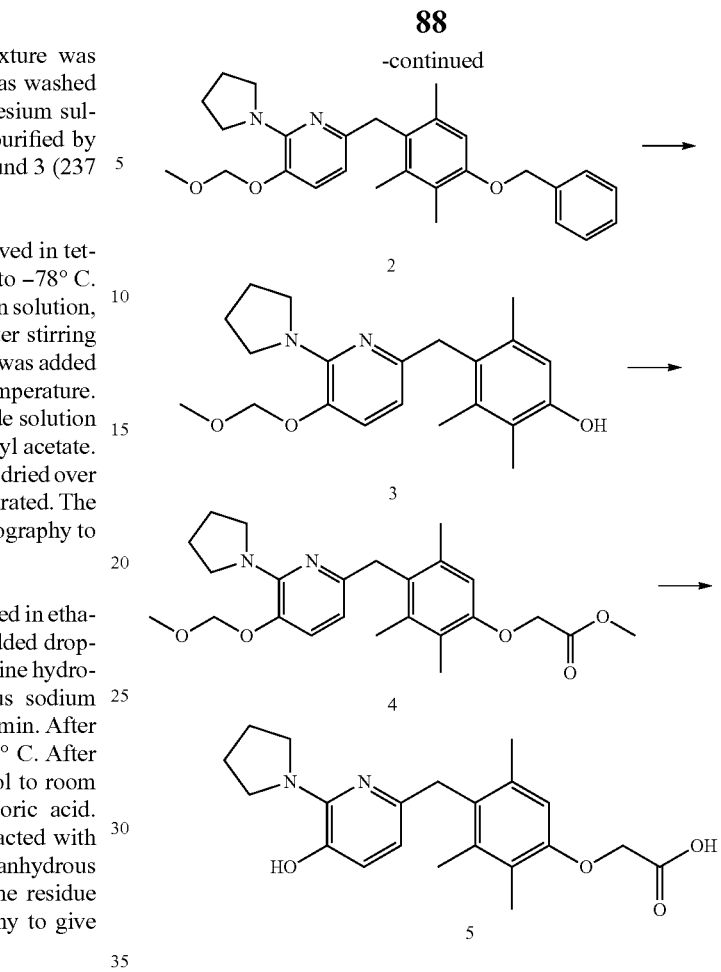

Compound 1 (206 mg, 0.500 mmol) was dissolved in dimethylsulfoxide (1 mL), pyrrolidine (356 mg, 5 mmol) was added, and the mixture was reacted in a microwave reactor at 160° C. for 2 hr. The mixture was allowed to cool to room temperature, ethyl acetate, and aqueous sodium bicarbonate solution were added and the mixture was stirred. The mixture was extracted with ethyl acetate, and the organic layer was washed with water and saturated brine, dried over anhydrous sodium sulfate, filtered, and concentrated. The residue was purified by silica gel column chromatography to give compound 2 (95.5 mg, 43%).

MS m/z 447 [M+H]⁺, APCI(+)

Compound 3 was synthesized by a method similar to that for compound 11 of Example 4.

MS m/z 357 [M+H]⁺, APCI(+)

Compound 4 was synthesized by a method similar to that for compound 12 of Example 4.

MS m/z 429 [M+H]⁺, APCI(+)

Compound 5 was synthesized by a method similar to that for compound 13 of Example 4.

MS m/z 371 [M+H]⁺, APCI(+)

Hydrobromide, hydrochloride, para-toluenesulfonate, methanesulfonate, benzenesulfonate, maleate and the like of the present compound can be produced by a general salt formation step.

Example 41

{4-[(6-cyclohexyl-5-hydroxypyridin-2-yl)methyl]-2,3,5-trimethylphenyl}acetic acid

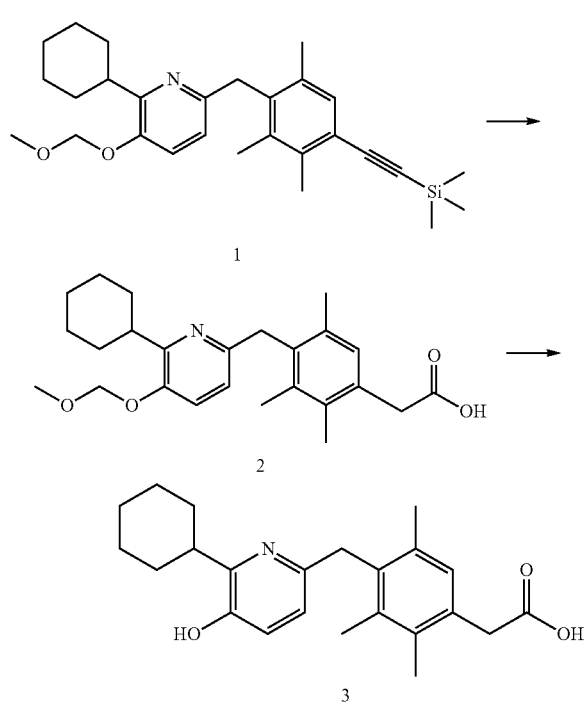

Borane-tetrahydrofuran complex (1M tetrahydrofuran solution, 1.55 mL) was purged with argon, ice-cooled, and cyclohexene (256 mg, 3.10 mmol) was added dropwise. Compound 1 (200 mg, 0.445 mmol) was dissolved in tetrahydrofuran (1.5 mL), added dropwise to the solution above, and the mixture was stirred at 0° C. for 2 hr. 1N Aqueous sodium hydroxide solution (1.26 mL) and methanol (1.5 mL) were combined and added 50 dropwise, 33% aqueous hydrogen peroxide solution (0.75 mL) was added dropwise, and the mixture was stirred at 0° C. for 1 hr. The mixture was concentrated, 1N hydrochloric acid and ethyl acetate were added and the mixture was stirred. The mixture was extracted with ethyl acetate, and the extract was dried over anhydrous sodium sulfate, filtered, and concentrated. The residue was purified by silica gel column chromatography to give compound 2 (149 mg, 81%).

MS m/z 410 [M−H]−, ESI(−)

Compound 3 was synthesized by a method similar to that for compound 13 of Example 4.

MS m/z 366 [M−H]−, ESI(−)

Hydrobromide, hydrochloride, para-toluenesulfonate, methanesulfonate, benzenesulfonate, maleate and the like of the present compound can be produced by a general salt formation step.

Example 42

4-[(6-cyclohexyl-5-hydroxypyridin-2-yl)methyl]-2,3,5-trimethylbenzoic acid

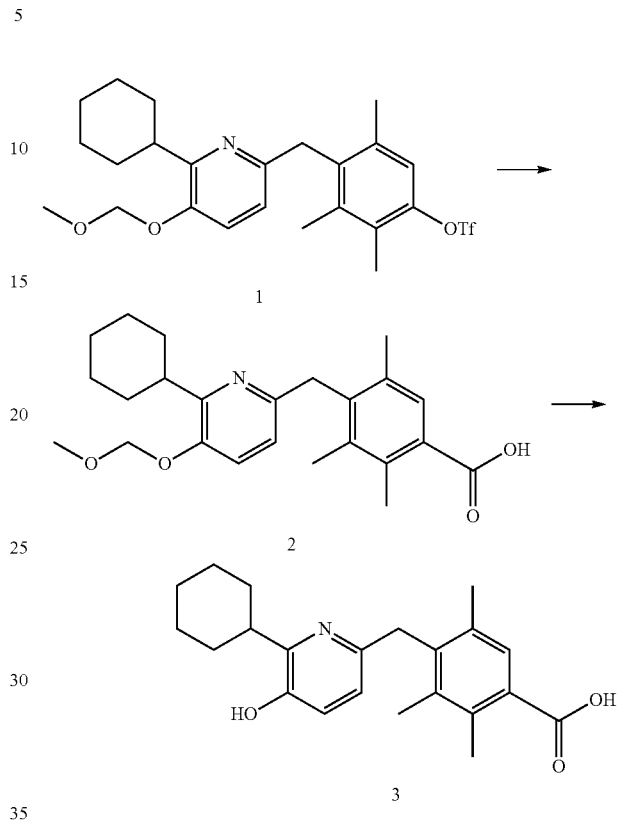

Compound 1 (251 mg, 0.50 mmol), molybdenum hexacarbonyl (264 mg, 1.0 mmol), palladium acetate (22 mg, 0.10 mmol), BINAP (62 mg, 0.10 mmol), and cesium carbonate (179 mg, 0.55 mmol) were suspended in toluene (5 mL) and, after purging with argon, methanol (320 mg, 10 mmol) and acetonitrile (2.5 mL) were added, and the mixture was stirred at 90° C. overnight. The mixture was allowed to cool to room temperature, iodine (254 mg, 1.0 mmol) was added and the mixture was stirred for 1 hr, and filtered through celite. Ethyl acetate, and aqueous sodium sulfite solution were added and the mixture was stirred for 30 min, and filtered through celite. The organic layer was washed with water and saturated brine, dried over anhydrous sodium sulfate, filtered, and concentrated. The residue was purified by silica gel column chromatography to give compound 2 (27 mg, 14%) and , corresponding methyl ester form (88 mg, 42%).

MS m/z 396 [M−H]−, ESI(−)

Compound 2 (26 mg, 0.066 mmol) was dissolved in tetrahydrofuran (0.8 mL). 6N Hydrochloric acid (0.2 mL) was added, and the mixture was heated to 50° C. After 3 hr, the mixture was allowed to cool to room temperature, saturated aqueous sodium hydrogen carbonate was added, and the mixture was extracted with ethyl acetate. The organic layer was washed with saturated aqueous ammonium chloride solution and water, dried over anhydrous sodium sulfate, filtered and concentrated. The residue was washed with ether-hexane to give compound 3 (17 mg, 76%).

MS m/z 352 [M−H]−, ESI(−)

Hydrobromide, hydrochloride, para-toluenesulfonate, methanesulfonate, benzenesulfonate, maleate and the like of the present compound can be produced by a general salt formation step.

Example 43

{2-chloro-4-[(6-cyclohexyl-5-hydroxypyridin-2-yl)methyl]-3,5-dimethylphenoxy}acetic acid

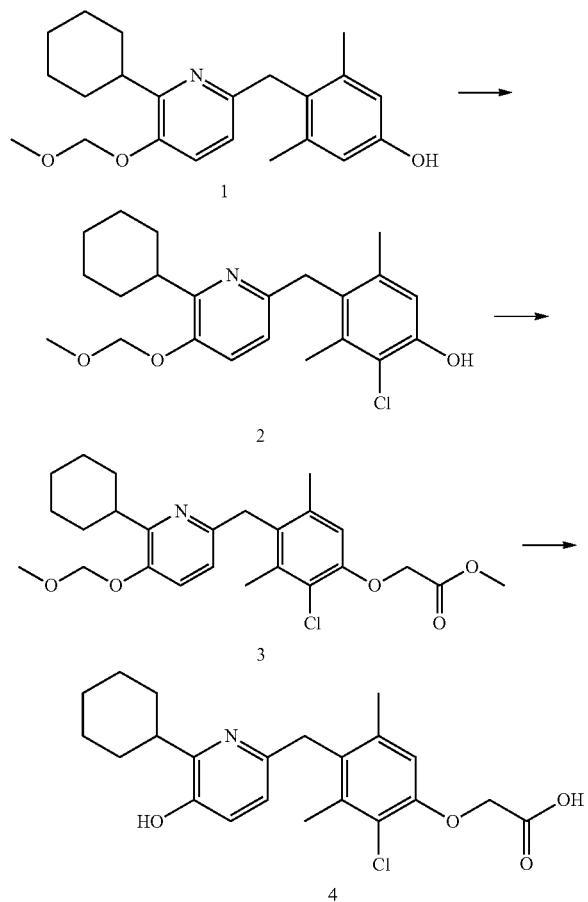

Compound 1 (1.00 g, 2.81 mmol) was dissolved in carbon tetrachloride (20 mL), and the mixture was cooled to 0° C. tert-Butyl hypochlorite (336 mg, 3.09 mmol) was slowly added dropwise, and the mixture was stirred for 2 hr. Water was added, and the mixture was extracted with ethyl acetate and the extract was washed with saturated brine, dried over anhydrous magnesium sulfate, filtered, and concentrated. The residue was purified by silica gel column chromatography to give compound 2 (312 mg, 28%).

MS m/z 390/392 [M+H]+, APCI(+)

Compound 2 (220 mg, 0.56 mmol) was dissolved in acetonitrile (3 mL), and methyl bromoacetate (130 mg, 0.850 mmol) and cesium carbonate (276 mg, 0.847 mmol) were added. After stirring for 4 hr, water was added, and the mixture was extracted with ethyl acetate and washed with saturated brine. The organic layer was dried over anhydrous magnesium sulfate, filtered, and concentrated. The residue was purified by silica gel column chromatography to give compound 3 (211 mg, 81%).

MS m/z 462/464 [M+H]+, APCI(+)

Compound 3 (211 mg, 0.457 mmol) was dissolved in methanol (2 mL) and tetrahydrofuran (2 mL). 6N Hydrochloric acid (2 mL) was added and the mixture was stirred at 60° C. for 4 hr. The mixture was allowed to cool to room temperature, and neutralized with 1N aqueous sodium hydroxide solution. After extraction with ethyl acetate, the organic layer was washed with saturated brine, dried over anhydrous magnesium sulfate, filtered and concentrated. The obtained residue was dissolved in methanol (2 mL) and tetrahydrofuran (2 mL), and 1N sodium hydroxide (2 mL) was added and the mixture was stirred at 60° C. for 1 hr. The mixture was allowed to cool to room temperature, neutralized with 1N hydrochloric acid, and extracted with ethyl acetate-tetrahydrofuran mixed solvent. The extract was dried over anhydrous magnesium sulfate, filtered and concentrated. The obtained residue was suspension washed with ether, and a powder obtained by filtration was dried under reduced pressure to give compound 4 (141 mg, 77%).

MS m/z 402/404 [M−H]−, ESI(−)

Hydrobromide, hydrochloride, para-toluenesulfonate, methanesulfonate, benzenesulfonate, maleate and the like of the present compound can be produced by a general salt formation step.

Example 44

{2-cyano-4-[(6-cyclohexyl-5-hydroxypyridin-2-yl)methyl]-3,5-dimethylphenoxy}acetic acid

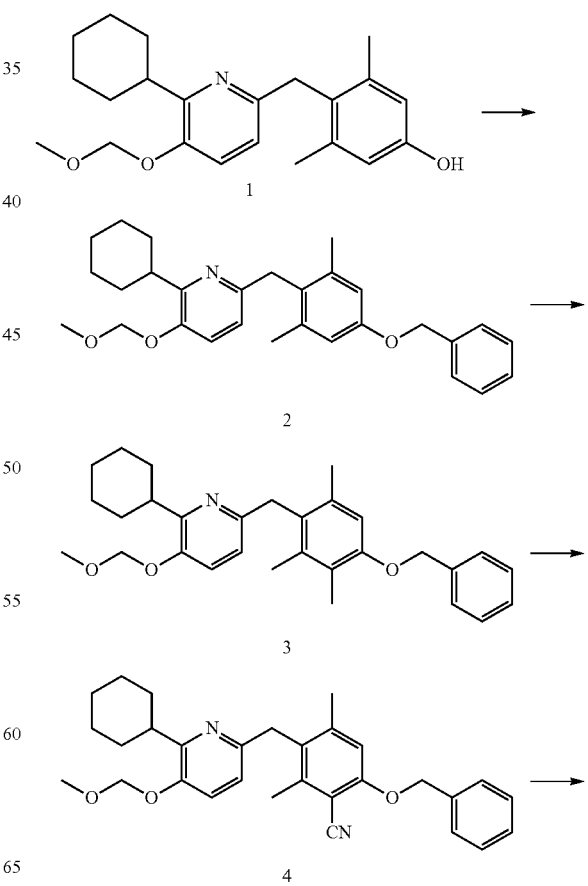

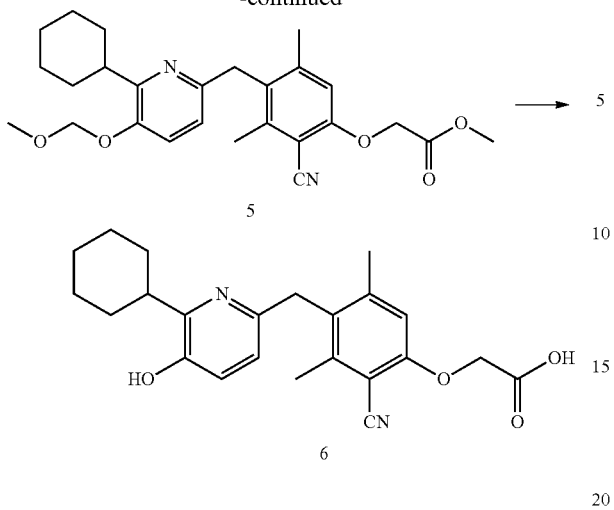

Compound 1 (3.80 g, 10.7 mmol) was dissolved in acetonitrile (40 mL), benzyl bromide (1.4 mL, 11.0 mmol), and cesium carbonate (5.23 g, 16.0 mmol) were added. After stirring overnight, the mixture was filtered through radiolite, and concentrated. The residue was purified by silica gel column chromatography to give compound 2 (4.55 g, 90%).

MS m/z 471 [M+H]$^+$, APCI(+)

Compound 2 (4.55 g, 10.2 mmol) was dissolved in dichloromethane (90 mL), and iodine (3.37 g, 13.2 mmol) and silver acetate (2.21 g, 13.2 mmol) were added. Under light shielding, the mixture was stirred overnight, and filtered through radiolite. The filtrate was washed successively with sodium thiosulfate aqueous solution, saturated aqueous sodium hydrogen carbonate, water and saturated brine, and dried over anhydrous magnesium sulfate, filtered, concentrated. The residue was purified by silica gel column chromatography to give compound 3 (5.43 g, 93%).

MS m/z 572 [M+H]$^+$, APCI(+)

Compound 3 (1.00 g, 1.75 mmol) was dissolved in degassed N,N'-dimethylformamide (20 mL), and copper(I) iodide (33 mg, 0.173 mmol), and zinc cyanide (411 mg, 3.50 mmol) were added, and the mixture was purged with argon. Tetrakis(triphenylphosphine)palladium(0) (102 mg, 0.0883 mmol) was added, and the mixture was stirred at 90° C. overnight. The mixture was allowed to cool to room temperature, saturated aqueous sodium hydrogen carbonate solution was added, and the mixture was filtered through radiolite. After extraction with ethyl acetate, the organic layer was washed successively with water and saturated brine, dried over anhydrous sodium sulfate, filtered, and concentrated. The residue was purified by silica gel column chromatography to give compound 4 (158 mg, 19%).

MS m/z 471 [M+H]$^+$, APCI(+)

Compound 5 was synthesized by a method similar to that for compound 8 of Example 2.

MS m/z 453 [M+H]$^+$, APCI(+)

Compound 6 was synthesized by a method similar to that for compound 13 of Example 4.

MS m/z 393 [M−H]−, ESI(−)

Hydrobromide, hydrochloride, para-toluenesulfonate, methanesulfonate, benzenesulfonate, maleate and the like of the present compound can be produced by a general salt formation step.

Example 45

({5-[(6-cyclohexyl-5-hydroxypyridin-2-yl)methyl]-3,4,6-trimethylpyridin-2-yl}oxy)acetic acid

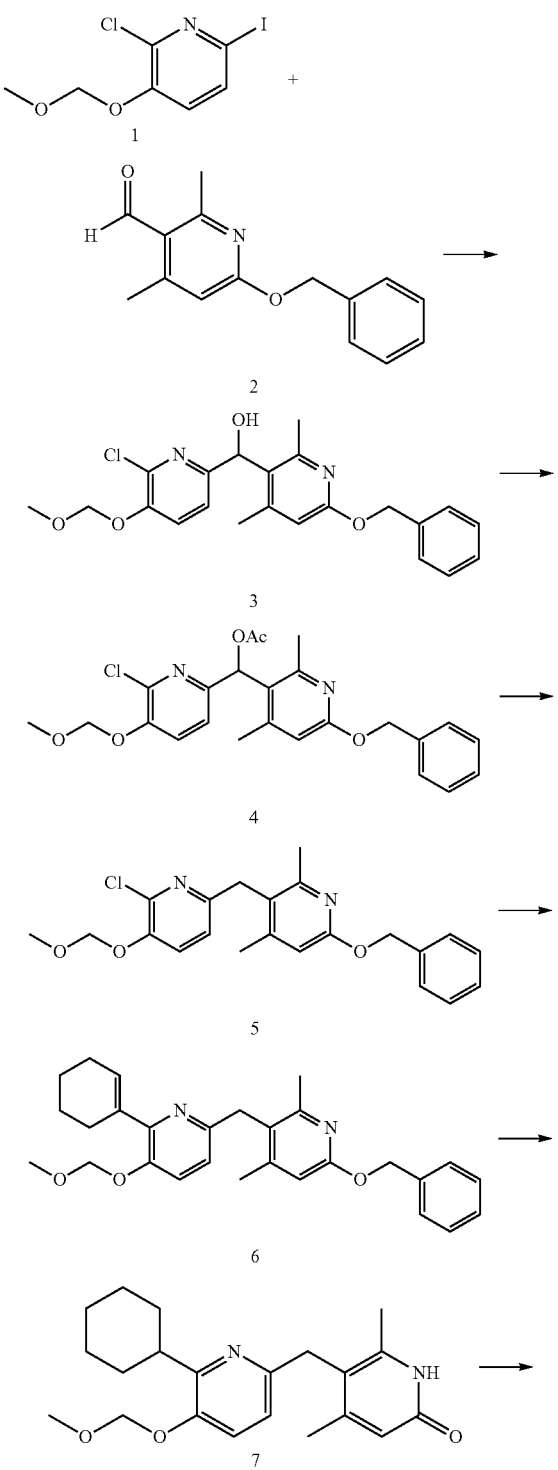

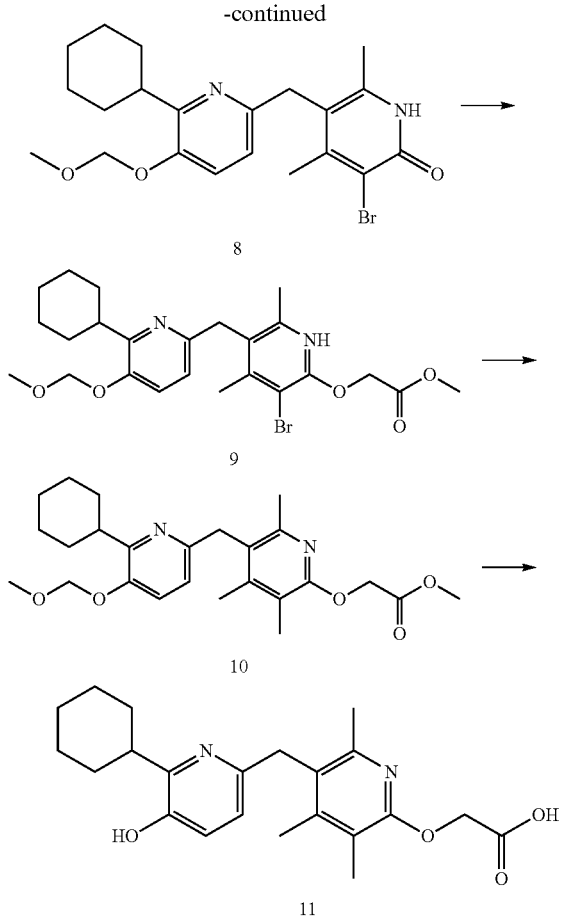

Compound 1 (3.30 g, 11.0 mmol) was dissolved in toluene (66 mL) and, after cooling to −78° C., n-butyllithium (2.6 M hexane solution, 4.45 mL, 11.6 mmol) was added, and the mixture was stirred. After 30 min, a solution of compound 2 (2.92 g, 12.1 mmol) in toluene was added dropwise by small portions, and the mixture was stirred for 1 hr and allowed to warm to room temperature. After stirring for 2 hr, saturated aqueous ammonium chloride solution was added, and the reaction mixture was extracted with ethyl acetate. The organic layer was washed with saturated brine, dried over anhydrous sodium sulfate, filtered and concentrated. The residue was purified by silica gel column chromatography to give compound 3 (3.03 g, 66%).

MS m/z 415/417 [M+H]+, APCI(+)

Compound 3 (3.02 g, 7.28 mmol) was dissolved in pyridine (2.30 g, 29.1 mmol), and acetic anhydride (2.23 g, 21.8 mmol) was added. After stirring overnight, the reaction mixture was concentrated, and the residue was dried azeotropically with toluene. The residue was purified by silica gel column chromatography to give compound 4 (3.17 g, 95%).
MS m/z 457/459 [M+H]+, APCI(+)

Compound 4 (3.17 g, 6.94 mmol) was dissolved in methylene chloride (63 mL), triethylsilane (968 mg, 8.32 mmol) was added and the mixture was ice-cooled. Boron trifluoride-diethyl ether complex (3.54 g, 25.0 mmol) was added dropwise over 1 hr. After stirring for 30 min, saturated aqueous sodium hydrogen carbonate was added, and the mixture was extracted with ethyl acetate. The organic layer was washed with saturated brine, dried over anhydrous sodium sulfate, filtered and concentrated. The residue was dissolved in aceto- nitrile (63 mL), chloromethyl methyl ether (558 mg, 6.94 mmol) and cesium carbonate (2.26 g, 6.94 mmol) was added. After stirring overnight, water was added, and the mixture was extracted with ethyl acetate. The organic layer was washed with saturated brine, dried over anhydrous sodium sulfate, filtered and concentrated. The residue was purified by silica gel column chromatography to give compound 5 (637 mg, 23%).

MS m/z 399/401 [M+H]+, APCI(+)

Compound 5 (610 mg, 1.53 mmol) was dissolved in 1,4-dioxane (12 mL), and cesium carbonate (1.49 g, 4.59 mmol), and 1-cyclohexeneboronic acid (304 mg, 2.29 mmol) were added, and the mixture was purged with argon. [1,1'-Bis(diphenylphosphino)ferrocene]dichloropalladium(II)-dichloromethane complex (125 mg, 0.15 mmol) was added, and the mixture was heated under reflux. After stirring overnight, the mixture was allowed to cool to room temperature, filtered through celite, and thoroughly washed with ethyl acetate. After concentration, the residue was purified by silica gel column chromatography to give compound 6 (586 mg, 86%).

MS m/z 445 [M+H]+, APCI(+)

Compound 6 (584 mg, 1.31 mmol) was dissolved in ethanol (58 mL) and, after purging with argon, 10% Pd/C (292 mg) was added. After purging with hydrogen, the mixture was stirred for 1 day. The reaction solution was filtered through celite, and washed with ethyl acetate. The filtrate was concentrated to give compound 7 (464 mg, 99%).

MS m/z 357 [M+H]+, APCI(+)

Compound 7 (460 mg, 1.29 mmol) was dissolved in chloroform (9 mL) and, after ice-cooling, N-bromosuccinimide (290 mg, 1.63 mmol) was added. After stirring for 3 hr, saturated aqueous sodium hydrogen carbonate was added, and the mixture was extracted with chloroform. The organic layer was washed with saturated brine, dried over anhydrous sodium sulfate, filtered and concentrated. The residue was purified by silica gel column chromatography to give compound 8 (546 mg, 97%).

MS m/z 435/437 [M+H]+, APCI(+)

Compound 8 (387 mg, 0.888 mmol) was dissolved in N,N'-dimethylformamide (8 mL), and methyl bromoacetate (215 mg, 1.33 mmol) and silver carbonate (735 mg, 2.66 mmol) were added, and the mixture was heated to 80° C. The mixture was stirred overnight, and filtered through celite. Water was added, and the mixture was extracted with ethyl acetate. The organic layer was washed with saturated brine, dried over anhydrous sodium sulfate, filtered and concentrated. The residue was purified by silica gel column chromatography to give compound 9 (360 mg, 80%).

MS m/z 507/509 [M+H]+, APCI(+)

Compound 9 (359 mg, 0.708 mmol) was dissolved in 1,4-dioxane (12 mL), and potassium carbonate (293 mg, 2.12 mmol), and trimethylboroxine (234 mg, 1.77 mmol) were added, and the mixture was purged with argon. [1,1'-Bis(diphenylphosphino)ferrocene]dichloropalladium(II)-dichloromethane complex (29.0 mg, 0.0354 mmol) was added, and the mixture was heated under reflux. After stirring overnight, the mixture was allowed to cool to room temperature. Water was added, and the mixture was extracted with ethyl acetate. The organic layer was washed with saturated brine, dried over anhydrous sodium sulfate, filtered and concentrated. The residue was purified by silica gel column chromatography to give compound 10 (302 mg, 96%).

MS m/z 443 [M+H]+, APCI(+)

Compound 10 (294 mg, 0.665 mmol) was dissolved in methanol (2.0 mL) and tetrahydrofuran (2.0 mL). 6N Hydrochloric acid (2.0 mL) was added, and the mixture was heated to 60° C. After stirring for 2 hr, the mixture was allowed to cool to room temperature. The mixture was neutralized with 4N aqueous sodium hydroxide solution, and extracted with ethyl acetate. The organic layer was washed with saturated brine, and dried over anhydrous sodium sulfate. After filtration, the filtrate was concentrated, and the residue was dissolved in methanol (6 mL). 2N Sodium hydroxide (1.0 mL) was added, and the mixture was heated to 60° C. and stirred for 2 hr. After allowing to cool to room temperature, the mixture was neutralized with 1N hydrochloric acid and extracted with ethyl acetate. The organic layer was washed with saturated brine, dried over anhydrous sodium sulfate, filtered and concentrated. The obtained residue was suspension washed with hexane to give compound 11 (223 mg, 87%).

MS m/z 383 [M−H]−, ESI(−)

Hydrobromide, hydrochloride, para-toluenesulfonate, methanesulfonate, benzenesulfonate, maleate and the like of the present compound can be produced by a general salt formation step.

Example 46

3-[({5-[(6-cyclohexyl-5-hydroxypyridin-2-yl)methyl]-3,4,6-trimethylpyridin-2-yl}oxy)methyl]-1,2,4-oxadiazol-5(4H)-one

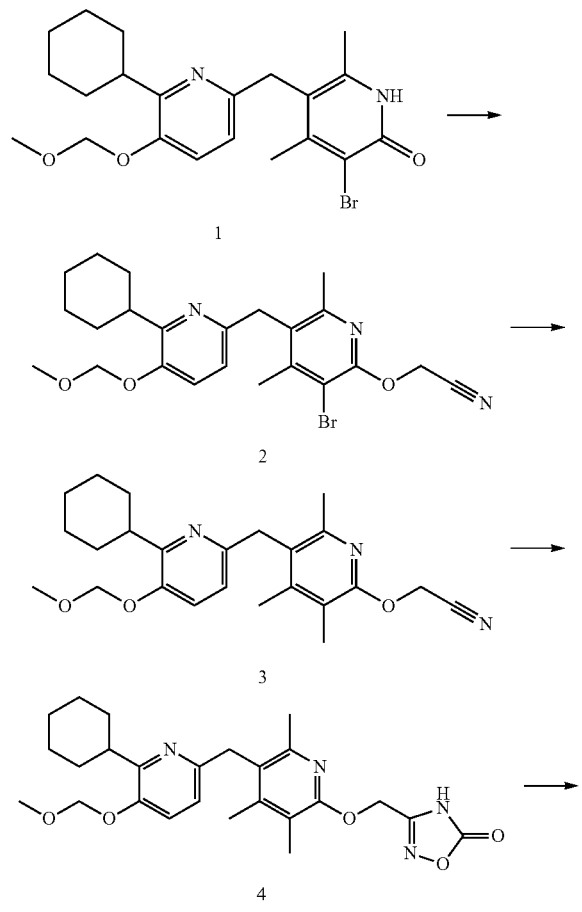

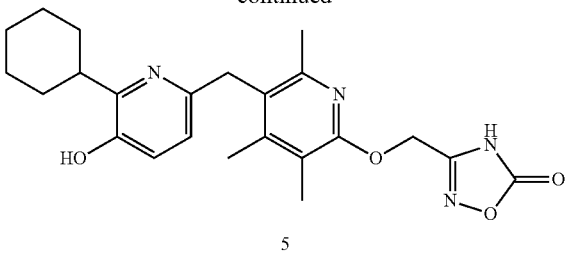

Compound 1 (154 mg, 0.354 mmol) was dissolved in N,N'-dimethylformamide (3 mL), and bromoacetonitrile (65.6 mg, 0.531 mmol) and silver carbonate (293 mg, 1.06 mmol) were added, and the mixture was heated to 80° C. The mixture was stirred overnight, and filtered through celite. Water was added, and the mixture was extracted with ethyl acetate. The organic layer was washed with saturated brine, dried over anhydrous sodium sulfate, filtered and concentrated. The residue was purified by silica gel column chromatography to give compound 2 (80 mg, 48%).

MS m/z 474/476 [M+H]+, APCI(+)

Compound 2 (80 mg, 0.168 mmol) was dissolved in 1,4-dioxane (2 mL), and potassium carbonate (70 mg, 0.504 mmol), and trimethylboroxine (55.6 mg, 0.420 mmol) were added, and the mixture was purged with argon. [1,1'-Bis (diphenylphosphino)ferrocene]dichloropalladium(II)-dichloromethane complex (6.90 mg, 0.00845 mmol) was added and the mixture was heated under reflux. After stirring overnight, the mixture was allowed to cool to room temperature. Water was added, and the mixture was extracted with ethyl acetate. The organic layer was washed with saturated brine, dried over anhydrous sodium sulfate, filtered and concentrated. The residue was purified by silica gel column chromatography to give compound 3 (61 mg, 89%).

MS m/z 410 [M+H]+, APCI(+)

Compound 3 (59.0 mg, 0.144 mmol) was dissolved in methanol (1 mL), and hydroxyamine hydrochloride (15.8 mg, 0.216 mmol) and sodium hydrogen carbonate (36.3 mg, 0.432 mmol) were added. After heating under reflux overnight, the mixture was allowed to cool to room temperature. Water was added, and the mixture was extracted with ethyl acetate. The organic layer was washed with saturated brine, dried over anhydrous sodium sulfate, filtered, and concentrated. The residue was dissolved in 1,4-dioxane (1 mL), and 1,1'-carbonyldiimidazole (35.0 mg, 0.216 mmol) was added. After stirring for 1 hr, the mixture was heated under reflux. After stirring for 5 hr, the mixture was allowed to cool to room temperature, water was added, saturated aqueous ammonium chloride solution was added, and the mixture was extracted with ethyl acetate. The organic layer was dried over anhydrous sodium sulfate, and concentrated. The residue was purified by silica gel column chromatography to give compound 4 (14.2 mg, 21%). Compound 4 (14.2 mg, 0.0303 mmol) was dissolved in methanol (1 mL) and tetrahydrofuran (1 mL). 6N Hydrochloric acid (0.5 mL) was added, and the mixture was heated to 60° C. After 3 hr, the mixture was allowed to cool to room temperature, and neutralized with 2N sodium hydroxide. The mixture was extracted with ethyl acetate, and the organic layer was washed with saturated brine, dried over anhydrous sodium sulfate, filtered, and concentrated. The residue was purified by silica gel column chromatography to give compound 5 (9.8 mg, 76%).

MS m/z 423 [M−H]−, ESI(−)

Hydrobromide, hydrochloride, para-toluenesulfonate, methanesulfonate, benzenesulfonate, maleate and the like of the present compound can be produced by a general salt formation step.

Example 47

(4-{[6-cyclohexyl-5-(formylamino)pyridin-2-yl]methyl}-2,3,5-trimethylphenoxy)acetic acid

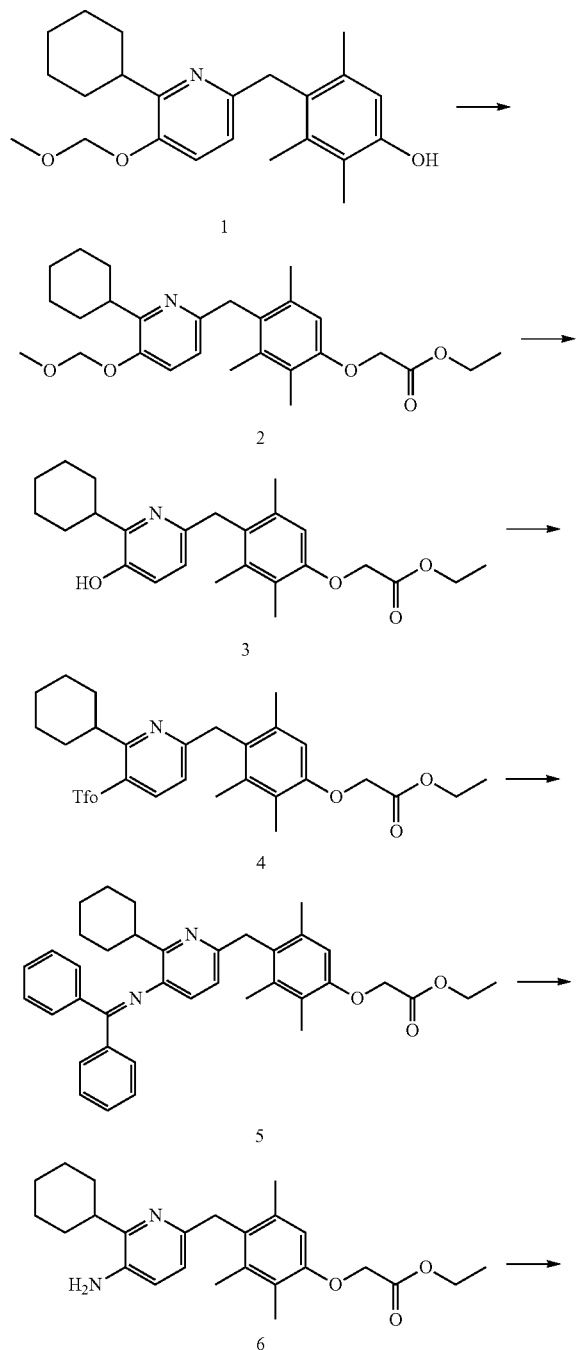

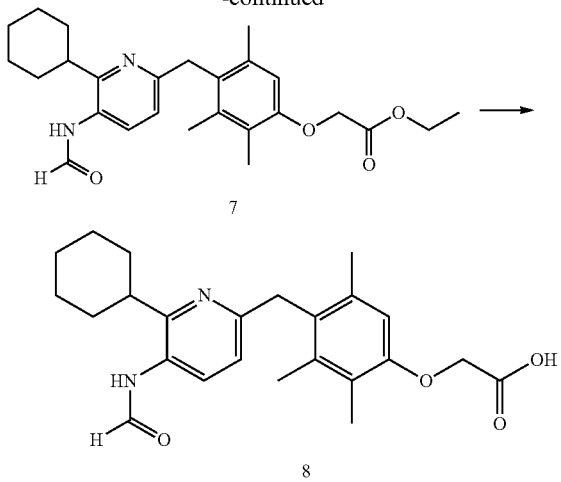

Compound 1 (1.94 g, 5.25 mmol) was dissolved in acetonitrile (39 mL), and ethyl bromoacetate (1.38 mg, 7.87 mmol) and cesium carbonate (5.13 g, 15.7 mmol) were added. After stirring overnight, water was added, and the mixture was extracted with ethyl acetate. The organic layer was washed with saturated brine, dried over anhydrous sodium sulfate, filtered, and concentrated. The residue was purified by silica gel column chromatography to give compound 2 (1.65 g, 69%).

MS m/z 456 [M+H]+, APCI(+)

Compound 2 (1.64 g, 3.60 mmol) and thioanisole (4.47 g, 36.0 mmol) were dissolved in dichloromethane (16 mL), trifluoromethanesulfonic acid (16 mL) was added, and the mixture was heated to 40° C. After stirring for 3 hr, the mixture was allowed to cool to room temperature, and neutralized with saturated aqueous sodium hydrogen carbonate. After extraction with ethyl acetate, the organic layer was washed with saturated brine, dried over anhydrous sodium sulfate, filtered, and concentrated. The residue was purified by silica gel column chromatography to give compound 3 (1.12 g, 76%).

MS m/z 412 [M+H]+, APCI(+)

Compound 3 (1.12 g, 2.72 mmol) and diisopropylethylamine (1.06 g, 8.17 mmol) were dissolved in methylene chloride (22 mL) and, after ice-cooling, trifluoromethanesulfonic anhydride (1.15 g, 4.09 mmol) was added. After stirring for 4 hr, the mixture was stirred overnight while allowing to warm to room temperature. Water was added, and the mixture was extracted with ethyl acetate. The organic layer was washed with saturated brine, dried over anhydrous sodium sulfate, filtered and concentrated. The residue was purified by silica gel column chromatography to give compound 4 (B76 mg, 59%).

MS m/z 544 [M+H]+, APCI(+)

Compound 4 (875 mg, 1.61 mmol) was dissolved in tetrahydrofuran (18 mL), and cesium carbonate (1.57 g, 4.83 mmol), benzophenone imine (583 mg, 3.22 mmol), (R)-BINAP (155 mg, 0.241 mmol), and palladium acetate (36.1 mg, 0.161 mmol) were added, and the mixture was purged with argon. The mixture was heated under reflux, and stirred overnight. The mixture was allowed to cool to room temperature, water was added, and the mixture was extracted with ethyl acetate. The organic layer was washed with saturated brine, dried over anhydrous sodium sulfate, filtered and concentrated. The residue was purified by silica gel column chromatography to give compound 5 (705 mg, 76%). Compound 5

(703 mg, 1.22 mmol) was dissolved in methanol (7 mL) and N,N'-dimethylformamide (7 mL), hydroxyamine hydrochloride (170 mg, 2.45 mmol), and sodium acetate (301 mg, 3.67 mmol) were added. After stirring overnight, saturated aqueous sodium hydrogen carbonate was added, and the mixture was extracted with ethyl acetate. The organic layer was washed with saturated brine, dried over anhydrous sodium sulfate, filtered and concentrated. The residue was purified by silica gel column chromatography to give compound 6 (445 mg, 89%).

MS m/z 411 [M+H]+, APCI(+)

A mixed solution of formic acid (122 mg, 2.60 mmol) and acetic anhydride (216 mg, 2.12 mmol) was heated to 60° C. After 2 hr, the mixture was ice-cooled and a solution of compound 6 (100 mg, 0.244 mmol) in tetrahydrofuran (2 mL) was added. After stirring for 1 hr, the mixture was allowed to warm to room temperature, and stirred overnight. Saturated aqueous sodium hydrogen carbonate was added, and the mixture was extracted with ethyl acetate. The organic layer was washed with saturated brine, dried over anhydrous sodium sulfate, filtered and concentrated. The residue was purified by silica gel column chromatography to give compound 7 (103 mg, 96%).

MS m/z 439 [M+H]+, APCI(+)

Compound 7 (100 mg, 0.228 mmol) was dissolved in methanol (2.0 mL) and, after ice-cooling, 1N sodium hydroxide (0.3 mL) was added. After stirring for 8 hr, the mixture was neutralized with 1N hydrochloric acid, and extracted with ethyl acetate. The organic layer was washed with saturated brine, dried over anhydrous sodium sulfate, filtered and concentrated. The obtained residue was suspension washed with diethyl ether-hexane mixed solution to give compound 8 (82 mg, 87%).

MS m/z 409 [M–H]–, ESI(–)

Hydrobromide, hydrochloride, para-toluenesulfonate, methanesulfonate, benzenesulfonate, maleate and the like of the present compound can be produced by a general salt formation step.

Example 48

[4-({6-cyclohexyl-5-[(methylsulfonyl)amino]pyridin-2-yl}methyl)-2,3,5-trimethylphenoxy]acetic acid

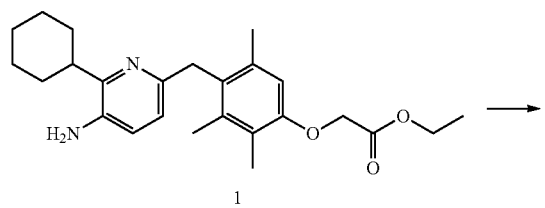

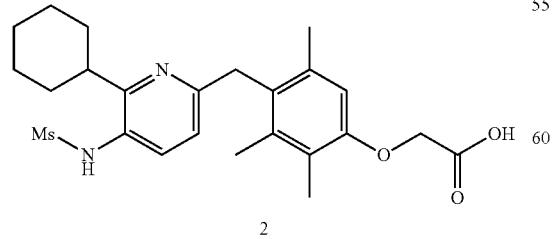

Compound 1 (100 mg, 0.244 mmol) and triethylamine (37.1 mg, 0.365 mmol) were dissolved in dichloromethane (2 mL) and, after ice-cooling, methanesulfonyl chloride (31.4 mg, 0.268 mmol) was added. After stirring for 3 hr, triethylamine (36.5 mg, 0.361 mmol) and methanesulfonyl chloride (14.8 mg, 0.132 mmol) were added. After stirring for 3 hr, water was added to the reaction solution, and the mixture was extracted with ethyl acetate. The organic layer was washed with saturated brine, dried over anhydrous sodium sulfate, filtered and concentrated. The residue was purified by silica gel column chromatography and the obtained residues were dissolved in methanol (2 mL)-tetrahydrofuran (2 mL) mixed solution and, after ice-cooling, 1N sodium hydroxide (0.5 mL) was added. After stirring overnight, respective reaction solutions were mixed together, and the mixture was neutralized with 1N hydrochloric acid, and extracted with ethyl acetate. The organic layer was washed with saturated brine, dried over anhydrous sodium sulfate, filtered and concentrated. The obtained residue was suspension washed with diethyl ether-hexane mixed solution to give compound 2 (87.6 mg, 78%).

MS m/z 459 [M–H]–, ESI(–)

Hydrobromide, hydrochloride, para-toluenesulfonate, methanesulfonate, benzenesulfonate, maleate and the like of the present compound can be produced by a general salt formation step.

Example 49

{4-[(6-cyclohexyl-5-hydroxypyridin-2-yl)methyl]-2-ethyl-3,5-dimethylphenoxy}acetic acid

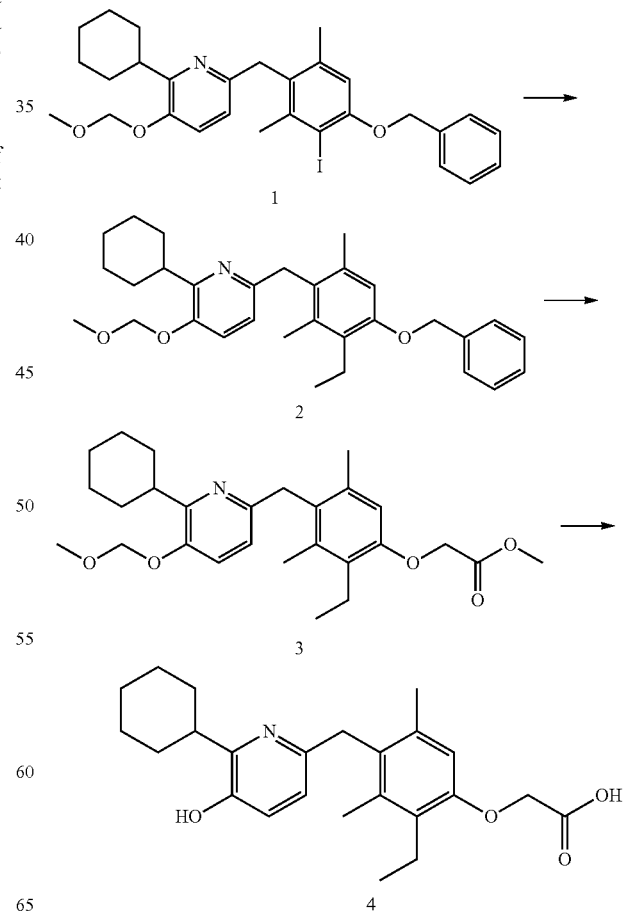

Compound 1 (1.00 g, 1.75 mmol) was dissolved in degassed 1,4-dioxane (20 mL), and potassium carbonate (1.45 g, 10.5 mmol), and ethylboronic acid (647 mg, 8.76 mmol) were added, and the mixture was purged with argon. [1,1'-Bis(diphenylphosphino)ferrocene]dichloropalladium (II) (256 mg, 0.350 mmol) was added, and the mixture was heated under reflux overnight. The mixture was allowed to cool to room temperature, and filtered through radiolite. Ethyl acetate was added, and the mixture was washed successively with water and saturated brine, dried over anhydrous sodium sulfate, filtered, and concentrated. The residue was purified by silica gel column chromatography to give compound 2 (326 mg, 39%).

MS m/z 474 [M+H]$^+$, APCI(+)

Compound 3 was synthesized by a method similar to that for compound 8 of Example 2.

MS m/z 456 [M+H]$^+$, APCI(+)

Compound 4 was synthesized by a method similar to that for compound 13 of Example 4.

MS m/z 396 [M−H]−, ESI(−)

Hydrobromide, hydrochloride, para-toluenesulfonate, methanesulfonate, benzenesulfonate, maleate and the like of the present compound can be produced by a general salt formation step.

Example 50

3-[{4-[(6-cyclohexyl-5-hydroxypyridin-2-yl)methyl]-3,5-dimethylphenyl}(methyl)amino]-3-oxopropanoic acid

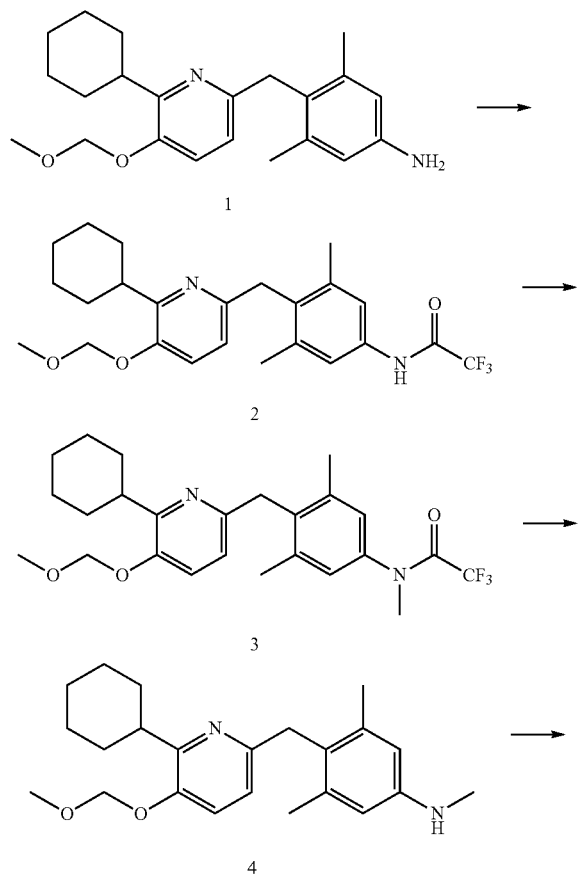

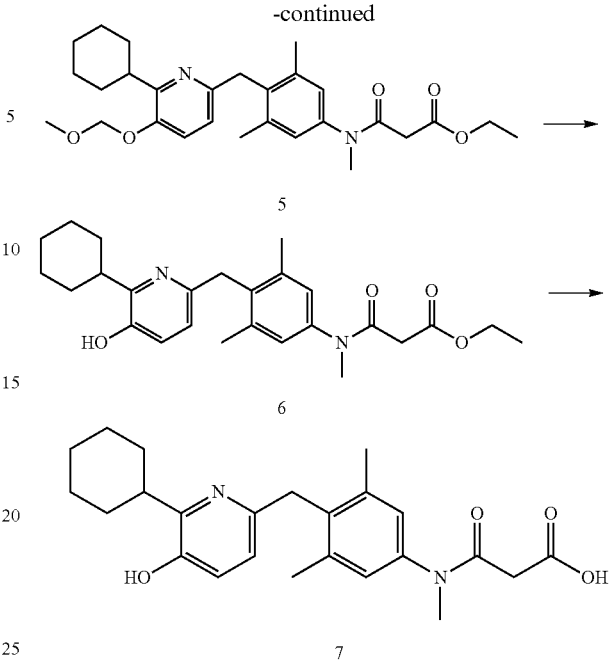

Compound 1 (108 mg, 0.305 mmol) and triethylamine (93.0 mg, 0.914 mmol) were dissolved in tetrahydrofuran (2 mL) and, after ice-cooling, trifluoroacetic anhydride (70.4 mg, 0.335 mmol) was added. After stirring for 3 hr, water was added to the reaction solution, and the mixture was extracted with chloroform. The organic layer was washed with saturated brine, dried over anhydrous sodium sulfate, filtered and concentrated. The residue was purified by silica gel column chromatography to give compound 2 (137 mg, 99%).

MS m/z 451 [M+H]+, APCI(+)

Compound 2 (130 mg, 0.289 mmol) and cesium carbonate (376 mg, 1.154 mmol) were dissolved in acetonitrile (3 mL), and iodomethane (123 mg, 0.866 mmol) was added. After stirring overnight, water was added to the reaction solution, and the mixture was extracted with chloroform. The organic layer was washed with saturated brine, dried over anhydrous sodium sulfate, filtered and concentrated. The residue was purified by silica gel column chromatography to give compound 3 (127 mg, 95%).

MS m/z 465 [M+H]+, APCI(+)

Compound 3 (125 mg, 0.269 mmol) was dissolved in methanol (2.0 mL)-tetrahydrofuran (3 mL) mixed solution and, after ice-cooling, 1N sodium hydroxide (0.32 mL) was added. After stirring for 3 hr, the reaction solution was neutralized with 1N hydrochloric acid, and extracted with ethyl acetate. The organic layer was washed with saturated brine, dried over anhydrous sodium sulfate, filtered and concentrated. The residue was purified by silica gel column chromatography to give compound 4 (99 mg, 99%).

MS m/z 369 [M+H]+, APCI(+)

Compound 4 (99.0 mg, 0.269 mmol) and triethylamine (81.6 mg, 0.806 mmol) were dissolved in dichloromethane (2 mL) and, after ice-cooling, ethyl 3-chloro-3-oxopropionate (910 mg, 6.04 mmol) was added. The mixture was stirred overnight while allowing to warm, and extracted with chloroform. The organic layer was washed with saturated brine, dried over anhydrous sodium sulfate, filtered and concentrated. The residue was purified by silica gel column chromatography to give compound 5 (71 mg, 55%).

MS m/z 483 [M+H]+, APCI(+)

Compound 5 (88.3 mg, 0.183 mmol) was dissolved in dichloromethane (1.0 mL), trifluoromethanesulfonic acid (1.0 mL) was added, and the mixture was heated to 40° C. After stirring for 3 hr, the mixture was allowed to cool to room temperature, and neutralized with saturated aqueous sodium hydrogen carbonate. After extraction with chloroform, the organic layer was washed with saturated brine, dried over anhydrous sodium sulfate, filtered, and concentrated. The residue was purified by silica gel column chromatography to give compound 6 (39.4 mg, 49%). Compound 6 (39.0 mg, 0.0889 mmol) was dissolved in methanol (0.80 mL) and, after ice-cooling, 1N sodium hydroxide (0.40 mL) was added. After stirring for 8 hr, the mixture was concentrated. The residue was washed with ethyl acetate, neutralized with 1N hydrochloric acid, and extracted with ethyl acetate. The organic layer was washed with saturated brine, dried over anhydrous sodium sulfate, filtered, and concentrated to give compound 7 (37.5 mg, 98%).

MS m/z 409 [M−H]−, ESI(−)

Hydrobromide, hydrochloride, para-toluenesulfonate, methanesulfonate, benzenesulfonate, maleate and the like of the present compound can be produced by a general salt formation step.

Example 51

{4-[(6-cyclohexyl-5-hydroxypyridin-2-yl)methyl]-2-methoxy-3,5-dimethylphenoxy}acetic acid

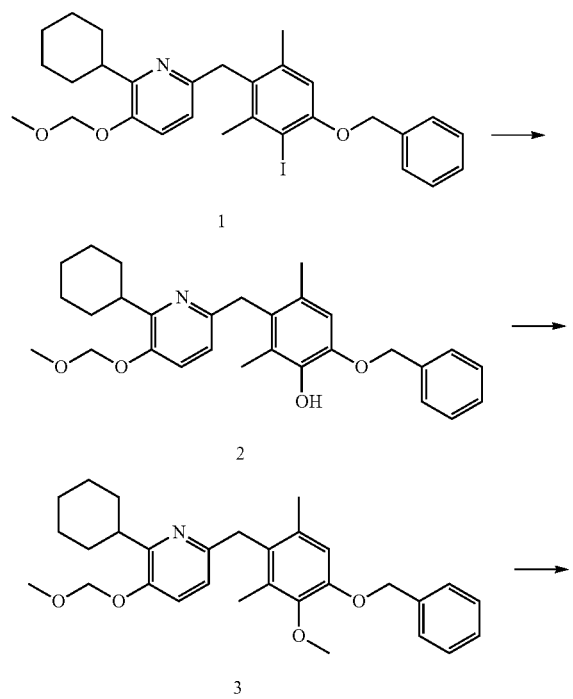

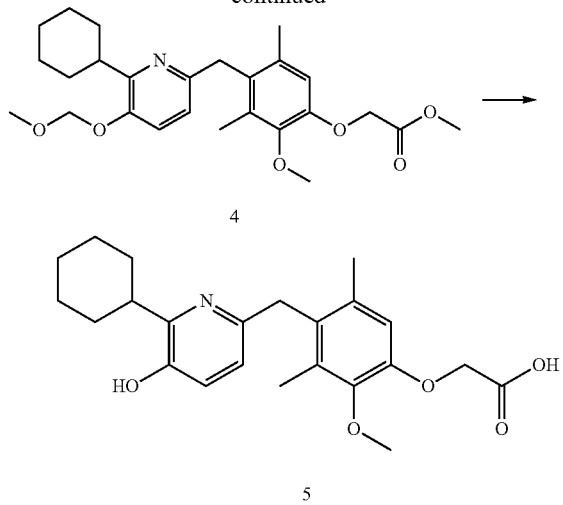

Compound 1 (1.00 g, 1.75 mmol) was dissolved in degassed 1,4-dioxane (18 mL), and water (18 mL), potassium hydroxide (216 mg, 3.85 mmol), and 2-di-tert-butylphosphino-2',4',6'-triisopropylbiphenyl (60.0 mg, 0.141 mmol) were added, and the mixture was purged with argon. Tris(dibenzylideneacetone)dipalladium(0) (32.0 mg, 0.0350 mmol) was added, and the mixture was heated under reflux overnight. The mixture was allowed to cool to room temperature, water was added, and the mixture was extracted with ethyl acetate. The organic layer was washed successively with water and saturated brine, dried over anhydrous sodium sulfate, filtered, and concentrated. The residue was purified by silica gel column chromatography to give compound 2 (469 mg, 58%).

MS m/z 462 [M+H]+, APCI(+)

Compound 2 (469 mg, 1.02 mmol) was dissolved in acetonitrile (10 mL), and methyl iodide (296 mg, 2.09 mmol) and cesium carbonate (500 mg, 1.53 mmol) were added. After stirring at room temperature for 2 hr, methyl iodide (296 mg, 2.09 mmol) was added, and the mixture was stirred for 2 hr. Water was added, and the mixture was extracted with ethyl acetate, and the extract was washed successively with water and saturated brine. The organic layer was dried over anhydrous magnesium sulfate, filtered, and concentrated. The residue was purified by silica gel column chromatography to give compound 3 (445 mg, 92%).

MS m/z 476 [M+H]+, APCI(+)

Compound 4 was synthesized by a method similar to that for compound 8 of Example 2.

MS m/z 458 [M+H]+, APCI(+)

Compound 5 was synthesized by a method similar to that for compound 13 of Example 4.

MS m/z 398 [M−H]−, ESI(−)

Hydrobromide, hydrochloride, para-toluenesulfonate, methanesulfonate, benzenesulfonate, maleate and the like of the present compound can be produced by a general salt formation step.

Example 52

3-({4-[(6-cycloheptyl-5-hydroxypyridin-2-yl)methyl]-3,5-dimethylphenyl}amino)-3-oxopropanoic acid

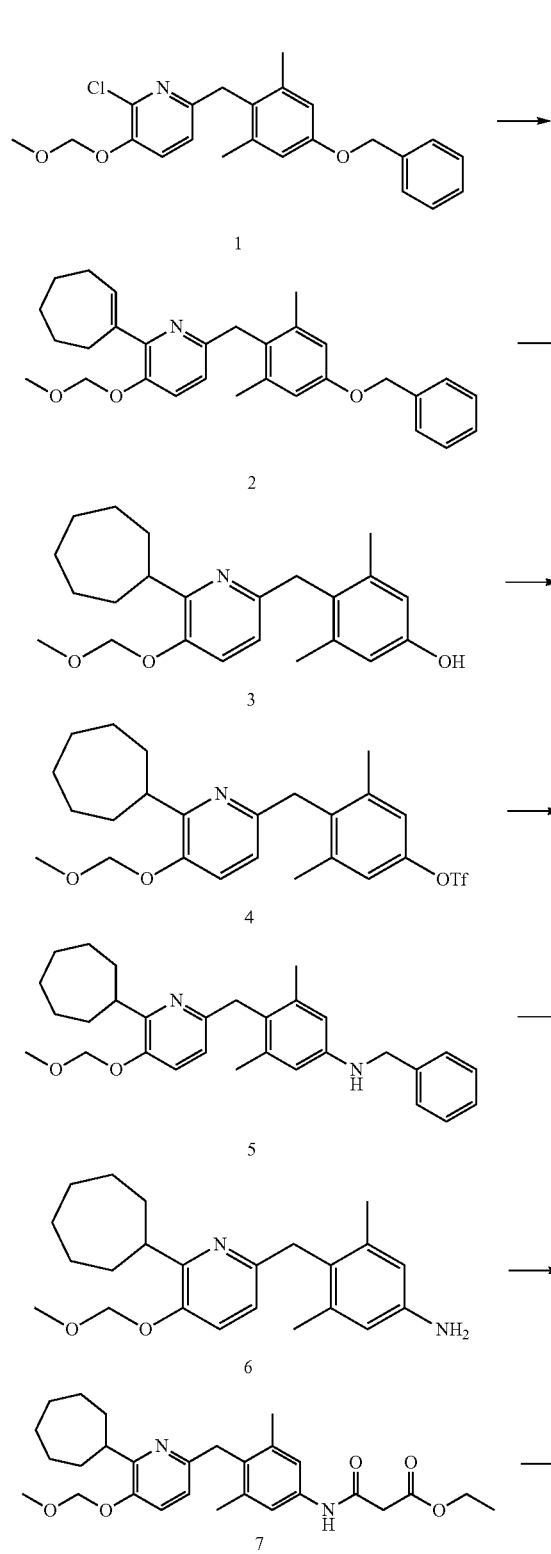

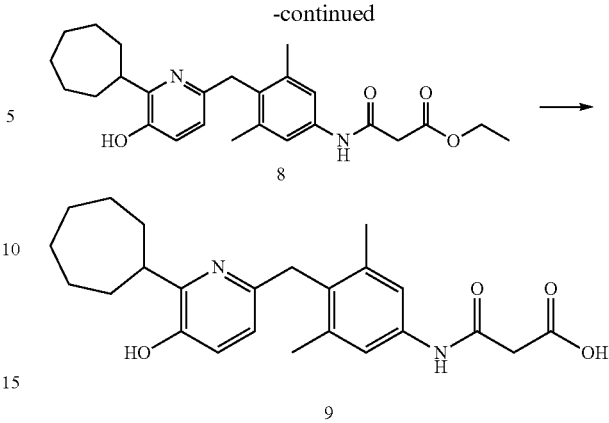

Compound 2 was synthesized by a method similar to that for compound 2 of Example 5.
MS m/z 458 [M+H]$^+$, APCI(+)

Compound 3 was synthesized by a method similar to that for compound 11 of Example 4.
MS m/z 370 [M+H]$^+$, APCI(+)

Compound 4 was synthesized by a method similar to that for compound 2 of Example 21.
MS m/z 502 [M+H]$^+$, APCI(+)

Compound 4 (2.22 g, 4.43 mmol) was dissolved in dioxane (22 mL), and potassium phosphate (5.64 g, 26.6 mmol), 2-di-tert-butylphosphinobiphenyl (844 mg, 1.77 mmol), and benzylamine (1.90 g, 17.7 mmol) were added, and the mixture was purged with argon.
Tris(dibenzylideneacetone)dipalladium(0) (810 mg, 0.885 mmol) was added, and the mixture was stirred at 100° C. overnight. The mixture was allowed to cool to room temperature, ethyl acetate and water were added and the mixture was filtered through radiolite. After extraction with ethyl acetate, the extract was washed successively with water and saturated brine, dried over anhydrous sodium sulfate, filtered, and concentrated. The residue was purified by silica gel column chromatography to give compound 5 (1.63 g, 81%).
MS m/z 459 [M+H]$^+$, APCI(+)

Compound 5 (1.71 g, 3.72 mmol) was dissolved in ethanol (34 mL) and acetic acid (8.5 mL) and, after purging with argon, 20% palladium hydroxide/carbon catalyst (854 mg) was added. After purging with hydrogen, the mixture was stirred for 7 hr, filtered through radiolite, and concentrated. The residue was purified by silica gel column chromatography to give compound 6 (1.08 g, 79%).
MS m/z 369 [M+H]$^+$, APCI(+)

Compound 7 was synthesized by a method similar to that for compound 5 of Example 21.
MS m/z 483 [M+H]$^+$, APCI(+)

Compound 7 (1.23 g, 2.56 mmol) and thioanisole (3.01 mL, 25.6 mmol) were dissolved in dichloromethane (12 mL) and, after ice-cooling, trifluoroacetic acid (12 mL) was added. After stirring at 40° C. for 2 hr, saturated aqueous sodium hydrogen carbonate was added, and the mixture was extracted with chloroform. The extract was washed successively with water and saturated brine, dried over anhydrous magnesium sulfate, filtered, and concentrated. The residue was purified by silica gel column chromatography to give compound 8 (0.92 g, 82%).
MS m/z 439 [M+H]$^+$, APCI(+)

Compound 8 (196 mg, 0.447 mmol) was dissolved in methanol (3.9 mL) and, after ice-cooling, 1N sodium hydroxide (0.89 mL) was added. The mixture was allowed to warm to room temperature, and stirred overnight, neutralized with saturated aqueous ammonium chloride solution, and extracted with ethyl acetate-methanol. The extract was dried over anhydrous magnesium sulfate, filtered, and concentrated. The obtained solid was washed with ether, and dried under reduced pressure to give compound 9 (187 mg, 100%).

MS m/z 409 [M−H]−, ESI(−)

Hydrobromide, hydrochloride, para-toluenesulfonate, methanesulfonate, benzenesulfonate, maleate and the like of the present compound can be produced by a general salt formation step.

Example 53

3-({4-[(6-cyclohexyl-5-hydroxypyridin-2-yl)methyl]-2,6-difluoro-3,5-dimethylphenoxy}methyl)-1,2,4-oxadiazol-5(4H)-one

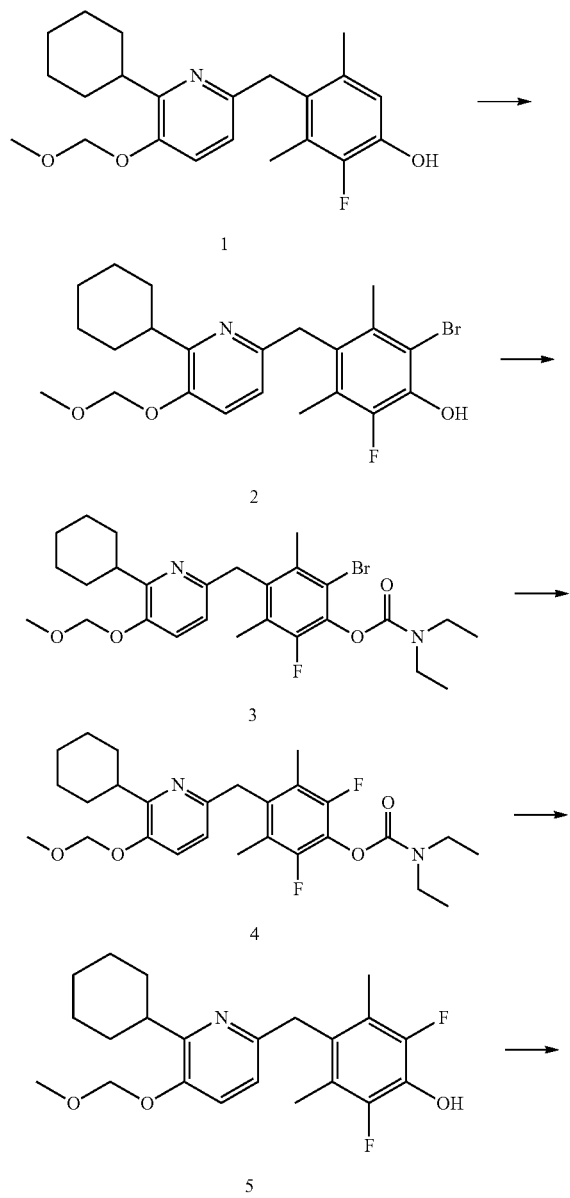

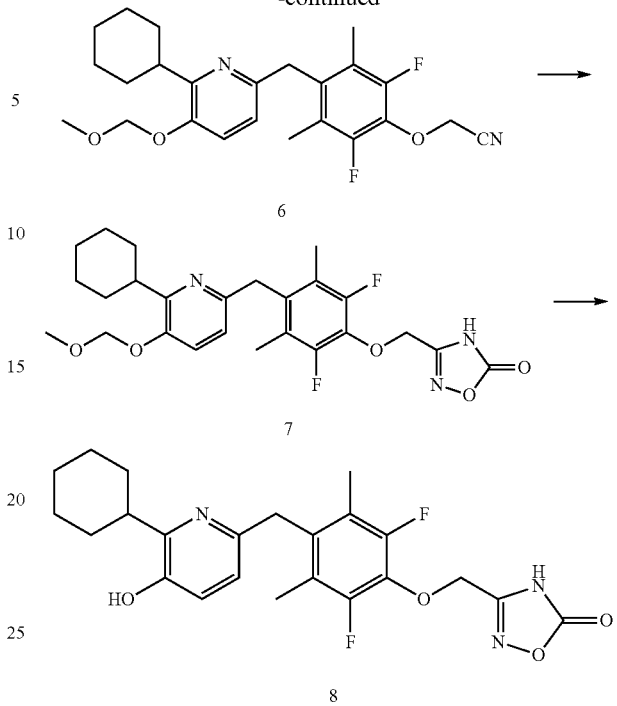

Compound 1 (1.00 g, 2.68 mmol) was dissolved in chloroform (10 mL), and ice-cooled. N-Bromosuccinimide (501 mg, 2.81 mmol) was added, and the mixture was stirred at room temperature for 4 hr. Water was added, and the mixture was extracted with ethyl acetate, and the extract was washed successively with water and saturated brine, dried over anhydrous sodium sulfate, filtered, and concentrated. The residue was purified by silica gel column chromatography to give compound 2 (925 mg, 76%).

MS m/z 452/454 [M+H]+, APCI(+)

Compound 2 (324 mg, 0.716 mmol) was dissolved in acetonitrile (7 mL), and diethylcarbamoyl chloride (147 mg, 1.08 mmol) and potassium carbonate (300 mg, 2.17 mmol) were added. The mixture was heated under reflux overnight, and allowed to cool to room temperature. Water was added, and the mixture was extracted with ethyl acetate, and the extract was washed successively with water and saturated brine. The organic layer was dried over anhydrous magnesium sulfate, filtered, and concentrated. The residue was purified by silica gel column chromatography to give compound 3 (302 mg, 76%).

MS m/z 551/553 [M+H]+, APCI(+)

Compound 3 (301 mg, 0.546 mmol) was dissolved in tetrahydrofuran (4 mL), cooled to −78° C., and n-butyllithium (hexane solution, 397 μL, 0.655 mmol) was slowly added dropwise. The mixture was stirred for 30 min. N-Fluorobenzenesulfonimide (517 mg, 0.610 mmol) dissolved in THF (2 mL) was slowly added dropwise, and the mixture was stirred for 3 hr, allowed to warm to room temperature, and stirred overnight. Saturated aqueous ammonium chloride solution was added, and the mixture was extracted with ethyl acetate. The organic layer was washed successively with water and saturated brine, dried over anhydrous sodium sulfate, filtered and concentrated. The residue was purified by silica gel column chromatography to give compound 4 (172 mg, 65%).

MS m/z 491 [M+H]+, APCI(+)

Compound 4 (172 mg, 0.351 mmol) was dissolved in ethanol (3.5 mL), potassium hydroxide (140 mg, 2.50 mmol) was added, the mixture was heated under reflux for 2 days. The mixture was allowed to cool to room temperature, and neutralized with saturated aqueous ammonium chloride solution. After extraction with ethyl acetate, the organic layer was washed successively with water and saturated brine, dried over anhydrous magnesium sulfate and filtered. The residue was purified by silica gel column chromatography to give compound 5 (84 mg, 61%).

MS m/z 392 [M+H]$^+$, APCI(+)

Compound 6 was synthesized by a method similar to that for compound 2 of Example 27.

MS m/z 431 [M+H]$^+$, APCI(+)

Compound 7 was synthesized by a method similar to that for compound 3 of Example 27.

MS m/z 488 [M−H]−, ESI(−)

Compound 8 was synthesized by a method similar to that for compound 4 of Example 27.

MS m/z 444 [M−H]−, ESI(−)

Hydrobromide, hydrochloride, para-toluenesulfonate, methanesulfonate, benzenesulfonate, maleate and the like of the present compound can be produced by a general salt formation step.

Example 54

3-({[2-chloro-4-[(6-cyclohexyl-5-hydroxypyridin-2-yl)methyl]-3,5-dimethylphenyl}amino)-3-oxopropanoic acid

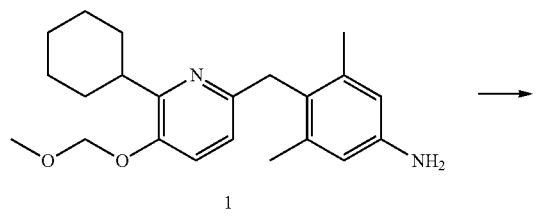
1

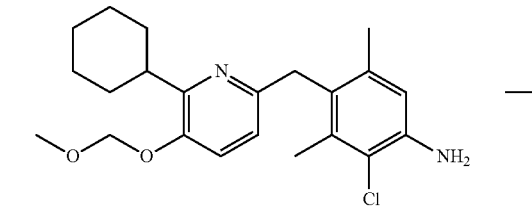
2

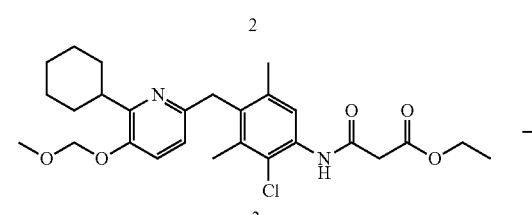
3

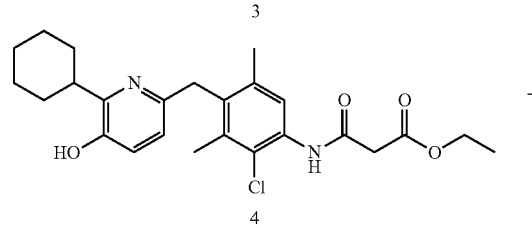
4

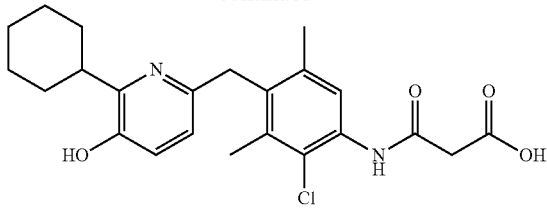
5

Compound 1 (3.50 g, 9.87 mmol) was dissolved in carbon tetrachloride (20 mL), and the mixture was ice-cooled. N-Chlorosuccinimide (1.45 g, 10.9 mmol) was added, and the mixture was stirred at room temperature for 3 hr. Chloroform was added, and the mixture was washed successively with water and saturated brine, dried over anhydrous sodium sulfate, filtered, and concentrated. The residue was purified by silica gel column chromatography to give compound 2 (2.32 g, 60%).

MS m/z 389/391 [M+H]$^+$, APCI(+)

Compound 3 was synthesized by a method similar to that for compound 5 of Example 21.

MS m/z 503/505 [M+H]$^+$, APCI(+)

Compound 4 was synthesized by a method similar to that for compound 8 of Example 52.

MS m/z 459/461 [M+H]$^+$, APCI(+)

Compound 5 was synthesized by a method similar to that for compound 9 of Example 52.

MS m/z 429/431 [M−H]−, ESI(−)

Hydrobromide, hydrochloride, para-toluenesulfonate, methanesulfonate, benzenesulfonate, maleate and the like of the present compound can be produced by a general salt formation step.

Example 55

3-({2-bromo-4-[(6-cyclohexyl-5-hydroxypyridin-2-yl)methyl]-3,5-dimethylphenyl}amino)-3-oxopropanoic acid

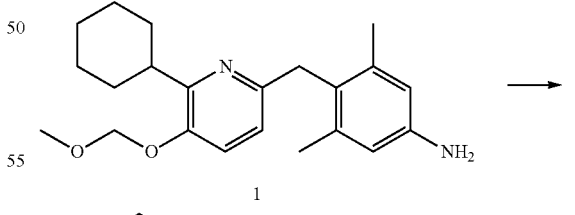
1

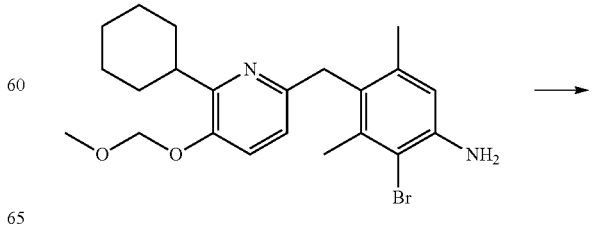
2

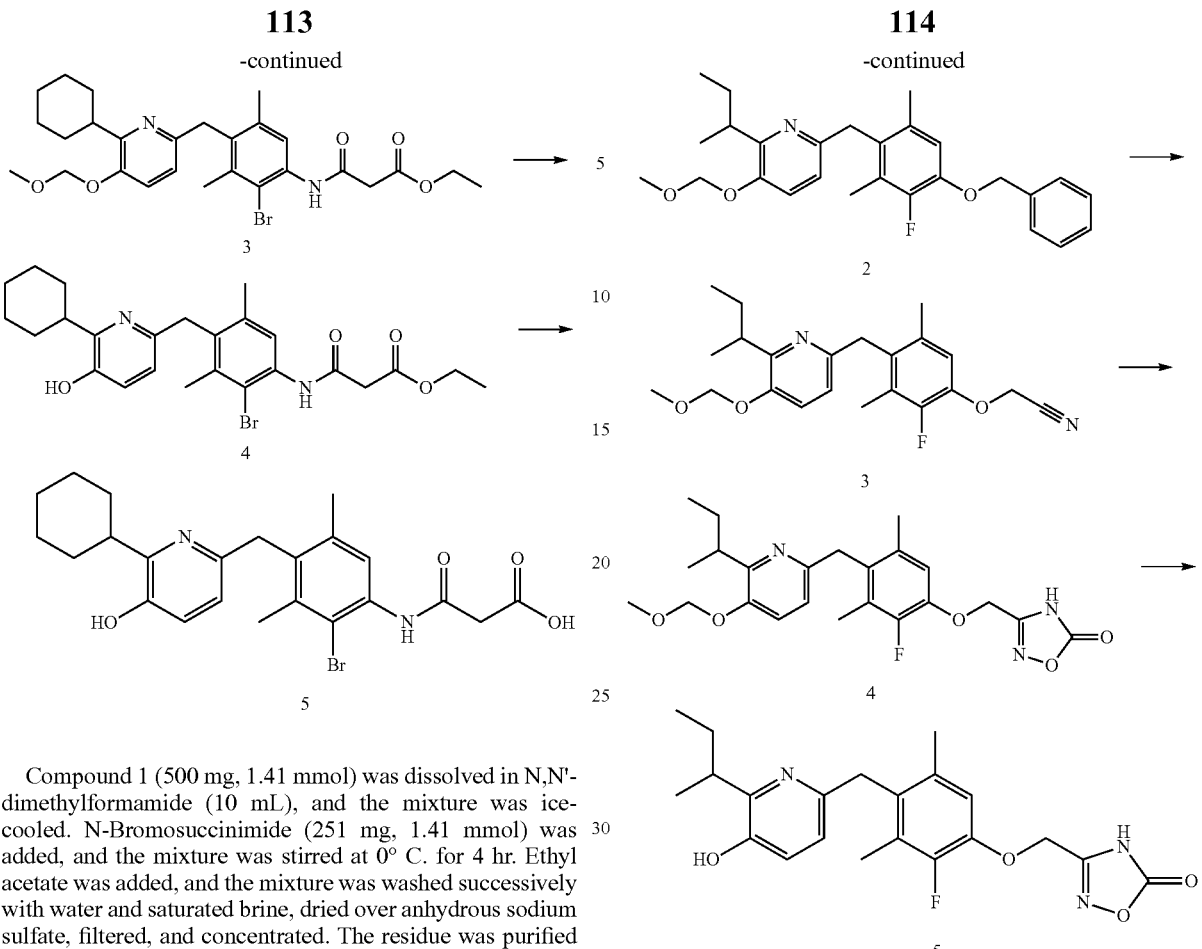

Compound 1 (500 mg, 1.41 mmol) was dissolved in N,N'-dimethylformamide (10 mL), and the mixture was ice-cooled. N-Bromosuccinimide (251 mg, 1.41 mmol) was added, and the mixture was stirred at 0° C. for 4 hr. Ethyl acetate was added, and the mixture was washed successively with water and saturated brine, dried over anhydrous sodium sulfate, filtered, and concentrated. The residue was purified by silica gel column chromatography to give compound 2 (555 mg, 91%).

MS m/z 433/435 [M+H]$^+$, APCI(+)

Compound 3 was synthesized by a method similar to that for compound 5 of Example 21.

MS m/z 547/549 [M+H]$^+$, APCI(+)

Compound 4 was synthesized by a method similar to that for compound 8 of Example 52.

MS m/z 503/505 [M+H]$^+$, APCI(+)

Compound 5 was synthesized by a method similar to that for compound 9 of Example 52.

MS m/z 473/475 [M−H]−, ESI(−)

Hydrobromide, hydrochloride, para-toluenesulfonate, methanesulfonate, benzenesulfonate, maleate and the like of the present compound can be produced by a general salt formation step.

Example 56

3-({4-[(6-sec-butyl-5-hydroxypyridin-2-yl)methyl]-2-fluoro-3,5-dimethylphenoxy}methyl)-1,2,4-oxadiazol-5(4H)-one

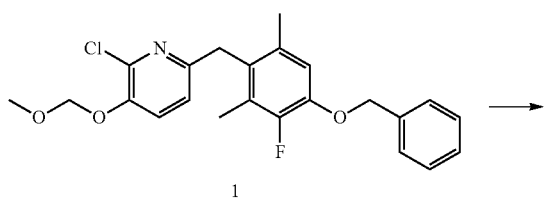

Compound 1 (508 mg, 1.22 mmol), copper(I) iodide (58.2 mg, 0.305 mmol), potassium iodide (121 mg, 0.733 mmol), and [1,1'-bis(diphenylphosphino)ferrocene]dichloropalladium(II) dichloromethane complex (49.9 mg, 0.0611 mmol) were purged with argon, and N,N-dimethylacetamide (10 mL) was added. sec-Butylzinc bromide (0.5 M tetrahydrofuran solution, 4.88 mL, 2.44 mmol) was added, and the mixture was heated to 60° C. One day later, the mixture was allowed to cool to room temperature. Water was added, and the mixture was extracted with ethyl acetate. The organic layer was washed with saturated brine, dried over anhydrous sodium sulfate, filtered and concentrated. The residue was purified by silica gel column chromatography to give compound 2 (333 mg, 62%).

MS m/z 438 [M+H]$^+$, APCI(+)

Compound 3 was synthesized by a method similar to that for compound 11 of Example 4 and compound 2 of Example 27.

MS m/z 387 [M+H]$^+$, APCI(+)

Compound 4 was synthesized by a method similar to that for compound 3 of Example 27.

MS m/z 444 [M−H]−, ESI(−)

Compound 5 was synthesized by a method similar to that for compound 4 of Example 27.

MS m/z 400 [M−H]−, ESI(−)

Hydrobromide, hydrochloride, para-toluenesulfonate, methanesulfonate, benzenesulfonate, maleate and the like of the present compound can be produced by a general salt formation step.

Example 57

3-{[2-fluoro-4-({5-hydroxy-6-[methyl(phenyl)amino]pyridin-2-yl}methyl)-3,5-dimethylphenoxy]methyl}-1,2,4-oxadiazol-5(4H)-one

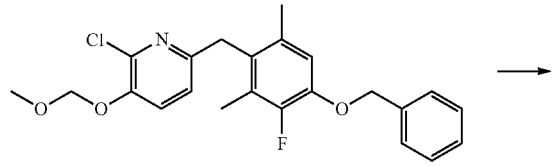

1

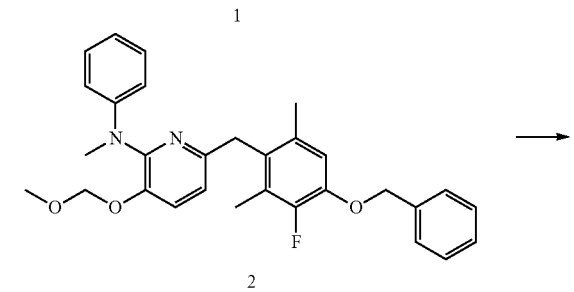

2

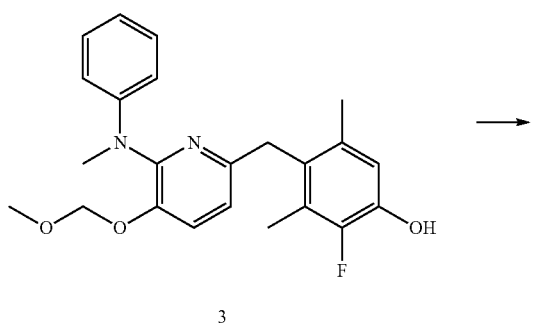

3

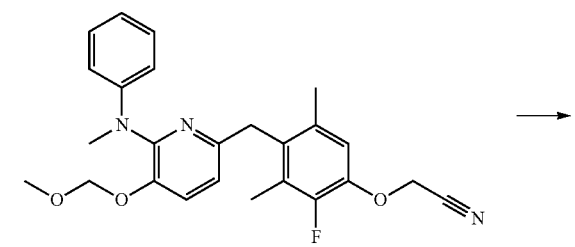

4

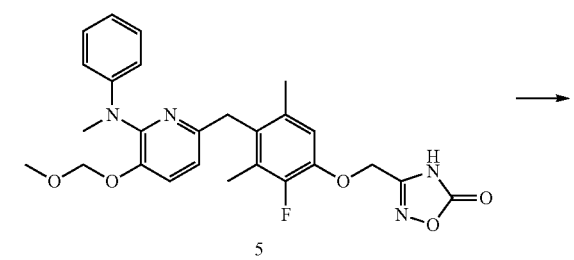

5

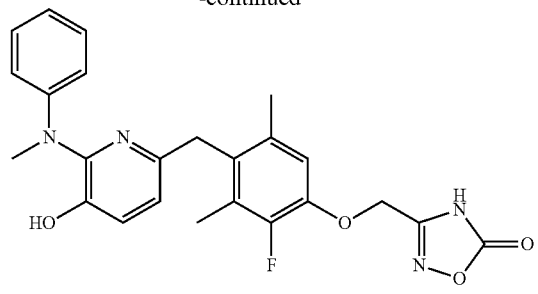

6

Compound 1 (208 mg, 0.500 mmol), N-methylaniline (80 mg, 0.75 mmol), tris(benzylideneacetone)dipalladium(0) (23 mg, 0.025 mmol), 4,5-bis(diphenylphosphino)-9,9-dimethylxanthene (43 mg, 0.075 mmol), and sodium t-butoxide (72 mg, 0.75 mmol) were purged with argon, toluene (5 mL) was added and the mixture was heated under reflux overnight. The mixture was allowed to cool to room temperature, ethyl acetate and water were added and the mixture was stirred and filtered through celite. The filtrate was extracted with ethyl acetate, and the organic layer was washed with water and saturated brine, dried over anhydrous sodium sulfate, filtered and concentrated. The residue was purified by silica gel column chromatography to give compound 2 (223 mg, 91%).

MS m/z 487 [M+H]$^+$, APCI(+)

Compound 3 was synthesized by a method similar to that for compound 11 of Example 4.

MS m/z 397 [M+H]$^+$, APCI(+)

Compound 4 was synthesized by a method similar to that for compound 2 of Example 27.

MS m/z 436 [M+H]$^+$, APCI(+)

Compound 5 was synthesized by a method similar to that for compound 3 of Example 27.

MS m/z 493 [M−H]−, ESI(−)

Compound 6 was synthesized by a method similar to that for compound 4 of Example 27.

MS m/z 449 [M−H]−, ESI(−)

Hydrobromide, hydrochloride, para-toluenesulfonate, methanesulfonate, benzenesulfonate, maleate and the like of the present compound can be produced by a general salt formation step.

Example 58

3-({3,5-dichloro-4-[(6-cyclohexyl-5-hydroxypyridin-2-yl)oxy]phenyl}amino)-3-oxopropanoic acid

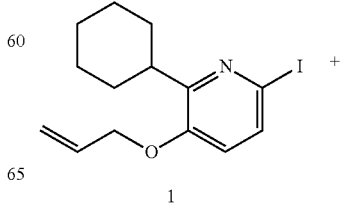

1

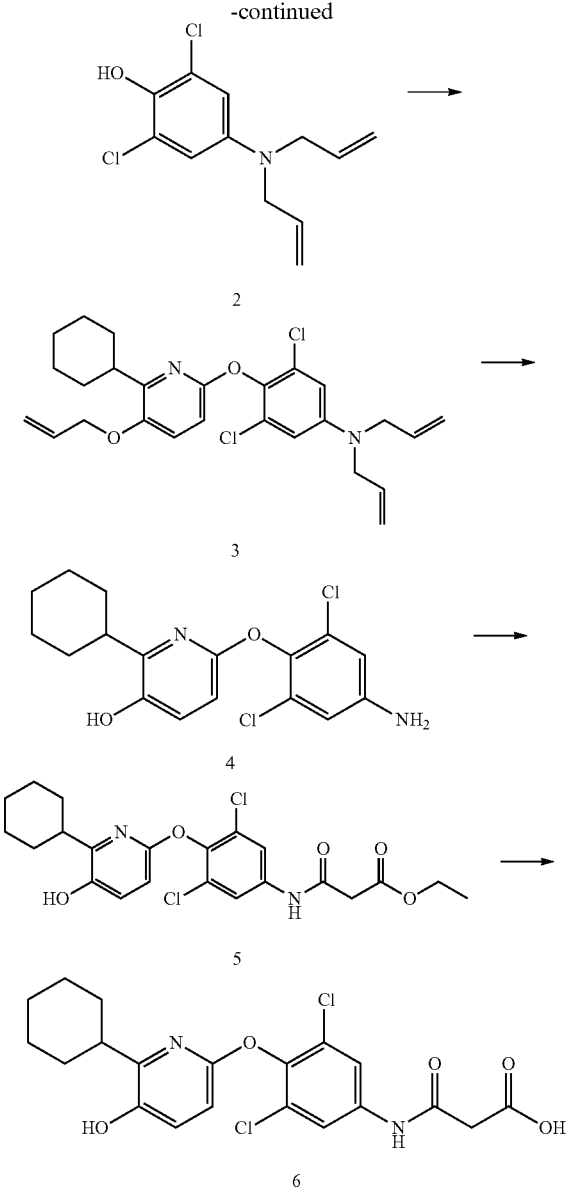

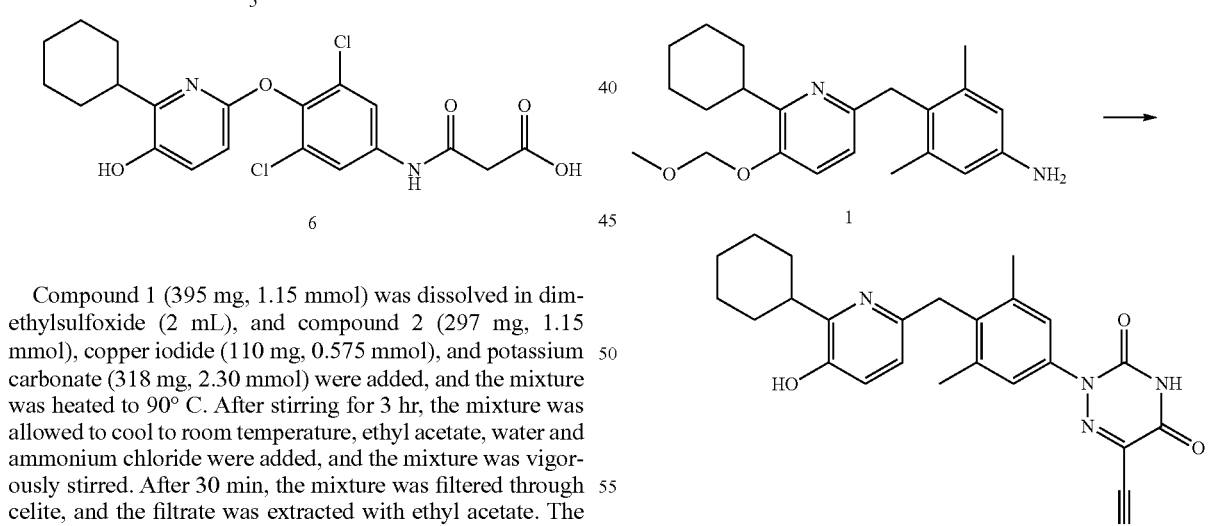

striphenylphosphinepalladium(0) (148 mg, 0.128 mmol) was added. After stirring for 4 hr, the mixture was allowed to cool to room temperature, and diluted with chloroform. The organic layer was washed with saturated aqueous sodium hydrogen carbonate and saturated brine, dried over anhydrous magnesium sulfate, filtered and concentrated. The residue was purified by silica gel column chromatography to give compound 4 (201 mg, 49%, 2 steps).

MS m/z 353/355 [M+H]$^+$, APCI(+)

Compound 4 (198 mg, 0.561 mmol) was dissolved in dichloromethane (3 mL) and tetrahydrofuran (3 mL), and pyridine (67 mg, 0.841 mmol) was added and the mixture was ice-cooled. Ethylmalonyl chloride (93 mg, 0.617 mmol) was added dropwise, and the mixture was stirred for 1 hr. Saturated aqueous sodium hydrogen carbonate was added, and the mixture was extracted with ethyl acetate. The organic layer was washed with saturated brine, dried over anhydrous magnesium sulfate, filtered and concentrated. The residue was purified by silica gel column chromatography to give compound 5 (217 mg, 83%).

MS m/z 467/469 [M+H]$^+$, APCI(+)

Compound 6 was synthesized by a method similar to that for compound 9 of Example 52.

MS m/z 437/439 [M−H]−, ESI(−)

Hydrobromide, hydrochloride, para-toluenesulfonate, methanesulfonate, benzenesulfonate, maleate and the like of the present compound can be produced by a general salt formation step.

Example 59

2-{4-[(6-cyclohexyl-5-hydroxypyridin-2-yl)methyl]-3,5-dimethylphenyl}-3,5-dioxo-2,3,4,5-tetrahydro-1,2,4-triazine-6-carbonitrile Compound 1 (395 mg, 1.15 mmol) was dissolved in dimethylsulfoxide (2 mL), and compound 2 (297 mg, 1.15 mmol), copper iodide (110 mg, 0.575 mmol), and potassium carbonate (318 mg, 2.30 mmol) were added, and the mixture was heated to 90° C. After stirring for 3 hr, the mixture was allowed to cool to room temperature, ethyl acetate, water and ammonium chloride were added, and the mixture was vigorously stirred. After 30 min, the mixture was filtered through celite, and the filtrate was extracted with ethyl acetate. The organic layer was washed with saturated brine, dried over anhydrous magnesium sulfate, filtered and concentrated. The residue was purified by silica gel column chromatography to give compound 3.

MS m/z 473/475 [M+H]$^+$, APCI(+)

Compound 3 was dissolved in dichloromethane (10 mL), N,N'-dimethylbarbituric acid (1.20 g, 7.68 mmol), and tetrakistriphenylphosphinepalladium(0) (148 mg, 0.128 mmol) were added, and the mixture was heated to 40° C. After stirring for 6 hr, tetrakistriphenylphosphinepalladium(0) (148 mg, 0.128 mmol) was added. After stirring for 17 hr, tetraki- To compound 1 (300 mg, 0.844 mmol) were added water (3 mL) and concentrated hydrochloric acid (3 mL) and the mixture was ice-cooled. Aqueous solution (1 mL) of sodium nitrite (72.8 mg, 1.05 mmol) was added dropwise and, after 30 min, ice-cooled aqueous solution (3 mL) of N-cyanoacetylurethane (145 mg, 0.928 mmol) and pyridine (3.0 mL, 38 mmol) was added. After 2 hr, the precipitated solid was filtered, washed with water and dried. To the obtained solid were added sodium acetate (350 mg, 4.27 mmol) and acetic acid (8 mL), and the mixture was heated to 120° C. After 3 hr, the mixture was allowed to cool to room temperature, saturated aqueous sodium hydrogen carbonate was added, and the mixture was extracted with ethyl acetate. The organic layer was washed with saturated brine, dried over anhydrous sodium sulfate, filtered and concentrated. The residue was purified by silica gel column chromatography. The obtained solid was suspension washed with ether-ethanol mixed solvent and dried to give compound 2 (78 mg, 21%).

MS m/z 432 [M+H]$^+$, APCI(+)

Hydrobromide, hydrochloride, para-toluenesulfonate, methanesulfonate, benzenesulfonate, maleate and the like of the present compound can be produced by a general salt formation step.

Example 60

3-[(2-fluoro-4-{[6-(2-fluoro-3-methylphenyl)-5-hydroxypyridin-2-yl]methyl}-3,5-dimethylphenoxy)methyl]-1,2,4-oxadiazol-5(4H)-one

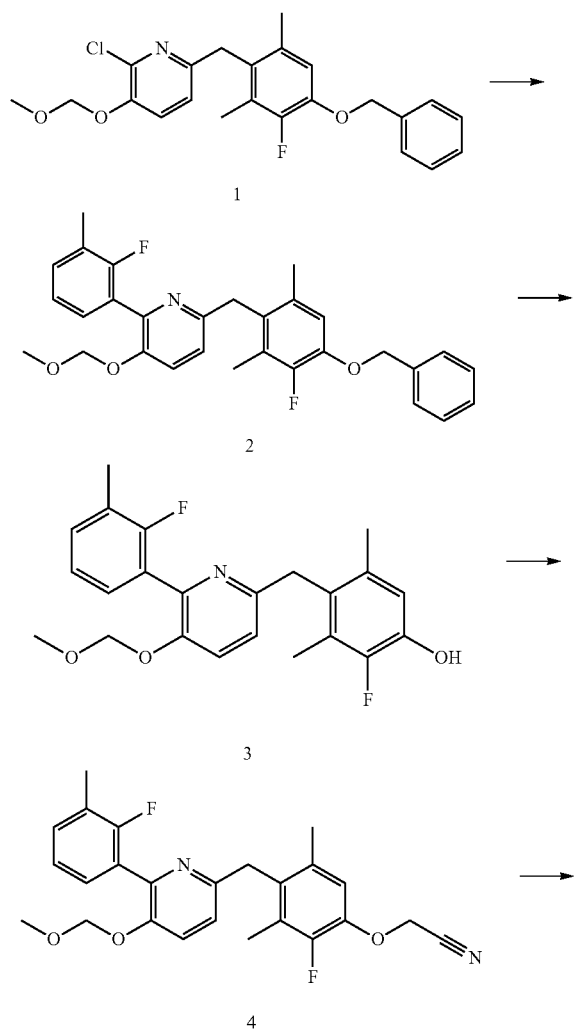

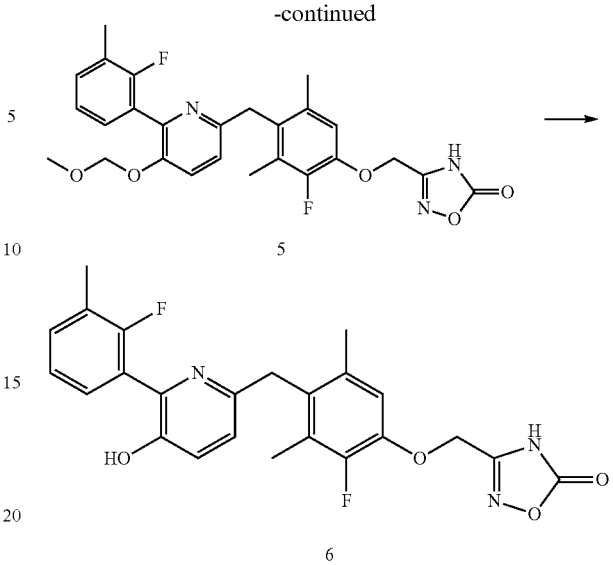

Compound 1 (208 mg, 0.50 mmol), 2-fluoro-3-methylphenylboronic acid (115 mg, 0.75 mmol), tetrakistriphenylphosphinepalladium(0) (58 mg, 0.05 mmol), and potassium carbonate (207 mg, 1.50 mmol) were purged with argon, suspended in water (0.7 mL) and 1,4-dioxane (2.8 mL), and the mixture was stirred at 90° C. for 1 hr. The mixture was allowed to cool to room temperature, ethyl acetate and water were added and the mixture was stirred and filtered through celite.

The filtrate was extracted with ethyl acetate, and the organic layer was washed with water and saturated brine, ChemElute filtered, and concentrated. The residue was purified by silica gel column chromatography to give compound 2 (233 mg, 95%).

MS m/z 490 [M+H]$^+$, APCI(+)

Compound 2 (232 mg, 0.47 mmol) was dissolved in ethanol (4 mL) and acetic acid (1 mL), and 5% Pd/C (90 mg) was added. After purging with hydrogen, the mixture was stirred for 4 hr, filtered and concentrated. The residue was purified by silica gel column chromatography to give compound 3 (153 mg, 81%).

MS m/z 400 [M+H]$^+$, APCI(+)

Compound 3 (152 mg, 0.38 mmol) was dissolved in s acetonitrile (4.5 mL), and bromoacetonitrile (81 mg, 0.68 mmol), and cesium carbonate (440 mg, 1.35 mmol) were added, and the mixture was stirred at room temperature for 1 hr. Water was added, and the mixture was extracted with ethyl acetate. The organic layer was washed with water and saturated brine, ChemElute filtered, and concentrated. The residue was purified by silica gel column chromatography to give compound 4 (160 mg, 96%).

MS m/z 439 [M+H]$^+$, APCI(+)

Compound 4 (158 mg, 0.36 mmol) was dissolved in methanol (1.5 mL), and tetrahydrofuran (0.5 mL), hydroxyamine hydrochloride (38 mg, 0.54 mmol) and sodium hydrogen carbonate (91 mg, 1.08 mmol) were added. After heating under reflux for 1.5 hr, the mixture was allowed to cool to room temperature, aqueous ammonium chloride solution and ethyl acetate were added and the mixture was stirred. The mixture was extracted with ethyl acetate, and the organic layer was washed with water and saturated brine, dried over anhydrous sodium sulfate, filtered, and concentrated. 1,4-Dioxane (3 mL) and then 1,1'-carbonyldiimidazole (88 mg, 0.54 mmol) were added. After stirring at room temperature for 1 hr, the mixture was heated under reflux for 2.5 hr. The mixture was allowed to cool to room temperature, ethyl acetate and water were added, and the mixture was neutralized with 5% hydrochloric acid. The mixture was extracted with ethyl acetate, and the organic layer was washed with water and saturated brine, dried over anhydrous sodium sulfate, filtered, and concentrated. The residue was purified by silica gel column chromatography to give compound 5 (163 mg, 91%).

MS m/z 496 [M−H]−, ESI(−)

Compound 5 (161 mg, 0.32 mmol) was dissolved in tetrahydrofuran (3.5 mL), 6N hydrochloric acid (0.75 mL) was added, and the mixture was stirred at 60° C. for 2 hr. The mixture was allowed to cool to room temperature, 2N sodium hydroxide (2.25 mL) was added and the mixture was stirred. Aqueous ammonium chloride solution was added. The mixture was extracted with ethyl acetate, and the organic layer was washed with water and saturated brine, dried over anhydrous sodium sulfate, filtered, and concentrated. The residue was purified by silica gel column chromatography to give compound 6 (135 mg, 92%).

MS m/z 452 [M−H]−, ESI(−)

Hydrobromide, hydrochloride, para-toluenesulfonate, methanesulfonate, benzenesulfonate, maleate and the like of the present compound can be produced by a general salt formation step.

Example 61

3-[(4-{[6-(4,4-difluoro-1-hydroxycyclohexyl)-5-hydroxypyridin-2-yl]methyl}-2-fluoro-3,5-dimethylphenoxy)methyl]-1,2,4-oxadiazol-5(4H)-one

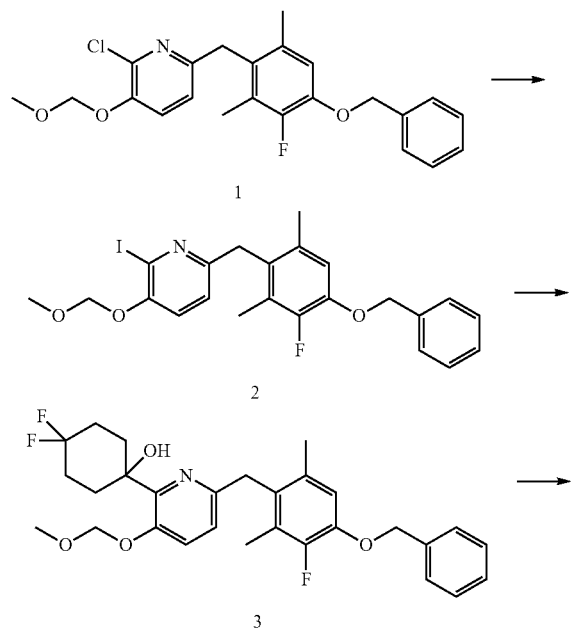

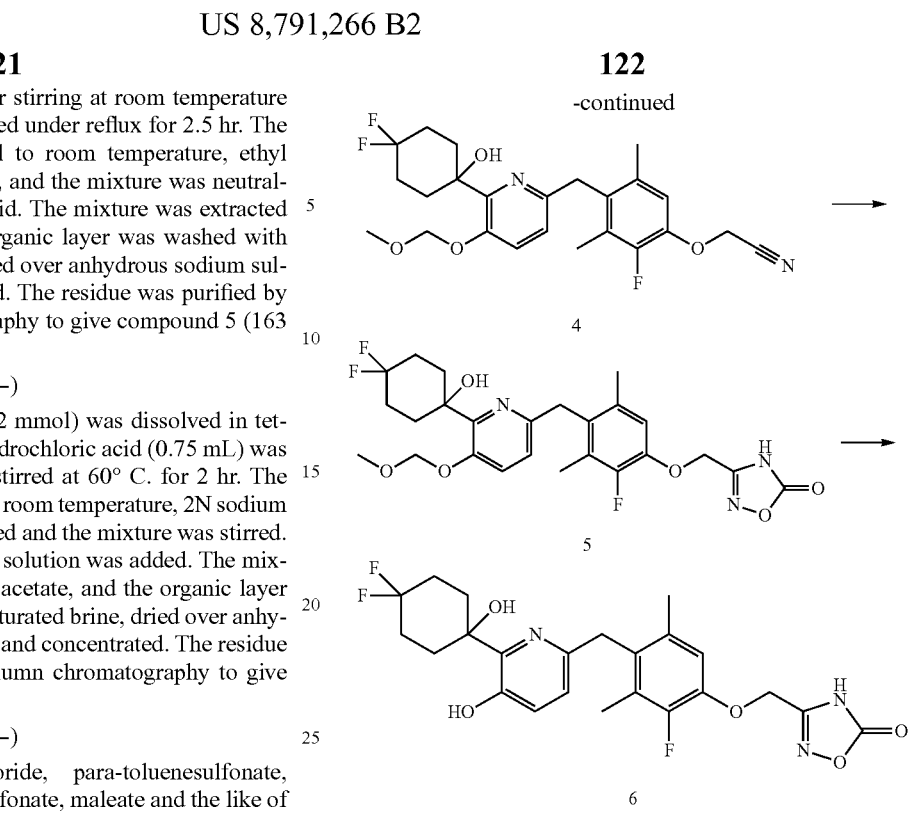

To compound 1 (508 mg, 1.22 mmol) were added sodium iodide (366 mg, 2.44 mmol) and copper(I) iodide (46.5 mg, 0.244 mmol) and (1R, 2R)-(−)-N,N'-dimethylcyclohexane-1,2-diamine (69.5 mg, 0.489 mmol), and the mixture was suspended in dioxane (2.5 mL). After purging with argon, the mixture was heated to 120° C. After 5 days, the mixture was allowed to cool to room temperature, sodium iodide (366 mg, 2.44 mmol) and copper(I) iodide (46.5 mg, 0.244 mmol) and (1R, 2R)-(−)-N,N'-dimethylcyclohexane-1,2-diamine (69.5 mg, 0.489 mmol) were added, and the mixture was heated to 120° C. After 1 day, the mixture was allowed to cool to room temperature, saturated aqueous ammonium chloride solution and ethyl acetate were added and the mixture was vigorously stirred. The obtained suspension was filtered through radiolite, and the residue was washed with ethyl acetate. The mixture was extracted with ethyl acetate, and the organic layer was washed with saturated brine, dried over anhydrous sodium sulfate, filtered and concentrated. The residue was purified by silica gel column chromatography to give compound 2 (331 mg, 53%).

MS m/z 508 [M+H]+, APCI(+)

Compound 2 (330 mg, 0.650 mmol) was dissolved in tetrahydrofuran (3 mL), cooled to −78° C., n-butyllithium (1.6 M hexane solution, 0.49 mL, 0.78 mmol) was slowly added dropwise, and the mixture was stirred for 1 hr. A solution (3 mL) of 4,4-difluorocyclohexanone (122 mg, 0.911 mmol) in tetrahydrofuran was slowly added dropwise, and the mixture was stirred for 1 hr, and heated to room temperature. After 1 hr, water was added, and the mixture was extracted with ethyl acetate. The organic layer was washed with saturated brine, dried over anhydrous sodium sulfate, filtered and concentrated. The residue was purified by silica gel column chromatography to give compound 3 (261 mg, 78%).

MS m/z 516 [M+H]+, APCI(+)

Compound 4 was synthesized by a method similar to that for compound 11 of Example 4 and compound 2 of Example 27.

MS m/z 465 [M+H]+, APCI(+)

Compound 5 was synthesized by a method similar to that for compound 3 of Example 27.

MS m/z 522 [M−H]−, ESI(−)

Compound 6 was synthesized by a method similar to that for compound 4 of Example 27.

MS m/z 478 [M−H]−, ESI(−)

Hydrobromide, hydrochloride, para-toluenesulfonate, methanesulfonate, benzenesulfonate, maleate and the like of the present compound can be produced by a general salt formation step.

Example 62

N-{4-[(6-cyclohexyl-5-hydroxypyridin-2-yl)methyl]-2,3,5-trimethylphenyl}glycine

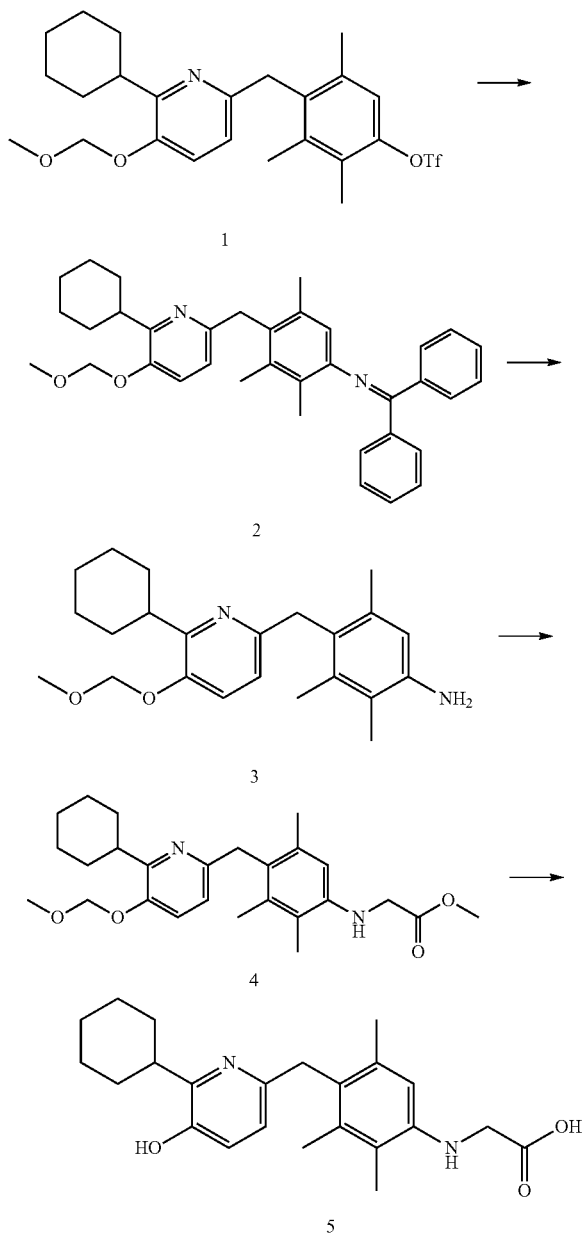

Compound 1 (2.00 g, 3.99 mmol) was dissolved in tetrahydrofuran (18 mL), and cesium carbonate (1.95 g, 5.98 mmol), benzophenone imine (867 mg, 4.79 mmol), (R)-BINAP (384 mg, 0.598 mmol), and palladium acetate (89.5 mg, 0.399 mmol) were added, and the mixture was purged with argon. The mixture was heated under reflux, and stirred overnight. The mixture was allowed to cool to room temperature, water was added, and the mixture was extracted with ethyl acetate. The organic layer was washed with saturated brine, dried over anhydrous sodium sulfate, filtered and concentrated. The residue was purified by silica gel column chromatography to give compound 2 (967 mg, 46%).

MS m/z 533 [M+H]+, APCI(+)

Compound 2 (1.78 g, 3.35 mmol) was dissolved in methanol (18 mL) and N,N'-dimethylformamide (18 mL). Hydroxyamine hydrochloride (466 mg, 6.71 mmol), and sodium acetate (826 mg, 10.1 mmol) were added. After stirring overnight, water was added, and the mixture was extracted with ethyl acetate. The organic layer was washed with saturated brine, dried over anhydrous sodium sulfate, filtered and concentrated. The residue was purified by silica gel column chromatography to give compound 3 (1.1B g, 95%).

MS m/z 369:M+H]+, APCI(+)

Compound 3 (200 mg, 0.542 mmol) was dissolved in acetonitrile (4 mL), and ethyl bromoacetate (104 mg, 0.675 mmol) and cesium carbonate (550 mg, 1.69 mmol) were added. After stirring for 7 hr, ethyl bromoacetate (104 mg, 0.675 mmol) and cesium carbonate (550 mg, 1.69 mmol) were added. After stirring overnight, ethyl bromoacetate (104 mg, 0.675 mmol) was added and the mixture was heated under reflux. After stirring for 7 hr, water was added, and the mixture was extracted with ethyl acetate. The organic layer was washed with saturated brine, dried over anhydrous sodium sulfate, filtered and concentrated. The residue was purified by silica gel column chromatography to give compound 4 (147 mg, 59%).

MS m/z 441 [M+H]+, APCI(+)

Compound 4 (141 mg, 0.319 mmol) was dissolved in methanol (0.6 mL) and tetrahydrofuran (0.6 mL). 6N Hydrochloric acid (1.0 mL) was added, and the mixture was heated to 60° C. After stirring for 2 hr, the mixture was allowed to cool to room temperature. The mixture was neutralized with 4N aqueous sodium hydroxide solution, and extracted with ethyl acetate. The organic layer was washed with saturated brine, and dried over anhydrous sodium sulfate. After filtration, the filtrate was concentrated, and the residue was dissolved in methanol (2.8 mL). 2N Sodium hydroxide (0.5 mL) was added, and the mixture was heated to 60° C. and stirred overnight. The mixture was allowed to cool to room temperature, 4N aqueous sodium hydroxide solution (3.0 mL) was added, and the mixture was concentrated. The residue was washed with ethyl acetate, neutralized with 1N hydrochloric acid and the precipitated solid was collected by filtration to give compound 5 (91.5 mg, 75%).

MS m/z 381 [M−H]−, ESI(−)

Hydrobromide, hydrochloride, para-toluenesulfonate, methanesulfonate, benzenesulfonate, maleate and the like of the present compound can be produced by a general salt formation step.

Example 63

({4-[(6-cyclohexyl-5-hydroxypyridin-2-yl)methyl]-3,5-dimethylphenoxy}methyl)phosphonic acid

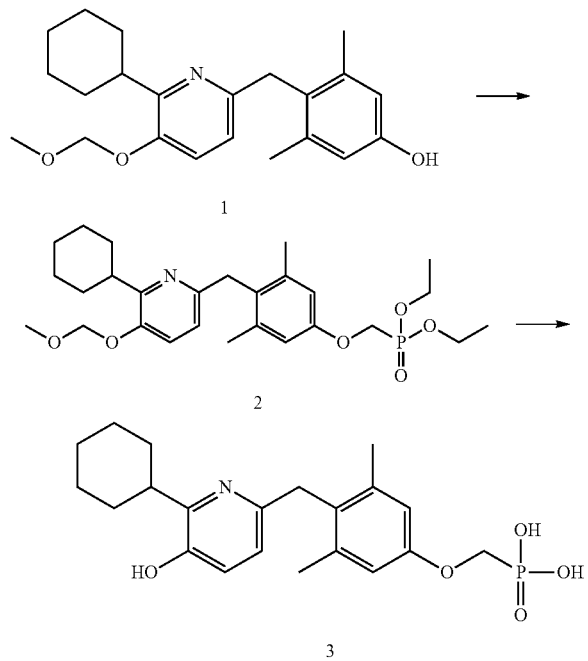

Example 64

N-{4-[(6-cyclohexyl-5-hydroxypyridin-2-yl)methyl]-3,5-dimethylbenzoyl}glycine

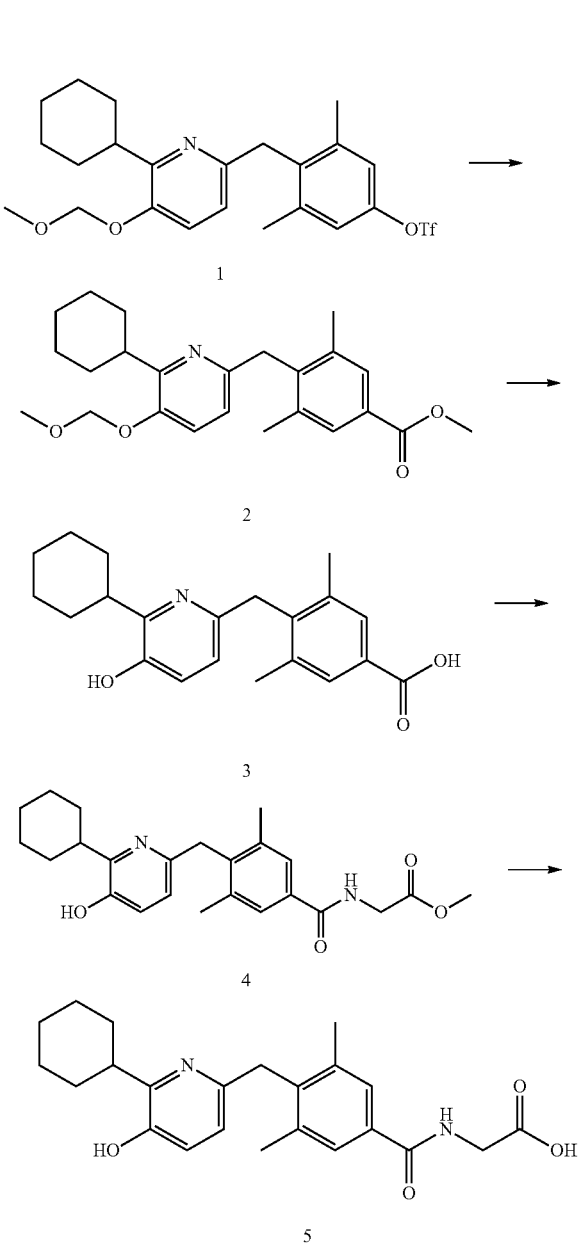

Compound 1 (300 mg, 0.844 mmol) was dissolved in N,N'-dimethylformamide (3 mL), and sodium hydride (mineral oil 60% dispersion, 40.5 mg, 1.01 mmol) was added. After stirring for 30 min, diethylphosphonomethyl triflate (104 mg, 0.675 mmol) was added. After stirring for 3 hr while allowing to cool, water was added, and the mixture was extracted with ethyl acetate. The organic layer was washed with saturated brine, dried over anhydrous sodium sulfate, filtered and concentrated. The residue was purified by silica gel column chromatography to give compound 2 (364 mg, 85%).

MS m/z 506 [M+H]+, APCI(+)

Compound 2 (363 mg, 0.718 mmol) was dissolved in dichloromethane (7.3 mL), and trimethylsilyl bromide (1.16 g, 7.180 mmol) was added. After stirring overnight, water (4.0 mL) and acetonitrile (4.0 mL) were added. After stirring overnight, the mixture was basified with 1N aqueous sodium hydroxide solution, and the aqueous layer was washed with ethyl acetate and neutralized with 1N hydrochloric acid. The precipitated solid was collected by filtration, and washed with ice water. The filtrate was ice-cooled, stood for 2 hr, and the precipitated solid was collected by filtration, and washed with ice water. The obtained solids were mixed, 6N hydrochloric acid (9.7 mL) was added and the mixture was heated under reflux. After stirring for 30 min, the mixture was basified with 4N aqueous sodium hydroxide solution, and the aqueous layer was washed with ethyl acetate, neutralized with 1N hydrochloric acid, and ice-cooled. After standing for 30 min, the precipitated solid was collected by filtration, and washed with ice water to give compound 3 (32.5 mg, 11%).

MS m/z 404 [M-H]-, ESI(-)

Hydrobromide, hydrochloride, para-toluenesulfonate, methanesulfonate, benzenesulfonate, maleate and the like of the present compound can be produced by a general salt formation step.

Compound 1 (4.26 g, 8.74 mmol) was dissolved in toluene (90 mL) and acetonitrile (45 mL), and purged with argon. Molybdenum hexacarbonyl (4.61 g, 17.5 mmol), palladium acetate (0.392 g, 1.75 mmol), BINAP (1.09 g, 1.75 mmol), cesium carbonate (3.13 g, 9.61 mmol), and methanol (5.60 g, 175 mmol) were added, and the mixture was heated to 90° C. After stirring for 16 hr, the mixture was allowed to cool to room temperature, iodine (4.44 g, 17.5 mmol) was added, and the mixture was vigorously stirred. After 2 hr, the mixture was filtered through celite, and ethyl acetate and saturated aqueous sodium thiosulfate solution were added to the filtrate, and the mixture was vigorously stirred. After 30 min, the mixture was filtered through celite, and the filtrate was extracted with ethyl acetate. The organic layer was washed with water and saturated brine, dried over anhydrous magnesium sulfate, filtered and concentrated. The residue was purified by silica gel column chromatography to give compound 2 (3.13 g, 90%).

MS m/z 398 [M+H]$^+$, APCI(+)

Compound 2 (1.12 g, 2.82 mmol) was dissolved in methanol (15 mL) and tetrahydrofuran (15 mL), 6N hydrochloric acid (15 mL) was added, and the mixture was heated to 50° C. After stirring for 22.5 hr, the mixture was heated to 60° C. After stirring for 2 hr, the mixture was allowed to cool to room temperature, and filtered through celite. The filtrate was neutralized with 2N aqueous sodium hydroxide solution, and concentrated. The residue was extracted with ethyl acetate, and the organic layer was washed with saturated brine, dried over anhydrous magnesium sulfate, filtered and concentrated. The obtained residue was dissolved in methanol (30 mL), 2N sodium hydroxide (14.1 mL, 28.2 mmol) was added, and the mixture was heated to 60° C. After stirring for 1.5 hr, the mixture was allowed to cool to room temperature, neutralized with 6N hydrochloric acid, and concentrated. The residue was extracted with ethyl acetate-tetrahydrofuran-methanol mixed solvent, and the organic layer was washed with saturated brine, dried over anhydrous magnesium sulfate, filtered and concentrated to give compound 3 (0.969 g, 100%).

MS m/z 338 [M−H]−, ESI(−)

Compound 3 (227 mg, 0.669 mmol) was dissolved in dichloromethane (7 mL) and N,N'-dimethylformamide (0.7 mL), and glycine methyl ester hydrochloride (126 mg, 1.00 mmol), 1-ethyl-3-(3-dimethylaminopropyl)carbodiimide hydrochloride (192 mg, 1.00 mmol), and 1-hydroxy-7-azabenzotriazole (137 mg, 1.00 mmol) were added and the mixture was ice-cooled. N-Methylmorpholine (135 mg, 1.34 mmol) was added, and the mixture was stirred for 10 min and heated to room temperature. After stirring for 18 hr, the mixture was concentrated. To the residue was added saturated aqueous ammonium chloride solution, and the mixture was extracted with ethyl acetate. The organic layer was washed with saturated aqueous sodium hydrogen carbonate, and saturated brine, dried over anhydrous magnesium sulfate, filtered and concentrated. The residue was purified by silica gel column chromatography to give compound 4 (183 mg, 67%).

MS m/z 411 [M+H]$^+$, APCI(+)

Compound 4 (180 mg, 0.438 mmol) was dissolved in methanol (4 mL), and 1N sodium hydroxide (0.877 mL, 0.877 mmol) was added. After stirring for 24 hr, the mixture was neutralized with 2N hydrochloric acid and concentrated. To the residue was added saturated brine, and the mixture was extracted with ethyl acetate-tetrahydrofuran mixed solvent. The organic layer was dried over anhydrous magnesium sulfate, filtered, and concentrated. The obtained residue was suspension washed with hexane-ether mixed solvent to give compound 5 (176 mg, 100%).

MS m/z 395 [M−H]−, ESI(−)

Hydrobromide, hydrochloride, para-toluenesulfonate, methanesulfonate, benzenesulfonate, maleate and the like of the present compound can be produced by a general salt formation step.

Example 65

{4-[(6-cyclohexyl-4-fluoro-5-hydroxypyridin-2-yl)methyl]-2,3,5-trimethylphenoxy}acetic acid

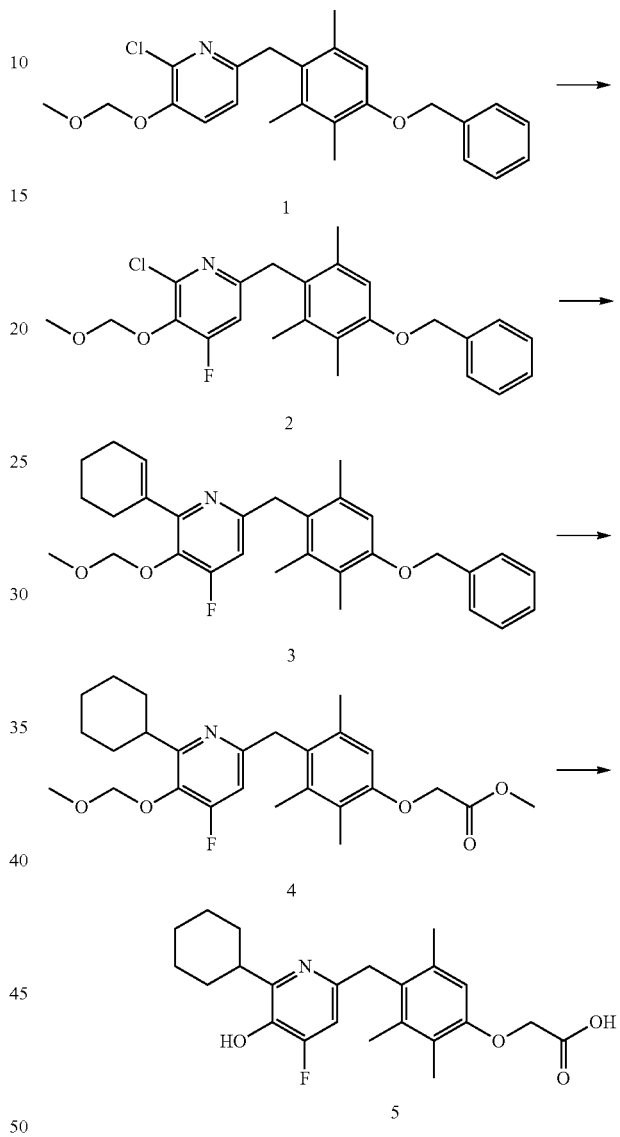

Compound 1 (439 mg, 1.06 mmol) was dissolved in tetrahydrofuran (8 and the mixture was cooled to −78° C. n-Butyllithium (1.6 M hexane solution, 0.75 mL, 1.1 mmol) was slowly added dropwise, and the mixture was stirred for 1 hr. N-Fluorobenzenesulfonimide (504 mg, 1.60 mmol) was added, and the mixture was stirred for 1 hr, and heated to room temperature. After 1 hr, water was added, and the mixture was extracted with ethyl acetate. The organic layer was washed with saturated brine, dried over anhydrous sodium sulfate, filtered and concentrated. The residue was purified by silica gel column chromatography to give compound 3 (375 mg, 82%).

MS m/z 430/432 [M+H]$^+$, APCI(+)

Compound 3 was synthesized by a method similar to that for compound 2 of Example 5.

MS m/z 476 [M+H]+, APCI(+)

Compound 4 was synthesized by a method similar to that for compound 8 of Example 2.

MS m/z 460 [M+H]+, APCI(+)

Compound 5 was synthesized by a method similar to that for compound 13 of Example 4.

MS m/z 400 [M−H]−, ESI(−)

Hydrobromide, hydrochloride, para-toluenesulfonate, methanesulfonate, benzenesulfonate, maleate and the like of the present compound can be produced by a general salt formation step.

Example 66

3-[(4-{[6-(3-ethoxyphenyl)-5-hydroxypyridin-2-yl]methyl}-2-fluoro-3,5-dimethylphenoxy)methyl]-1,2,4-oxadiazol-5(4H)-one

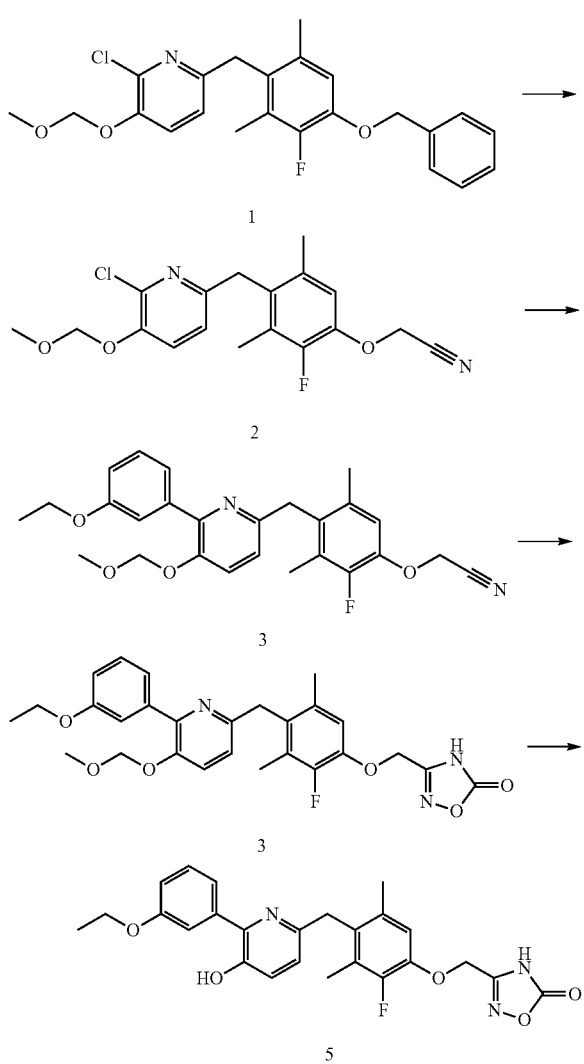

Compound 1 (6.24 g, 15.0 mmol) was dissolved in tetrahydrofuran (150 mL), 5% Pd/C (1.36 g) was added and the mixture was purged with hydrogen, and stirred for 4 hr, filtered and concentrated. The obtained residue was dissolved in acetonitrile (170 mL). Cesium carbonate (8.48 g, 26 mmol), and bromoacetonitrile (2.71 g, 23 mmol) were added, and the mixture was stirred at room temperature for 1.5 hr. Ethyl acetate, and water were added and the mixture was stirred and extracted with ethyl acetate. The organic layer was washed with water and saturated brine, dried over anhydrous sodium sulfate, filtered, and concentrated. The residue was purified by silica gel column chromatography to give compound 2 (4.65 g, 85%).

MS m/z 365/367 [M+H]+, APCI(+)

Compound 2 (128 mg, 0.35 mmol), 3-ethoxyphenylboronic acid (88 mg, 0.53 mmol), [1,1'-bis(diphenylphosphino)ferrocene]dichloropalladium(II) dichloromethane complex (29 mg, 0.04 mmol), and cesium carbonate (342 mg, 1.05 mmol) were measured and purged with argon, suspended in dioxane (3.5 mL) and heated under reflux overnight. The mixture was allowed to cool to room temperature, filtered through celite, washed with aqueous ammonium chloride solution and saturated brine, ChemElute filtered, and concentrated. The residue was purified by silica gel column chromatography to give compound 3 (132 mg, 82%).

MS m/z 451 [M+H]+, APCI(+)

Compound 3 (129 mg, 0.29 mmol) was dissolved in methanol (1.5 mL), and tetrahydrofuran (0.5 mL), hydroxyamine hydrochloride (30 mg, 0.43 mmol) and sodium hydrogen carbonate (227 mg, 0.86 mmol) were added. After heating under reflux for 1.5 hr, the mixture was allowed to cool to room temperature, aqueous ammonium chloride solution, and ethyl acetate were added and the mixture was stirred. The mixture was extracted with ethyl acetate, and the organic layer was washed with water and saturated brine, dried over anhydrous sodium sulfate, filtered, and concentrated. 1,4-Dioxane (3 mL) and then 1,1'-carbonyldiimidazole (70 mg, 0.43 mmol) were added. After stirring at room temperature for 1 hr, the mixture was heated under reflux for 2.5 hr. The mixture was allowed to cool to room temperature, ethyl acetate, and water were added, and the mixture was neutralized with 5% hydrochloric acid. The mixture was extracted with ethyl acetate, and the organic layer was washed with water and saturated brine, dried over anhydrous sodium sulfate, filtered, and concentrated. The residue was purified by silica gel column chromatography to give compound 4 (124 mg, 85%).

MS m/z 508 [M−H]−, ESI(−)

Compound 4 (123 mg, 0.24 mmol) was dissolved in ethanol (3.5 mL), 6N hydrochloric acid (0.6 mL) was added, and the mixture was stirred at 50° C. for 5 hr. The mixture was allowed to cool to room temperature, and neutralized with 2N sodium hydroxide (1.8 mL). Ethyl acetate, and aqueous ammonium chloride solution were added and the mixture was stirred. The mixture was extracted with ethyl acetate, and the organic layer was washed with water and saturated brine, dried over anhydrous sodium sulfate, filtered, and concentrated. The residue was purified by silica gel column chromatography to give compound 5 (75 mg, 67%).

MS m/z 464 [M−H]−, ESI(−)

Hydrobromide, hydrochloride, para-toluenesulfonate, methanesulfonate, benzenesulfonate, maleate and the like of the present compound can be produced by a general salt formation step.

Example 67

N-{4-[(6-cyclohexyl-5-hydroxypyridin-2-yl)methyl]-3,5-dimethylbenzyl}glycine

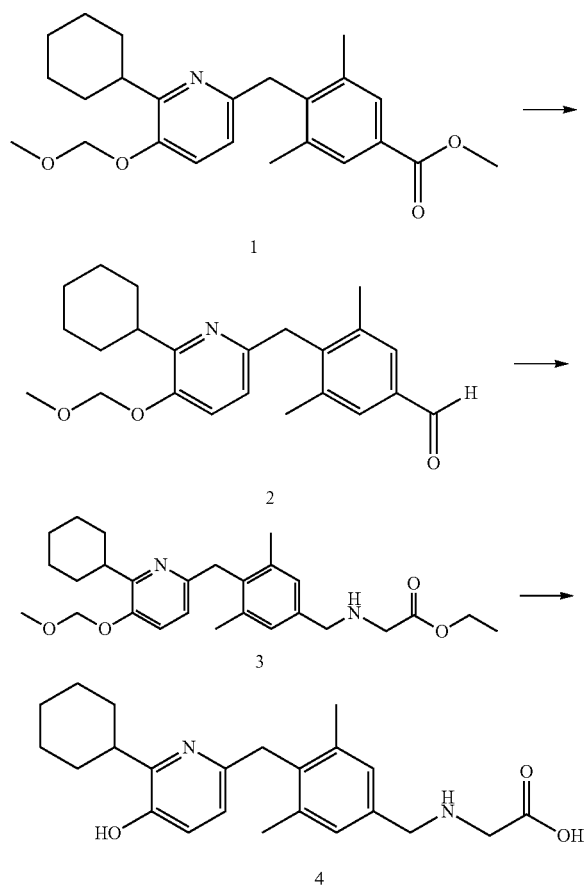

Under an argon atmosphere, compound 1 (700 mg, 1.8 mmol) was dissolved in toluene (4 mL), and the mixture was ice-cooled. Sodium bis(2-methoxyethoxy)aluminum hydride (3.6 M toluene solution, 1.0 mL, 3.6 mmol) and 1-methylpiperidine (0.44 mL, 4.0 mmol) were mixed and added to a toluene solution of compound 1. The mixture was stirred for 1 hr while allowing to warm to room temperature, water was added and the mixture to was filtered through radiolite. The aqueous layer was extracted with ethyl acetate. The organic layer was washed with saturated brine, dried over anhydrous sodium sulfate, filtered and concentrated. The residue was purified by silica gel column chromatography to give compound 2 (379 mg, 57%).

MS m/z 368 [M+H]$^+$, APCI(+)

Compound 2 (100 mg, 0.27 mmol) was dissolved in ethanol (1 mL). Sodium acetate (90 mg, 1.1 mmol), glycine ethyl ester hydrochloride (175 mg, 1.3 mmol) and sodium cyanoborohydride (27 mg, 0.43 mmol) were added and the mixture was stirred overnight. Saturated aqueous sodium hydrogen carbonate solution was added, and the mixture was extracted with ethyl acetate. The organic layer was washed with saturated brine, dried over anhydrous sodium sulfate, filtered and concentrated. The residue was purified by silica gel column chromatography to give compound 3 (61 mg, 50%).

MS m/z 455 [M+H]$^+$, APCI(+)

Compound 4 was synthesized by a method similar to that for compound 13 of Example 4.

MS m/z 381 [M−H]$^+$, APCI(+)

Hydrobromide, hydrochloride, para-toluenesulfonate, methanesulfonate, benzenesulfonate, maleate and the like of the present compound can be produced by a general salt formation step.

Example 68

3-[({4-[(5-hydroxy-6-phenylpyridin-2-yl)(methoxy)methyl]-5-methyl-2,3-dihydro-1-benzofuran-7-yl}oxy)methyl]-1,2,4-oxadiazol-5(4H)-one

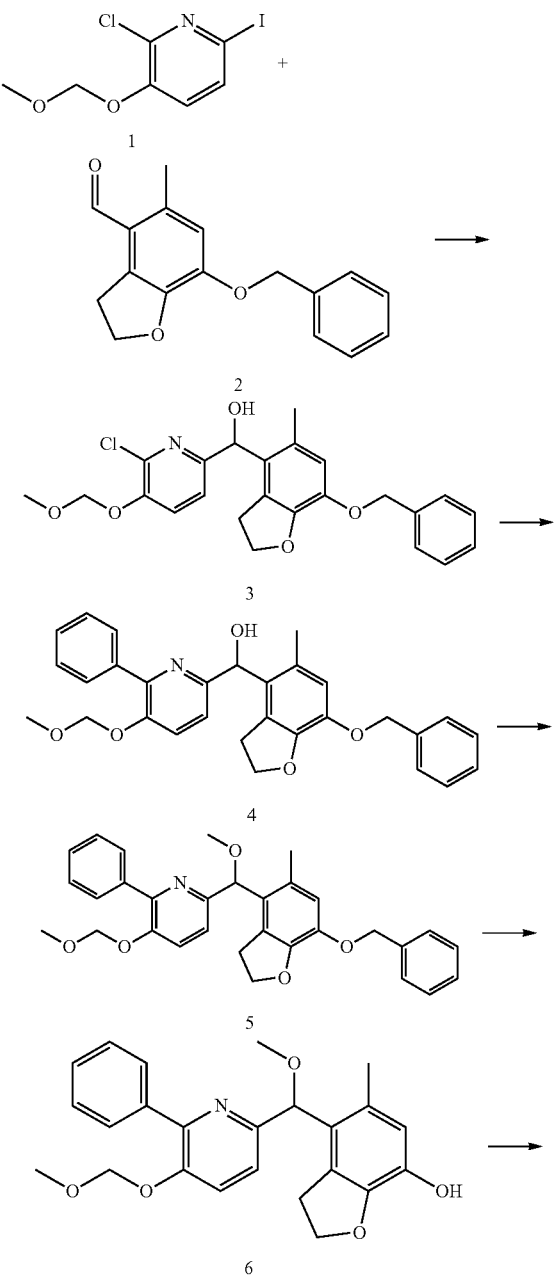

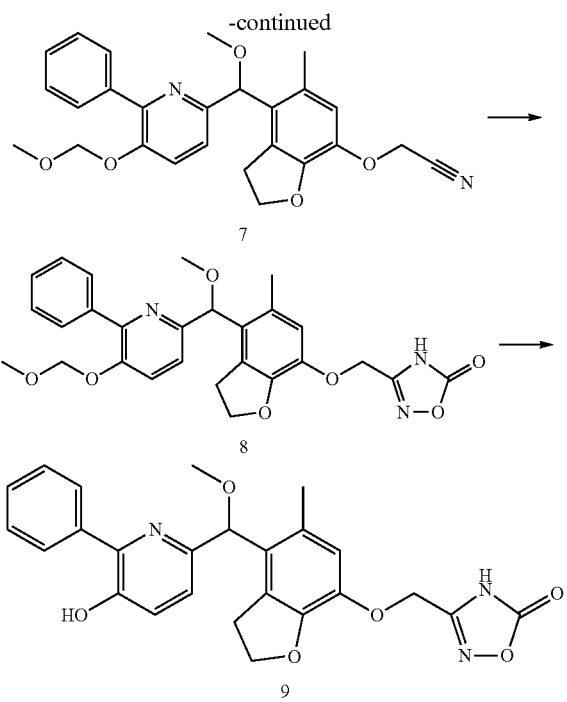

15

Compound 1 (3.22 g, 10.75 mmol) was dried azeotropically with toluene and, after purging with argon, dissolved in toluene (90 mL) and the mixture was cooled to −78° C. n-Butyllithium (1.57 M hexane solution, 6.85 mL, 10.7 mmol) was slowly added dropwise, and the mixture was stirred for 30 min. A solution of compound 2 (2.62 g, 9.77 mmol) in toluene (10 mL) was added dropwise, and the mixture was stirred for 1 hr while allowing to warm to room temperature. Aqueous ammonium chloride solution was added, and the mixture was extracted with ethyl acetate. The organic layer was washed with water and saturated brine, dried over anhydrous sodium sulfate, filtered, and concentrated. The residue was purified by silica gel column chromatography to give compound 3 (3.75 g, 87%).

MS m/z 442/444 [M+H]$^+$, APCI(+)

Compound 3 (221 mg, 0.500 mmol), phenylboronic acid (91 mg, 0.75 mmol), tetrakistriphenylphosphinepalladium(0) (58 mg, 0.05 mmol), and potassium carbonate (207 mg, 1.5 mmol) were purged with argon, dioxane (2.8 mL), and water (0.7 mL) were added, and the mixture was stirred at 90° C. overnight. The mixture was allowed to cool to room temperature, ethyl acetate, and water were added, and the mixture was stirred and filtered through celite. The filtrate was extracted with ethyl acetate, and the organic layer was washed with water and saturated brine, dried over anhydrous sodium sulfate, filtered, and concentrated. The residue was purified by silica gel column chromatography to give compound 4 (231 mg, 96%).

MS m/z 484 [M+H]$^+$, APCI(+)

Compound 4 (85 mg, 0.18 mmol) was dissolved in tetrahydrofuran (2 mL), and the mixture was ice-cooled. Sodium hydride (mineral oil 60% dispersion, 7.7 mg, 0.19 mmol) was added and the mixture was stirred for 10 min. Methyl iodide (37 mg, 0.27 mmol) was added, and the mixture was stirred for 2 hr while allowing to warm to room temperature. Methyl iodide (19 mg, 0.13 mmol), and sodium hydride (mineral oil 60% dispersion, 3 mg, 0.07 mmol) were added, and the mixture was further stirred for 1 hr. Ethyl acetate, and water were added, and the mixture was stirred, and extracted with ethyl acetate. The organic layer was washed with water and saturated brine, dried over anhydrous sodium sulfate, filtered, and concentrated. The residue was purified by silica gel column chromatography to give compound 5 (76 mg, 86%).

MS m/z 498 [M+H]$^+$, APCI(+)

Compound 6 was synthesized by a method similar to that for compound 11 of Example 4.

MS m/z 408 [M+H]$^+$, APCI(+)

Compound 7 was synthesized by a method similar to that for compound 2 of Example 27.

MS m/z 447 [M+H]$^+$, APCI(+)

Compound 8 was synthesized by a method similar to that for compound 3 of Example 27.

MS m/z 504 [M−H]$^-$, ESI(−)

Compound 9 was synthesized by a method similar to that for compound 4 of Example 27.

MS m/z 460 [M−H]$^-$, ESI(−)

Hydrobromide, hydrochloride, para-toluenesulfonate, methanesulfonate, benzenesulfonate, maleate and the like of the present compound can be produced by a general salt formation step.

Example 69

3-[({4-[[6-(2-fluoro-3-methylphenyl)-5-hydroxypyridin-2-yl](hydroxy)methyl]-5-methyl-2,3-dihydro-1-benzofuran-7-yl}oxy)methyl]-1,2,4-oxadiazol-5(4H)-one

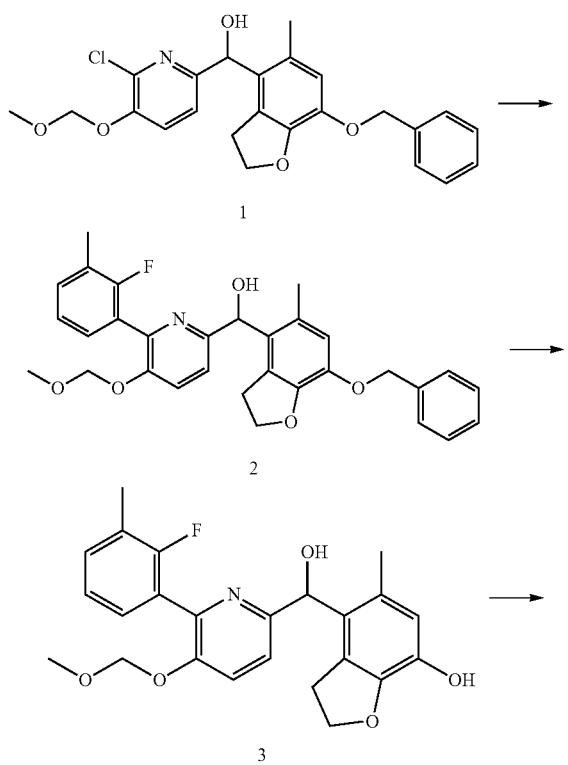

135

-continued

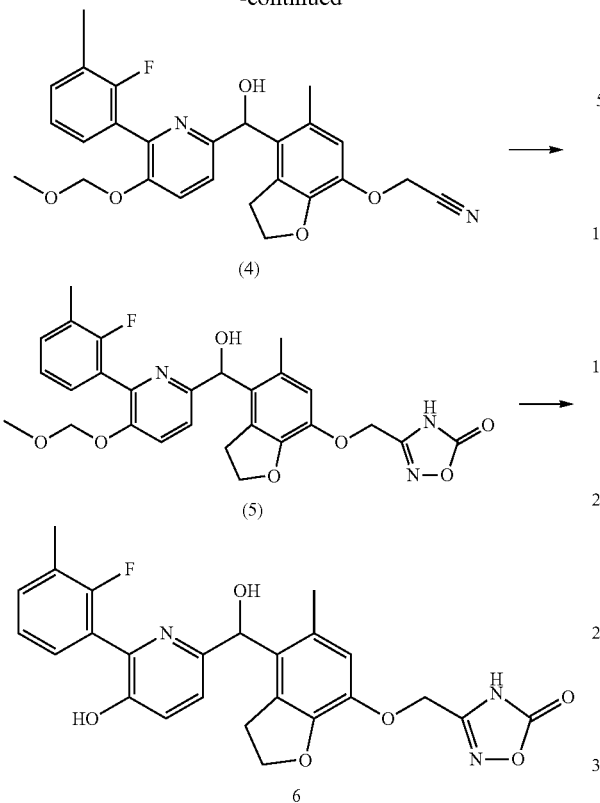

Compound 1 (221 mg, 0.500 mmol), 2-fluoro-3-methylphenylboronic acid (115 mg, 0.75 mmol), tetrakistriphenylphosphinepalladium(0) (58 mg, 0.05 mmol), and potassium carbonate (207 mg, 1.5 mmol) were purged with argon, 1,4-dioxane (2.8 mL), and water (0.7 mL) were added, and the mixture was stirred at 90° C. overnight. The mixture was allowed to cool to room temperature, ethyl acetate, and water were added, and the mixture was stirred and filtered through celite. The filtrate was extracted with ethyl acetate, and the organic layer was washed with water and saturated brine, dried over anhydrous sodium sulfate, filtered, and concentrated. The residue was purified by silica gel column chromatography to give compound 2 (246 mg, 95%).

MS m/z 516 [M+H]$^+$, APCI(+)

Compound 3 was synthesized by a method similar to that for compound 11 of Example 4.

MS m/z 426 [M+H]$^+$, APCI(+)

Compound 4 was synthesized by a method similar to that for compound 2 of Example 27.

MS m/z 465 [M+H]$^+$, APCI(+)

Compound 5 was synthesized by a method similar to that for compound 3 of Example 27.

MS m/z 522 [M−H]−, ESI(−)

Compound 6 was synthesized by a method similar to that for compound 4 of Example 27.

MS m/z 478 [M−H]−, ESI(−)

Hydrobromide, hydrochloride, para-toluenesulfonate, methanesulfonate, benzenesulfonate, maleate and the like of the present compound can be produced by a general salt formation step.

136

Example 70

{3-bromo-2-fluoro-4-[(5-hydroxy-6-phenylpyridin-2-yl)methyl]-5-methylphenoxy}acetic acid

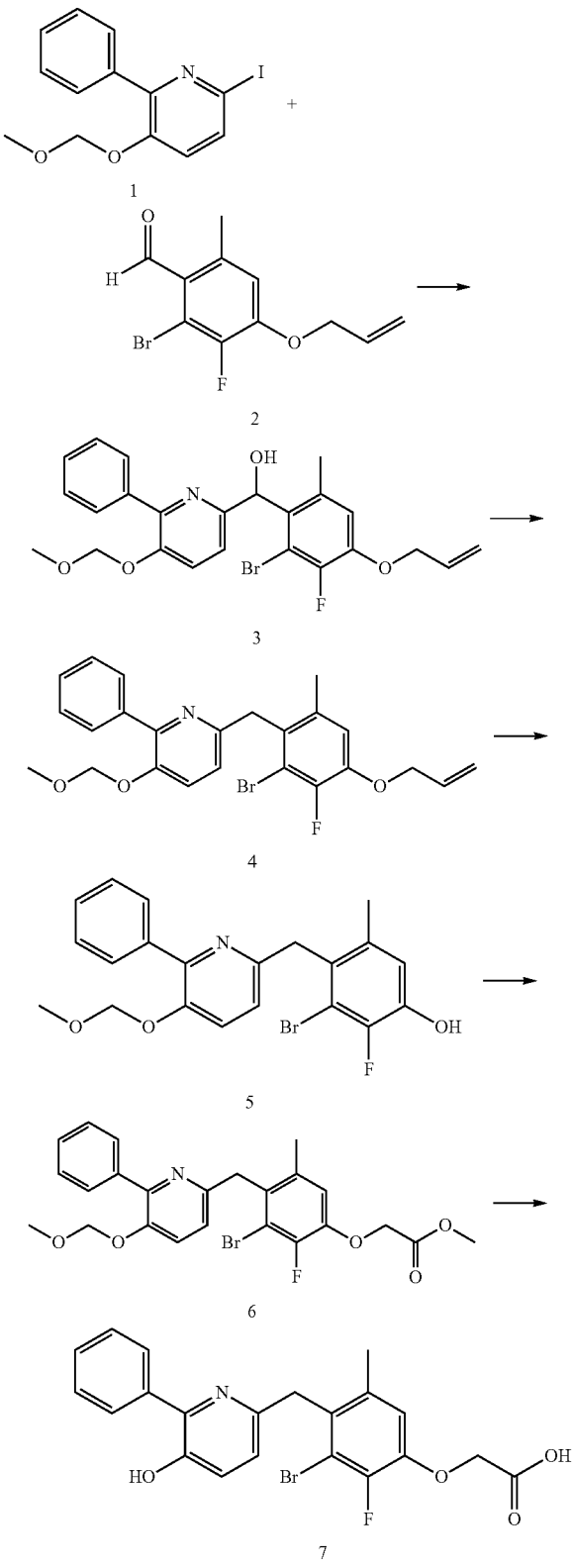

Compound 1 (571 mg, 1.67 mmol) was dissolved in tetrahydrofuran (1.7 mL) and, after ice-cooling, isopropylmagnesium chloride-lithium chloride (1.3 M tetrahydrofuran solution, 1.29 mL, 1.67 mmol) was added dropwise. After stirring for 1 hr, isopropylmagnesium chloride-lithium chloride (1.3 M tetrahydrofuran solution, 0.64 mL, 0.835 mmol) was added dropwise. After stirring for 1 hr, compound 2 (457 mg, 1.67 mmol) was added. After stirring for 45 min, the mixture was heated to room temperature. After stirring for 14 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 3.

MS m/z 488/490 [M+H]+, APCI(+)

Compound 3 was dissolved in dichloromethane (15 mL), triethylamine (292 mg, 2.88 mmol) was added and the mixture was ice-cooled. Methanesulfonyl chloride (247 mg, 2.16 mmol) was added dropwise, and the mixture was heated to room temperature. After stirring for 1 hr, triethylamine (146 mg, 1.44 mmol) and methanesulfonyl chloride (124 mg, 1.08 mmol) were added. After stirring for 30 min, triethylamine (146 mg, 1.44 mmol) and methanesulfonyl chloride (124 mg, 1.08 mmol) were added. After stirring for 30 min, saturated aqueous sodium hydrogen carbonate was added, and the mixture was extracted with ethyl acetate. The organic layer was washed with saturated brine, dried over anhydrous magnesium sulfate, filtered and concentrated. The residue was dissolved in dichloromethane (15 mL), triethylsilane (201 mg, 1.73 mmol) was added and the mixture was ice-cooled. Silver trifluoromethanesulfonate (444 mg, 1.73 mmol) was added and, after stirring for 45 min, saturated aqueous sodium hydrogen carbonate and saturated brine were added, and the mixture was vigorously stirred. After 15 min, the mixture was filtered through celite, and the filtrate was extracted with chloroform. The organic layer was washed with saturated brine, dried over anhydrous magnesium sulfate, filtered and concentrated. The residue was purified by silica gel column chromatography to give compound 4 (389 mg, 49%, 2step).

MS m/z 472/474 [M+H]+, APCI(+)

Compound 4 (386 mg, 0.817 mmol) was dissolved in tetrahydrofuran (8 mL), and N-methylmorpholine (107 mg, 1.23 mmol) and tetrakistriphenylphosphinepalladium(0) (47 mg, 0.0409 mmol) were added. After stirring for 30 min, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 5 (317 mg, 90%).

MS m/z 432/434 [M+H]+, APCI(+)

Compound 6 was synthesized by a method similar to that for compound 12 of Example 4.

MS m/z 504/506 [M+H]+, APCI(+)

Compound 7 was synthesized by a method similar to that for compound 13 of Example 4.

MS m/z 444/446 [M−H]−, ESI(−)

Hydrobromide, hydrochloride, para-toluenesulfonate, methanesulfonate, benzenesulfonate, maleate and the like of the present compound can be produced by a general salt formation step.

Example 71

3-[(4-{[6-(3,3-difluorocyclohexyl)-5-hydroxypyridin-2-yl]methyl}-2-fluoro-3,5-dimethylphenoxy)methyl]-1,2,4-oxadiazol-5(4H)-one

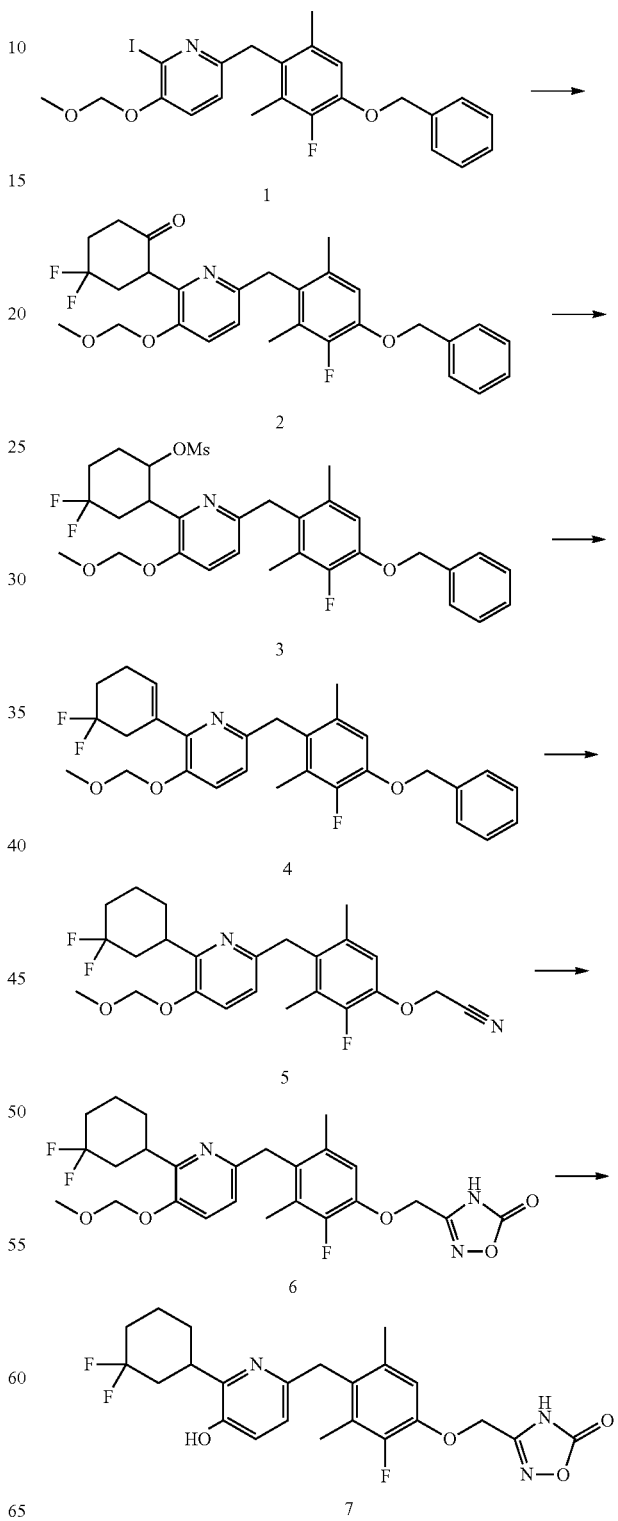

To compound 1 (497 mg, 0.980 mmol) were added 4,4-difluorocyclohexanone (314 mg, 2.34 mmol), sodium tert-butoxide (225 mg, 2.34 mmol), palladium acetate (26 mg, 0.12 mmol), and 2-(dicyclohexylphosphino)-2'-methylbiphenyl (85 mg, 0.23 mmol). Toluene (12 mL) was added, and the mixture was purged with argon and heated to 80° C. After 18 hr, the mixture was allowed to cool to room temperature, water and 6N hydrochloric acid were added, and the mixture was extracted with ethyl acetate. The organic layer was washed with saturated brine, dried over anhydrous sodium sulfate, filtered and concentrated. The residue was purified by silica gel column chromatography to give compound 2 (165 mg, 32%).

MS m/z 514 [M+H]$^+$, APCI(+)

Compound 2 (165 mg, 0.322 mmol) was dissolved in methanol (3 mL), and sodium borohydride (24.4 mg, 0.644 mmol) was added.

After 5 hr, saturated aqueous ammonium chloride solution was added, and the mixture was extracted with ethyl acetate. The organic layer was dried over anhydrous sodium sulfate, filtered, concentrated, and dried. To the obtained residue was added dichloromethane (3 mL), and triethylamine (0.27 mL, 1.93 mmol), trimethylamine hydrochloride (3 mg, 0.03 mmol), and methanesulfonyl chloride (0.074 mL, 0.96 mmol) were added. After 15 hr, saturated aqueous sodium hydrogen carbonate was added, and the mixture was extracted with chloroform. The organic layer was dried over anhydrous sodium sulfate, filtered, and concentrated. The residue was purified by silica gel column chromatography to give diastereomers (61 mg, 32%, 36 mg, 19%) of compound 3.

MS m/z 594 [M+H]$^+$, APCI(+)

Compound 3 (59 mg, 0.099 mmol) was dissolved in N,N'-dimethylformamide (1.2 mL), and 1,8-diazabicyclo[5.4.0]undec-7-ene (0.030 mL, 0.20 mmol) was added. The mixture was heated to 60° C. and, after 3 hr, heated to 100° C. One day later, the mixture was allowed to cool to room temperature, 1N hydrochloric acid was added, and the mixture was extracted with ethyl acetate. The organic layer was washed with saturated brine, dried over anhydrous sodium sulfate, filtered and concentrated. The residue was purified by silica gel 30 column chromatography to give compound 4 (31 mg, 63%).

MS m/z 498 [M+H]$^+$, APCI(+)

Compound 5 was synthesized by a method similar to that for compound 11 of Example 4 and compound 2 of Example 27.

MS m/z 449 [M+H]$^+$, ESI(+)

Compound 6 was synthesized by a method similar to that for compound 3 of Example 27.

MS m/z 506 [M−H]−, ESI(−)

Compound 7 was synthesized by a method similar to that for compound 4 of Example 27.

MS m/z 462 [M−H]−, ESI(−)

Hydrobromide, hydrochloride, para-toluenesulfonate, methanesulfonate, benzenesulfonate, maleate and the like of the present compound can be produced by a general salt formation step.

Example 72

3-({5-ethyl-2-fluoro-4-[(5-hydroxy-6-phenylpyridin-2-yl)methyl]-3-methylphenoxy)methyl)-1,2,4-oxadiazol-5(4H)-one

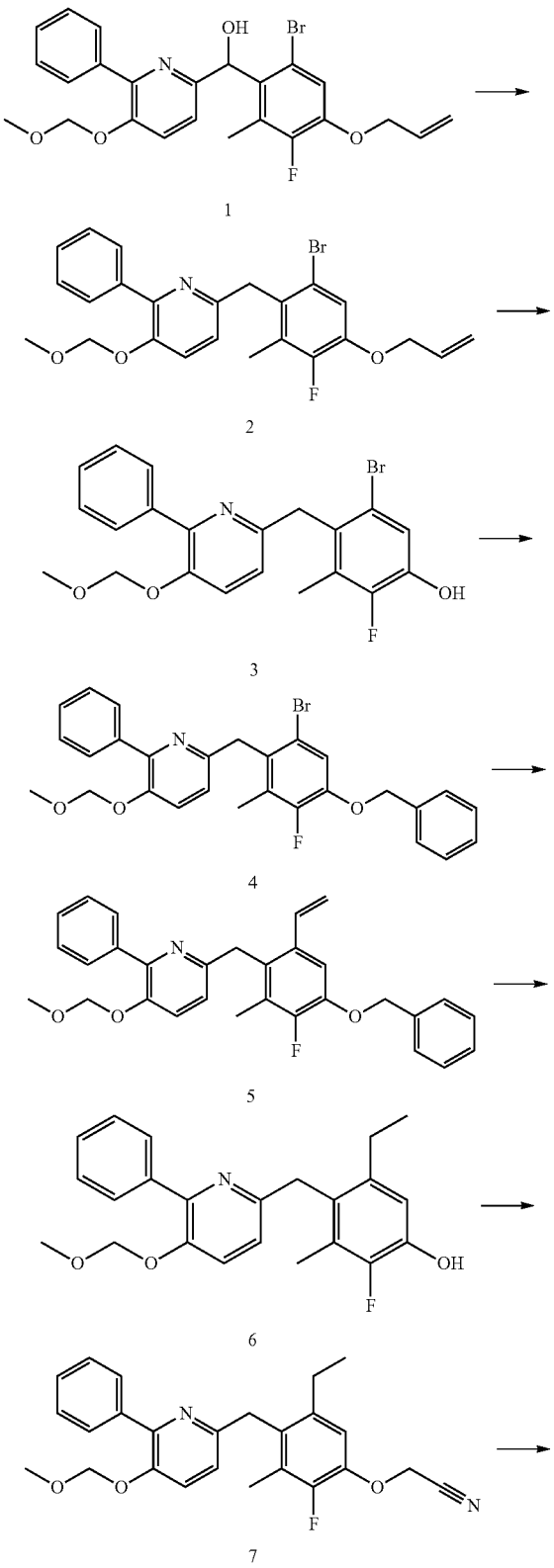

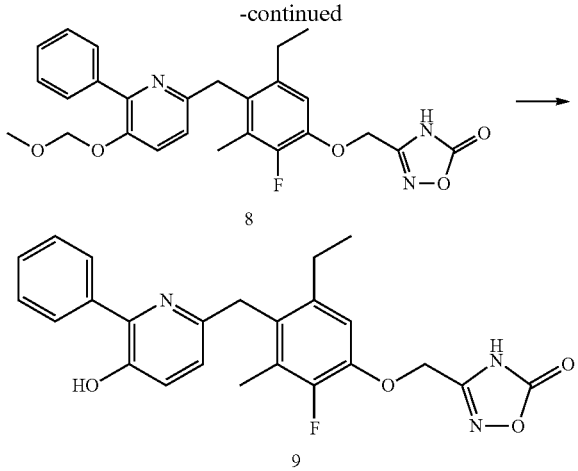

Compound 1 (1.6 g, 3.4 mmol) was dissolved in dichloromethane (33 ml), and the mixture was ice-cooled. Methanesulfonyl chloride (0.78 mL, 10 mmol) and triethylamine (1.9 ml, 14 mmol) were added, and the mixture was allowed to warm to room temperature. Further, methanesulfonyl chloride (0.40 mL, 5.2 mmol) and triethylamine (0.95 mL, 6.8 mmol) were added and, after stirring overnight, saturated aqueous ammonium chloride solution was added, and the mixture was extracted with ethyl acetate. The organic layer was washed with saturated brine, dried over anhydrous sodium sulfate, filtered and concentrated. The residue was purified by silica gel column chromatography. The obtained residue (1.7 g) was dissolved in dichloromethane (34 mL), and the mixture was ice-cooled. Under an argon atmosphere, triethylsilane (0.81 mL, 5.1 mmol) and silver trifluoromethanesulfonate (1.3 g, 5.1 mmol) were added and the mixture was stirred for 1 hr. Saturated aqueous sodium hydrogen carbonate solution was added, and the mixture was filtered through radiolite. The aqueous layer was extracted with ethyl acetate. The organic layer was washed with saturated brine, dried over anhydrous sodium sulfate, filtered and concentrated. The residue was purified by silica gel column chromatography to give compound 2 (970 mg, 60%).

MS m/z 472/474 [M+H]$^+$, APCI(+)

Under an argon atmosphere, compound 2 (970 mg, 2.10 mmol) was dissolved in tetrahydrofuran (21 mL), and morpholine (0.28 mL, 3.2 mmol) and tetrakistriphenylphosphine-palladium(0) (119 mg, 0.11 mmol) were added. After stirring for 6 hr, saturated aqueous ammonium chloride solution was added, and the mixture was extracted with ethyl acetate. The organic layer was washed with saturated brine, dried over anhydrous sodium sulfate, filtered and concentrated. The residue was purified by short silica gel column chromatography to give compound 3 (745 mg, 82%).

MS m/z 432/434 [M+H]$^+$, APCI(+)

Compound 4 was synthesized by a method similar to that for compound 3 of Example 2.

MS m/z 522/524 [M+H]$^+$, APCI(+)

Under an argon atmosphere, compound 4 (630 mg, 1.2 mmol) was dissolved in dimethoxyethane (13 mL) and water (1.3 ml). Tetrakistriphenylphosphine(0) (139 mg, 0.12 mmol) and vinylboronic acid pinacol ester (462 mg, 3.0 mmol) and cesium carbonate (1.1 g, 3.6 mmol) were added and the mixture was heated to 90° C. and stirred overnight. Saturated aqueous ammonium chloride solution was added, and the mixture was extracted with ethyl acetate. The organic layer was washed with saturated brine, dried over anhydrous sodium sulfate, filtered and concentrated. The residue was purified by short silica gel column chromatography to give compound 5 (457 mg, 81%).

MS m/z 470 [M+H]$^+$, APCI(+)

Compound 6 was synthesized by a method similar to that for compound 11 of Example 4.

MS m/z 382 [M+H]$^+$, APCI(+)

Compound 7 was synthesized by a method similar to that for compound 2 of Example 27.

MS m/z 421 [M+H]$^+$, APCI(+)

Compound 8 was synthesized by a method similar to that for compound 3 of Example 27.

MS m/z 478 [M−H]$^+$, APCI(+)

Compound 9 was synthesized by a method similar to that for compound 4 of Example 27.

MS m/z 434 [M+H]$^+$, APCI(+)

Hydrobromide, hydrochloride, para-toluenesulfonate, methanesulfonate, benzenesulfonate, maleate and the like of the present compound can be produced by a general salt formation step.

Example 73

{4-[(6-cyclohexyl-3-fluoro-5-hydroxypyridin-2-yl)methyl]-2,3,5-trimethylphenoxy}acetic acid

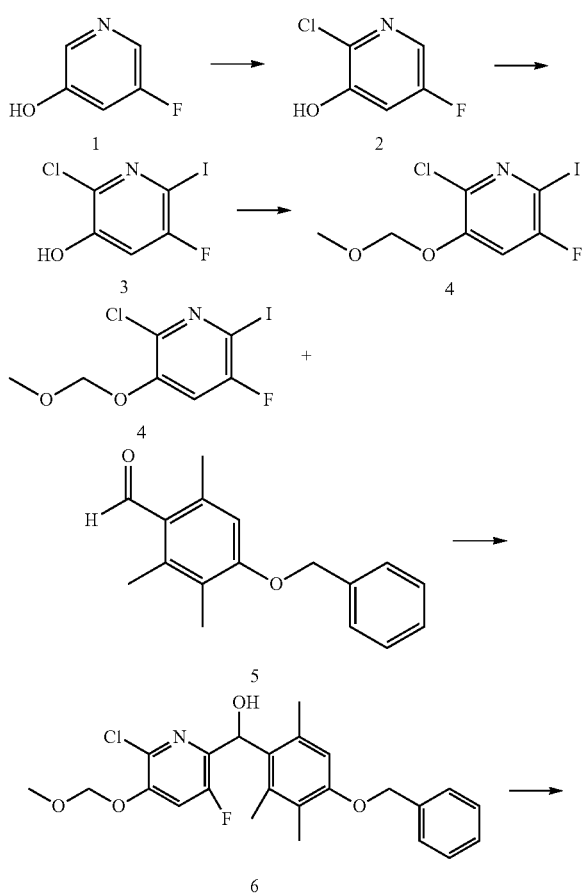

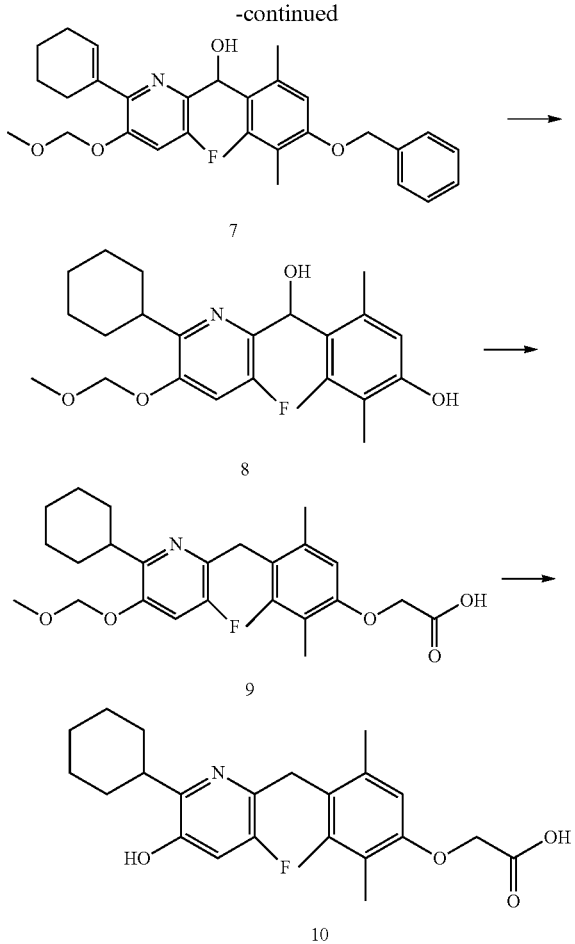

Compound 1 (880 mg, 7.78 mmol) was suspended in water (13 mL) and the suspension was ice-cooled. Sodium hydroxide (560 mg, 14.0 mmol) was added to give a solution, 5% aqueous sodium hypochlorite solution (11.6 mL, 7.78 mmol) was added dropwise over 5 min. After stirring for 10 min, the mixture was heated to room temperature. After stirring for 20 hr, the mixture was ice-cooled, and 5% aqueous sodium hypochlorite solution (2.32 mL, 1.56 mmol) was added dropwise. After stirring for 10 min, the mixture was heated to room temperature. After stirring for 72 hr, 6N hydrochloric acid was added to adjust to pH 2, and the mixture was extracted with ethyl acetate. The organic is layer was dried over anhydrous magnesium sulfate, filtered and concentrated to give compound 2.

MS m/z 148/150 [M+H]$^+$, APCI(+)

Compound 2 was suspended in water (7 mL), and potassium carbonate (2.01 g, 14.6 mmol) was added to give a solution. Iodine (1.06 g, 4.16 mmol) was added, and the mixture was stirred for 18 hr. Saturated aqueous sodium thiosulfate solution was added. 6N Hydrochloric acid was added to adjust to pH 2, and the mixture was extracted with ethyl acetate. The organic layer was dried over anhydrous magnesium sulfate, filtered and concentrated to give compound 3.

MS m/z 272/274 [M−H]−, ESI(−)

Compound 3 was dissolved in acetonitrile (20 mL) and tetrahydrofuran (20 mL), cesium carbonate (5.47 g, 16.8 mmol) and chloromethyl methyl ether (676 mg, 8.39 mmol) were added. After stirring for 14 hr, the mixture was filtered through celite. The filtrate was concentrated, and the residue was purified by silica gel column chromatography to give compound 4.

MS m/z 318/320 [M+H]$^+$, APCI(+)

Compound 4 was dissolved in toluene (40 mL), and the mixture was cooled to −78° C. n-Butyllithium (1.67M hexane solution, 2.23 mL, 3.72 mmol) was added dropwise over 5 min, and the mixture was stirred for 25 min. Compound 5 (0.945 g, 3.72 mmol) was dissolved in toluene (5 mL) and the mixture was added dropwise over 5 min. After stirring for 25 min, the mixture was heated to room temperature. After stirring for 1 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 6 (1.57 g, 45%, 4 steps).

MS m/z 428/430 [M+H−H$_2$O]$^+$, APCI(+)

Compound 6 (1.03 g, 2.31 mmol) was dissolved in 1,4-dioxane (16 ml), and water (4 ml), potassium carbonate (958 mg, 6.93 mmol), and 1-cyclohexeneboronic acid (440 mg, 3.46 mmol) were added, and the mixture was purged with argon. Tetrakistriphenylphosphinepalladium(0) (80 mg, 0.0693 mmol) was added, and the mixture was heated to 90° C. After stirring for 2 hr, 1-cyclohexeneboronic acid (440 mg, 3.46 mmol) and tetrakistriphenylphosphinepalladium(0) (160 mg, 0.139 mmol) were added. After stirring for 1.5 hr, the mixture was allowed to cool to room temperature, and filtered through celite. The filtrate was diluted with ethyl acetate, washed with saturated aqueous sodium hydrogen carbonate, and saturated brine, dried over anhydrous magnesium sulfate, filtered and concentrated. The residue was purified by silica gel column chromatography to give compound 7 (963 mg, 84%).

MS m/z 492 [M+H]$^+$, APCI(+)

Compound 7 (960 mg, 1.95 mmol) was dissolved in pyridine (3 mL), acetic anhydride (3 mL) was added, and the mixture was heated to 80° C. After stirring for 3 hr, the mixture was heated to 100° C. After stirring for 1 hr, the reaction mixture was concentrated, and dried azeotropically with toluene. The residue was dissolved in acetic acid (20 mL) and, after purging with argon, 20% palladium hydroxide carbon (312 mg) was added. After purging with hydrogen, the mixture was stirred for 16 hr, and 20% palladium hydroxide carbon (312 mg) was added. After purging with hydrogen, the mixture was stirred for 9 hr, filtered through celite and thoroughly washed with ethyl acetate. The filtrate was concentrated, and dried azeotropically with toluene. The residue was purified by silica gel column chromatography to give compound 8 (537 mg, 71%).

MS m/z 388 [M+H]$^+$, APCI(+)

Compound 9 was synthesized by a method similar to that for compound 12 of Example 4.

MS m/z 460 [M+H]$^+$, APCI(+)

Compound 10 was synthesized by a method similar to that for compound 13 of Example 4.

MS m/z 400 [M−H]−, ESI(−)

Hydrobromide, hydrochloride, para-toluenesulfonate, methanesulfonate, benzenesulfonate, maleate and the like of the present compound can be produced by a general salt formation step.

Example 74

3-[(5-ethyl-4-{[6-(3-ethylphenyl)-5-hydroxypyridin-2-yl]methyl}-2-fluoro-3-methylphenoxy)methyl]-1,2,4-oxadiazol-5(4H)-one

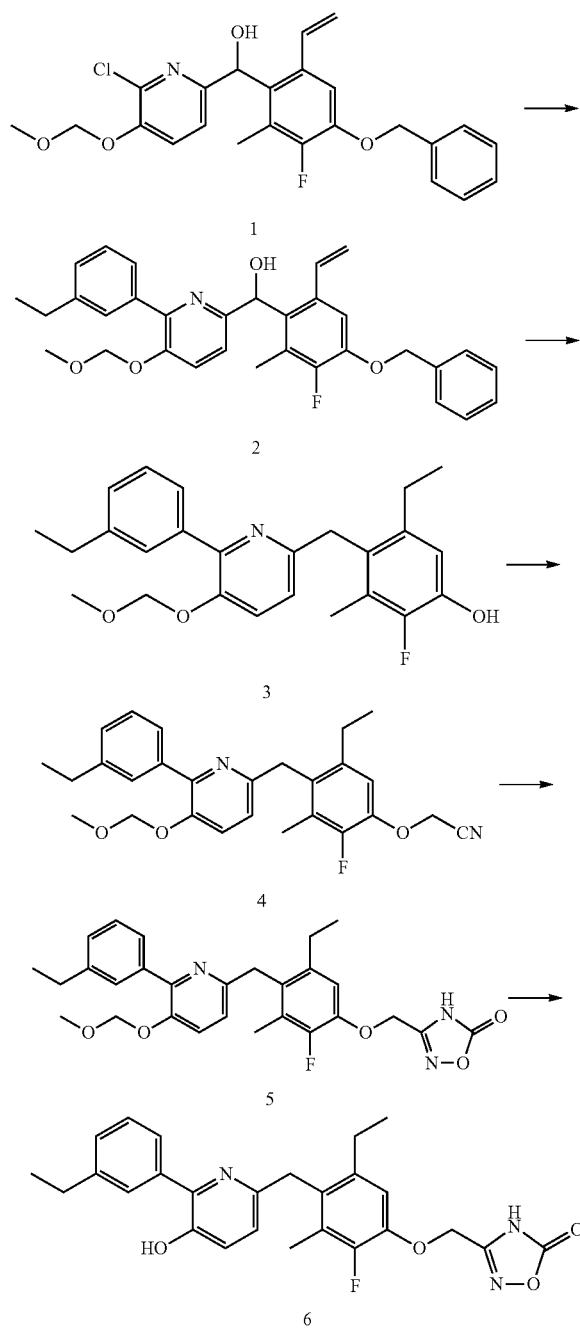

Compound 1 (206 mg, 0.464 mmol) was dissolved in 1,4-dioxane (4 mL), and water (1 ml), potassium carbonate (192 mg, 1.39 mmol), and 3-ethylphenylboronic acid (104 mg, 0.696 mmol) were added, and the mixture was purged with argon. Tetrakistriphenylphosphinepalladium(0) (54 mg, 0.046 mmol) was added, and the mixture was heated to 90° C. After stirring for 14 hr, the mixture was allowed to cool to room temperature. Saturated aqueous sodium hydrogen carbonate was added, and the mixture was extracted with ethyl acetate. The organic layer was washed with saturated brine, dried over anhydrous magnesium sulfate, filtered and concentrated. The residue was purified by silica gel column chromatography to give compound 2 (88 mg, 37%).

MS m/z 514 [M+H]$^+$, APCI(+)

Compound 2 (86 mg, 0.167 mmol) was dissolved in pyridine (1.5 mL), acetic anhydride (1.5 mL) was added, and the mixture was heated to 100° C. After stirring for 2 hr, the reaction mixture was concentrated, and dried azeotropically with toluene. The residue was dissolved in acetic acid (3 ml) and, after purging with argon, 20% palladium hydroxide carbon (28 mg) was added. After purging with hydrogen, the mixture was stirred for 5 hr, and 20% palladium hydroxide carbon (28 mg) was added. After purging with hydrogen, the mixture was stirred for 20 hr, filtered through celite, and thoroughly washed with ethyl acetate and methanol. The filtrate was concentrated, and dried azeotropically with toluene. The residue was purified by silica gel column chromatography to give compound 3 (53 mg, 78%).

MS m/z 410 [M+H]$^+$, APCI(+)

Compound 4 was synthesized by a method similar to that for compound 2 of Example 27.

MS m/z 449 [M+H]$^+$, APCI(+)

Compound 5 was synthesized by a method similar to that for compound 3 of Example 27.

MS m/z 506 [M−H]$^-$, ESI(−)

Compound 6 was synthesized by a method similar to that for compound 4 of Example 27.

MS m/z 462 [M−H]$^-$, ESI(−)

Hydrobromide, hydrochloride, para-toluenesulfonate, methanesulfonate, benzenesulfonate, maleate and the like of the present compound can be produced by a general salt formation step.

Example 75

[2-fluoro-4-({5-hydroxy-6-[1-(methoxymethyl)cyclohexyl]pyridin-2-yl}methyl)-3,5-dimethylphenoxy]acetic acid

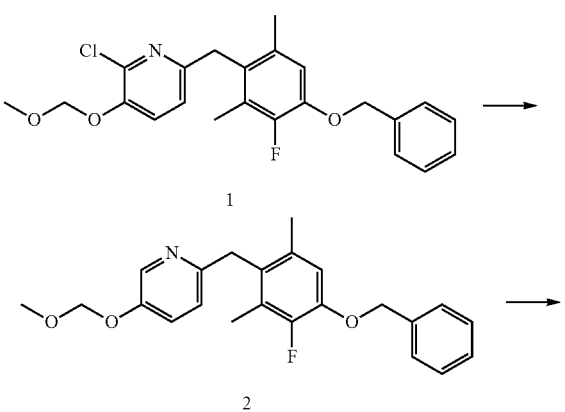

-continued

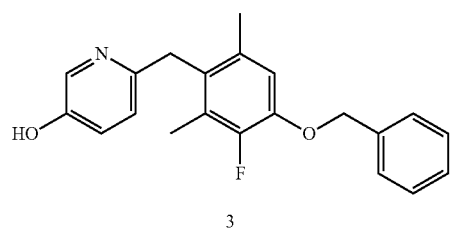

3

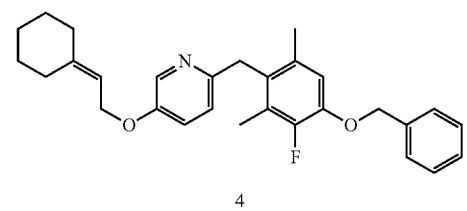

4

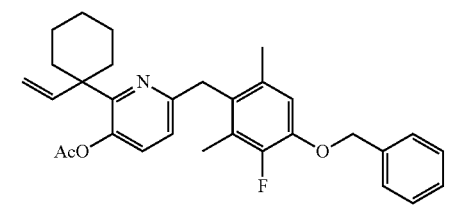

5

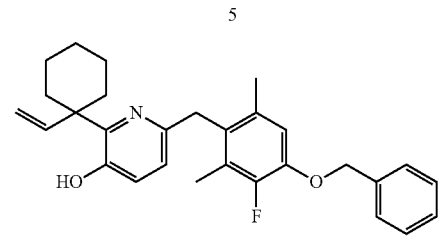

6

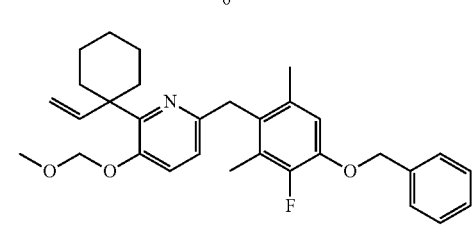

7

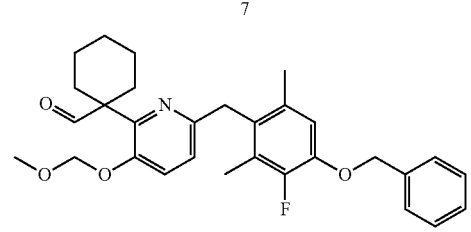

8

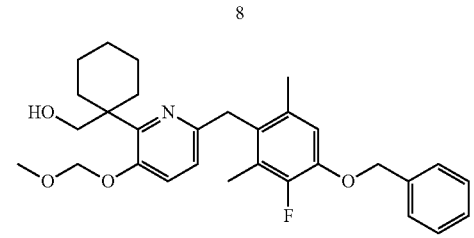

9

-continued

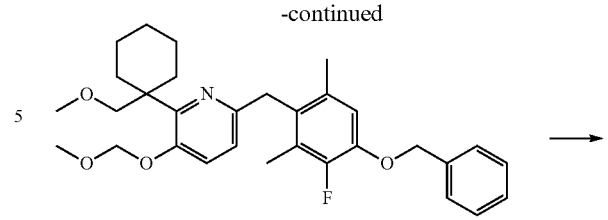

10

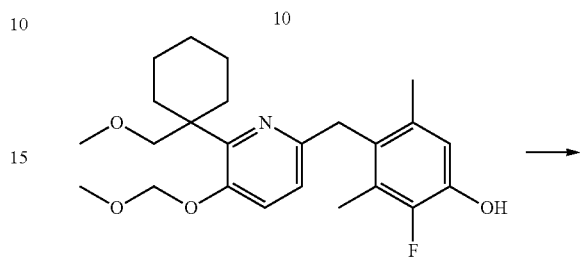

11

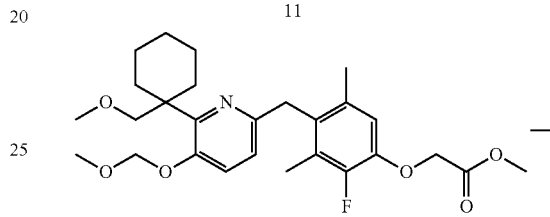

12

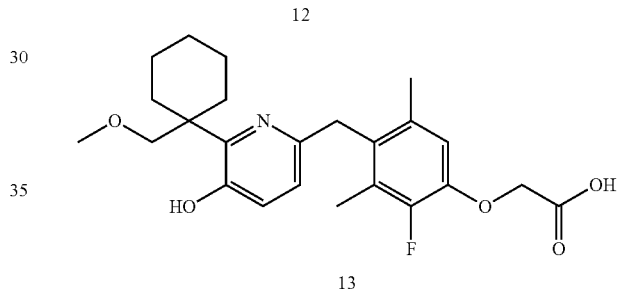

13

Compound 1 (3.30 g, 7.93 mmol) was dissolved in tetrahydrofuran (50 mL), and [1,1'-bis(diphenylphosphino)ferrocene]dichloropalladium(II) (581 mg, 0.793 mmol) was added. After ice-cooling, tert-butylmagnesium chloride (1.02 M tetrahydrofuran solution, 23.3 mL, 23.8 mmol) was added dropwise over 10 min. After stirring for 5 min, the mixture was heated to room temperature. After stirring for 20 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 2 (2.33 g, 77%).

MS m/z 382 [M+H]$^+$, APCI(+)

Compound 2 (2.33 g, 6.11 mmol) was dissolved in methanol (30 ml) and tetrahydrofuran (30 mL), and 6N hydrochloric acid (30 mL) was added. After stirring for 20 hr, the mixture was neutralized with 4N aqueous sodium hydroxide solution. Sodium chloride was added, and the mixture was extracted with ethyl acetate. The organic layer was dried over anhydrous magnesium sulfate, filtered and concentrated to give compound 3 (2.02 g, 98%).

MS m/z 338 [M+H]$^+$, APCI(+)

Compound 3 (2.06 g, 6.11 mmol) was dissolved in N,N'-dimethylformamide (30 mL) and, after ice-cooling, sodium hydride (mineral oil 60% dispersion, 366 mg, 9.16 mmol)

was added. After stirring for 2 hr, the mixture was heated to room temperature. After stirring for 2 hr, (2-bromoethylidene)cyclohexane (purity 80%, 2.16 g, 9.16 mmol) was added dropwise. After stirring for 18 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 4 (2.40 g, 88%).

MS m/z 446 [M+H]$^+$, APCI(+)

Compound 4 (850 mg, 1.92 mmol) was dissolved in acetic anhydride (4 mL), and potassium acetate (567 mg, 5.77 mmol) was added and the mixture was heated to 200° C. in a microwave reactor. After stirring for 2 hr, the mixture was allowed to cool to room temperature. Water was added, and the mixture was dried azeotropically with toluene. To the residue was added ethyl acetate, and the mixture was filtered through celite. The filtrate was extracted with ethyl acetate, and the organic layer was washed with saturated aqueous sodium hydrogen carbonate, and saturated brine, dried over anhydrous magnesium sulfate, filtered and concentrated. The residue was purified by silica gel column chromatography to give compound 5 (531 mg, 57%).

MS m/z 484 [M+H]$^+$, APCI(+)

Compound 5 (1.58 g, 3.24 mmol) was dissolved in methanol (16 mL), and the mixture was ice-cooled. Potassium carbonate (1.34 g, 9.72 mmol) was added, and the mixture was heated to room temperature. After stirring for 2 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 6 (1.15 g, 80%).

MS m/z 446 [M+H]$^+$, APCI(+)

Compound 6 (1.15 g, 2.58 mmol) was dissolved in acetonitrile (13 mL), and cesium carbonate (2.52 g, 7.74 mmol) and chloromethyl methyl ether (312 mg, 3.87 mmol) were added. The mixture was stirred for 30 min, and filtered through celite. The filtrate was concentrated, and the residue was purified by silica gel column chromatography to give compound 7 (1.18 g, 94%).

MS m/z 490 [M+H]$^+$, APCI(+)

Compound 7 (200 mg, 0.408 mmol) was dissolved in acetone (4 mL), and water (1 ml) and N-methylmorpholine-N-oxide (96 mg, 0.817 mmol) were added and the mixture was ice-cooled. Osmium tetraoxide (2.5% tert-butyl alcohol solution, 42 mg, 0.00408 mmol) was added, and the mixture was heated to room temperature. After stirring for 1.5 hr, osmium tetraoxide (2.5% tert-butyl alcohol solution, 42 mg, 0.00408 mmol) was added. After stirring for 3.5 hr, N-methylmorpholine-N-oxide (144 mg, 1.23 mmol) was added. After stirring for 15 hr, pyridine (65 mg, 0.817 mmol) and osmium tetraoxide (2.5% tert-butyl alcohol solution, 42 mg, 0.00408 mmol) were added. After stirring for 1.5 hr, N-methylmorpholine-N-oxide (144 mg, 1.23 mmol) was added. After stirring for 3.5 hr, osmium tetraoxide (2.5% tert-butyl alcohol solution, 42 mg, 0.00408 mmol) was added. After stirring for 2.5 hr, saturated aqueous sodium thiosulfate solution was added, and the mixture was extracted with ethyl acetate. The organic layer was washed with saturated brine, dried over anhydrous magnesium sulfate, filtered and concentrated. The residue was dissolved in tetrahydrofuran (4 mL), and water (0.8 ml) was added. After ice-cooling, sodium periodate (131 mg, 0.613 mmol) was added. After stirring for 3.5 hr, sodium periodate (44 mg, 0.204 mmol) was added. After stirring for 30 min, the mixture was heated to room temperature. After stirring for 2 hr, the mixture was filtered through celite, and diluted with ethyl acetate. The organic layer was washed with saturated brine, dried over anhydrous magnesium sulfate, filtered and concentrated. The residue was purified by silica gel column chromatography to give compound 8 (181 mg, 90%).

MS m/z 492 [M+H]$^+$, APCI(+)

Compound 8 (179 mg, 0.364 mmol) was dissolved in methanol (4 mL) and tetrahydrofuran (1 mL) and, after ice-cooling, sodium borohydride (21 mg, 0.546 mmol) was added. After stirring for 15 min, the mixture was heated to room temperature, stirred for 30 min, and saturated aqueous ammonium chloride solution was added. The mixture was extracted with ethyl acetate. The organic layer was washed with saturated brine, dried over anhydrous magnesium sulfate, filtered and concentrated. The residue was purified by silica gel column chromatography to give compound 9 (171 mg, 95%).

MS m/z 494 [M+H]$^+$, APCI(+)

Compound 9 (169 g, 0.342 mmol) was dissolved in tetrahydrofuran (4 mL) and, after ice-cooling, sodium hydride (mineral oil 60% dispersion, 27 mg, 0.685 mmol) was added. After stirring for 30 min, iodomethane (146 mg, 1.03 mmol) was added dropwise, and the mixture was heated to room temperature. After stirring for 2.5 hr, sodium hydride (mineral oil 60% dispersion, 68 mg, 1.71 mmol) and iodomethane (292 mg, 2.05 mmol) were added. After stirring for 20 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 10 (157 mg, 90%).

MS m/z 508 [M+H]$^+$, APCI(+)

Compound 11 was synthesized by a method similar to that for compound 11 of Example 4.

MS m/z 418 [M+H]$^+$, APCI(+)

Compound 12 was synthesized by a method similar to that for compound 12 of Example 4.

MS m/z 490 [M+H]$^+$, APCI(+)

Compound 13 was synthesized by a method similar to that for compound 13 of Example 4.

MS m/z 430 [M−H]−, ESI(−)

Hydrobromide, hydrochloride, para-toluenesulfonate, methanesulfonate, benzenesulfonate, maleate and the like of the present compound can be produced by a general salt formation step.

Example 76

(4-{[6-(4,4-difluorocyclohexyl)-5-hydroxypyridin-2-yl]methyl}-2,3,5-trimethylphenoxy)acetic acid

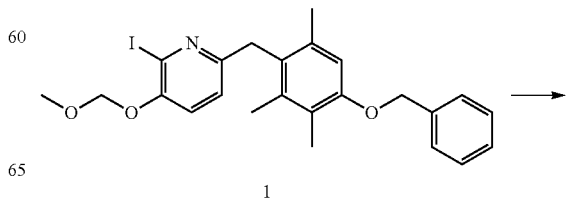

1

-continued

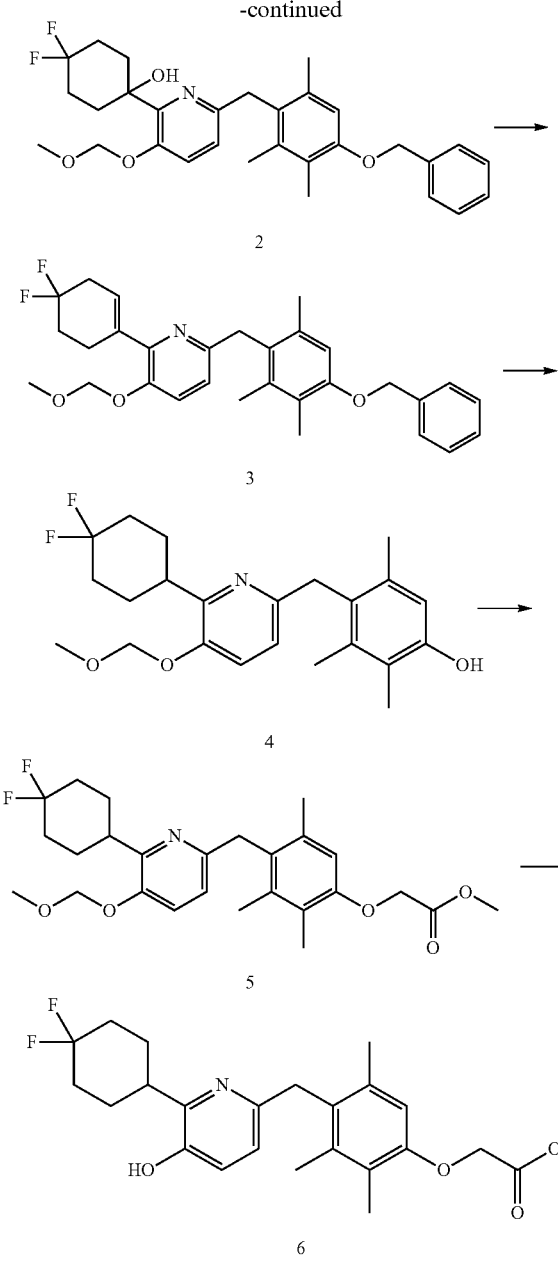

Compound 1 (460 mg, 0.902 mmol) was dissolved in tetrahydrofuran (4 mL), cooled to −78° C., n-butyllithium (1.6 M hexane solution, 0.79 mL, 1.2 mmol) was slowly added dropwise, and the mixture was stirred for 30 min. A solution (2 mL) of 4,4-difluorocyclohexanone (193 mg, 1.44 mmol) in tetrahydrofuran was slowly added dropwise. After stirring for 30 min, the mixture was heated to room temperature. After 1 hr, saturated aqueous ammonium chloride solution was added, and the mixture was extracted with ethyl acetate. The organic layer was washed with saturated brine, dried over anhydrous sodium sulfate, filtered and concentrated. The residue was purified by silica gel column chromatography to give compound 2.

MS m/z 512 [M+H]$^+$, APCI(+)

Compound 2 was dissolved in toluene (2.6 ml,), and p-toluenesulfonic acid monohydrate (164 mg, 0.864 mmol) and molecular sieves 4A (500 mg) were added and the mixture was heated under reflux. After 1 day, the mixture was allowed to cool to room temperature, and filtered. The filtrate was washed with saturated aqueous sodium hydrogen carbonate and saturated brine, dried over anhydrous sodium sulfate, filtered, concentrated and dried. To the obtained residue were added acetonitrile (2.6 mL) and chloromethyl methyl ether (0.096 mL, 1.2 mmol). Cesium carbonate (413 mg, 1.27 mmol) was added, and the mixture was stirred for 5 hr. Water was added, and the mixture was extracted with ethyl acetate. The organic layer was washed with saturated brine, dried over anhydrous sodium sulfate, filtered and concentrated. The residue was purified by silica gel column chromatography to give compound 3.

MS m/z 494 [M+H]$^+$, APCI(+)

Compound 3 was dissolved in ethanol (2 mL) and acetic acid (1mL), 20% palladium hydroxide/carbon (120 mg) was added. After purging with hydrogen, the mixture was stirred for 15 hr, filtered through radiolite, and washed with ethyl acetate. The filtrate was concentrated and the obtained residue was purified by silica gel column chromatography to give compound 4 (40 mg, 11%, 3 steps).

MS m/z 406[M+H]$^+$, APCI(+)

Compound 5 was synthesized by a method similar to that for compound 12 of Example 4.

MS m/z 478 [M+H]$^+$, APCI(+)

Compound 6 was synthesized by a method similar to that for compound 13 of Example 4.

MS m/z 418 [M−H]−, ESI(−)

Hydrobromide, hydrochloride, para-toluenesulfonate, methanesulfonate, benzenesulfonate, maleate and the like of the present compound can be produced by a general salt formation step.

Example 77

(2-fluoro-4-{[5-hydroxy-6-(1-hydroxyethyl)pyridin-2-yl]methyl}-3,5-dimethylphenoxy)acetic acid

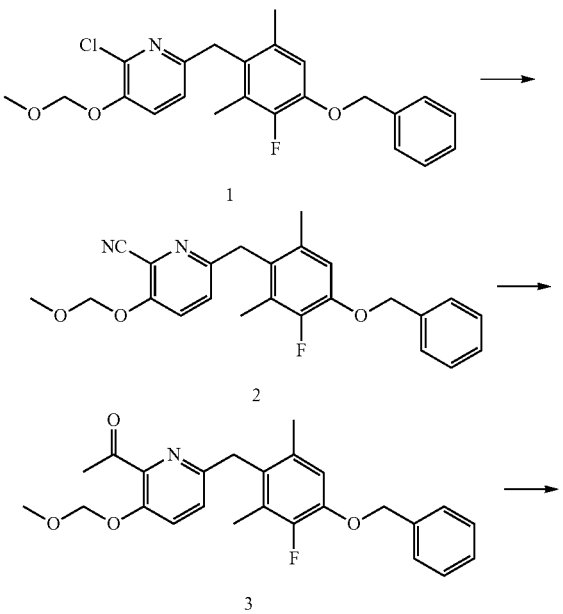

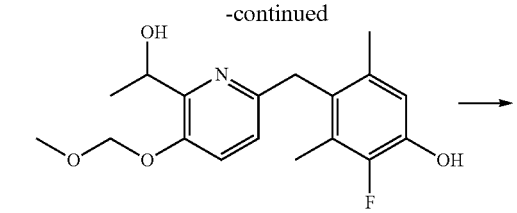

4

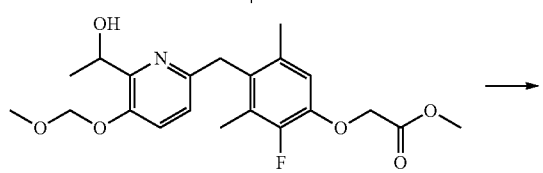

5

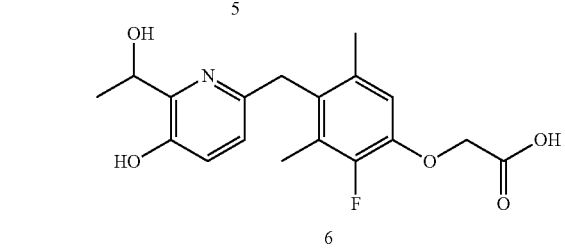

6

Compound 1 (4.15 g, 10 mmol), zinc cyanide (705 mg, 6 mmol), zinc powder (392 mg, 6 mmol), 1,1'-bis(diphenylphosphino)ferrocene (1.1 g, 2 mmol), and bis(benzylideneacetone)palladium(0) (575 mg, 1 mmol) were measured and, after purging with argon, N,N-dimethylacetamide (25 ml) was added and the mixture was stirred at 120° C. for 4 hr. The mixture was allowed to cool to room temperature, and ethyl acetate, and aqueous ammonium chloride solution were added. The mixture was stirred and filtered through celite. The filtrate was extracted with ethyl acetate, and the organic layer was washed with water and saturated brine, dried over anhydrous sodium sulfate, filtered, and concentrated. The residue was purified by silica gel column chromatography to give compound 2 (2.24 g, 55%).

MS m/z 407 [M+H]+, APCI(+)

Compound 2 (250 mg, 0.62 mmol) was dissolved in tetrahydrofuran (2.5 mL) and, after purging with argon, ice-cooled. Methyl magnesium bromide (3 M ether solution, 0.7 ml, 2.1 mmol) was added dropwise, and the mixture was allowed to warm to room temperature, and stirred for 3 hr. Aqueous ammonium chloride solution, and ethyl acetate were added and the mixture was stirred, and extracted with ethyl acetate. The organic layer was washed with water and saturated brine, dried over anhydrous sodium sulfate, filtered, and concentrated. The residue was purified by silica gel column chromatography to give compound 3 (156 mg, 60%).

MS m/z 424 [M+H]+, APCI(+)

Compound 3 (144 mg, 0.34 mmol) was dissolved in ethanol (2.8 mL) and acetic acid (0.7 mL), and 5% Pd/C (30 mg) was added. After purging with hydrogen, the mixture was stirred for 3 hr, filtered and concentrated. The residue was purified by silica gel column chromatography to give compound 4 (103 mg, 90%).

MS m/z 336 [M+H]+, APCI(+)

Compound 5 was synthesized by a method similar to that for compound 12 of Example 4.

MS m/z 408 [M+H]+, APCI(+)

Compound 6 was synthesized by a method similar to that for compound 13 of Example 4.

MS m/z 348 [M-H]-, ESI(-)

Hydrobromide, hydrochloride, para-toluenesulfonate, methanesulfonate, benzenesulfonate, maleate and the like of the present compound can be produced by a general salt formation step.

Example 78

(4-{[5-hydroxy-6-(3-methylcyclohexyl)-pyridin-2-yl]methyl}-2,3,5-trimethylphenoxy)acetic acid

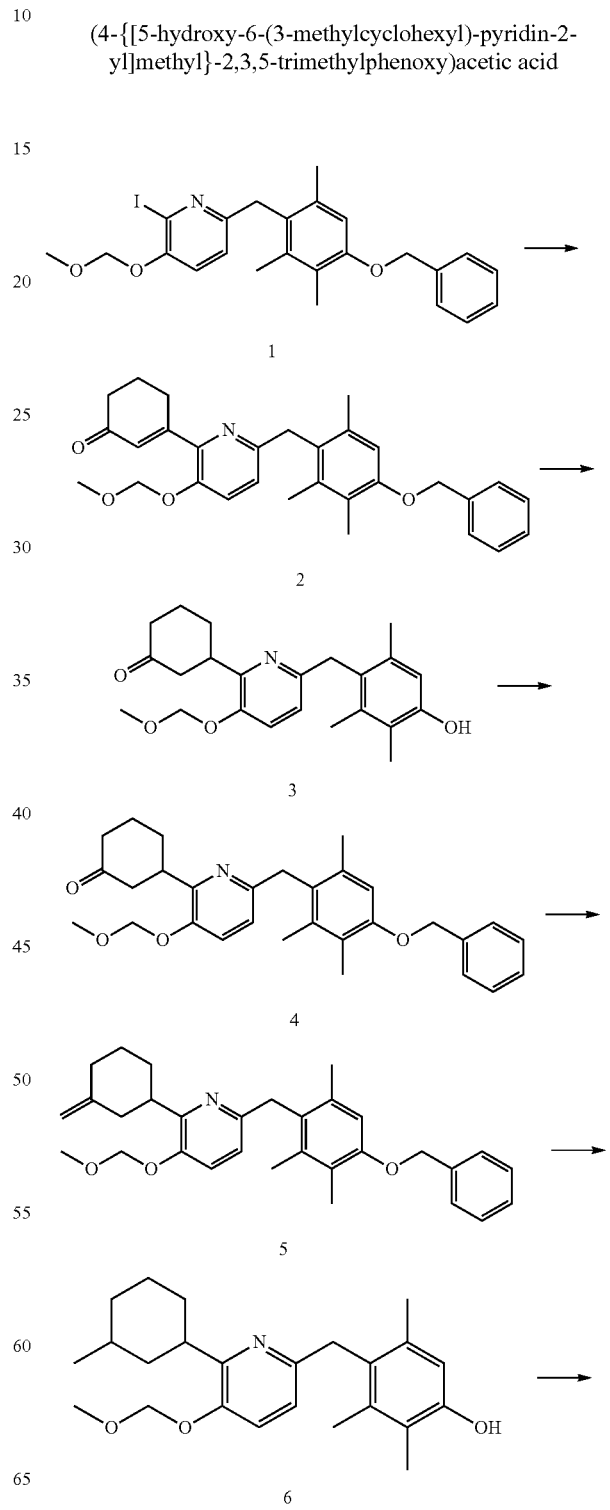

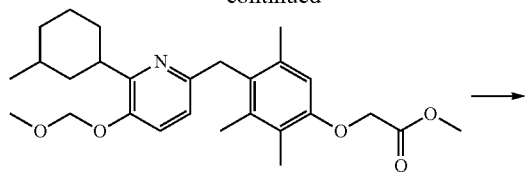

7

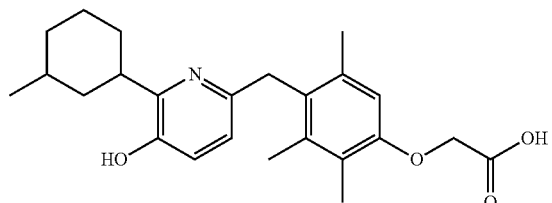

8

Under an argon atmosphere, compound 1 (226 mg, 0.45 mmol) was dissolved in tetrahydrofuran (0.5 mL) and ice-cooled. Isopropylmagnesium bromide.lithium chloride mixture (1.3 M tetrahydrofuran solution, 0.52 mL, 0.68 mmol) was added and the mixture was stirred for 1 hr. A solution of 3-ethoxy-2-cyclohexenone (95 mg, 0.68 mmol) in tetrahydrofuran (0.5 mL) was added. The mixture was stirred for 2 hr while allowing to warm to room temperature. 1N Hydrochloric acid was added, and the mixture was extracted with ethyl acetate. The organic layer was washed with saturated brine, dried over anhydrous sodium sulfate, filtered and concentrated. The residue was purified by silica gel column chromatography to give compound 2 (190 mg, 90%).

MS m/z 472 [M+H]$^+$, APCI(+)

Compound 3 was synthesized by a method similar to that for compound 11 of Example 4.

MS m/z 384 [M+H]$^+$, APCI(+)

Compound 4 was synthesized by a method similar to that for compound 3 of Example 2.

MS m/z 474 [M+H]$^+$, APCI(+)

Methyltriphenylphosphine bromide (759 mg, 2.1 mmol) and potassium tert-butoxide (238 mg, 2.1 mmol) were suspended in toluene (12 mL) and the mixture was stirred with heating in an argon atmosphere at 100° C. After allowing to cool to room temperature, 6 mL thereof was added to a solution of compound 4 (100 mg, 0.21 mmol) in toluene (3 ml,), and the mixture was stirred for 30 min. Water was added, and the mixture was extracted with ethyl acetate. The organic layer was washed with saturated brine, dried over anhydrous sodium sulfate, filtered and concentrated. The residue was purified by silica gel column chromatography to give compound 5 (89 mg, 90%). MS m/z 472 [M+H]$^+$, APCI(+)

Compound 6 was synthesized by a method similar to that for compound 11 of Example 4.

MS m/z 384 [M+H]$^+$, APCI(+)

Compound 7 was synthesized by a method similar to that for compound 12 of Example 4.

MS m/z 456 [M+H]$^+$, APCI(+)

Compound 8 was synthesized by a method similar to that for compound 13 of Example 4.

MS m/z 396 [M−H]−, ESI(−)

Hydrobromide, hydrochloride, para-toluenesulfonate, methanesulfonate, benzenesulfonate, maleate and the like of the present compound can be produced by a general salt formation step.

Example 79

(4-{[5-hydroxy-6-(3-methoxycyclohexyl)-pyridin-2-yl]methyl}-2,3,5-trimethylphenoxy)acetic acid

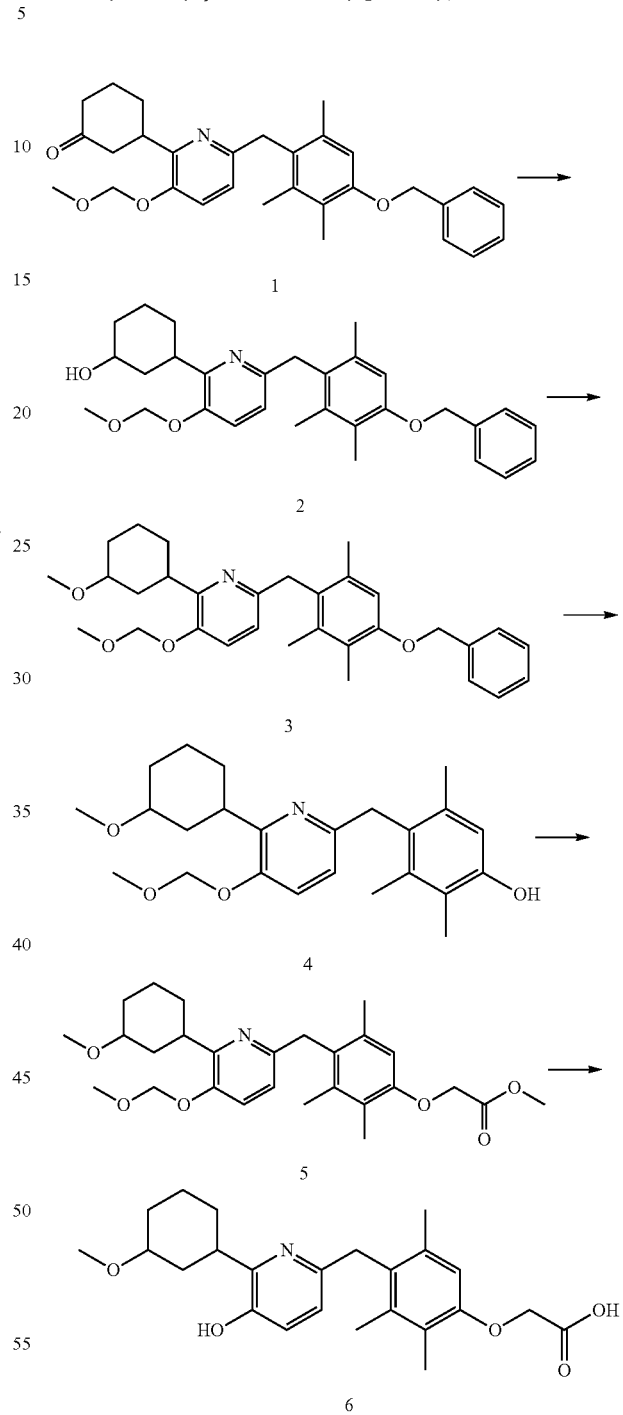

Under an argon atmosphere, compound 1 (133 mg, 0.28 mmol) was dissolved in tetrahydrofuran (1 mL), and the mixture was cooled to −78° C. Potassium tri(sec-butyl)borohydride (1 M tetrahydrofuran solution, 0.4 mL, 0.40 mmol) was added and the mixture was stirred for 30 min, and allowed to warm to room temperature. Saturated aqueous ammonium chloride solution was added, and the mixture was extracted with ethyl acetate. The organic layer was washed with saturated brine, dried over anhydrous sodium sulfate, filtered and concentrated. The residue was purified by silica gel column chromatography to give compound 2 (82 mg, 62%).

MS m/z 476 [M+H]+, APCI(+)

Compound 2 (74 mg, 0.15 mmol) was dissolved in tetrahydrofuran (1.5 mL). Iodomethane (0.087 mL, 0.93 mmol) and sodium hydride (mineral oil 60% dispersion, 12 mg, 0.30 mmol) were added and the mixture was stirred overnight. Saturated aqueous ammonium chloride solution was added, and the mixture was extracted with ethyl acetate. The organic layer was washed with saturated brine, dried over anhydrous sodium sulfate, filtered and concentrated. The residue was purified by silica gel column chromatography to give compound 3 (73 mg, 99%).

MS m/z 490 [M+H]+, APCI(+)

Compound 4 was synthesized by a method similar to that for compound 11 of Example 4.

MS m/z 400 [M+H]+, APCI(+)

Compound 5 was synthesized by a method similar to that for compound 12 of Example 4.

MS m/z 472 [M+H]+, APCI(+)

Compound 6 was synthesized by a method similar to that for compound 13 of Example 4.

MS m/z 412 [M−H]−, ESI(−)

Hydrobromide, hydrochloride, para-toluenesulfonate, methanesulfonate, benzenesulfonate, maleate and the like of the present compound can be produced by a general salt formation step.

The compounds of Example 80-Example 300 were produced according to production methods 1-14, and the above-mentioned Examples and Reference Examples. Hydrobromide, hydrochloride, para-toluenesulfonate, methanesulfonate, benzenesulfonate, maleate and the like of the compounds of Example 80-Example 300 can be produced via conventional salt formation steps.

TABLE 1

| Example | | MASS |
|---|---|---|
| Example 80 | 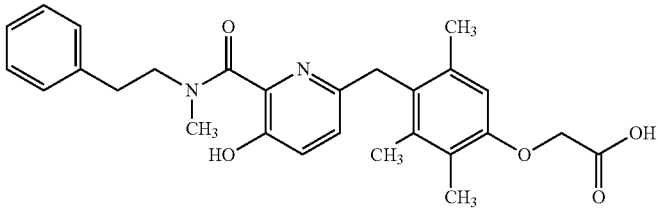 [SMILES: Cc1cc(OCC(=O)O)c(C)c(C)c1Cc1ccc(O)c(C(=O)N(C)CCc2ccccc2)n1] | 461 [M − H]−, ESI (−) |
| Example 81 | 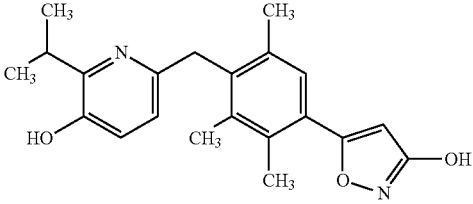 [SMILES: Cc1cc(-c2cc(O)no2)c(C)c(C)c1Cc1ccc(O)c(C(C)C)n1] | 351 [M − H]−, ESI (−) |
| Example 82 | 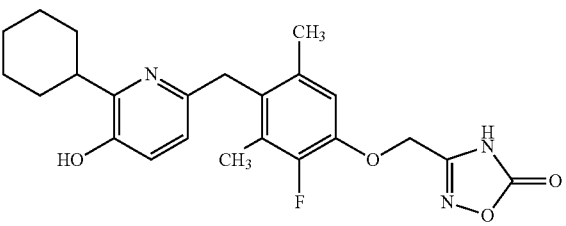 | 426 [M − H]−, ESI (−) |
| Example 83 | 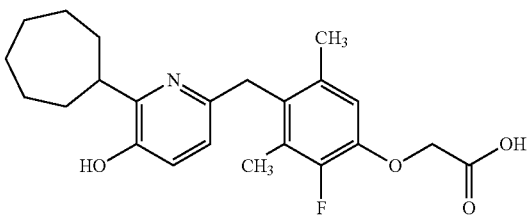 [SMILES: Cc1cc(OCC(=O)O)c(F)c(C)c1Cc1ccc(O)c(C2CCCCCC2)n1] | 400 [M − H]−, ESI (−) |
| Example 84 | 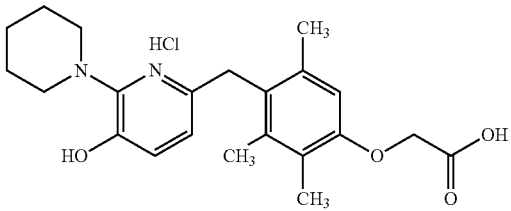 | 383 [M − H]−, ESI (−) |

TABLE 1-continued

| Example | | MASS |
|---|---|---|
| Example 85 | (structure) | 440 [M – H]–, ESI (–) |
| Example 86 | (structure) | 420 [M – H]–, ESI (–) |
| Example 87 | (structure) | 470 [M – H]–, ESI (–) |
| Example 88 | (structure) | 442/444 [M – H]–, ESI (–) |
| Example 89 | (structure) | 380 [M – H]–, ESI (–) |
| Example 90 | (structure) | 430 [M – H]–, ESI (–) |
| Example 91 | (structure) | 434 [M – H]–, ESI (–) |

TABLE 1-continued

| Example | MASS |
|---|---|
| Example 92 | 396 [M − H]−, ESI (−) |
| Example 93 | 470 [M − Na]−, ESI (−) |
| Example 94 | 426 [M − H]−, ESI (−) |
| Example 95 | 436 [M − H]−, ESI (−) |
| Example 96 | 466 [M − H]−, ESI (−) |
| Example 97 | 436 [M − H]−, ESI (−) |

TABLE 1-continued

| Example | | MASS |
|---|---|---|
| Example 98 | (structure) | 415 [M + H]+, ESI (+) |
| Example 99 | (structure) | 394 [M − H]−, ESI (−) |
| Example 100 | (structure) | 408 [M − H]−, ESI (−) |
| Example 101 | (structure) | 412 [M − H]−, ESI (−) |
| Example 102 | (structure) | 416 [M − H]−, ESI (−) |
| Example 103 | (structure) | 434 [M − H]−, ESI (−) |
| Example 104 | (structure) | 448 [M − H]−, ESI (−) |

TABLE 1-continued
| Example | | MASS |
|---|---|---|
| Example 105 | 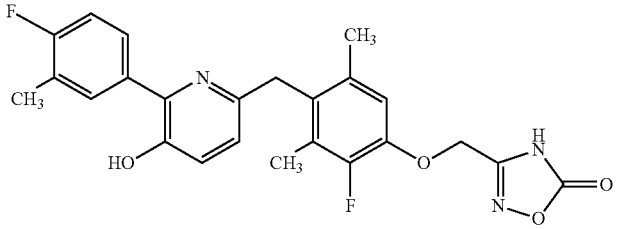 [SMILES: Cc1cc(-c2nc(Cc3c(C)cc(OCc4noc(=O)[nH]4)c(F)c3C)ccc2O)ccc1F] | 452 [M − H]−, ESI (−) |
| Example 106 | 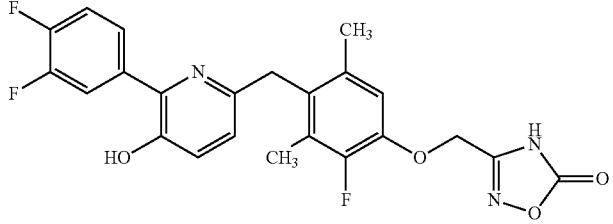 [SMILES: Cc1cc(OCc2noc(=O)[nH]2)c(F)c(C)c1Cc1ccc(O)c(-c2ccc(F)c(F)c2)n1] | 456 [M − H]−, ESI (−) |
| Example 107 | 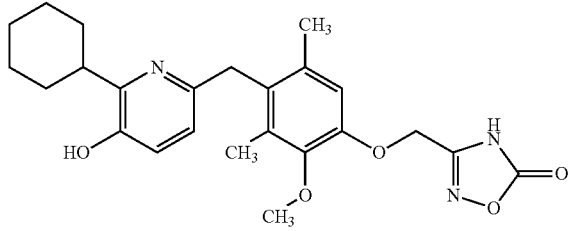 [SMILES: COc1c(OCc2noc(=O)[nH]2)cc(C)c(Cc2ccc(O)c(C3CCCCC3)n2)c1C] | 438 [M − H]−, ESI (−) |
| Example 108 | 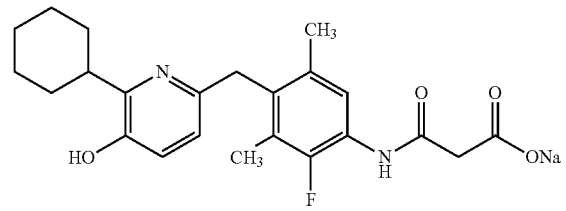 | 413 [M − Na]−, ESI (−) |
| Example 109 | 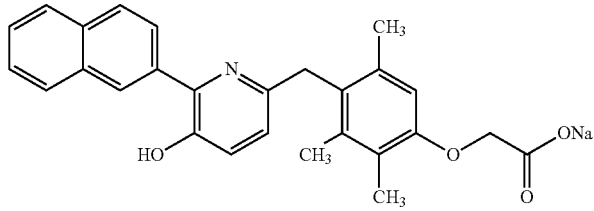 | 426 [M − Na]−, ESI (−) |
| Example 110 | 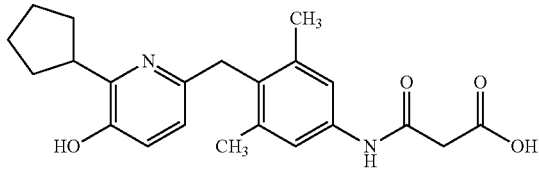 [SMILES: Cc1cc(NC(=O)CC(=O)O)cc(C)c1Cc1ccc(O)c(C2CCCC2)n1] | 381 [M − H]−, ESI (−) |
| Example 111 | 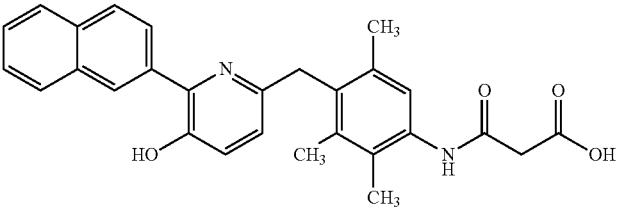 | 439 [M − H]−, ESI (−) |

TABLE 1-continued

| Example | MASS |
|---|---|
| Example 112 | 407 [M − H]−, ESI (−) |
| Example 113 | 373 [M − H]−, ESI (−) |
| Example 114 | 383 [M − H]−, ESI (−) |
| Example 115 | 420 [M − Na]−, ESI (−) |
| Example 116 | 396 [M − H]−, ESI (−) |
| Example 117 | 436 [M − H]−, ESI (−) |
| Example 118 | 427 [M − H]−, ESI (−) |

TABLE 1-continued

| Example | | MASS |
|---|---|---|
| Example 119 | | 404 [M − H]−, ESI (−) |
| Example 120 | | 412 [M − H]−, ESI (−) |
| Example 121 | | 376 [M − H]−, ESI (−) |
| Example 122 | | 390 [M − H]−, ESI (−) |
| Example 123 | | 390 [M − H]−, ESI (−) |
| Example 124 | | 394 [M − H]−, ESI (−) |

TABLE 1-continued

| Example | | MASS |
|---|---|---|
| Example 125 | | 434 [M − H]−, ESI (−) |
| Example 126 | | 434 [M − H]−, ESI (−) |
| Example 127 | | 438 [M − H]−, ESI (−) |
| Example 128 | | 356 [M − H]−, ESI (−) |
| Example 129 | | 396 [M − H]−, ESI (−) |
| Example 130 | | 374 [M − H]−, ESI (−) |

TABLE 1-continued

| Example | | MASS |
|---|---|---|
| Example 131 | (structure) | 427 [M − H]−, ESI (−) |
| Example 132 | (structure) | 409 [M − Na]−, ESI (−) |
| Example 133 | (structure) | 414 [M − H]−, ESI (−) |
| Example 134 | (structure) | 448 [M − Na]−, ESI (−) |
| Example 135 | (structure) | 455 [M − H]−, ESI (−) |
| Example 136 | (structure) | 398 [M − H]−, ESI (−) |

TABLE 1-continued

| Example | | MASS |
|---|---|---|
| Example 137 | | 412 [M – H]–, ESI (–) |
| Example 138 | | 414 [M – H]–, ESI (–) |
| Example 139 | | 408 [M – H]–, ESI (–) |
| Example 140 | | 438 [M – Na]–, ESI (–) |
| Example 141 | | 412 [M – Na]–, ESI (–) |
| Example 142 | | 456 [M – Na]–, ESI (–) |

TABLE 1-continued

| Example | | MASS |
|---|---|---|
| Example 143 | | 525/527 [M − H]−, ESI (−) |
| Example 144 | | 447/229 [M − H]−, ESI (−) |
| Example 145 | | 450 [M − H]−, ESI (−) |
| Example 146 | | 488 [M − H]−, ESI (−) |
| Example 147 | | 450 [M − H]−, ESI (−) |
| Example 148 | | 488 [M − H]−, ESI (−) |

TABLE 1-continued

| Example | | MASS |
|---|---|---|
| Example 149 | [structure] | 452 [M − H]−, ESI (−) |
| Example 150 | [structure] | 456 [M − H]−, ESI (−) |
| Example 151 | [structure] | 456 [M − H]−, ESI (−) |
| Example 152 | [structure] | 394 [M − H]−, ESI (−) |
| Example 153 | [structure] | 429/431 [M − Na]−, ESI (−) |
| Example 154 | [structure] | 452 [M − Na]−, ESI (−) |

181 182
TABLE 1-continued
| Example | | MASS |
|---|---|---|
| Example 155 | 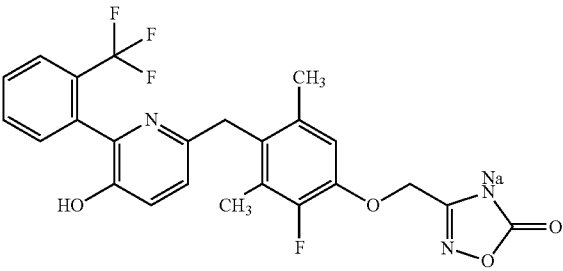 | 4881 [M − Na]−, ESI (−) |
| Example 156 | 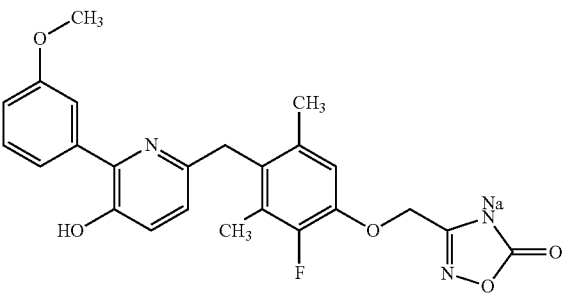 | 450 [M − Na]−, ESI (−) |
| Example 157 | 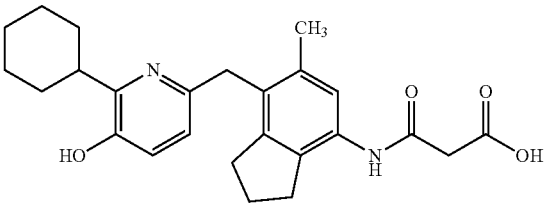 [SMILES: Cc1cc(NC(=O)CC(=O)O)c2c(c1Cc1ccc(O)c(C3CCCCC3)n1)CCC2] | 421 [M − H]−, ESI (−) |
| Example 158 | 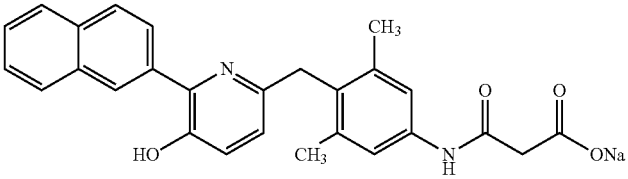 | 439 [M − Na]−, ESI (−) |
| Example 159 | 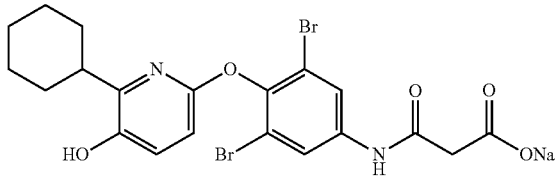 | 525/527 [M − Na]−, ESI (−) |
| Example 160 | 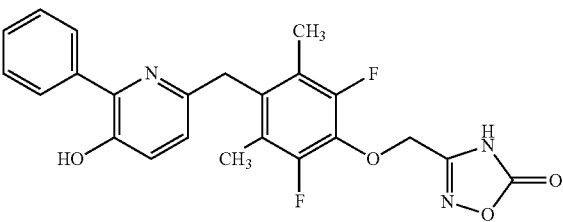 [SMILES: Cc1c(F)c(OCc2noc(=O)[nH]2)c(F)c(C)c1Cc1ccc(O)c(-c2ccccc2)n1] | 438 [M − H]−, ESI (−) |

TABLE 1-continued

| Example | | MASS |
|---|---|---|
| Example 161 | | 456 [M – H]–, ESI (–) |
| Example 162 | | 404 [M – H]–, ESI (–) |
| Example 163 | | 409 [M – H]–, ESI (–) |
| Example 164 | | 425 [M – H]–, ESI (–) |
| Example 165 | | 435 [M – H]–, ESI (–) |
| Example 166 | | 400 [M – H]–, ESI (–) |
| Example 167 | | 464/466 [M – H]–, ESI (–) |

TABLE 1-continued

| Example | MASS |
|---|---|
| Example 168 | 428 [M − H]−, ESI (−) |
| Example 169 | 460 [M − H]−, ESI (−) |
| Example 170 | 418 [M − H]−, ESI (−) |
| Example 171 | 394 [M − H]−, ESI (−) |
| Example 172 | 406 [M − H]−, ESI (−) |
| Example 173 | 410/412 [M − H]−, ESI (−) |

TABLE 1-continued

| Example | | MASS |
|---|---|---|
| Example 174 | | 412 [M – H]–, ESI (–) |
| Example 175 | | 430 [M – H]–, ESI (–) |
| Example 176 | | 404 [M – H]–, ESI (–) |
| Example 177 | | 4081 [M – H]–, ESI (–) |
| Example 178 | | 408 [M – H]–, ESI (–) |
| Example 179 | | 424 [M – H]–, ESI (–) |

TABLE 1-continued
| Example | | MASS |
|---|---|---|
| Example 180 | 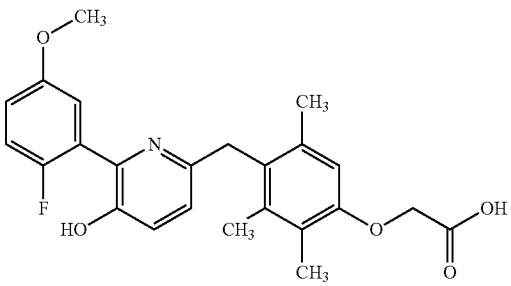 | 4241 [M − H]−, ESI (−) |
| Example 181 | 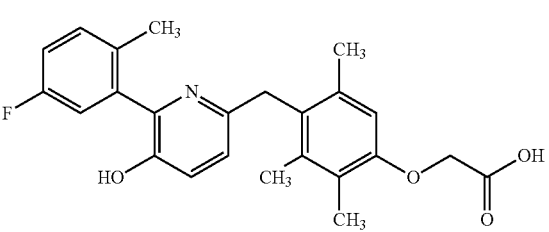 [SMILES: Cc1ccc(F)cc1-c1nc(Cc2c(C)cc(OCC(=O)O)c(C)c2C)ccc1O] | 408 [M − H]−, ESI (−) |
| Example 182 | 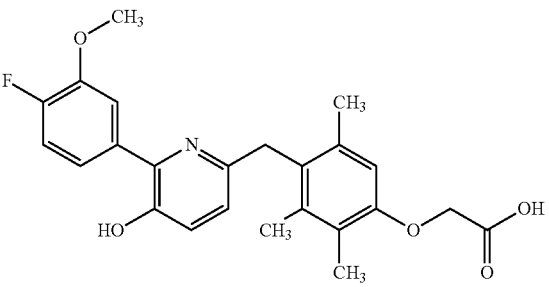 [SMILES: COc1cc(-c2nc(Cc3c(C)cc(OCC(=O)O)c(C)c3C)ccc2O)ccc1F] | 424 [M − H]−, ESI (−) |
| Example 183 | 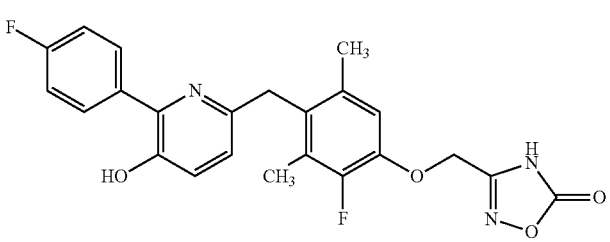 [SMILES: Cc1cc(OCc2noc(=O)[nH]2)c(F)c(C)c1Cc1ccc(O)c(-c2ccc(F)cc2)n1] | 438 [M − H]−, ESI (−) |
| Example 184 | 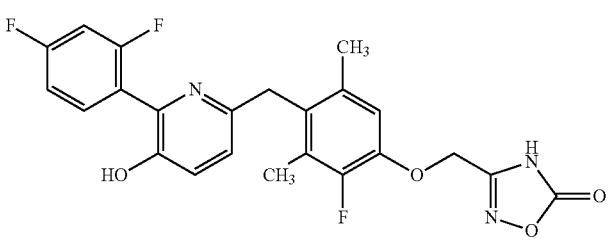 [SMILES: Cc1cc(OCc2noc(=O)[nH]2)c(F)c(C)c1Cc1ccc(O)c(-c2ccc(F)cc2F)n1] | 456 [M − H]−, ESI (−) |
| Example 185 | 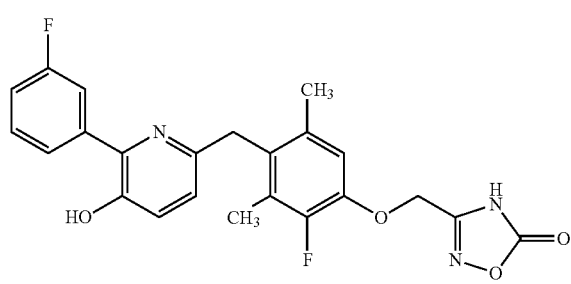 [SMILES: Cc1cc(OCc2noc(=O)[nH]2)c(F)c(C)c1Cc1ccc(O)c(-c2cccc(Cl)c2)n1] | 438 [M − H]−, ESI (−) |

TABLE 1-continued

| Example | MASS |
|---|---|
| Example 186 | 456 [M − H]−, ESI (−) |
| Example 187 | 452 [M − H]−, ESI (−) |
| Example 188 | 474 [M − H]−, ESI (−) |
| Example 189 | 506 [M − H]−, ESI (−) |
| Example 190 | 506 [M − H]−, ESI (−) |

TABLE 1-continued

| Example | MASS |
|---|---|
| Example 191 | 474 [M − H]−, ESI (−) |
| Example 192 | 474 [M − H]−, ESI (−) |
| Example 193 | 408 [M − H]−, ESI (−) |
| Example 194 | 408 [M − H]−, ESI (−) |
| Example 195 | 424 [M − H]−, ESI (−) |
| Example 196 | 456 [M − H]−, ESI (−) |

TABLE 1-continued

| Example | | MASS |
|---|---|---|
| Example 197 | [structure] | 448 [M − H]−, ESI (−) |
| Example 198 | [structure] | 452 [M − H]−, ESI (−) |
| Example 199 | [structure] | 472/474 [M − H]−, ESI (−) |
| Example 200 | [structure] | 468 [M − H]−, ESI (−) |
| Example 201 | [structure] | 468 [M − H]−, ESI (−) |

TABLE 1-continued

| Example | | MASS |
|---|---|---|
| Example 202 | (structure) | 448 [M – H]–, ESI (–) |
| Example 203 | (structure) | 464 [M – H]–, ESI (–) |
| Example 204 | (structure) | 504 [M – H]–, ESI (–) |
| Example 205 | (structure) | 454/456 [M – H]–, ESI (–) |
| Example 206 | (structure) | 489 [M – H]–, ESI (–) |

TABLE 1-continued
| Example | | MASS |
|---|---|---|
| Example 207 | 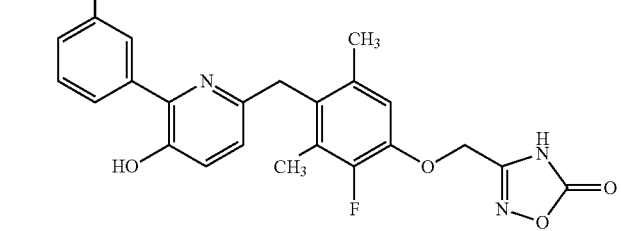 | 491 [M − H]−, ESI (−) |
| Example 208 | 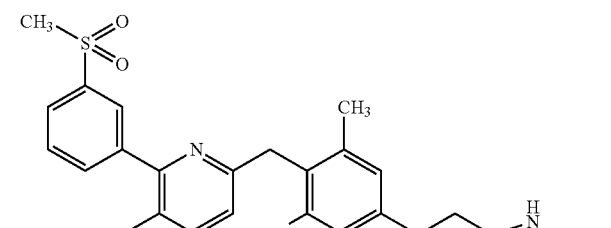 | 498 [M − H]−, ESI (−) |
| Example 209 | 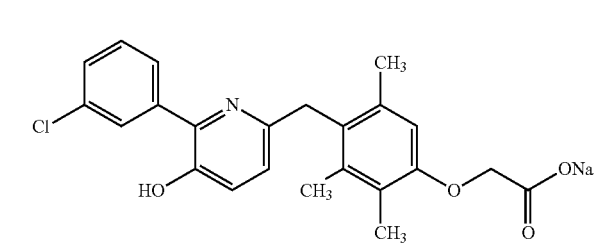 | 410/412 [M − Na]−, ESI (−) |
| Example 210 | 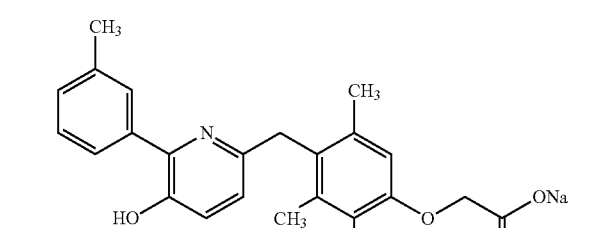 | 390 [M − Na]−, ESI (−) |
| Example 211 | 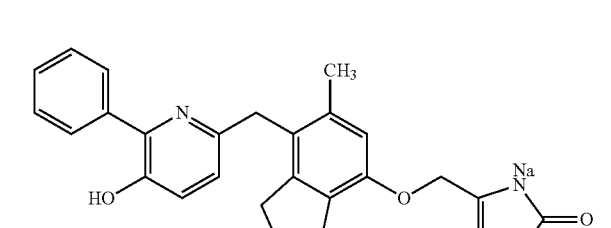 | 430 [M − Na]−, ESI (−) |

TABLE 1-continued

| Example | MASS |
|---|---|
| Example 212 | 462 [M − H]−, ESI (−) |
| Example 213 | 400/402 [M − H]−, ESI (−) |
| Example 214 | 440 [M − H]−, ESI (−) |
| Example 215 | 484 [M − H]−, ESI (−) |
| Example 216 | 426 [M + H]+, APCI (+) |

TABLE 1-continued

| Example | MASS |
|---|---|
| Example 217 | 458 [M + H]+, APCI (+) |
| Example 218 | 444 [M − H]−, ESI (−) |
| Example 219 | 434 [M − H]−, ESI (−) |
| Example 220 | 434 [M − H]−, ESI (−) |
| Example 221 | 420 [M − H]−, ESI (−) |

TABLE 1-continued
| Example | | MASS |
|---|---|---|
| Example 222 | 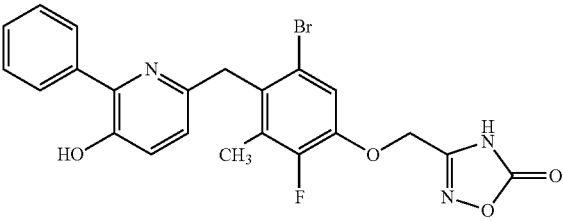 [SMILES: Cc1c(F)c(OCc2noc(=O)[nH]2)cc(Br)c1Cc1ccc(O)c(-c2ccccc2)n1] | 484/486 [M − H]−, ESI (−) |
| Example 223 | 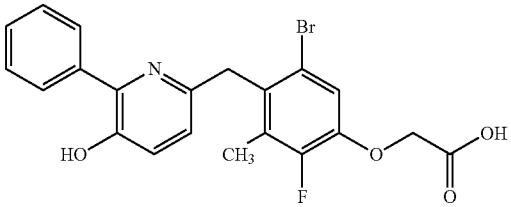 [SMILES: Cc1c(F)c(OCC(=O)O)cc(Br)c1Cc1ccc(O)c(-c2ccccc2)n1] | 444/446 [M − H]−, ESI (−) |
| Example 224 | 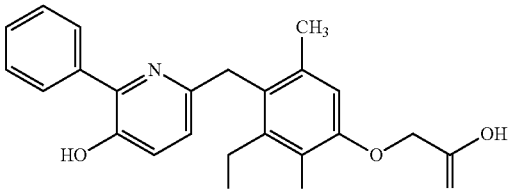 | 394 [M − H]−, ESI (−) |
| Example 225 | 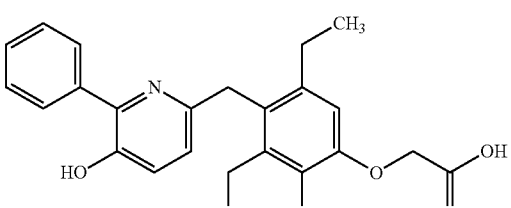 | 408 [M − H]−, ESI (−) |
| Example 226 | 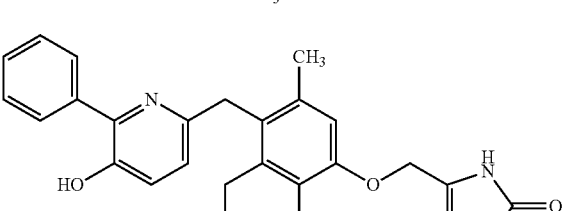 | 434 [M − H]−, ESI (−) |
| Example 227 | 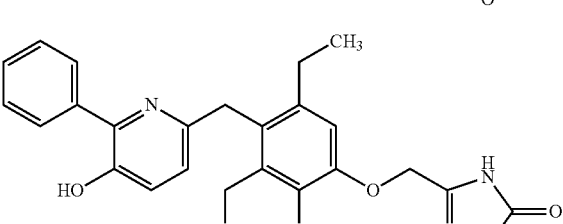 | 448 [M − H]−, ESI (−) |
| Example 228 | 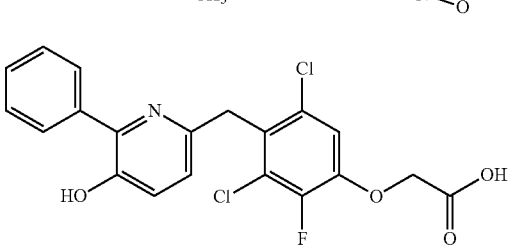 | 420/422 [M − H]−, ESI (−) |

TABLE 1-continued

| Example | | MASS |
|---|---|---|
| Example 229 | | 460/462 [M – H]–, ESI (–) |
| Example 230 | | 400/402 [M – H]–, ESI (–) |
| Example 231 | | 394 [M – H]–, ESI (–) |
| Example 232 | | 440 [M – H]–, ESI (–) |
| Example 233 | | 482 [M – H]–, ESI (–) |
| Example 234 | | 482 [M – H]–, ESI (–) |

TABLE 1-continued

| Example | MASS |
|---|---|
| Example 235 | 496 [M − H]−, ESI (−) |
| Example 236 | 478 [M − H]−, ESI (−) |
| Example 237 | 478 [M − H]−, ESI (−) |
| Example 238 | 482 [M − H]−, ESI (−) |
| Example 239 | 496 [M − H]−, ESI (−) |

TABLE 1-continued

| Example | | MASS |
|---|---|---|
| Example 240 | [structure] | 506 [M − H]−, ESI (−) |
| Example 241 | [structure] | 445 [M − H]−, ESI (−) |
| Example 242 | [structure] | 391 [M − H]−, ESI (−) |
| Example 243 | [structure] | 405 [M − H]−, ESI (−) |
| Example 244 | [structure] | 421 [M − H]−, ESI (−) |

TABLE 1-continued

| Example | MASS |
|---|---|
| Example 245 | 416 [M − H]−, ESI (−) |
| Example 246 | 478 [M − H]−, ESI (−) |
| Example 247 | 522 [M − H]−, ESI (−) |
| Example 248 | 496 [M − H]−, ESI (−) |
| Example 249 | 466 [M − H]−, ESI (−) |

TABLE 1-continued

| Example | | MASS |
|---|---|---|
| Example 250 | [structure] | 466 [M − H]−, ESI (−) |
| Example 251 | [structure] | 522 [M − H]−, ESI (−) |
| Example 252 | [structure] | 406 [M − H]−, ESI (−) |
| Example 253 | [structure] | 502 [M − H]−, ESI (−) |
| Example 254 | [structure] | 478 [M − H]−, ESI (−) |

TABLE 1-continued

| Example | | MASS |
|---|---|---|
| Example 255 | | 418 [M − H]−, ESI (−) |
| Example 256 | | 508/510 [M − H]−, ESI (−) |
| Example 257 | | 548/550 [M − H]−, ESI (−) |
| Example 258 | | 448 [M − H]−, ESI (−) |
| Example 259 | | 464 [M − H]−, ESI (−) |
| Example 260 | | 520 [M − H]−, ESI (−) |

TABLE 1-continued

| Example | MASS |
|---|---|
| Example 261 | 440 [M − H]−, ESI (−) |
| Example 262 | 452 [M − H]−, ESI (−) |
| Example 263 | 502 [M − H]−, ESI (−) |
| Example 264 | 466 [M − H]−, ESI (−) |
| Example 265 | 466 [M − H]−, ESI (−) |
| Example 266 | 478 [M − H]−, ESI (−) |

TABLE 1-continued

| Example | MASS |
|---------|------|
| Example 267 | 464 [M − Na]−, ESI (−) |
| Example 268 | 470 [M − H]−, ESI (−) |
| Example 269 | 408 [M − H]−, ESI (−) |
| Example 270 | 404 [M − H]−, ESI (−) |
| Example 271 | 424/426 [M − H]−, ESI (−) |
| Example 272 | 396 [M − H]−, ESI (−) |

TABLE 1-continued

| Example | MASS |
|---|---|
| Example 273 | 446/448 [M − H]−, ESI (−) |
| Example 274 | 410 [M − H]−, ESI (−) |
| Example 275 | 402/404 [M − H]−, ESI (−) |
| Example 276 | 388 [M − H]−, ESI (−) |
| Example 277 | 446/448 [M − H]−, ESI (−) |
| Example 278 | 426 [M − H]−, ESI (−) |

TABLE 1-continued
| Example | | MASS |
|---|---|---|
| Example 279 | 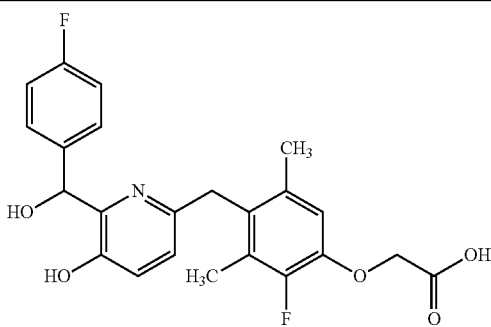 | 428 [M − H]−, ESI (−) |
| Example 280 | 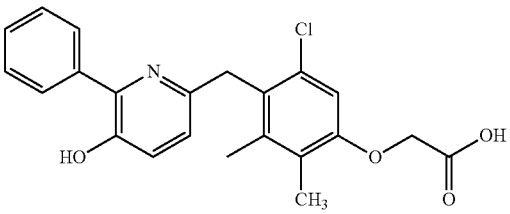 [SMILES: Cc1c(OCC(=O)O)cc(Cl)c(Cc2ccc(O)c(-c3ccccc3)n2)c1C] | 396/398 [M − H]−, ESI (−) |
| Example 281 | 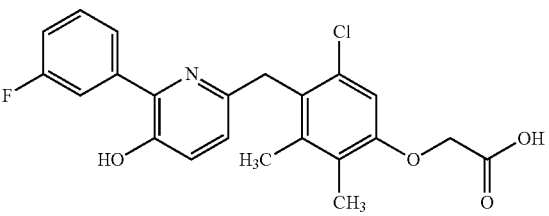 [SMILES: Cc1c(OCC(=O)O)cc(Cl)c(Cc2ccc(O)c(-c3cccc(F)c3)n2)c1C] | 414/416 [M − H]−, ESI (−) |
| Example 282 | 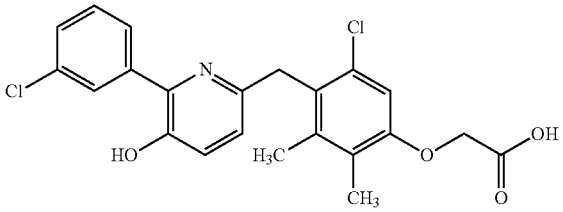 [SMILES: Cc1c(OCC(=O)O)cc(Cl)c(Cc2ccc(O)c(-c3cccc(Cl)c3)n2)c1C] | 430/432 [M − H]−, ESI (−) |
| Example 283 | 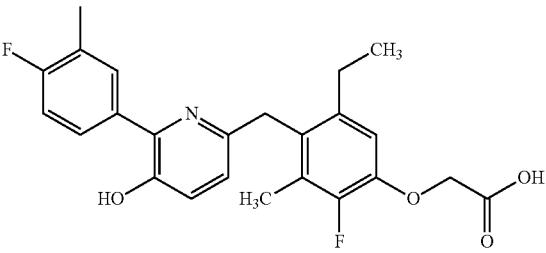 [SMILES: CCc1cc(OCC(=O)O)c(F)c(C)c1Cc1ccc(O)c(-c2ccc(F)c(C)c2)n1] | 426 [M − H]−, ESI (−) |
| Example 284 | 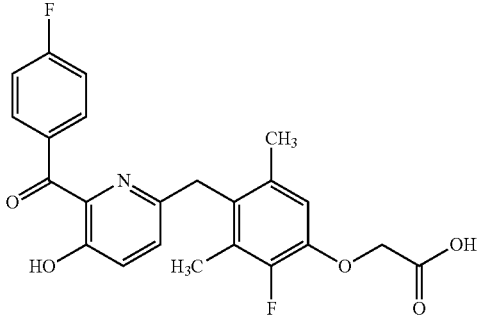 [SMILES: Cc1cc(OCC(=O)O)c(F)c(C)c1Cc1ccc(O)c(C(=O)c2ccc(F)cc2)n1] | 426 [M − H]−, ESI (−) |

TABLE 1-continued

| Example | | MASS |
|---|---|---|
| Example 285 | (structure) | 412 [M − H]−, ESI (−) |
| Example 286 | (structure) | 426 [M − H]−, ESI (−) |
| Example 287 | (structure) | 396 [M − H]−, ESI (−) |
| Example 288 | (structure) | 402/404 [M − H]−, ESI (−) |
| Example 289 | (structure) | 456 [M − H]−, ESI (−) |
| Example 290 | (structure) | 452 [M − H]−, ESI (−) |

TABLE 1-continued

| Example | MASS |
|---|---|
| Example 291 | 466 [M − H]−, ESI (−) |
| Example 292 | 436 [M − H]−, ESI (−) |
| Example 293 | 442/444 [M − H]−, ESI (−) |
| Example 294 | 466 [M − H]−, ESI (−) |
| Example 295 | 468 [M − H]−, ESI (−) |
| Example 296 | 437 [M − H]−, ESI (−) |

TABLE 1-continued

| Example | MASS |
|---|---|
| Example 297 | 397 [M − H]−, ESI (−) |
| Example 298 | 408 [M − H]−, ESI (−) |
| Example 299 | 422 [M − Na]−, ESI (−) |
| Example 300 | 386 [M − Na]−, ESI (−) |

The following compounds are included in the compound represented by the formula [I], and can be produced according to production methods 1-14, the above-mentioned Examples, and Reference Examples.

di[(2,2-dimethylpropanoyloxy)methyl]({4-[(5-hydroxy-6-isopropylpyridin-2-yl)methyl]-3,5-dimethylphenoxy}methyl)phosphonate;

di[(2,2-dimethylpropanoyloxy)methyl]({4-[(6-cyclohexyl-5-hydroxypyridin-2-yl)methyl]-3,5-dimethylphenoxy}methyl)phosphonate;

di[(2,2-dimethylpropanoyloxy)methyl]({4-[(6-cycloheptyl-5-hydroxypyridin-2-yl)methyl]-3,5-dimethylphenoxy}methyl)phosphonate;

di[(2,2-dimethylpropanoyloxy)methyl]({4-[(5-hydroxy-6-isopropylpyridin-2-yl)methyl]-2,3,5-trimethylphenoxy}methyl)phosphonate;

di[(2,2-dimethylpropanoyloxy)methyl]({4-[(6-cyclohexyl-5-hydroxypyridin-2-yl)methyl]-2,3,5-trimethylphenoxy}methyl)phosphonate;

di[(2,2-dimethylpropanoyloxy)methyl]({4-[(6-cycloheptyl-5-hydroxypyridin-2-yl)methyl]-2,3,5-trimethylphenoxy}methyl)phosphonate;

di[(2,2-dimethylpropanoyloxy)methyl]({2-fluoro-4-[(5-hydroxy-6-isopropylpyridin-2-yl)methyl]-3,5-dimethylphenoxy}methyl)phosphonate;

di[(2,2-dimethylpropanoyloxy)methyl]({4-[(6-cyclohexyl-5-hydroxypyridin-2-yl)methyl]-2-fluoro-3,5-dimethylphenoxy}methyl)phosphonate;

di[(2,2-dimethylpropanoyloxy)methyl]({4-[(6-cycloheptyl-5-hydroxypyridin-2-yl)methyl]-2-fluoro-3,5-dimethylphenoxy}methyl)phosphonate;

N,N'-bis[(ethoxycarbonyl)methyl]({4-[(5-hydroxy-6-isopropylpyridin-2-yl)methyl]-3,5-dimethylphenoxy}methyl)phosphonic acid diamide;

N,N'-bis[ethoxycarbonyl)methyl]({4-[(6-cyclohexyl-5-hydroxypyridin-2-yl)methyl]-3,5-dimethylphenoxy}methyl)phosphonic acid diamide;

N,N'-bis[(ethoxycarbonyl)methyl]({4-[(6-cycloheptyl-5-hydroxypyridin-2-yl)methyl]-3,5-dimethylphenoxy}methyl)phosphonic acid diamide;

N,N'-bis[(ethoxycarbonyl)methyl]({4-[(5-hydroxy-6-isopropylpyridin-2-yl)methyl]-2,3,5-trimethylphenoxy}methyl)phosphonic acid diamide;

N,N'-bis[(ethoxycarbonyl)methyl]({4-[(6-cyclohexyl-5-hydroxypyridin-2-yl)methyl]-2,3,5-trimethylphenoxy}methyl)phosphonic acid diamide;

N,N'-bis[(ethoxycarbonyl)methyl]({4-[(6-cycloheptyl-5-hydroxypyridin-2-yl)methyl]-2,3,5-trimethylphenoxy}methyl)phosphonic acid diamide;

N,N'-bis[(ethoxycarbonyl)methyl]({2-fluoro-4-[(5-hydroxy-6-isopropylpyridin-2-yl)methyl]-3,5-dimethylphenoxy}methyl)phosphonic acid diamide;

N,N'-bis[(ethoxycarbonyl)methyl]({4-[(6-cyclohexyl-5-hydroxypyridin-2-yl)methyl]-2-fluoro-3,5-dimethylphenoxy}methyl)phosphonic acid diamide;

N,N'-bis[(ethoxycarbonyl)methyl]({4-[(6-cycloheptyl-5-hydroxypyridin-2-yl)methyl]-2-fluoro-3,5-dimethylphenoxy}methyl)phosphonic acid diamide;

6-(4-{[4-(3-chlorophenyl)-2-oxido-1,3,2-dioxaphosphinan-2-yl]methoxy}-2,6-dimethylbenzyl)-2-isopropylpyridin-3-ol;

6-(4-{[4-(3-chlorophenyl)-2-oxido-1,3,2-dioxaphosphinan-2-yl]methoxy}-2,6-dimethylbenzyl)-2-cyclohexylpyridin-3-ol;

6-(4-{[4-(3-chlorophenyl)-2-oxido-1,3,2-dioxaphosphinan-2-yl]methoxy}-2,6-dimethylbenzyl)-2-cycloheptylpyridin-3-ol;

6-(4-{[4-(3-chlorophenyl)-2-oxido-1,3,2-dioxaphosphinan-2-yl]methoxy}-2,3,6-trimethylbenzyl)-2-isopropylpyridin-3-ol;

6-(4-{[4-(3-chlorophenyl)-2-oxido-1,3,2-dioxaphosphinan-2-yl]methoxy}-2,3,6-trimethylbenzyl)-2-cyclohexylpyridin-3-ol;

6-(4-{[4-(3-chlorophenyl)-2-oxido-1,3,2-dioxaphosphinan-2-yl]methoxyl-2,3,6-trimethylbenzyl)-2-cycloheptylpyridin-3-ol;

6-(4-{[4-(3-chlorophenyl)-2-oxido-1,3,2-dioxaphosphinan-2-yl]methoxy}-3-fluoro-2,6-dimethylbenzyl)-2-isopropylpyridin-3-ol;

6-(4-{[4-(3-chlorophenyl)-2-oxido-1,3,2-dioxaphosphinan-2-yl]methoxy}-3-fluoro-2,6-dimethylbenzyl)-2-cyclohexylpyridin-3-ol;

6-(4-{[4-(3-chlorophenyl)-2-oxido-1,3,2-dioxaphosphinan-2-yl]methoxy}-3-fluoro-2,6-dimethylbenzyl)-2-cycloheptylpyridin-3-ol;

3-{[4-({6-[(4-fluorophenyl)(hydroxy)methyl]-5-hydroxypyridin-2-yl}methyl)-3,5-dimethylphenyl]amino}-3-oxopropanoic acid;

3-{[4-({6-[(4-fluorophenyl)(hydroxy)methyl]-5-hydroxypyridin-2-yl}methyl)-2,3,5-trimethylphenyl]amino}-3-oxopropanoic acid;

3-{[2-fluoro-4-({6-[(4-fluorophenyl)(hydroxy)methyl]-5-hydroxypyridin-2-yl}methyl)-3,5-dimethylphenyl]amino}-3-oxopropanoic acid;

{[4-({6-[(4-fluorophenyl)(hydroxy)methyl]-5-hydroxypyridin-2-yl}methyl)-3,5-dimethylphenyl]amino}(oxo)acetic acid;

{[4-({6-[(4-fluorophenyl)(hydroxy)methyl]-5-hydroxypyridin-2-yl}methyl)-2,3,5-trimethylphenyl]amino}(oxo)acetic acid;

{[2-fluoro-4-({6-[(4-fluorophenyl)(hydroxy)methyl]-5-hydroxypyridin-2-yl}methyl)-3,5-dimethylphenyl]amino}(oxo)acetic acid;

2-{4-[(5-hydroxy-6-isopropylpyridin-2-yl)methyl]-3,5-dimethylphenyl}-3,5-dioxo-2,3,4,5-tetrahydro-1,2,4-triazine-6-carbonitrile;

2-{4-[(6-cycloheptyl-5-hydroxypyridin-2-yl)methyl]-3,5-dimethylphenyl}-3,5-dioxo-2,3,4,5-tetrahydro-1,2,4-triazine-6-carbonitrile;

2-{4-[(5-hydroxy-6-isopropylpyridin-2-yl)methyl]-2,3,5-trimethylphenyl}-3,5-dioxo-2,3,4,5-tetrahydro-1,2,4-triazine-6-carbonitrile;

2-{4-[(6-cyclohexyl-5-hydroxypyridin-2-yl)methyl]-2,3,5-trimethylphenyl}-3,5-dioxo-2,3,4,5-tetrahydro-1,2,4-triazine-6-carbonitrile;

2-{4-[(6-cycloheptyl-5-hydroxypyridin-2-yl)methyl]-2,3,5-trimethylphenyl}-3,5-dioxo-2,3,4,5-tetrahydro-1,2,4-triazine-6-carbonitrile;

2-{2-fluoro-4-[(5-hydroxy-6-isopropylpyridin-2-yl)methyl]-3,5-dimethylphenyl}-3,5-dioxo-2,3,4,5-tetrahydro-1,2,4-triazine-6-carbonitrile;

2-{4-[(6-cyclohexyl-5-hydroxypyridin-2-yl)methyl]-2-fluoro-3,5-dimethylphenyl}-3,5-dioxo-2,3,4,5-tetrahydro-1,2,4-triazine-6-carbonitrile;

2-{4-[(6-cycloheptyl-5-hydroxypyridin-2-yl)methyl]-2-fluoro-3,5-dimethylphenyl}-3,5-dioxo-2,3,4,5-tetrahydro-1,2,4-triazine-6-carbonitrile.

The compounds of Example 2-1-Example 2-17 were produced according to production methods 1 - 14, and the above-mentioned Examples and Reference Examples.

TABLE 2

| Example | MASS |
|---|---|
| Example 2-1 | 488 [M + H]+, APCI(+) |
| Example 2-2 | 462/464 [M + Na]+, ESI(+) |

TABLE 2-continued

| Example | | MASS |
|---|---|---|
| Example 2-3 | (structure) | 488/490 [M + H]+, ESI(+) |
| Example 2-4 | (structure) | 444/446 [M + H]+, ESI(+) |
| Example 2-5 | (structure) | 444/446 [M + H]+, ESI(+) |
| Example 2-6 | (structure) | 486 [M + H]+, ESI(+) |
| Example 2-7 | (structure) | 502 [M + H]+, ESI(+) |
| Example 2-8 | (structure) | 444/446 [M + H]+, ESI(+) |
| Example 2-9 | (structure) | 442/444 [M + H]+, ESI(+) |

TABLE 2-continued
| Example | | MASS |
|---|---|---|
| Example 2-10 | 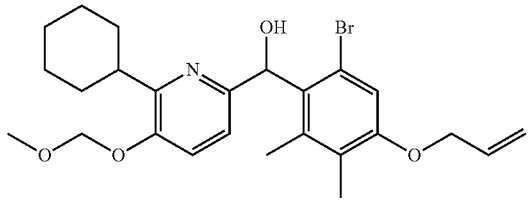 [SMILES: C=CCOc1cc(Br)c(C(O)c2ccc(OCOC)c(C3CCCCC3)n2)c(C)c1C] | 490/492 [M + H]+, ESI(+) |
| Example 2-11 | 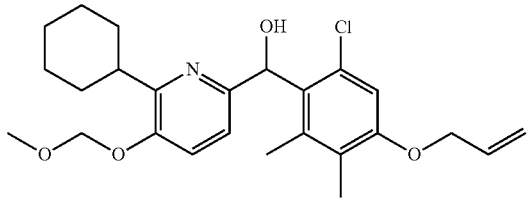 [SMILES: C=CCOc1cc(Cl)c(C(O)c2ccc(OCOC)c(C3CCCCC3)n2)c(C)c1C] | 446/448 [M + H]+, ESI(+) |
| Example 2-12 | 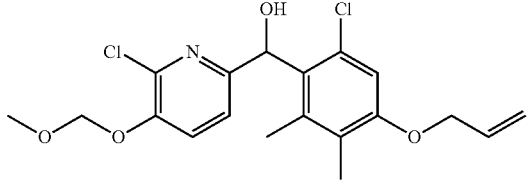 [SMILES: C=CCOc1cc(Cl)c(C(O)c2ccc(OCOC)c(Cl)n2)c(C)c1C] | 398/400 [M + H]+, APCI(+) |
| Example 2-13 | 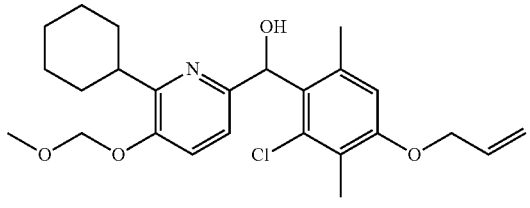 [SMILES: C=CCOc1cc(C)c(C(O)c2ccc(OCOC)c(C3CCCCC3)n2)c(Cl)c1C] | 446/448 [M + H]+, APCI(+) |
| Example 2-14 | 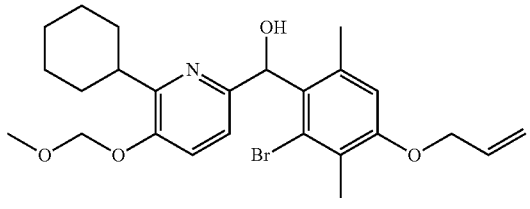 [SMILES: C=CCOc1cc(C)c(C(O)c2ccc(OCOC)c(C3CCCCC3)n2)c(Br)c1C] | 490/492 [M + H]+, APCI(+) |
| Example 2-15 | 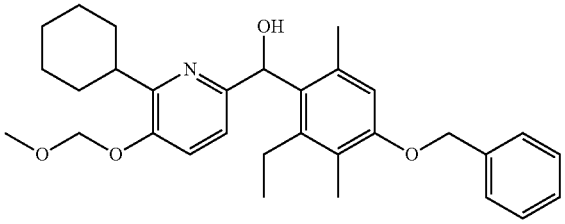 [SMILES: CCc1c(C)c(OCc2ccccc2)cc(C)c1C(O)c1ccc(OCOC)c(C2CCCCC2)n1] | 490 [M + H]+, APCI(+) |
| Example 2-16 | 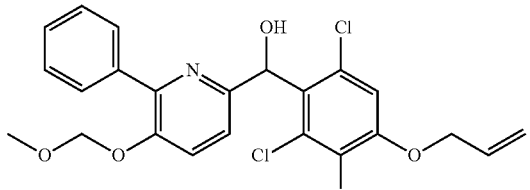 | 464/466 [M + H]+, APCI(+) |

TABLE 2-continued

| Example | | MASS |
|---|---|---|
| Example 2-17 | 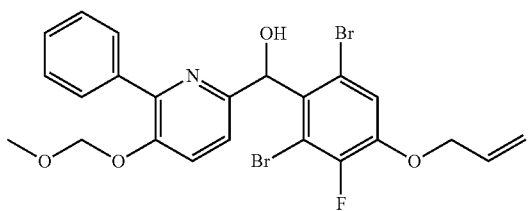 [SMILES: C=CCOc1cc(Br)c(C(O)c2ccc(OCOC)c(-c3ccccc3)n2)c(Br)c1F] | 552/554/556 [M + H]+, APCI(+) |

Reference Example 1

6-[(4-benzyloxy-2,6-dimethyl)phenylhydroxymethyl]-2-chloro-3-methoxymethoxypyridine

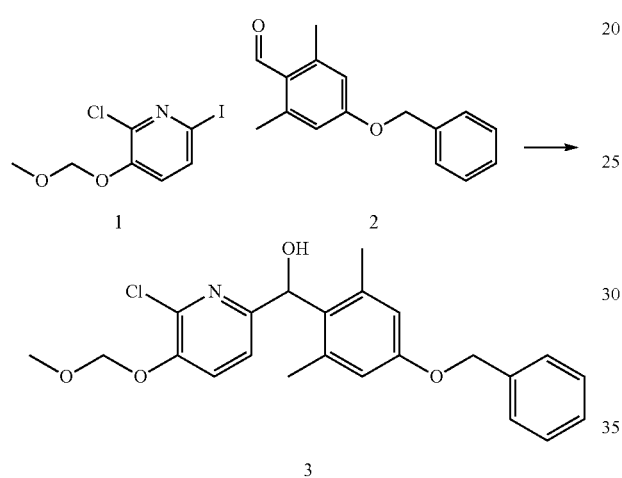

Compound 1 (CAS No. 199168-10-0, 344 mg, 1.15 mmol) was dissolved in toluene (8 mL), and the mixture was cooled to −78° C. n-Butyllithium (1.65 M hexane solution, 0.7 mL, 1.15 mmol) was slowly added dropwise, and the mixture was stirred for 30 min. Compound 2 (CAS No. 28924-92-7, 251 mg, 1.04 mmol) was dissolved in toluene (2 mL), and the mixture was added dropwise over 5 min. After stirring for 30 min, the mixture was heated to room temperature. After 2 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 3 (308 mg, 71%).

MS m/z 414/416 [M+H]+, APCI(+)

Reference Example 2

4-benzyloxy-3-fluoro-2,6-dimethylbenzaldehyde

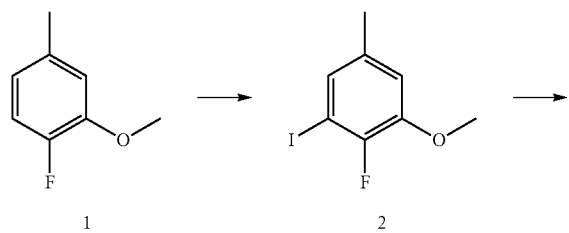

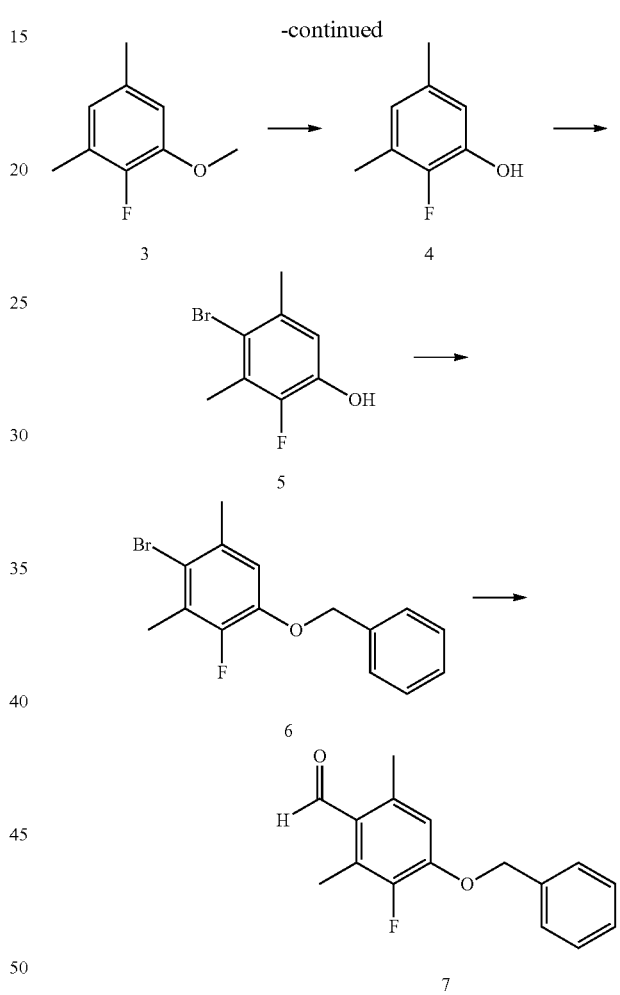

2-Fluoro-5-methylanisole (1.00 g, 7.14 mmol) and N,N,N′,N″,N″-pentamethyldiethylenetriamine (1.36 g, 7.85 mmol) were dissolved in tetrahydrofuran (20 mL) and the mixture was cooled to −78° C. n-Butyllithium (1.20 M hexane solution, 6.55 mL, 7.86 mmol) was slowly added dropwise, and the mixture was stirred for 2 hr. Iodine (3.63 g, 14.3 mmol) dissolved in tetrahydrofuran (4 mL) was slowly added dropwise, and the mixture was stirred for 30 min and heated to room temperature. Saturated aqueous sodium thiosulfate solution was added, and the mixture was extracted with ethyl acetate, the extract was washed with water and saturated brine, dried over anhydrous magnesium sulfate, filtered and concentrated. The residue was purified by silica gel column chromatography to give compound 2 (1.68 g, 88%). Compound 2 (1.68 g, 6.31 mmol), potassium carbonate (2.20 g, 15.9 mmol), and trimethylboroxine (1.98 g, 15.8 mmol) were dissolved in dioxane (32 mL), and the mixture was purged with argon. [1,1'-Bis(diphenylphosphino)ferrocene]dichloropalladium(II) dichloromethane complex (258 mg, 0.316 mmol) was added and the mixture was heated under reflux. After stirring for 15 hr, the mixture was allowed to cool to room temperature, filtered through radiolite, and concentrated. The residue was purified by silica gel column chromatography to give compound 3 (715 mg, 74%)

MS m/z 155 [M+H]+, APCI(+)

Compound 3 (714 mg, 4.63 mmol) was dissolved in methylene chloride, and the mixture was stirred cooled to 0° C., and boron tribromide (1.0 M methylene chloride solution, 9.30 mL, 9.30 mmol) was added dropwise. After stirring for 1 hr, the mixture was warmed to room temperature. Water was added, and the mixture was extracted twice with chloroform. The extract was washed with saturated brine, dried over anhydrous magnesium sulfate, filtered and concentrated. The residue was purified by silica gel column chromatography to give compound 4 (434 mg, 69%).

MS m/z 139 [M–H]–, ESI(–)

Compound 4 (433 g, 3.09 mmol) was dissolved in methylene chloride (6.5 mL) and methanol (4.3 mL), and tetra-n-tribromide (1.56 g, 3.24 mmol) was added. After stirring for 2 hr, water was added, and the mixture was extracted with diethyl ether. The extract was washed with saturated brine, dried over anhydrous sodium sulfate, filtered, and concentrated. The residue was purified by silica gel column chromatography to give compound 5 (573 mg, 85%).

MS m/z 217/219 [M–H]–, ESI(–)

Compound 5 (571 mg, 2.61 mmol) was dissolved in acetonitrile (6.5 and benzyl bromide (491 mg, 2.87 mmol) and cesium carbonate (1.28 g, 3.93 mmol) were added. After stirring for 2 hr, water was added, and the mixture was extracted with ethyl acetate. The organic layer was washed with saturated brine, dried over anhydrous sodium sulfate, filtered, and concentrated. The residue was purified by silica gel column chromatography to give compound 6 (783 mg, 97%).

MS m/z 326/328 [M+NH4]+, APCI(+)

Compound 6 (782 mg, 2.53 mmol) was dissolved in tetrahydrofuran (13 mL), and the mixture was cooled to −78° C. n-Butyllithium (1.2 M hexane solution, 3.16 mL, 3.79 mmol) was slowly added dropwise, and the mixture was stirred for 10 min. N,N-Dimethylformamide (555 mg, 7.59 mmol) was slowly added dropwise, and the mixture was stirred for 10 min, and heated to room temperature. Saturated aqueous ammonium chloride solution was added, and the mixture was extracted with ethyl acetate. The organic layer was washed with saturated brine, dried over anhydrous sodium sulfate, filtered and concentrated. The residue was purified by silica gel column chromatography to give compound 7 (464 mg, 71%).

MS m/z 259 [M+H]+, APCI(+)

Reference Example 3

6-(benzyloxy)-2,4-dimethylnicotinaldehyde

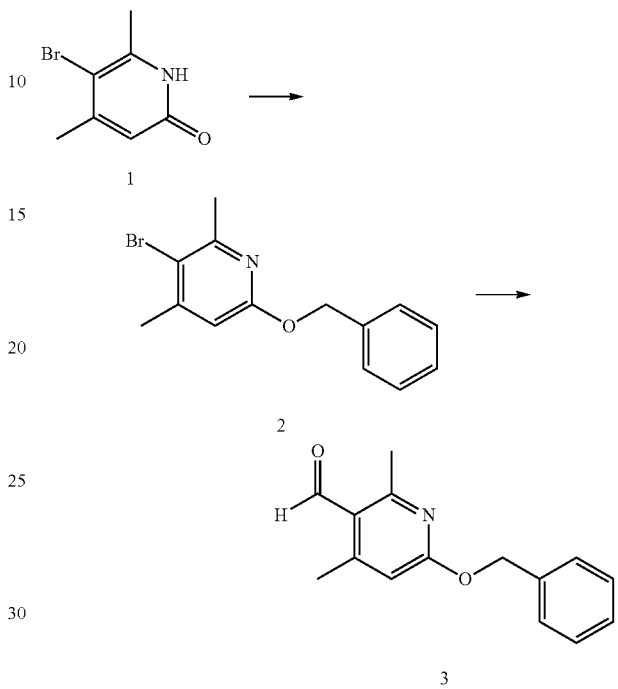

Compound 1 (10.0 g, 49.5 mmol) and silver carbonate (27.3 g, 99.0 mmol) were dissolved in N,N'-dimethylformamide (100 mL), benzyl bromide (8.89 g, 52.0 mmol) was added, and the mixture was heated to 80° C. After stirring overnight, the mixture was filtered through celite. Water was added, and the mixture was extracted with ethyl acetate. The organic layer was washed with saturated brine, dried over anhydrous sodium sulfate, filtered, and concentrated. The residue was purified by silica gel column chromatography to give compound 2 (12.5 g, 87%).

MS m/z 292/294 [M+H]+, APCI(+)

Compound 2 (5.00 g, 17.1 mmol) was dissolved in tetrahydrofuran (100 mL), and the mixture was cooled to −78° C. n-Butyllithium (2.6 M hexane solution, 7.24 mL, 18.8 mmol) was added dropwise over 10 min, and the mixture was stirred for 15 min. N,N'-Dimethylformamide (6.25 g, 85.6 mmol) was added dropwise by small portions, and the mixture was stirred for 1 hr and warm to room temperature. After stirring for 2 hr, saturated aqueous ammonium chloride solution was added, and the mixture was extracted with ethyl acetate. The organic layer was washed with saturated brine, dried over anhydrous sodium sulfate, filtered and concentrated. The residue was purified by silica gel column chromatography to give compound 3 (3.06 g, 74%).

MS m/z 242 [M+H]+, APCI(+)

Reference Example 4

2,6-dichloro-4-(diallylamino)phenol

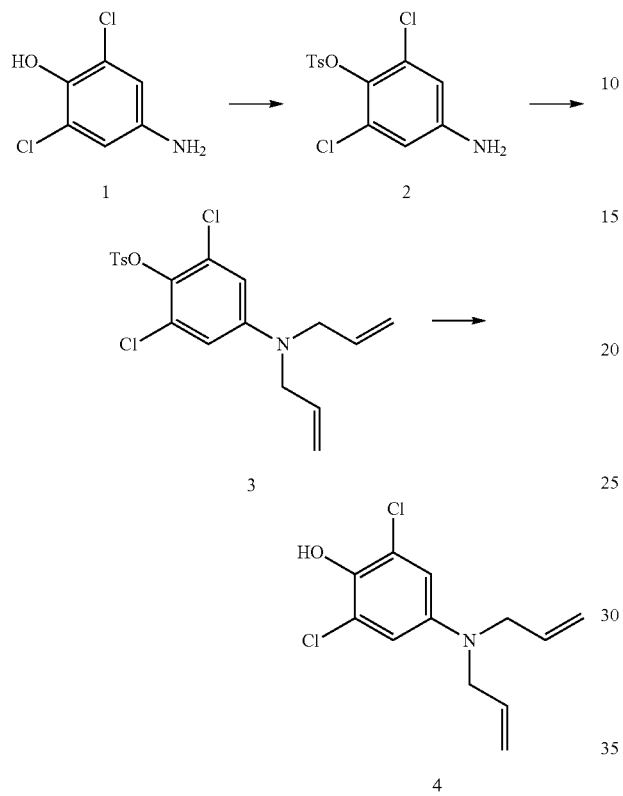

Compound 1 (3.14 g, 17.6 mmol) was suspended in dichloromethane (60 mL), and the suspension was ice-cooled. Triethylamine (2.68 g, 26.5 mmol) was added to give a solution, to which p-toluenesulfonyl chloride (3.36 g, 17.6 mmol) was added. After stirring for 30 min, saturated aqueous sodium hydrogen carbonate was added, and the mixture was extracted with chloroform. The organic layer was washed with saturated brine, dried over anhydrous magnesium sulfate, filtered and concentrated. The residue was purified by silica gel column chromatography to give compound 2 (5.53 g, 94%).

MS m/z 332/334 [M+H]$^+$, APCI(+)

Compound 2 (5.53 g, 16.6 mmol) was dissolved in N,N'-dimethylformamide (30 mL), and potassium carbonate (6.90 g, 49.9 mmol), sodium iodide (2.50 g, 16.6 mmol), and allyl bromide (4.84 g, 40.0 mmol) were added, and the mixture was heated to 50° C. After stirring for 6.5 hr, allyl bromide (2.42 g, 20.0 mmol) was added. After stirring for 16.5 hr, allyl bromide (2.42 g, 20.0 mmol) was added, and the mixture was heated to 70° C. After stirring for 16.5 hr, potassium carbonate (6.90 g, 49.9 mmol) and allyl bromide (4.84 g, 40.0 mmol) were added. After stirring for 22 hr, the mixture was allowed to cool to room temperature, filtered through celite, and diluted with ethyl acetate. The organic layer was washed with saturated brine, dried over anhydrous magnesium sulfate, filtered and concentrated. The residue was purified by silica gel column chromatography to give compound 3 (4.71 g, 69%).

MS m/z 412/414 [M+H]$^+$, APCI(+)

Compound 3 (1.08 g, 2.62 mmol) was dissolved in methanol (9 ml), potassium hydroxide (1.47 g, 26.2 mmol) was added, and the mixture was heated to 70° C. After stirring for 20 min, the mixture was allowed to cool to room temperature, and neutralized with 6N hydrochloric acid. After extraction with ethyl acetate, the organic layer was washed with saturated brine, dried over anhydrous magnesium sulfate, filtered and concentrated. The residue was purified by silica gel column chromatography to give compound 4 (575 mg, 85%).

MS m/z 258/260 [M+H]$^+$, APCI(+)

Reference Example 5

4-(allyloxy)-2,6-dibromo-3-fluorobenzaldehyde

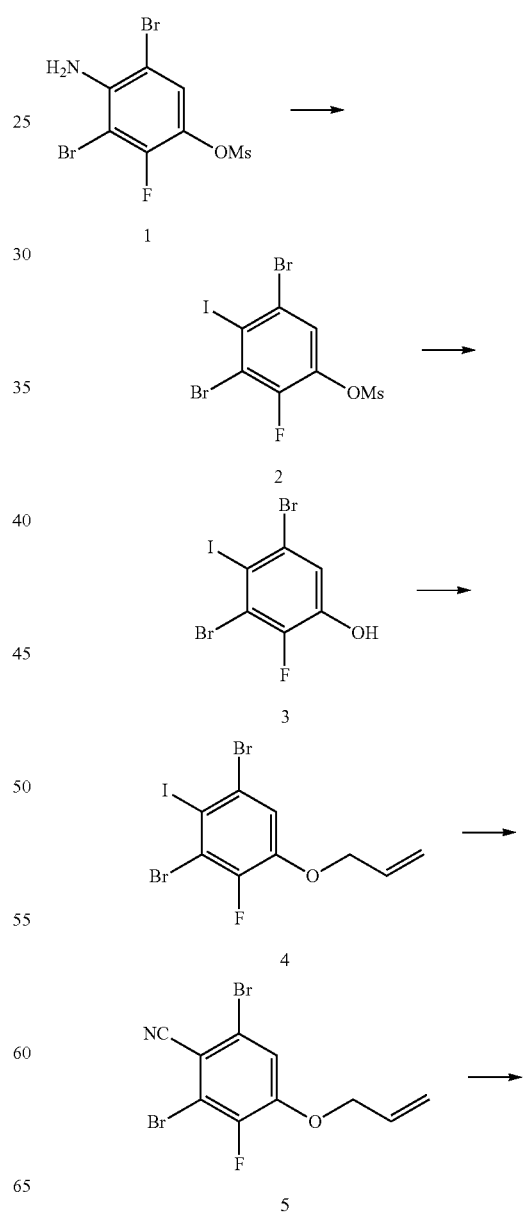

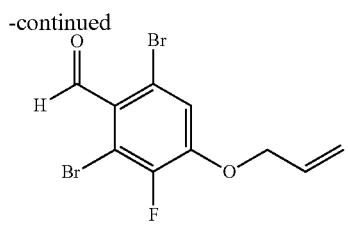

Compound 1 (5.00 g, 13.8 mmol) was dissolved in acetonitrile (25 ml), and added dropwise to an ice-cooled mixed solution of sulfuric acid (25 ml) and water (25 ml) over 15 min. After stirring for 20 min, an ice-cooled mixed solution of sodium nitrite (1.71 g, 24.8 mmol) and water (15 mL) was added dropwise over 7 min. After stirring for 15 min, the mixture was added to a mixed solution of potassium iodide (8.00 g, 48.2 mmol) and water (25 mL). After stirring for 50 min, water was added, and the mixture was extracted with chloroform. The organic layer was washed with saturated aqueous sodium carbonate solution, saturated aqueous sodium thiosulfate solution, and saturated brine, dried over anhydrous magnesium sulfate, filtered and concentrated. The residue was purified by silica gel column chromatography to give compound 2 (5.60 g, 86%).

MS m/z490/492/494 $[M+NH_4]^+$, APCI(+)

Compound 2 (5.08 g, 10.7 mmol) was dissolved in methanol (40 mL) and, after ice-cooling, 5N aqueous sodium hydroxide solution (6.43 mL, 32.2 mmol) was added, and the mixture was heated to room temperature. After stirring for 1 hr, the mixture was concentrated. The residue was acidified with 1N hydrochloric acid. After extraction with ethyl acetate, the organic layer was washed with saturated brine, dried over anhydrous magnesium sulfate, filtered and concentrated. The residue was purified by silica gel column chromatography to give compound 3 (4.04 g, 95%).

MS m/z393/395/397 $[M-H]-$, ESI(−)

Compound 3 (4.04 g, 10.2 mmol) was dissolved in acetonitrile (50 mL), and cesium carbonate (6.65 g, 20.4 mmol) and allyl bromide (1.85 g, 15.3 mmol) were added. After stirring for 4 hr, the mixture was filtered through celite. The filtrate was concentrated, and the residue was purified by silica gel column chromatography to give compound 4 (3.92 g, 88%).

Compound 4 (3.92 g, 8.99 mmol) was dissolved in N,N'-dimethylformamide (30 mL), and copper cyanide (1.61 g, 18.0 mmol) and L-proline (1.04 g, 8.99 mmol) were added, and the mixture was heated to 80° C. After stirring for 24 hr, the mixture was allowed to cool to room temperature. Ethyl acetate and aqueous ammonia were added, and the mixture was vigorously stirred. After 30 min, saturated brine was added, and the mixture was extracted with ethyl acetate. The organic layer was washed with saturated brine, dried over anhydrous magnesium sulfate, filtered and concentrated. The residue was purified by silica gel column chromatography to give compound 5 (2.43 g, 81%).

Compound 5 (1.18 g, 3.53 mmol) was dissolved in toluene (20 mL) and, after ice-cooling, diisobutylaluminum hydride (1M toluene solution, 5.28 ml, 5.28 mmol) was added dropwise over 5 min. After stirring for 50 min, methanol was added dropwise, and the mixture was allowed to cool to room temperature. 1M Sulfuric acid (50 mL) and ethyl acetate (100 mL) were added, and the mixture was vigorously stirred. After 1 hr, the mixture was extracted with ethyl acetate, and the organic layer was washed with water and saturated brine, dried over anhydrous magnesium sulfate, filtered and concentrated. The residue was purified by silica gel column chromatography to give compound 6 (1.04 g, 87%).

MS m/z351/353/355 $[M+H+MeOH-H_2O]^+$, APCI(+)

Reference Example 6

2-cyclohexyl-6-iodo-3-(methoxymethoxy)pyridine

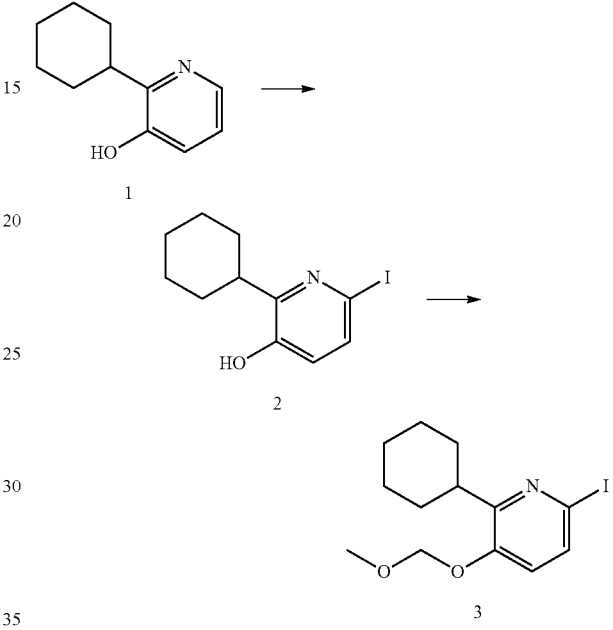

Compound 1 (8.52 g, 48.1 mmol) was suspended in acetonitrile (160 mL) and water (30 mL), and sodium iodide (8.65 g, 57.7 mmol) was added and the mixture was ice-cooled. Sodium hydroxide (1.92 g, 48.1 mmol) was added to give a solution, to which 5% aqueous sodium hypochlorite solution (71.6 mL, 48.1 mmol) was added dropwise over 15 min. After stirring for 10 min, the mixture was heated to room temperature. After stirring for 50 min, 5% aqueous sodium hypochlorite solution (21.5 mL, 14.4 mmol) was added dropwise over 5 min. After stirring for 15 min, 5% aqueous sodium hypochlorite solution (21.5 mL, 14.4 mmol) was added dropwise over 5 min. After stirring for 20 min, sodium iodide (2.16 g, 14.4 mmol) was added, and 5% aqueous sodium hypochlorite solution (21.5 mL, 14.4 mmol) was added dropwise over 5 min. After stirring for 20 min, 5% aqueous sodium hypochlorite solution (14.3 mL, 9.61 mmol) was added dropwise over 5 min. After stirring for 15 min, the mixture was neutralized with 6N hydrochloric acid, concentrated, and extracted with ethyl acetate. The organic layer was washed with saturated aqueous sodium thiosulfate solution, and saturated brine, dried over anhydrous magnesium sulfate, filtered and concentrated. The residue was purified by silica gel column chromatography to give compound 2 (9.46 g, 65%).

MS m/z 304 $[M+H]^+$, APCI(+)

Compound 2 (9.46 g, 31.2 mmol) was dissolved in acetonitrile (80 mL) and tetrahydrofuran (80 mL), and cesium carbonate (15.3 g, 46.8 mmol) and chloromethyl methyl ether (3.01 g, 37.4 mmol) were added. After stirring for 14.5 hr, chloromethyl methyl ether (1.00 g, 12.5 mmol) was added. After stirring for 1.5 hr, the mixture was filtered through celite. The filtrate was concentrated, and the residue was purified by silica gel column chromatography to give compound 3 (10.2 g, 94%).

MS m/z 348 [M+H]$^+$, APCI(+)

Reference Example 7

4-(allyloxy)-2,6-dichloro-3-fluorobenzaldehyde

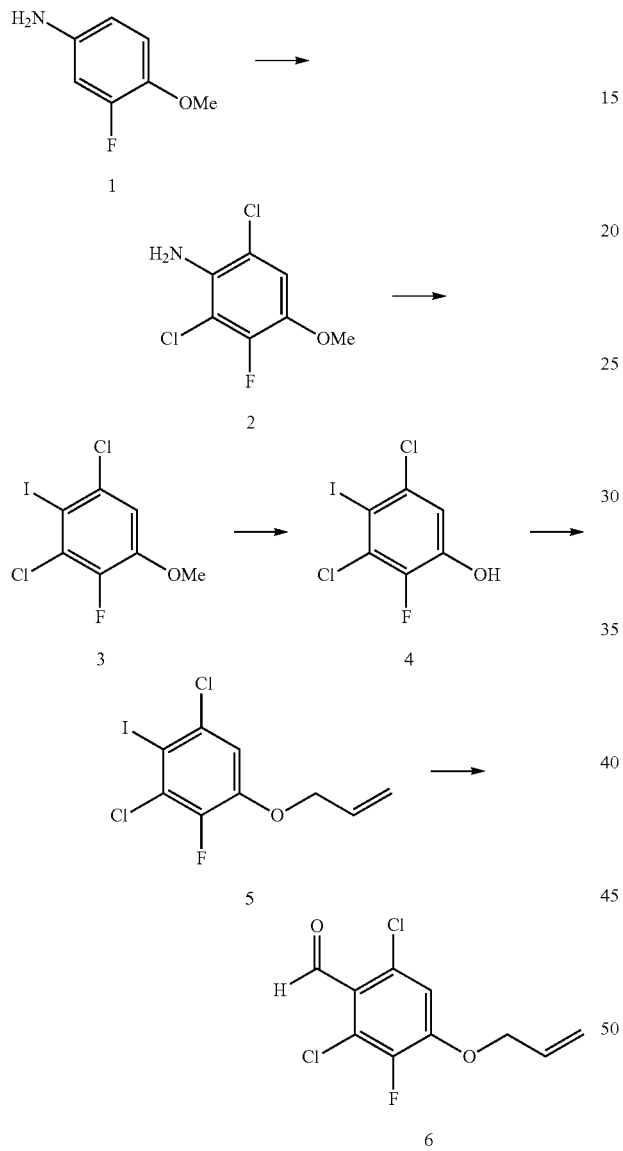

Compound 1 (431 mg, 2.10 mmol) was dissolved in dichloromethane (11 mL) and, after ice-cooling, tert-butyl hypochlorite (456 mg, 4.20 mmol) was added dropwise. After stirring for 30 min, tert-butyl hypochlorite (46 mg, 0.420 mmol) was added dropwise. After stirring for 20 min, saturated aqueous sodium thiosulfate solution was added, and the mixture was extracted with chloroform. The organic layer was washed with saturated brine, dried over anhydrous magnesium sulfate, filtered and concentrated. The residue was purified by silica gel column chromatography to give compound 2 (475 mg, 82%).

MS m/z 274/276/278 [M+H]$^+$, APCI(+)

Compound 2 (472 mg, 1.72 mmol) was dissolved in acetonitrile (3 mL), and the mixture was added dropwise to an ice-cooled mixed solution of sulfuric acid (3 mL) and water (3 mL) over 5 min. After stirring for 10 min, an ice-cooled mixed solution of sodium nitrite (214 mg, 3.10 mmol) and water (1.5 mL) was added dropwise over 2 min. After stirring for 20 min, the mixture was added at once to an ice-cooled mixed solution of potassium iodide (1.00 g, 6.03 mmol) and water (3 mL). After stirring for 5 min, the mixture was heated to room temperature. After stirring for 45 min, water was added, and the mixture was extracted with chloroform. The organic layer was washed with saturated aqueous sodium carbonate solution, saturated aqueous sodium thiosulfate solution, and saturated brine, dried over anhydrous magnesium sulfate, filtered and concentrated. The residue was purified by silica gel column chromatography to give compound 3 (563 mg, 85%).

Compound 3 (560 mg, 1.45 mmol) was dissolved in methanol (7 mL), and 5N aqueous sodium hydroxide solution (1.45 mL, 7.27 mmol) was added. After stirring for 1 hr, the mixture was concentrated. The residue was dissolved in water and adjusted to pH 2 with 6N Hydrochloric acid. The resulting solid was collected by filtration, washed with cold water and dried to give compound 4 (434 mg, 97%).

MS m/z 305/307 [M−H]−, ESI(−)

Compound 4 (432 mg, 1.41 mmol) was dissolved in acetonitrile (10 mL), and cesium carbonate (1.38 g, 4.22 mmol) and allyl bromide (255 mg, 2.11 mmol) were added. After stirring for 6 hr, the mixture was filtered through celite. The filtrate was concentrated, and the residue was purified by silica gel column chromatography to give compound 5 (458 mg, 94%).

Compound 5 (455 mg, 1.31 mmol) was dissolved in toluene (13 mL), and the mixture was cooled to −78° C. n-Butyllithium (1.65 M hexane solution, 0.874 mL, 1.44 mmol) was added dropwise over 3 min. After stirring for 15 min, N,N'-dimethylformamide (0.479 g, 6.56 mmol) was added dropwise. After stirring for 10 min, the mixture was heated to room temperature. After stirring for 1 hr, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 6 (167 mg, 51%).

MS m/z 263/265 [M+H+MeOH−H$_2$O]$^+$, APCI(+)

Reference Example 8

4-(benzyloxy)-2,6-diethyl-3-fluorobenzaldehyde

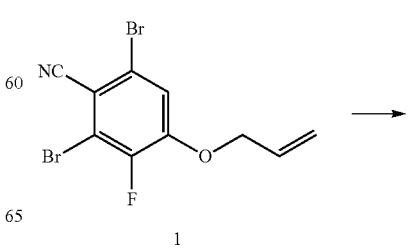

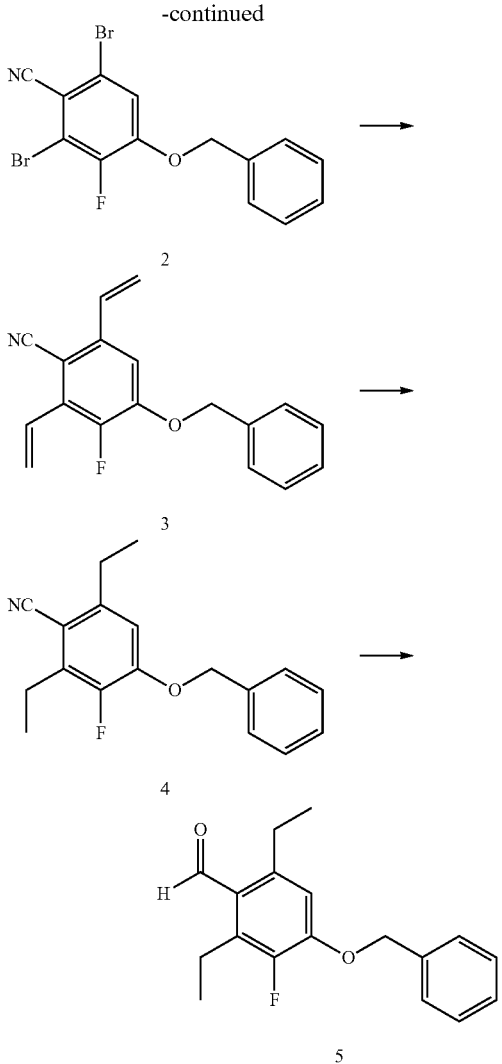

Compound 1 (640 mg, 1.91 mmol) was dissolved in tetrahydrofuran (20 ml,), and N-methylmorpholine (250 mg, 2.87 mmol) and tetrakistriphenylphosphinepalladium(0) (110 mg, 0.0955 mmol) were added. After stirring for 20 min, the mixture was concentrated. The residue was dissolved in ethyl acetate. The organic layer was washed with 1N hydrochloric acid, and saturated brine, dried over anhydrous magnesium sulfate, filtered and concentrated. The residue was dissolved in acetonitrile (20 mL), and cesium carbonate (1.87 g, 5.73 mmol) and benzyl bromide (490 mg, 2.87 mmol) were added. After stirring for 16 hr, the mixture was filtered through celite. The filtrate was concentrated, and the residue was purified by silica gel column chromatography to give compound 2 (601 mg, 82%).

Compound 2 (299 mg, 0.777 mmol) was dissolved in dimethoxyethane (8 mL), and water (0.8 mL), cesium carbonate (1.52 g, 4.66 mmol), and vinylboronic acid pinacol ester (598 mg, 3.88 mmol) were added, and the mixture was purged with argon. Tetrakistriphenylphosphinepalladium(0) (179 mg, 0.155 mmol) was added, and the mixture was heated to 90° C. After stirring for 16 hr, water (0.8 mL), vinylboronic acid pinacol ester (299 mg, 1.94 mmol), and tetrakistriphenylphosphinepalladium(0) (90 mg, 0.0777 mmol) were added. After stirring for 8 hr, the mixture was allowed to cool to room temperature, saturated aqueous ammonium chloride solution was added, and the mixture was extracted with ethyl acetate. The organic layer was washed with saturated brine, dried over anhydrous magnesium sulfate, filtered and concentrated. The residue was purified by silica gel column chromatography to give compound 3 (129 mg, 59%).

MS m/z 280 [M+H]$^+$, APCI(+)

Compound 3 (126 mg, 0.451 mmol) was dissolved in tetrahydrofuran (5 mL) and, after purging with argon, palladium carbon-ethylenediamine complex (13 mg) was added. After purging with hydrogen, the mixture was stirred for 6 hr, filtered through celite and thoroughly washed with ethyl acetate. The filtrate was concentrated, and the residue was dissolved in tetrahydrofuran (5 mL) and, after purging with argon, palladium carbon-ethylenediamine complex (40 mg) was added. After purging with hydrogen, the mixture was stirred for 14 hr, filtered through celite and thoroughly washed with ethyl acetate. The filtrate was concentrated, and the residue was dissolved in acetonitrile (5 mL), and cesium carbonate (441 mg, 1.35 mmol) and benzyl bromide (77 mg, 0.451 mmol) were added. After stirring for 4 hr, the mixture was filtered through celite. The filtrate was concentrated, and the residue was purified by silica gel column chromatography to give compound 4 (113 mg, 88%).

MS m/z 284 [M+H]$^+$, APCI(+)

Compound 4 (214 mg, 0.755 mmol) was dissolved in toluene (4 mL) and, after ice-cooling, diisobutylaluminum hydride (1 M toluene solution, 1.13 mL, 1.13 mmol) was added dropwise over 3 min. After stirring for 1 hr, diisobutylaluminum hydride (1 M toluene solution, 1.13 mL, 1.13 mmol) was added dropwise over 3 min. After stirring for 25 min, diisobutylaluminum hydride (1 M toluene solution, 0.755 mL, 0.755 mmol) was added dropwise. After stirring for 20 min, methanol was added dropwise, and the mixture was allowed to cool to room temperature. 1M Sulfuric acid and ethyl acetate were added, and the mixture was vigorously stirred. After 1 hr, 50% sulfuric acid and 6N hydrochloric acid were added, and the mixture was vigorously stirred. After one night, the mixture was extracted with ethyl acetate, and the organic layer was washed with water, and saturated brine, dried over anhydrous magnesium sulfate, filtered and concentrated. The residue was purified by silica gel column chromatography to give compound 5 (54 mg, 25%).

MS m/z 287 [M+H]$^+$, APCI(+)

The compounds of Reference Example 9 - Reference Example 27 were produced according to production methods 1-14, and the above-mentioned Examples and Reference Examples.

TABLE 3

| Ref. Ex. | | MASS |
| --- | --- | --- |
| Reference Example 9 | (structure) | 255 [M + H]+, APCI(+) |

TABLE 3-continued

| Ref. Ex. | | MASS |
|---|---|---|
| Reference Example 10 | (2,3-dihydrobenzofuran with CHO, methyl, and O-benzyl substituents) | 269 [M + H]+, APCI(+) |
| Reference Example 11 | (indane with CHO, methyl, and O-benzyl substituents) | 267 [M + H]+, APCI(+) |
| Reference Example 12 | (benzaldehyde with methyl, vinyl, F, and O-benzyl substituents) | 271 [M + H]+, APCI(+) |
| Reference Example 13 | (benzaldehyde with vinyl, methyl, F, and O-benzyl substituents) | 271 [M + H]+, APCI(+) |
| Reference Example 14 | (benzaldehyde with ethyl, methyl, and O-benzyl substituents) | 269 [M + H]+, APCI(+) |
| Reference Example 15 | (benzaldehyde with methyl, ethyl, methyl, and O-benzyl substituents) | 269 [M + H]+, APCI(+) |
| Reference Example 16 | (benzaldehyde with Br, methyl, F, and O-allyl substituents) | 273/275 [M + H]+, APCI(+) |
| Reference Example 17 | (benzaldehyde with methyl, Br, F, and O-allyl substituents) | 273/275 [M + H]+, APCI(+) |
| Reference Example 18 | (benzaldehyde with Cl, methyl, F, and O-allyl substituents) | 243/245 [M + H + MeOH—H2O]+, APCI(+) |
| Reference Example 19 | (benzaldehyde with methyl, Cl, F, and O-allyl substituents) | 243/245 [M + H + MeOH—H2O]+, APCI(+) |
| Reference Example 20 | (benzaldehyde with Br, methyl, methyl, and O-allyl substituents) | 269/271 [M + H]+, APCI(+) |
| Reference Example 21 | (benzaldehyde with Cl, methyl, methyl, and O-allyl substituents) | 225/227 [M + H]+, APCI(+) |
| Reference Example 22 | (phenol with 2,6-diBr and N,N-diallylamino substituent) | 346/348 [M + H]+, APCI(+) |
| Reference Example 23 | (benzaldehyde with methyl, methyl, Br, and O-allyl substituents) | 269/271 [M + H]+, APCI(+) |

TABLE 3-continued

| Ref. Ex. | | MASS |
|---|---|---|
| Reference Example 24 | (structure) | 225/227 [M + H]+, APCI(+) |
| Reference Example 25 | (structure) | 308 [M + H]+, APCI(+) |
| Reference Example 26 | (structure) | 344 [M + H]+, APCI(+) |
| Reference Example 27 | (structure) | 342 [M + H]+, APCI(+) |

Experimental Example

Transcription Activation Test of Human Thyroid Hormone Receptors α1 (TRα1) and β1 (TRβ1)

pcDNA3.1 vector (manufactured by Invitrogen) that expresses TRα1 or β1 cloned from human liver-derived cells, and firefly luciferase expression vector pDR4-LuC (manufactured by Stratagene) having a thyroid hormone response sequence to be a reporter were transfected into 293T cells cultured in Dulbecco's modified Eagle medium (DMEM) containing 10% of activated carbon/dextran-treated fetal bovine serum (FBS) by using Lipofectamine2000 (manufactured by Invitrogen). After 16 hr, the cells were plated again in a 96 well plate, and the medium was exchanged with DMEM containing 0.1% activated carbon/dextran-treated FBS. After 3 more hr, a compound diluted with dimethyl sulfoxide solution was added, and the luciferase activity after 24 hr was measured.

As a positive control, 3,3',5-triiodo-L-thyronine ($T_3$), which is a biological ligand, was used. The transcription activation action of the compound on TRα1 and TRβ1 was shown by each $EC_{50}$ value and the maximum luciferase activity value relative to the maximum luciferase activity value of $T_3$ as 100. The results are shown in the following Tables.

TABLE 4

| Example | TRβ (μM) | selectivity |
|---|---|---|
| 1 | 0.003 | B |
| 2 | 0.002 | B |
| 3 | 0.02 | A |
| 4 | 0.0005 | B |
| 5 | 0.0005 | A |
| 6 | 0.05 | B |
| 7 | 0.001 | A |
| 8 | 0.05 | A |
| 9 | 0.007 | C |
| 10 | 0.03 | B |
| 11 | 0.001 | B |
| 12 | 0.0007 | B |
| 13 | 0.0003 | A |
| 14 | 0.01 | B |
| 15 | 0.009 | B |
| 16 | 0.02 | B |
| 17 | 0.02 | B |
| 18 | 2 | C |
| 19 | 0.005 | B |
| 20 | 0.004 | C |
| 21 | 0.03 | B |
| 22 | 0.2 | A |
| 23 | 0.01 | A |
| 24 | 0.03 | B |
| 25 | 0.001 | C |
| 26 | 0.006 | C |
| 27 | 0.0003 | C |
| 28 | 0.0002 | C |
| 29 | 0.002 | A |
| 30 | 0.002 | A |
| 31 | 0.0002 | B |
| 32 | 0.0004 | B |
| 33 | 0.008 | B |
| 34 | 0.0004 | B |
| 35 | 0.009 | B |
| 36 | 0.003 | C |
| 37 | 0.0001 | B |
| 41 | 0.004 | B |
| 42 | 0.3 | B |
| 44 | 0.2 | B |
| 45 | 0.005 | A |
| 52 | 0.006 | A |
| 54 | 0.006 | A |
| 60 | 0.0006 | A |
| 62 | 0.004 | B |
| 64 | 0.08 | B |
| 65 | 0.01 | A |
| 73 | 0.0002 | A |
| 80 | 0.1 | B |
| 81 | 0.0001 | B |
| 92 | 0.001 | A |
| 107 | 0.01 | C |
| 117 | 0.002 | B |
| 118 | 0.02 | B |
| 131 | 0.004 | A |
| 136 | 0.001 | C |
| 152 | 0.005 | B |
| 171 | 0.002 | A |
| 173 | 0.0004 | A |
| 191 | 0.006 | A |
| 206 | 0.003 | A |
| 216 | 0.004 | A |
| 236 | 0.003 | A |
| 256 | 0.003 | A |
| 268 | 0.001 | B |
| 269 | 0.0007 | A |

Selectivity (TRα/TRβ):
A: 5<(TRα/TRβ)
B: 2<(TRα/TRβ)<5
C: 2>(TRα/TRβ)

Industrial Applicability

The heterocyclic derivative of the present invention shows a thyroid hormone β receptor agonist action, and can be a medicament effective for the prophylaxis or treatment of the diseases relating to the action.

This application is based on patent application No. 2009-102259 filed in Japan, the contents of which are encompassed in full herein.

The invention claimed is:
1. A compound represented by the formula:

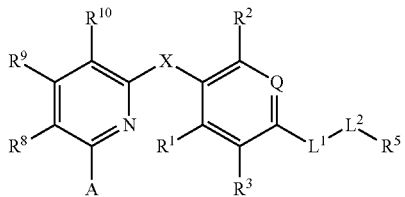

wherein

A is optionally substituted alkyl, optionally substituted carbocyclic group, optionally substituted aryl, optionally substituted heterocyclic group, optionally substituted heteroaryl, optionally substituted amino, or optionally substituted carbamoyl, X is optionally substituted methylene, —O— or —S—, Q is C—$R^4$, $L^1$ is single bond, methylene, —CH=CH—, —O—, —CO—, —$NR^{11}$—, —$NR^{11}$CO—, —$CONR^{11}$—, —$CH_2NR^{11}$— or —S—, $L^2$ is single bond, —$CR^6R^7$—, or divalent heterocyclic group, $R^1$ and $R^2$ are the same or different and each is hydrogen, alkyl, alkenyl or halogen, $R^3$ and $R^4$ are the same or different and each is hydrogen, alkyl, alkoxy, cyano or halogen, $R^1$ and $R^3$ are optionally bonded to form carbocycle or heterocycle, $R^5$ is a carboxyl group, an alkoxycarbonyl group or bioisosteric group of carboxyl group, wherein the bioisosteric group is selected from the group consisting of the following formulae:

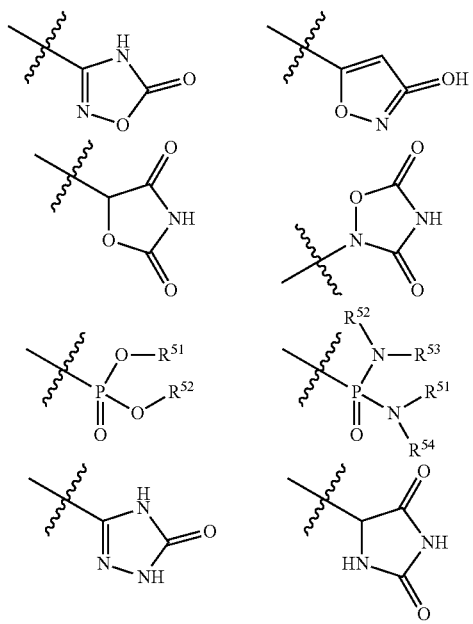

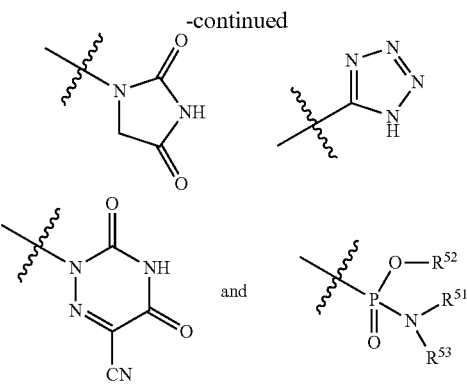

wherein $R^{51}$ and $R^{52}$ are the same or different and each is alkyl optionally substituted by alkanoyloxy or alkoxycarbonyl, or hydrogen, $R^{51}$ and $R^{52}$ may be bonded to form heterocycle optionally substituted by aryl optionally substituted by halogen, and $R^{53}$ and $R^{54}$ are the same or different and each is alkyl or hydrogen, $R^6$ and $R^7$ are the same or different and each is hydrogen, optionally substituted alkyl or halogen, or $R^6$ and $R^7$ are bonded to form cycloalkane or heterocycle, $R^8$ is hydroxy, alkanoylamino or alkylsulfonylamino, $R^9$ and $R^{10}$ are the same or different and each is hydrogen, alkyl or halogen, and $R^{11}$ is hydrogen or alkyl, or a pharmacologically acceptable salt thereof.

2. The compound according to claim 1, wherein the substituent of the optionally substituted alkyl for A is the same or different 1-3 groups selected from aryl optionally substituted by 1-3 groups selected from alkyl, halogen, alkoxy, alkanoyl, and cyano;

a heterocyclic group optionally substituted by 1-3 groups selected from alkyl, halogen, alkoxy, alkanoyl, and cyano;

heteroaryl optionally substituted by 1-3 groups selected from alkyl, halogen, alkoxy, alkanoyl, and cyano;

cycloalkyl optionally substituted by 1-3 groups selected from alkyl, halogen, alkoxy, alkanoyl, and cyano;

hydroxy;

alkoxy;

halogen;

amino group optionally substituted by 1 or 2 alkyl; and oxo, the substituent of the optionally substituted aryl, optionally substituted carbocyclic group, optionally substituted heterocyclic group and optionally substituted heteroaryl group for A is the same or different 1-3 groups selected from alkyl optionally substituted by hydroxy, alkoxy, cycloalkyl or halogen;

alkenyl optionally substituted by alkoxy or cycloalkyl;

cycloalkyl optionally substituted by alkyl, alkoxy or cycloalkyl;

alkoxy optionally substituted by alkoxy, cycloalkyl or halogen;

cycloalkyloxy optionally substituted by alkyl, alkoxy or cycloalkyl;

halogen;

cyano;

hydroxy;

oxo;

heterocycle;

alkylsulfonyl; and mono or dialkylcarbamoyl, the substituent of the optionally substituted amino for A is the same or different 1 or 2 alkyl optionally substituted by alkoxy, cycloalkyl or halogen;

alkenyl optionally substituted by alkoxy or cycloalkyl;

cycloalkyl optionally substituted by alkyl, alkoxy or cycloalkyl;

alkanoyl optionally substituted by alkoxy, cycloalkyl or halogen; or aryl optionally substituted by alkyl, alkoxy or cycloalkyl, the substituent of the optionally substituted carbamoyl for A is the same or different 1 or 2 alkyl optionally substituted by aryl, the substituent of the optionally substituted alkyl for $R^6$ or $R^7$ is alkoxy, hydroxy or halogen, and the substituent of the optionally substituted methylene for X is alkoxy or hydroxy, or a pharmacologically acceptable salt thereof.

3. The compound according to claim 2, wherein A is optionally substituted alkyl, optionally substituted carbocyclic group, optionally substituted aryl, optionally substituted heterocyclic group or optionally substituted heteroaryl, Q is C—$R^4$, $R^1$ and $R^2$ are the same or different and each is alkyl or halogen, $R^3$ and $R^4$ are the same or different and each is hydrogen, alkyl or halogen, X is methylene, —O— or —S—, $R^5$ is a carboxyl group, an alkoxycarbonyl group, or bioisosteric group of carboxyl group, wherein the bioisosteric group is selected from the group consisting of the following formulae:

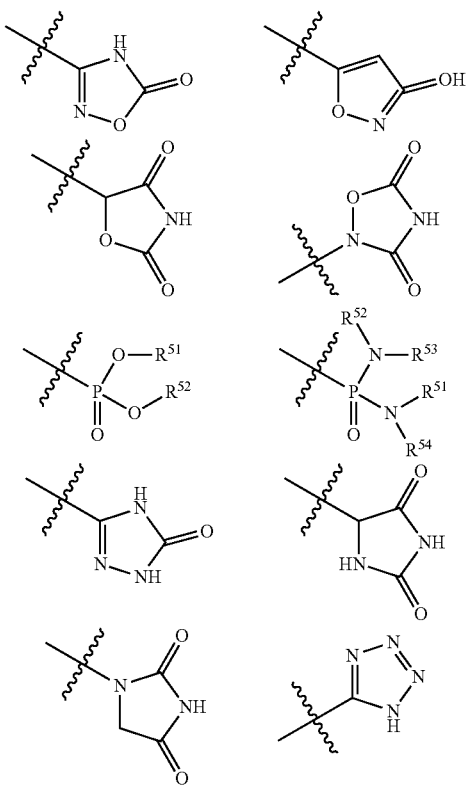

-continued

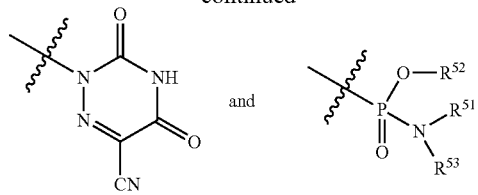

wherein $R^{51}$ and $R^{52}$ are the same or different and each is alkyl optionally substituted by alkanoyloxy or alkoxycarbonyl, or hydrogen, $R^{51}$ and $R^{52}$ may be bonded to form heterocycle optionally substituted by aryl optionally substituted by halogen, and $R^{53}$ and $R^{54}$ are the same or different and each is alkyl or hydrogen, $L^1$ is a single bond, methylene, —CH=CH—, —O—, —NH—, —NHCO— or —S—, $L^2$ is a single bond, —$CR^6R^7$—, or divalent heterocyclic group, $R^6$ and $R^7$ are the same or different and each is hydrogen, alkyl or halogen, or $R^6$ and $R^7$ are bonded to form cycloalkane or heterocycle together with the adjacent carbon, $R^8$ is hydroxy, and $R^9$ and $R^{10}$ are hydrogen, or a pharmacologically acceptable salt thereof.

4. The compound according to claim 1, wherein A is an optionally substituted carbocyclic group, or a pharmacologically acceptable salt thereof.

5. The compound according to claim 1, wherein A is optionally substituted aryl, or a pharmacologically acceptable salt thereof.

6. The compound according to claim 4, wherein the optionally substituted carbocyclic group is optionally substituted cycloalkyl, or a pharmacologically acceptable salt thereof.

7. The compound according to claim 1, wherein A is optionally substituted alkyl, or a pharmacologically acceptable salt thereof.

8. The compound according to claim 1, wherein A is optionally substituted heterocyclic group, or a pharmacologically acceptable salt thereof.

9. The compound according to claim 1, wherein A is optionally substituted heteroaryl, or a pharmacologically acceptable salt thereof.

10. The compound according to claim 1, wherein X is methylene, or a pharmacologically acceptable salt thereof.

11. The compound according to claim 1, wherein $R^1$ and $R^2$ are the same group, or a pharmacologically acceptable salt thereof.

12. The compound according to claim 1, wherein $R^1$ and $R^2$ are the same or different and each is alkyl, or a pharmacologically acceptable salt thereof.

13. The compound according to claim 1, wherein $R^1$ and $R^3$ are bonded to form carbocycle or heterocycle, or a pharmacologically acceptable salt thereof.

14. The compound according to claim 1, wherein $R^8$ is hydroxy, or a pharmacologically acceptable salt thereof.

15. (4-{[5-Hydroxy-6-(2-naphthyl)pyridin-2-yl]methyl}-3,5-dimethylphenoxy)acetic acid;
{4-[(6-cyclopentyl-5-hydroxypyridin-2-yl)methyl]-2,3,5-trimethylphenoxy}acetic acid;
{4-[(6-cyclohexyl-5-hydroxypyridin-2-yl)methyl]-2,3,5-trimethylphenoxy}acetic acid;
{2-bromo-4- [(6-cyclohexyl-5-hydroxypyridin-2-yl)methyl]-3,5-dimethylphenoxy}acetic acid;

3-({4-[(5-hydroxy-6-phenylpyridin-2-yl)methyl]-3,5-dimethylphenyl}amino)-3-oxopropanoic acid;

3-({4-[(6-cyclohexyl-5-hydroxypyridin-2-yl)methyl]-3,5-dimethylphenyl}amino)-3-oxopropanoic acid;

3-[(4-{[5-hydroxy-6-(2-naphthyl)pyridin-2-yl]methyl}-3,5-dimethylphenoxy)methyl]-1,2,4-oxadiazol-5(4H)-one;

3-[(4-{[5-hydroxy-6-(5,6,7,8-tetrahydronaphthalen-2-yl)pyridin-2-yl]methyl}-3,5-dimethylphenoxy)methyl]-1,2,4-oxadiazol-5(4H)-one;

3-({4-[(6-cycloheptyl-5-hydroxypyridin-2-yl)methyl]-3,5-dimethylphenyl}amino)-3-oxopropanoic acid;

N-[2-chloro-4-(6-cyclohexyl-5-hydroxy-pyridin-2-ylmethyl)-3,5-dimethyl-phenyl]amino-3-oxopropanoic acid;

3-[(2-fluoro-4-{[6-(2-fluoro-3-methylphenyl)-5-hydroxypyridin-2-yl]methyl}-3,5-dimethylphenoxy)methyl]-1,2,4-oxadiazol-5(4H)-one;

{4-[(6-cyclohexyl-4-fluoro-5-hydroxypyridin-2-yl)methyl]-2,3,5-trimethylphenoxy}acetic acid;

{4-[(6-cyclohexyl-3-fluoro-5-hydroxypyridin-2-yl)methyl]-2,3,5-trimethylphenoxy}acetic acid;

{4-[(6-cycloheptyl-5-hydroxypyridin-2-yl)methyl]-2,3,5-trimethylphenoxy}acetic acid;

3-({4-[(6-cycloheptyl-5-hydroxypyridin-2-yl)methyl]-2-fluoro-3,5-dimethylphenyl}amino)-3-oxopropanoic acid;

{4-[6-(3-fluoro-phenyl)-5-hydroxy-pyridin-2-ylmethyl]-2,3,5-trimethyl-phenoxy}acetic acid;

(4-{[6-(3-chlorophenyl)-5-hydroxypyridin-2-yl]methyl}-2,3,5-trimethylphenoxy)acetic acid;

3-{2-fluoro-4-[5-hydroxy-6-(2,3,4-trifluoro-phenyl)-pyridin-2-ylmethyl]-3,5-dimethyl-phenoxymethyl}-1,2,4-oxadiazol-5(4H)-one;

3-[(2-fluoro-4-{[5-hydroxy-6-(3-pyrrolidin-1-ylphenyl)pyridin-2-yl]methyl}-3,5-dimethylphenoxy)methyl]-1,2,4-oxadiazol-5(4H)-one;

2-{4-[(5-hydroxy-6-phenylpyridin-2-yl)methyl]-3,5-dimethylphenyl}-3,5-dioxo-2,3,4,5-tetrahydro-1,2,4-triazine-6-carbonitrile;

3-{2-fluoro-4-[5-hydroxy-6-(3-propoxy-phenyl)-pyridin-2-ylmethyl]-3,5-dimethyl-phenoxymethyl}-1,2,4-oxadiazol-5(4H)-one;

[3,5-dibromo-2-fluoro-4-(5-hydroxy-6-phenyl-pyridin-2-ylmethyl)-phenoxy]acetic acid;

(5-ethyl-4-{[6-(3-fluorophenyl)-5-hydroxypyridin-2-yl]methyl}-2,3-dimethylphenoxy)acetic acid, or a pharmacologically acceptable salt thereof.

16. A pharmaceutical composition comprising:
the compound according to claim 1, or a pharmacologically acceptable salt thereof, as an active ingredient; and
a pharmaceutically acceptable carrier.

17. The compound according to claim 3, wherein X is methylene, and $R^8$ is hydroxyl, or a pharmacologically acceptable salt thereof.

18. The compound according to claim 17, wherein -$L^1$-$L^2$-$L^5$ is Selected from the group consisting of the following formulae:

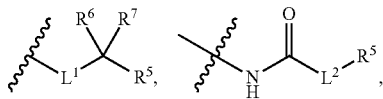

or a pahramacologically acceptable salt thereof.

19. The compound according to claim 18, wherein A is optionally substituted cycloalkyl, or a pharmacologically acceptable salt thereof.

* * * * *

UNITED STATES PATENT AND TRADEMARK OFFICE
CERTIFICATE OF CORRECTION

PATENT NO. : 8,791,266 B2  Page 1 of 1
APPLICATION NO. : 13/265137
DATED : July 29, 2014
INVENTOR(S) : Shinji Kawata et al.

It is certified that error appears in the above-identified patent and that said Letters Patent is hereby corrected as shown below:

IN THE CLAIMS:

In claim 1, at column 255, immediately below line 41, change the right-hand formula

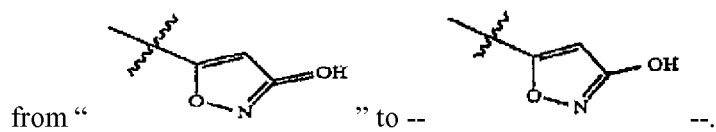

In claim 3, at column 257, immediately below line 35, change the right-hand formula

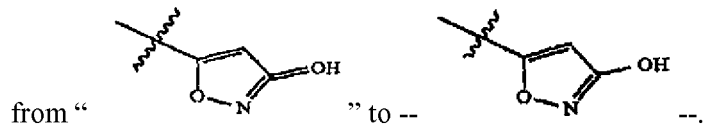

In claim 18, at column 260, lines 21-22, change "-$L^1$-$L^2$-$L^5$" to -- -$L^1$-$L^2$-$R^5$ --.

Signed and Sealed this
Twenty-fourth Day of February, 2015

Michelle K. Lee
*Deputy Director of the United States Patent and Trademark Office*